United States Patent
Sato et al.

(10) Patent No.: US 6,291,452 B1
(45) Date of Patent: Sep. 18, 2001

(54) 1,4-BENZODIAZEPINONES AND THEIR USES AS CCK ANTAGONISTS

(75) Inventors: Yoshinari Sato, Takaishi; Seiichiro Tabuchi, Nishinomiya; Hitoshi Mitsui, Nara-ken; Ikuyo Katsumi, Osaka; Naoko Yamamoto, Nishinomiya, all of (JP)

(73) Assignees: Fujisawa Pharmacetical Co., Ltd.; Nippon Shokubai Co., Ltd., both of Osaka (JP)

( * ) Notice: Subject to any disclaimer, the term of this patent is extended or adjusted under 35 U.S.C. 154(b) by 0 days.

(21) Appl. No.: 09/269,752

(22) PCT Filed: Sep. 29, 1997

(86) PCT No.: PCT/JP97/03483

§ 371 Date: Apr. 30, 1999

§ 102(e) Date: Apr. 30, 1999

(87) PCT Pub. No.: WO98/15535

PCT Pub. Date: Apr. 16, 1998

(30) Foreign Application Priority Data

Oct. 8, 1996 (AU) .............................. PO2843/96

(51) Int. Cl.[7] .................... A61K 31/5513; C07D 243/24
(52) U.S. Cl. ............................ 514/221; 540/509
(58) Field of Search ............................ 514/221; 540/509

(56) References Cited

U.S. PATENT DOCUMENTS

| | | | |
|---|---|---|---|
| 4,970,207 | 11/1990 | Sato et al. ............................ | 514/211 |
| 4,981,847 | 1/1991 | Sato et al. ............................ | 514/211 |
| 5,155,101 | 10/1992 | Sato et al. ............................ | 514/211 |
| 5,248,679 | 9/1993 | Sato et al. ............................ | 514/220 |
| 5,264,433 | 11/1993 | Sato et al. ............................ | 514/221 |
| 5,322,842 | 6/1994 | Sato et al. ............................ | 514/220 |
| 5,360,802 | * 11/1994 | Chambers et al. .................... | 514/221 |
| 5,382,664 | 1/1995 | Sato et al. ............................ | 540/509 |
| 5,401,737 | 3/1995 | Sato et al. ............................ | 514/220 |
| 5,410,049 | * 4/1995 | Chambers et al. .................... | 540/504 |
| 5,451,582 | * 9/1995 | Chambers et al. .................... | 514/221 |
| 5,461,048 | 10/1995 | Sato et al. ............................ | 514/211 |
| 5,556,969 | * 9/1996 | Chambers et al. .................... | 540/509 |
| 5,569,654 | * 10/1996 | Armour et al. ....................... | 514/221 |
| 5,597,915 | * 1/1997 | Chambers et al. .................... | 540/509 |
| 5,681,833 | * 10/1997 | Castro Pineiro et al. ........... | 514/215 |
| 5,763,437 | 6/1998 | Sato et al. ............................ | 514/221 |
| 5,929,071 | * 7/1999 | Salata, Jr. ............................ | 514/221 |

FOREIGN PATENT DOCUMENTS

| | | | |
|---|---|---|---|
| 514 133 | * 11/1992 | (EP) . | |
| WO 93/16999 | * 9/1993 | (WO) . | |
| WO 95/28399 | * 10/1995 | (WO) . | |

OTHER PUBLICATIONS

Bright et al. (Synth. Commun. (1996), 26(22), 4195–4209).*

* cited by examiner

*Primary Examiner*—Bruck Kifle
(74) *Attorney, Agent, or Firm*—Oblon, Spivak, McClelland, Maier & Neustadt, P.C.

(57) ABSTRACT

Benzodiazepine derivatives of the formula:

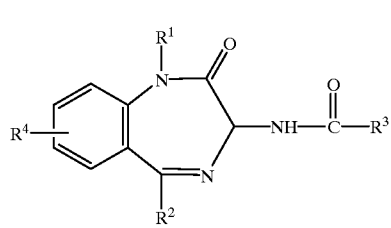

wherein $R^2$ is alkyl or cycloalkyl-alkyl when $R^4$ is hydrogen, or $R^2$ is a variety of specified groups when $R^4$ is alkyl, halogen or dialkylamino, are useful as cholecystokinin antagonists.

12 Claims, No Drawings

1,4-BENZODIAZEPINONES AND THEIR USES AS CCK ANTAGONISTS

TECHNICAL FIELD

This invention relates to new benzodiazepine derivatives or a pharmaceutically acceptable salts thereof which are useful as a medicament.

BACKGROUND ART

Some benzodiazepine derivatives have been known as described, for example, in European Patent Application Publication No. 349949 and International Publication No. WO 96/04254.

DISCLOSURE OF INVENTION

This invention relates to new benzodiazepine derivatives or pharmaceutically acceptable salts thereof.

More particularly, it relates to new benzodiazepine derivatives and pharmaceutically acceptable salts thereof which are selective cholecystokinin-B (CCK-B) antagonists or cholecystokinin-A and B (CCK-A/B) antagonists and therefore useful as therapeutical and/or preventive agents for disorders of appetite regulatory systems (e.g., anorexia, etc.), disorders associated with intestinal smooth muscle hyperactivity (e.g., irritable bowel syndrome, sphineter spasm, etc.), panic disorder, psychosis (e.g., schizophrenia, etc.), pancreatitis, etc. and also useful as analgesics.

The benzodiazepine derivatives of this invention can be represented by the following formula (I):

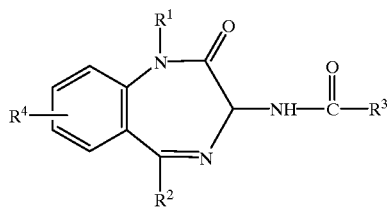

(I)

Wherein
$R^1$ is
(1) lower alkyl;
(2) hydroxy(lower)alkyl;
(3) protected hydroxy(lower)alkyl;
(4) heterocyclic(lower)alkyl which may have one or more suitable substituent(s);
(5) aryl(lower)alkyl which may have one or more suitable substituent(s);
(6) carboxy(lower)alkyl;
(7) protected carboxy(lower)alkyl; or (8)

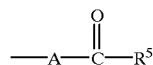

[wherein
A is lower alkylene and
$R^5$ is
(a) lower alkyl,
(b) $C_3$–$C_8$ cycloalkyl,
(c) adamantyl,
(d) aryl which may have one or more suitable substituent (s),
(e) amino which may have one or two suitable substituent(s),
(f) azabicyclo[3.2.2]nonyl, or
(g) saturated heteromonocyclic group containing at least one nitrogen atom, which may have one or more suitable substituent(s)],
$R^2$ is
(1) lower alkyl,
(2) $C_3$–$C_8$ cycloalkyl,
(3) lower alkoxy(lower)alkyl,
(4) $C_3$–$C_8$ cycloalkyl(lower)alkyl,
(5) N,N-di(lower)alkylamino(lower)alkyl,
(6) lower alkylpiperazinyl(lower)alkyl,
(7) lower alkylthio(lower)alkyl,
(8) hydroxy(lower)alkyl,
(9) protected hydroxy(lower)alkyl,
(10) azabicyclo[3.2.2]nonyl(lower)alkyl,
(11) aryl which may have one or more suitable substituent(s),
(12) cyano,
(13) lower alkanoyl,
(14) carboxy(lower)alkenyl, or
(15) protected carboxy(lower)alkenyl,
$R^3$ is indolyl or -NH-$R^6$ [wherein $R^6$ is
(1) aryl which may have one or more suitable substituent(s),
(2) pyridyl which may have one or more suitable substituent(s), or
(3) $C_3$–$C_8$ cycloalkyl], and
$R^4$ is
(1) hydrogen,
(2) lower alkyl,
(3) halogen, or
(4) di(lower)alkylamino,
with proviso that when $R^4$ is hydrogen, then $R^2$ is lower alkyl or $C_3$–$C_8$ cycloalkyl(lower)alkyl,
or a pharmaceutically acceptable salt thereof.

According to the present invention, the new benzodiazepine derivatives (I) can be prepared by the processes which are illustrated in the following scheme.

Process 1

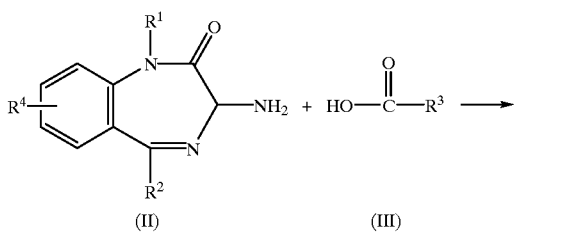

(II)    (III)

or its reactive derivative at the amino group or a salt thereof    or its reactive derivative or a salt thereof

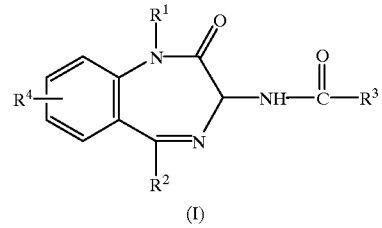

(I)
or a salt thereof

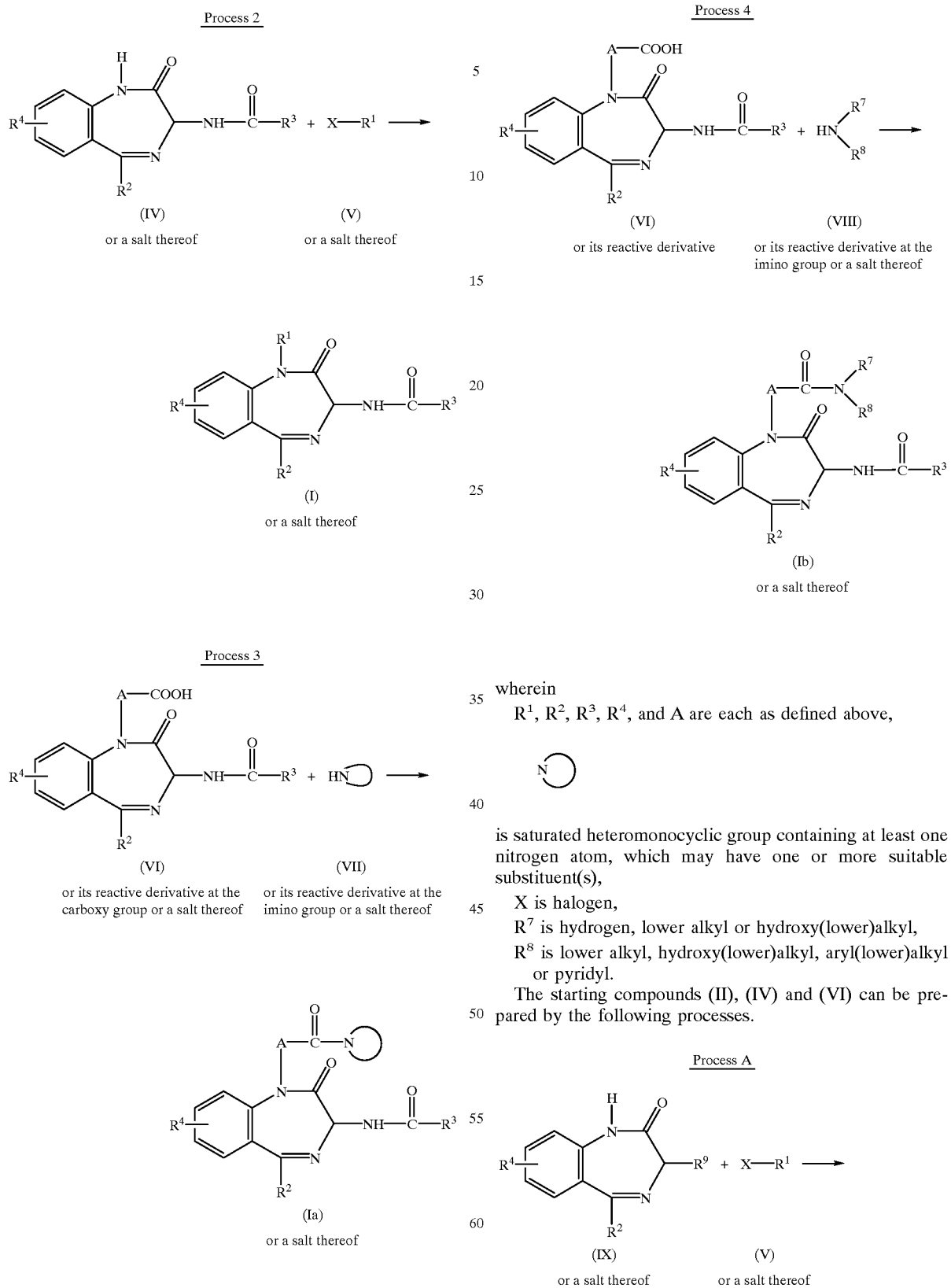

wherein
R[1], R[2], R[3], R[4], and A are each as defined above,

[ring N symbol]

is saturated heteromonocyclic group containing at least one nitrogen atom, which may have one or more suitable substituent(s),
X is halogen,
R[7] is hydrogen, lower alkyl or hydroxy(lower)alkyl,
R[8] is lower alkyl, hydroxy(lower)alkyl, aryl(lower)alkyl or pyridyl.

The starting compounds (II), (IV) and (VI) can be prepared by the following processes.

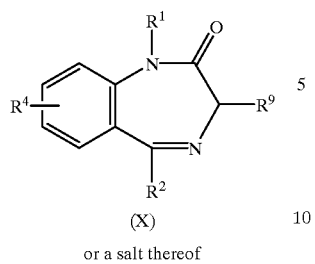

(X)

or a salt thereof

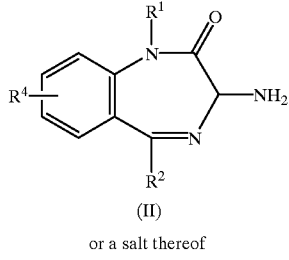

(II)

or a salt thereof

Process B

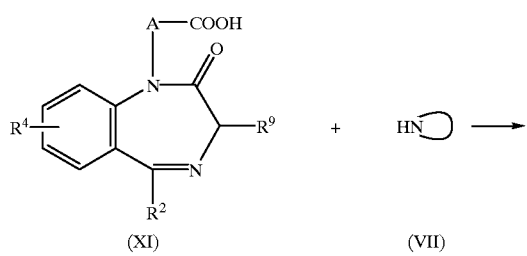

(XI)     (VII)

or its reactive derivative at the    or its reactive derivative at the
carboxy group or a salt thereof    imino group or a salt thereof

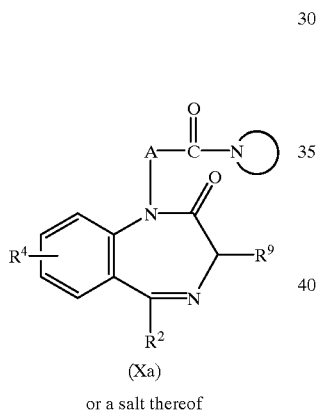

(Xa)

or a salt thereof

Process C

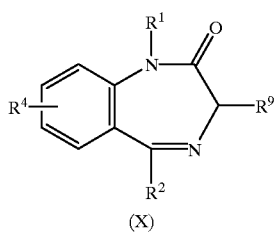

(X)

or a salt thereof

| Elimination reaction of the amino protective group

Process D

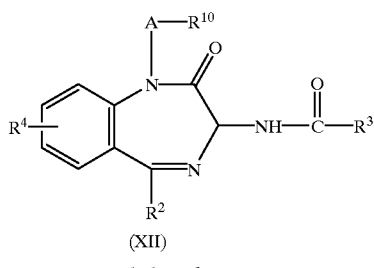

(XII)

or a salt thereof

| Elimination reaction of the carboxy protective group

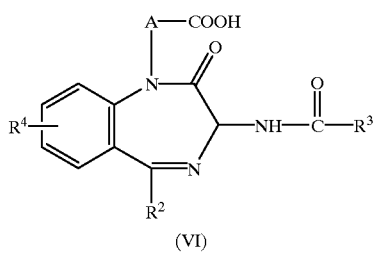

(VI)

Process E

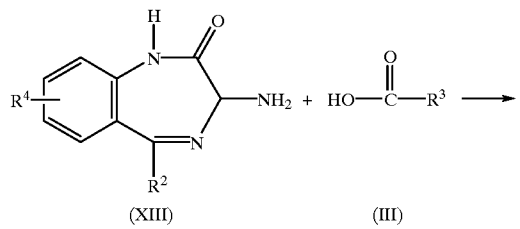

(XIII)     (III)

or its reactive derivative at the    or its reactive derivative
amino group or a salt thereof    or a salt thereof

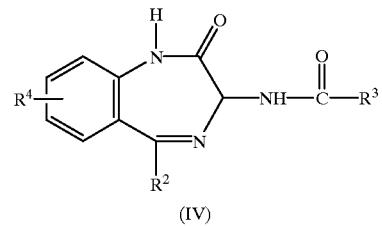

(IV)

or a salt thereof wherein $R^1$, $R^2R^3$, $R^4$, X,

and A are each as defined above,
$R^9$ is protected amino, and
$R^{10}$ is protected carboxy.

With regard to the object compound (I), in case that the compound (I) has the group of the formula:

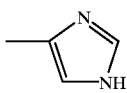

in $R^1$, said group can also exist in the tautomeric form and such tautomeric equilibrium can be represented by the following scheme.

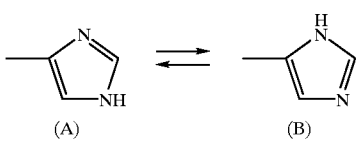

Both of the above tautomeric isomers are included within the scope of the present invention. In the present specification and claim, the compounds including the group of such tautomeric isomers are represented for the convenient sake by one expression of the group of the formula (A).

Further, in case that the compound (I) has the group of the formula:

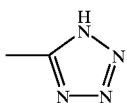

in $R^6$, said group can also exist in the tautomeric from and such tautomeric equilibrium can be represented by the following scheme.

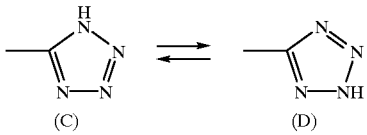

Both of the above tautomeric isomers are included within the scope of the present invention. In the present specification and claim, the compounds including the group of such tautomeric isomers are represented for the convenient sake by one expression of the group of the formula (C).

BEST MODE FOR CARRYING OUT THE INVENTION

Suitable pharmaceutically acceptable salts of the object compound (I) are conventional non-toxic salts and include a metal salts such as an alkali metal salt (e.g., sodium salt, potassium salt, etc.) and an alkaline earth metal salt (e.g., calcium salt, magnesium salt, etc.), an ammonium salt, an organic base salt (e.g., trimethylamine salt, triethylamine salt, pyridine salt, picoline salt, dicyclohexylamine salt, N,N'-dibenzylethylene diamine salt, etc.), an organic acid salt (e.g., acetate, maleate, lartrate, methanesulfonate, benzenesulfonate, formate, toluenesulfonate, trifluoroacetate, etc.), an inorganic acid salt (e.g., hydrochloride, hydrobromide, sulfate, phosphate, etc.), a salt with an amino acid (e.g., arginine, aspartic acid, glutamic acid, etc.), and the like.

In the above and subsequent descriptions of the present specification, suitable examples and illustrations of the various definitions which the present invention include within the scope thereof are explained in detail as follows.

The term "lower" is intended to mean 1 to 6 carbon atom(s), unless otherwise indicated.

Suitable "lower alkyl" may include methyl, ethyl, propyl, isopropyl, butyl, isobutyl, sec-butyl, t-butyl, 3-methylbutyl, pentyl, t-pentyl, hexyl and the like.

Suitable "hydroxy protective group" in "protected hydroxy(lower)alkyl" may include acyl, which includes aliphatic acyl group and acyl group containing an aromatic or heterocyclic ring.

And, suitable examples of the said acyl may be lower alkanoyl (e.g., formyl, acetyl, propionyl, butyryl, isobutyryl, valeryl, isovaleryl, oxalyl, succinyl, pivaloyl, etc.); lower alkoxycarbonyl (e.g., methoxycarbonyl, ethoxycarbonyl, propoxycarbonyl, isopropoxycarbonyl, butoxycarbonyl, tert-butoxycarbonyl, pentyloxycarbonyl, hexyloxycarbonyl, etc.); lower alkanesulfonyl (e.g., mesyl, ethanesulfonyl, propanesulfonyl, isopropanesulfonyl, butanesulfonyl, etc.); arenesulfonyl (e.g., benzenesulfonyl, tosyl, etc.); aroyl (e.g., benzoyl, toluoyl, xyloyl, naphthoyl, phthaloyl, indancarbonyl, etc.); ar(lower)alkanoyl (e.g., phenylacetyl, phenylpropionyl, etc.); ar(lower)alkoxycarbonyl (e.g., benzyloxycarbonyl, phenethyloxycarbonyl, etc.), and the like.

Suitable "heterocyclic group" may include saturated or unsaturated, monocyclic or polycyclic heterocyclic group containing at least one hetero-atom such as an oxygen, sulfur, nitrogen atom and the like. And especially preferable helerocyclic group may be heterocyclic group such as unsaturated 3 to 8-membered heteromonocyclic group containing 1 to 4 nitrogen atom(s), for example, pyrrolyl, pyrrolinyl, imidazolyl, pyrazolyl, pyridyl and its N-oxide, pyperidyl, pyrimidinyl, pyrazinyl, dihydropyridazinyl, tetrahydropyridazinyl, triazolyl (e.g., 1H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), dihydrotriazinyl (e.g., 4,5-dihydro-1,2,4-triazinyl, 2,5-dihydro-1,2,4-triazinyl, etc.), etc.;

saturated 3 to 8-membered heteromonocyclic group containing 1 to 4 nitrogen atom(s), for example, pyrrolidinyl, imidazolidinyl, piperidino, piperazinyl, azacycloheptyl, azacyclooetyl, etc.;

unsaturated condensed heterocyclic group containing 1 to 5 nitrogen atom(s), for example, indolyl, isoindolyl, indolinyl, isoindolinyl, indolizynyl, benzimidazolyl, quinolyl, isoquinolyl, indazolyl, benzotriazolyl, tetrazolopyridyl, tetrazolopyridazinyl (e.g.,tetrazolo[1,5-b]pyridazinyl, etc.,), dihydrotriazolopyridazinyl, etc.,;

unsaturated 3 to 8-membered heteromonocyclic group containing 1 to 2 oxygen atom(s) and 1 to 3 nitrogen atom(s), for example, oxazolyl, isoxazolyl, dihydroisoxazolyl, oxadiazolyl (e.g., 1,2,4-oxadiazolyl, 1,3,4-oxadiazolyl, 2,5-oxadiazolyl, etc.,), etc.,;

saturated 3 to 8-membered heteromonocyclic group containing 1 to 2 oxygen atom(s) and 1 to 3 nitrogen atom(s), for example, morpholinyl, etc.,;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered heteromonocyclic group containing 1 to 2 sulfur atom(s) and 1 to 3 nitrogen atom(s), for example, 1,3-thiazolyl, 1,2-thiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl), etc.,;

saturated 3 to 8-membered heteromonocyclic group containing 1 to 2 sulfur atom(s) and 1 to 3 nitrogen atom(s), for example, thiazolidinyl, etc.,;

unsaturated 3 to 8-membered heteromonocyclic group containing an oxygen atom, for example furyl, etc.;

unsaturated 3 to 8-membered heteromonocyclic group containing a sulfur atom, for example, thienyl, etc.;

unsaturated condensed heteromonocyclic group containing 1 to 2 sulfur atom(s) and 1 to 3 nitrogen atom(s), for example, benzothiazolyl, benzothiadiazolyl, etc., and the like.

Suitable "aryl" may include phenyl, naphthyl, and the like.

Suitable "protected carboxy" may include esterified carboxy and the like.

Suitable example of the ester moiety of an esterified carboxy may be the ones such as lower alkyl ester (e.g. methyl ester, ethyl ester, propyl ester, isopropyl ester, butyl ester, isobutyl ester, tert-butyl ester, pentyl ester, hexyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1 (or 2 or 3 or 4)-acetoxybutyl ester, 1 (or 2)-propionyloxyethyl ester, 1(or 2 or 3)-propionyloxypropyl ester, 1(or 2)-butyryloxyethyl ester, 1(or 2)-isobutyryloxyethyl ester, 1(or 2)-pivaloyloxyethyl ester, 1(or 2)-hexanoyloxyethyl ester, iso-butyryloxymethyl ester, 2-ethylbutyryloxymethyl ester, 3,3-dimethylbutyryloxymethyl ester, 1(or 2)-pentanoyloxyethyl ester, etc.], lower alkanesulfonyl (lower)alkyl ester (e.g. 2-mesylethyl ester, etc.), mono(or di or tri)-halo(lower)alkyl ester (e.g. 2-iodoethyl ester, 2,2,2-trichloroethyl ester, etc.), lower alkoxycarbonyloxy(lower) alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), lower alkylthio (lower)alkyl ester (e.g. methylthiomethyl ester, 1-(or 2-)methylthioethyl ester, 1-(or 2- or 3-)methylthiopropyl ester, 1-(or 2- or 3- or 4-)methylthiobutyl ester, 1-(or 2- or 3- or 4-or 5-)methylthiopentyl ester, 1-(or 2- or 3- or 4- or 5- or 6-)methylthiohexyl ester, ethyl-thiomethyl ester, 1-(or 2-)ethylthioethyl ester, 1-(or 2- or 3-)ethylthiopropyl ester, propylthiomethyl ester, 1-(or 2-)propylthioethyl ester, 1-(or 2- or 3-)propylthiopropyl ester, etc.), phthalidylidene(lower) alkyl ester, or (5-lower alkyl-2-oxo-1,3-dioxol-4-yl)(lower) alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, etc.); lower alkynyl ester (e.g. ethynyl ester, propynyl ester, etc.); ar(lower)alkyl ester which may have at least one suitable substituent(s) such as mono(or di or tri)phenyl(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.); aryl ester which may have at least one suitable substituent(s) (e.g. phenyl ester, 4-chlorophenyl ester, tolyl ester, tert-butylphenyl ester, xylyl ester, mesityl ester, cumenyl ester, etc.); phthalidyl ester; and the like.

Suitable "lower alkylene" may include straight or branched one having 1 to 6 carbon atom(s), such as methylene, ethylene, trimethylene, tetramethylene, pentamethylene, hexamethylene, or the like, preferably one having 1 to 4 carbon atom(s).

Suitable "$C_3$–$C_8$ cycloalkyl" may include cyclopropyl, cyclobutyl, cyclopentyl, cyclohexyl, cycloheptyl and cyclooctyl.

Suitable "saturated heteromonocyclic group containing at least one nitrogen atom" may include saturated 3 to 8-membered heteromonocyclic group containing 1 to 4 nitrogen atom(s), for example, pyrrolidinyl, imidazolidinyl, piperidino, piperidyl, piperazinyl, azacycloheptyl, azacyclooetyl, etc.;

saturated 3 to 8-membered heteromonocyclic group containing 1 to 2 oxygen atom(s) and 1 to 3 nitrogen atom(s), for example, morpholinyl, etc.;

saturated 3 to 8-membered heteromonocyclic group containing 1 to 2 sulfur atom(s) and 1 to 3 nitrogen atom(s), for example, thiazolidinyl, etc., and the like.

Suitable "lower alkoxy" may include methoxy, ethoxy, propoxy, isopropoxy, butoxy, t-butoxy, pentyloxy, t-pentyloxy, hexyloxy, and the like.

Suitable "substituent" in the terms "heterocyclic(lower) alkyl which may have one or more suitable substituent(s)", "aryl(lower)alkyl which may have one or more suitable substituent(s)", "aryl which may have one or more suitable substituent(s)", "amino which may have one or more suitable substituent(s)", "saturated heteromonocyclic group containing at least one nitrogen atom, which may have one or more suitable substituent(s)", and "pyridyl which may have one or more suitable substituent(s)" may include lower alkyl (which is exemplified above), acyl (which is exemplified above), hydroxy, lower alkoxy (which is exemplified above), carboxy(lower)alkoxy, protected carboxy(lower) alkoxy, nitro, amino, diacylamino, hydroxy(lower)alkyl, aryl(lower)alkyl, carbamoyl, oxo, aryl (which is exemplified above), mono or di substituted carbamoyl (which is exemplified above), heterocyclic group (which is exemplified below), heterocyclic carbonyl(lower)alkyl, halogen (e.g., chlorine, bromine, fluorine and iodine), lower alkylthio (e.g., methylthio, ethylthio, propylthio, butylthio, pentylthio, etc.), carboxy, protected carboxy (which is exemplified above), triphenyl(lower)alkyltetrazolyl, hydroxyimino(lower)alkyl (e.g., hydroxyiminomethyl, hydroxyiminoethyl, etc.), sulfo (lower)alkyl (e.g., sulfomethyl, sulfoethyl, etc.), tetrazolyl (lower)alkyl, di(lower)alkylamino (e.g., N,N-dimethylamino, etc.), and the like.

Suitable examples of the said mono or di substituted carbamoyl may be mono or di(lower)alkylcarbamoyl (e.g., methylcarbamoyl, dimethylcarbamoyl, ethylcarbamoyl, diethylcarbamoyl, N-methyl-N-ethylcarbamoyl, propylcarbamoyl, dipropylcarbamoyl, isopropylcarbamoyl, butylcarbamoyl, pentylcarbamoyl, hexylcarbamoyl, etc.), heterocyclic carbamoyl (e.g., tetrazolylcarbamoyl, etc.,), mono or di(carboxy)(lower)alkylcarbamoyl (e.g., carboxymethylcarbamoyl, 1-carboxyethylcarbamoyl, 2-carboxyethylcarbamoyl, 1,3-dicarboxypropylcarbamoyl, etc.,), mono or di (lower alkoxycarbonyl)(lower) alkylcarbamoyl (e.g., 1,3-diethoxycarbonylpropylcarbamoyl,etc.), mono or di (protected carboxy)(lower)alkylcarbamoyl (wherein "protected carboxy" is exemplified above), mono or di {(lower) alkyl}amino(lower)alkylcarbamoyl (e.g., 2-dimethylaminoethylcarbamoyl, etc.), and the like.

Suitable "lower alkanoyl" may include formyl, acetyl, propionyl, butyryl, isobutyryl, valeryl, isovaleryl, pivaloyl and the like.

Suitable "lower alkenyl" may include vinyl, propenyl, butenyl, pentenyl, hexenyl and the like.

Suitable "amino protective group" in "protected amino" may include acyl (which is exemplified above) and the like.

The preferred embodiments of the object compound (I) are as follows:

$R^1$ is
(1) lower alkyl;
(2) hydroxy(lower)alkyl;
(3) acyloxy(lower)alkyl;
(4) heterocyclic(lower)alkyl which may have one or more substituent(s) selected from the group consisting of lower alkyl and acyl;
(5) aryl(lower)alkyl which may have one or more acyl(s);
(6) carboxy(lower)alkyl;
(7) esterified carboxy(lower)alkyl; or

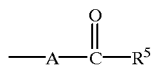

(8)

[wherein
A is lower alkylene and
$R^5$ is
(a) lower alkyl,
(b) $C_3$–$C_8$ cycloalkyl,
(c) adamantyl,
(d) aryl which may have one or more substituent(s) selected from the group consisting of lower alkyl, hydroxy, lower alkoxy, carboxy(lower)alkoxy, protected carboxy(lower)alkoxy, nitro, amino and diacylamino,
(e) amino which may have one or two substituent(s) selected from the group consisting of lower alkyl, hydroxy(lower)alkyl, aryl(lower)alkyl and pyridyl,
(f) azabicyclo[3.2.2]nonyl, or
(g) saturated heteromonocyclic group containing at least one nitrogen atom, which may have one or more substituent(s) selected from the group consisting of carbamoyl, acyl, hydroxy, oxo, aryl, aryl(lower)alkyl, lower alkyl, hydroxy(lower)alkyl, di(lower)alkylcarbamoyl, heterocyclic group, and heterocycliccarbonyl(lower)alkyl], $R^2$ is
(1) lower alkyl,
(2) $C_3$–$C_8$ cycloalkyl,
(3) lower alkoxy(lower)alkyl,
(4) $C_3$–$C_8$ cycloalkyl(lower)alkyl,
(5) N,N-di(lower)alkylamino(lower)alkyl,
(6) lower alkylpiperazinyl(lower)alkyl,
(7) lower alkylthio(lower)alkyl,
(8) hydroxy(lower)alkyl,
(9) acyloxy(lower)alkyl,
(10) azabicyclo[3.2.2]nonyl(lower)alkyl,
(11) aryl which may have one or more halogen(s),
(12) cyano,
(13) lower alkanoyl,
(14) carboxy(lower)alkenyl, or
(15) esterified carboxy(lower)alkenyl, $R^3$ is indolyl or -NH-$R^6$ [wherein $R^6$ is
(1) aryl which may have one or more substituent(s) selected from the group consisting of lower alkyl, hydroxy, lower alkoxy, lower alkylthio, hydroxy(lower)alkyl, acyl, halogen, carboxy, protected carboxy, tetrazolyl, triphenyl(lower)alkyltetrazolyl, hydroxyimino(lower)alkyl, sulfo(lower)alkyl, tetrazolyl(lower)alkyl and di(lower)alkylamino,
(2) pyridyl which may have one or more lower alkyl(s), or
(3) $C_3$–$C_8$ cycloalkyl], $R^4$ is
(1) hydrogen,
(2) lower alkyl,
(3) halogen or
(4) di(lower)alkylamino,
with proviso that when $R^4$ is hydrogen, then $R^2$ is lower alkyl or $C_3$–$C_8$ cycloalkyl(lower)alkyl,
or a pharmaceutically acceptable salt thereof.

The more preferred embodiments of the object compound (I) are as follows:

$R^1$ is
(1) lower alkyl;
(2) hydroxy(lower)alkyl;
(3) lower alkanoyloxy(lower)alkyl;
(4) heterocyclic(lower)alkyl which may have one or more substituent(s) selected from the group consisting of lower alkyl and lower alkanoyl;
(5) aryl(lower)alkyl which may have one or more lower alkanoyl(s);
(6) carboxy(lower)alkyl;
(7) lower alkoxycarbonyl(lower)alkyl; or

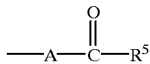

(8)

[wherein
A is lower alkylene and
$R^5$ is
(a) lower alkyl,
(b) $C_3$–$C_8$ cycloalkyl,
(c) adamantyl,
(d) aryl which may have one or more substituent(s) selected from the group consisting of lower alkyl, hydroxy, lower alkoxy, carboxy(lower)alkoxy, lower alkoxycarbonyl(lower)alkoxy, nitro, amino and di(lower alkanoyl)amino,
(e) amino which may have one or two substituent(s) selected from the group consisting of lower alkyl, hydroxy(lower)alkyl, phenyl(lower)alkyl and pyridyl,
(f) azabicyclo[3.2.2]nonyl, or
(g) saturated heteromonocyclic group containing at least one nitrogen atom, which may have one or more substituent(s) selected from the group consisting of carbamoyl, lower alkanoyl, hydroxy, oxo, phenyl, phenyl(lower)alkyl, lower alkyl, hydroxy(lower)alkyl, di(lower)alkylcarbamoyl, piperidyl, pyridyl, pyrimidinyl and pyrrolidinylcarbonyl(lower)alkyl, $R^2$ is
- (1) lower alkyl,
- (2) $C_3$–$C_8$ cycloalkyl,
- (3) lower alkoxy(lower)alkyl,
- (4) $C_3$–$C_8$ cycloalkyl(lower)alkyl,
- (5) N,N-di(lower)alkylamino(lower)alkyl,
- (6) lower alkylpiperazinyl(lower)alkyl,
- (6) lower alkylpiperazinyl(lower)alkyl,
- (7) lower alkylthio(lower)alkyl,
- (8) hydroxy(lower)alkyl,
- (9) lower alkanoyloxy(lower)alkyl,
- (10) azabicyclo[3.2.2]nonyl(lower)alkyl, or
- (11) aryl which may have one or more halogen(s),
- (12) cyano,
- (13) lower alkanoyl,
- (14) carboxy(lower)alkenyl, or
- (15) lower alkoxycarbonyl(lower)alkenyl, $R^3$ is indolyl or -NH-$R^6$ [wherein $R^6$ is
- (1) aryl which may have one or more substituent(s) selected from the group consisting of lower alkyl, hydroxy, lower alkoxy, lower alkylthio, hydroxy(lower)alkyl, lower alkanoyl, halogen, carboxy, esterified carboxy, tetrazolyl, triphenyl(lower)alkyltetrazolyl, hydroxyimino(lower)alkyl, sulfo(lower)alkyl, tetrazolyl(lower)alkyl, and di(lower)alkylamido,
- (2) pyridyl which may have one or more lower alkyl(s), or
- (3) $C_3$–$C_8$ cycloalkyl], $R^4$ is
- (1) hydrogen,
- (2) lower alkyl,
- (4) di(lower)alkylamino, with proviso that when $R^4$ is hydrogen, then $R^2$ is lower alkyl or $C_3$–$C_8$ cycloalkyl(lower)alkyl,
or a pharmaceutically acceptable salt thereof.

And the more preferred embodiments of the object compound (I) are as follows:
wherein
$R^1$ is
- (1) methyl,
- (2) hydroxyethyl,
- (3) acetoxyethyl,
- (4) pyridylmethyl, imidazolylmethyl or thienylmethyl, each of which may have one or more substituent(s) selected from the group consisting of methyl and acetyl,
- (5) benzyl which may have one or more substituent(s) selected from the group consisting of acetyl,
- (6) carboxymethyl,
- (7) ethoxycarbonylmethyl or t-butoxycarbonylmethyl, or (8)

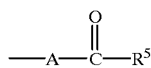

[wherein
A is methylene, and
$R^5$ is
- (a) methyl, ethyl or t-butyl,
- (b) cyclopropyl, cyclopentyl, cyclohexyl, cycloheptyl or cyclooctyl,
- (c) adamantyl,
- (d) phenyl which may have one or more substituent(s) selected from the group consisting of methyl, hydroxy, methoxy, carboxymethoxy, ethoxycarbonylmethoxy, nitro, amino and diacetylamino,
- (e) amino which may have one or two substituent(s) selected from the group consisting of methyl, ethyl, t-butyl, isopropyl, hydroxyethyl, isobutyl, 1-methyl-1-phenylethyl and pyridyl,
- (f) azabicyclo[3.2.2]nonyl, or
- (g) pyrrolidinyl, piperidyl, azacycloheptyl, azacyclooetyl, piperazinyl or morpholinyl, each of which may have one or more substituent(s) selected from the group consisting of carbamoyl, acetyl, hydroxy, oxo, phenyl, benzyl, methyl, hydroxymethyl, hydroxyethyl, diethylcarbamoyl, piperidyl, pyridyl, pyrimidinyl and pyrrolidinylcarbonylmethyl], $R^2$ is
- (1) methyl, ethyl, isopropyl, isobutyl, butyl or isopentyl,
- (2) cyclopropyl or cyclohexyl,
- (3) methoxymethyl,
- (4) cyclohexylmethyl,
- (5) N,N-dimethylaminomethyl,
- (6) methylpiperazinylmethyl,
- (7) methylthiomethyl,
- (8) hydroxymethyl,
- (9) acetoxymethyl,
- (10) (3-azabicyclo[3.2.2]non-3-yl)methyl,
- (11) phenyl which may have one or more fluorine(s),
- (12) cyano,
- (13) formyl,
- (14) carboxyvinyl, or
- (15) ethoxycarbonylvinyl, $R^3$ is indolyl or -NH-$R^6$ [wherein $R^6$ is
- (1) phenyl which may have one or more substituent(s) selected from the group consisting of methyl, hydroxy, methoxy, methylthio, hydroxymethyl, formyl, acetyl, chlorine, bromine, carboxy, t-butoxycarbonyl, tetrazolyl, triphenylmethyltetrazolyl, hydroxyiminomethyl, hydroxyiminoethyl, sulfoethyl, tetrazolylmethyl and N,N-dimethylamino,
- (2) pyridyl which may have one or more methyl(s), or
- (3) cyclohexyl], $R^4$ is
- (1) hydrogen,
- (2) methyl, ethyl or isopropyl,
- (3) chlorine, or
- (4) N,N-dimethylamino, with proviso that when $R^4$ is hydrogen, then $R^2$ is isopropyl, isobutyl, methyl, isopentyl, ethyl, butyl or cyclohexylmethyl, or a pharmaceutically acceptable salt thereof.

And the more preferred embodiments of the object compound (I) are as follows:

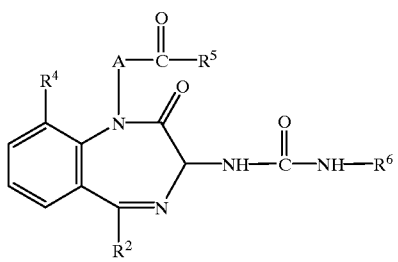

wherein
R² is lower alkyl or C₃–C₈ cycloalkyl,
R⁴ is lower alkyl,
R₅ is C₃–C₈ cycloalkyl,
R⁶ is lower alkylphenyl and
A is lower alkylene,
or a pharmaceutically acceptable salt thereof.

And the most preferred embodiments of the object compound (I) are as follows:

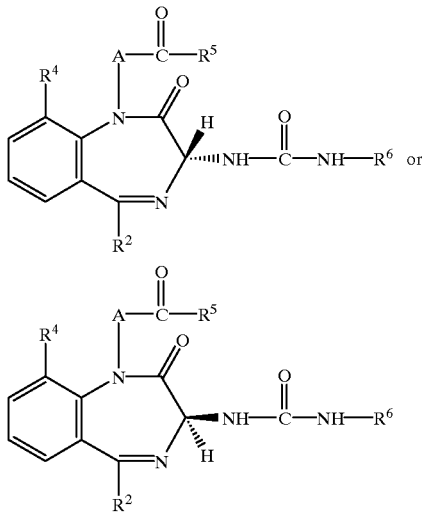

wherein
R² is lower alkyl or C₃–C₈ cycloalkyl,
R⁴ is lower alkyl,
R₅ is C₃–C₈ cycloalkyl,
R⁶ is lower alkylphenyl and
A is lower alkylene,
or a pharmaceutically acceptable salt thereof.

The processes for preparing the object compound (I) and the starting compounds of the present invention are explained in detail in the following.

10 Process 1

The compound (I) or a salt thereof can be prepared by reacting the compound (II) or its reactive derivative at the amino group or a salt thereof with the compound (III) or its reactive derivative or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as N,N-bis(trimethylsilyl)acetamide, N-trimethylsilylacetamide or the like; a derivative formed by the reaction of the compound (II) with phosphorus trichloride or phosgene and the like.

Suitable reactive derivative of the compound (III) may include an acid halide, an acid anhydride, an activated amide, an activated ester, isocyanate, and the like. The suitable example may be an acid chloride, an acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfonic acid (e.g., methanesulfonic acid, ethanesulfonic acid, etc.), sulfuric acid, alkylcarbonic acid, aliphatic carboxylic acid (e.g., pivalic acid, pentanoic acid, isopentanoic acid, 2-ethylbutyric acid, trichloroacetic acid, etc.) or aromatic carboxylic acid (e.g., benzoic acid, etc.); a symmetrical acid anhydride; an activated amide with imidazole, 4-substituted imidazole, dimethylpyrazole, triazole or tetrazole; an activated ester (e.g., cyanomethyl ester, methoxymethyl ester, dimethyliminomethyl [(CH₃)₂N⁺=CH] ester, vinyl ester, propargyl ester, phenyl ester, p-nitrophenyl ester, 2,4-dinitrophenyl ester, trichlorophenyl ester, pentachlorophenyl ester, mesylphenyl ester, phenylazophenyl ester, pyranyl ester, pyridyl ester, piperidyl ester, etc.); an ester with a N-hydroxy compound (e.g., N,N-dimethylhydroxylamine, 1-hydroxy-2-(1H)-pyridone, N-hydroxysuccinimide, N-hydroxybenzotriazole, N-hydroxyphtalimide, 1-hydroxy-6-chloro-1H-benzotriazole, etc.); isocyanate of the formula R³—N=C=O (in which R³ is as defined above), and the like. These reactive derivatives can optionally be selected according to the kind of the compound (III) to be used.

Suitable salts of the compounds (II) and (III) can be referred to the ones as exemplified for the compound (I).

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely affect the reaction. These conventional solvents may also be used in a mixture with water.

When the compound (III) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarobodiimide, N,N'-diisopropylcarbodiimide; N-ethyl-N'-(3-dimethylaminopropyl)carbodiimide; N,N'-carbonylbis-(2-methylimidazole); N,N'-carbonyldiimidazole, pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)aklylmorphorine, N,N-di(lower)alkylbenzylamine, or the like. The reaction temperature is not critical, and the reaction is usually carried out under cooling to heating.

The compound (III) or its reactive derivative, or a salt thereof can be prepared in accordance with the method disclosed in the Preparations described later or similar manners thereto.

Process 2

The compound (I) or a salt thereof can be prepared by reacting the compound (IV) or a salt thereof with a compound (V) or a salt thereof.

This reaction can be referred to that of Examples 3,6, 8–10.

Process 3

The compound (Ia) or a salt thereof can be prepared by reacting the compound (VI) or its reactive derivative at the carboxy group or a salt thereof with the compound (VII) or its reactive derivative at the imino group or a salt thereof.

Suitable reactive derivative at the carboxy group of the compound (VI) may include the same one as illustrated in the explanation of the Process 1.

Suitable reactive derivative at the imino group of the compound (VII) may be adequately selected from the reactive derivative at the amino group that is illustrated in the explanation for the Process 1.

Suitable salts of the compounds (VI) and (VII) can be referred to the ones as exemplified for the compound (I).

The reaction is usually carried out in the presence of base.

Suitable base may include an inorganic base such as alkali metal hydride (e.g., sodium hydride, etc.), alkali metal hydroxide (e.g., sodium hydroxide, potassium hydroxide, etc.), alkaline earth metal hydroxide (e.g., magnesium hydroxide, calcium hydroxide, etc.), alkali metal carbonate (e.g., sodium carbonate, potassium carbonate, etc.), alkaline earth metal carbonate (e.g., magnesium carbonate, calcium carbonate, etc.), alkali metal bicarbonate (e.g., sodium bicarbonate, potassium bicarbonate, etc.), alkali metal acetate (e.g., sodium acetate, potassium acetate, etc.), alkaline earth metal phosphate (e.g., magnesium phosphate, calcium phosphate, etc.), alkali metal hydrogen phosphate (e.g., disodium hydrogen phosphate, dipotassium hydrogen phosphate, etc.), or the like, and an organic base such as trialkylamine (e.g., trimethylamine, triethylamine etc.), picoline, N-methylpyrrolidine, N-methyl-morpholine, or the like.

The reaction is usually carried out in a solvent such as alcohol (e.g., methanol, ethanol, etc.), benzene, N,N-dimethylformamide, tetrahydrofuran, diethyl ether or any other solvent which does not adversely affect the reaction.

The reaction temperature is not critical and the reaction is usually carried out under cooling to heating.

Process 4

The compound (Ib) or a salt thereof can be prepared by reacting the compound (VI) or its reactive derivative at the carboxy group or a salt thereof with the compound (VIII) or its reactive derivative at the imino group or a salt thereof.

Suitable reactive derivative at the carboxy group of the compound (VI) and suitable reactive derivative at the imino group of the compound (VIII) may include the same one as illustrated in the explanation of the Process 1.

Suitable salts of the compounds (VI) and (VIII) can be referred to the ones as exemplified for the compound (I).

The reaction can be referred to that of the aforementioned Process 3.

It is to be noted that the compound (I) may include one or more stereoisomers due to asymmetric carbon atoms, and all of such isomers and mixture thereof are included within the scope of this invention. It is also to be noted that the compound (I) may include a solvate, e.g., hydrate, etc.

Process A

The compound (X) or a salt thereof can be prepared by reacting the compound (IX) or a salt thereof with the compound (V) or a salt thereof. This reaction can be referred to that of aforementioned Process 2.

Process B

The compound (Xa) or a salt thereof can be prepared by reacting the compound (XI) or its reactive derivative at the carboxy group or a salt thereof with the compound (VII) or its reactive derivative at the imino group or a salt thereof. This reaction can be referred to that of Preparation 59-5.

Process C

The compound (II) or a salt thereof can be prepared by subjecting the compound (X) or a salt thereof to elimination reaction of the amino protective group. This elimination reaction can be referred to that of Preparations 13-4, 15-2, 16-11 and 17-4.

Process D

The compound (VI) or a salt thereof can be prepared by subjecting the compound (XII) or a salt thereof to elimination reaction of the carboxy protective group. This elimination reaction can be referred to that of Preparation 59-4.

Process E

The compound (IV) or a salt thereof can be prepared by reacting the compound (XIII) or its reactive derivative at the amino group or a salt thereof with the compound (III) or its reactive derivative or a salt thereof.

The reaction can be referred to that of the aforementioned Process 1.

The compound (XIII) or its reactive derivative at the amino group or a salt thereof can be prepared in accordance with the method disclosed in the Preparations described later or similar manners thereto.

The object compound (I) and pharmaceutically acceptable salts thereof are selective CCK-B antagonists or CCK-A/B antagonists.

Further, it is expected that the object compound (I) and pharmaceutically acceptable salts thereof have gastrin antagonism and are useful as therapeutical and/or preventive agents for ulcers such as gastric ulcer, duodenal ulcer, excess gastric secretion, zollinger-Ellison Syndrome, non-ulcer dyspepsia, gastroesophageal reflux disease, etc.

In order to show the utility of the object compound (I), pharmacological activity of the representative compound thereof is shown in the following.

Experiment 1

I Test Compound
  (1) N-[(3RS)-1-(3-azabicyclo[3.2.2]non-3-yl) carbonylmethyl-2,3-dihydro-5-isopropyl-2-oxo-1H-1, 4-benzodiazepin-3-yl]-N'-(3-methylthiophenyl)urea
  (2) N-[(3RS)-1-(3-azabicyclo[3.2.2]non-3-yl) carbonylmethyl-2,3-dihydro-5-acetoxymethyl-9-methyl-2-oxo-1H-1,4-benzodiazepin-3-yl]-N'-(3-methylphenyl)urea

[II] Test:
  $^{125}$I]CCK-8 binding to guinea-pig cerebral cortical membranes

Test Method (i) Membrane Preparation

Guinea-pigs were killed by decapitation and bled to death. Cerebral cortex was removed, minced in a small quantity of 50 mM Tris-HCl buffer (pH 7.4), and homogenized in 20 vol. of the buffer by a glass-teflon homogenizer. The homogenate was centrifuged at 30000 × g, (16000 rpm) for 10 minutes. The pellet was then resuspended in the same buffer by a glass-teflon homogenizer and recentrifuged at 30000 × g for 10 minutes. This procedure (washings) was repeated twice more. The final pellet (membrane) was suspended in incubation medium (see below) so as to obtain a final protein concentration of 4 mg/ml and frozen at −80° C. All manipulations were done at 0–4° C.

(ii) Receptor Binding Assay

The composition of incubation medium was as follows:
10 mM HEPES (pH 6.5), 5 mM $MgCl_2$, 1 mM EGTA, 130 mM NaCl and 0.25 mg/ml bacitracin. Frozen membranes were thawed and aliquots (400 μg protein) were incubated for 60 minutes under shaking at 37° C. in plastic tubes in 500 μL of incubation medium with 50 pM $^{125}$I-CCK-8 in the presence or absence of test compound ($1 \times 10^{-8}$ M). To determine the non-specific binding, CCK-8 at 1μM was added. Each assay was performed in duplicate. Reaction mixture was filtered through a Whatman GF/B glass filter to stop the reaction. After washing the filter with 50 mM Tris-HCl (pH 7.4) buffer containing 0.1% BSA, the radioactivity of the filter was countered. Non-specific binding was subtracted from total binding to yield specific binding. The effect of the test compound was expressed as % inhibition of specific $^{125}$I-CCK-8 binding.

Test Result

Inhibition (%):

test compound(1): 97.3% test compound(2): 97%

Experiment 2

[I] Test Compound (A) N-[(3RS)-1-cyclohexylcarbonylmethyl-2,3-dihydro-5,9-dimethyl-2-oxo-1H-1,4-benzodiazepin-3-yl-N'-(3-methylphenyl)urea (B) N-[(3RS)-1-cyclohexylcarbonylmethyl-2,3-dihydro-5-ethyl-9-methyl-2-oxo-1H-1,4-benzodiazepin-3-yl]-N'-(3-methylphenyl)urea (C) N-[(3R)-1-cyclohexylcarbonylmethyl-5-ethyl-9-methyl-2-oxo-2,3-dihydro-1H-1,4-benzodiazepin-3-yl]-N'-(3-methylphenyl)urea (D) N-[(3RS)-1-cyclohexylcarbonylmethyl-5-cyclopropyl-2,3-dihydro-9-methyl-2-oxo-1H-1,4-benzodiazepin-3-yl]-N'-(3-methylphenyl)urea

[II] Tests:

Receptor binding studies and gastric emptying in mice

Test Method

The tests were carried out in accordance with the method described at pages 571 to 572 in the following literature;

Harunobu Ito, Hajime Sogabe et al., The Journal of Pharmacology and Experimental Therapeutics, 571, No. 2, Vol.268 (1994).

Test results are shown in the table 1.

TABLE 1

Biological evaluation results

| Compound | $IC_{50}$(nM) for CCK-B | $IC_{50}$(nM) for CCK-A | selectivity A/B | Gastric emptying $ID_{50}$(mg/Kg) |
|---|---|---|---|---|
| (A) | 3.7 | 1.1 | 0.30 | 0.4 |
| (B) | 1.6 | 0.9 | 0.56 | 0.4 |
| (C) | 1.0 | 0.3 | 0.30 | 0.23 |
| (D) | 1.1 | 2.0 | 1.82 | 1.8 |

The object compound (I) or pharmaceutically acceptable salts thereof can usually be administered to mammals including human being in the form of a conventional pharmaceutical composition such as capsule, micro-capsule, tablet, granule, powder, troche, syrup, aerosol, inhalation, solution, injection, suspension, emulsion, suppository or the like.

The pharmaceutical composition of this invention can contain various organic or inorganic carrier materials, which are conventionally used for pharmaceutical purpose, such as excipient (e.g., sucrose, starch, mannit, sorbit, lactose, glucose, cellulose, talc, calcium phosphate, calcium carbonate, etc.), binding agent (cellulose, methyl cellulose, hydroxypropyl cellulose, polypropylpyrrolidone, gelatin, gum arabic, polyethyleneglycol, sucrose, starch, etc.), disintegrator (e.g., starch, carboxymethyl cellulose, calcium salt of carboxymethyl cellulose, hydroxypropylstarch, sodium glycole-starch, sodium bicarbonate, calcium phosphate, calcium citrate, etc.), lubricant (e.g., magnesium stearate, talc, sodium lauryrsulfate, etc.), flavoring, agent (e.g., citric acid, menthol, glycine, orange powders, etc.), preservative (e.g., sodium benzoate, sodium bisulfite, methylparaben, propylparaben, etc.), stabilizer (e.g., citric acid, sodium citrate, acetic acid, etc.), suspending agent (e.g., methyl cellulose, polyvinylpyrrolidone, aluminum stearate, etc.), dispersing agent, aqueous diluting agent (e.g., water), base wax (e.g., cacao butter, polyethyleneglycol, white petrolatum, etc.).

The effective ingredient may usually be administered with a unit dose of 0.01 mg/kg to 50 mg/kg, 1 to 4 times a day. However, the above dosage may be increased or decreased according to age, weight, conditions of the patient or the administering method.

The following Preparations and Examples are given only for the purpose of illustrating the present invention in more detail.

Preparation 1-1

To a suspension of magnesium turnings (7.53 g) in dry ether (100 ml) was added dropwise a solution of isopropyl bromide (36.87 g) in dry ether (50 ml) at reflux temperature for 1 hour. The mixture was heated at the same temperature for 1 hour and then allowed to cool to 5~10° C. in an ice bath. To the mixture was added dropwise a solution of 2-aminobenzonitrile (11.81 g) in dry tetrahydrofuran (100 ml) at the same temperature for 1 hour. The mixture was stirred additionally 1 hour and then heated under reflux for 3 hours. The reaction mixture was allowed to cool to 5~10° C. in an ice bath. A 3N aqueous hydrochloric acid was added dropwise to the mixture for 1 hour and then heated under reflux for 3 hours. The resultant mixture was concentrated in vacuo to remove the organic solvent. The residue was extracted with chloroform (2×300 ml). The extracts were combined and washed with a brine (2×100 ml). Dryness over magnesium sulfate and evaporation gave a crude product. The product was purified by column chromatography on silica gel with chloroform. The fractions containing the desired product were combined and evaporated in vacuo to afford a pure 2-isopropylcarbonylaniline (15.35 g) as a colorless oil.

$^1$H-NMR ($CDCl_3$, δ): 1.20 (6H, d, J=6.8Hz), 3.56–3.60 (1H, m), 6.30 (2H, br), 6.63–6.67 (2H, m), 7.22–7.27 (1H, m) 7.77 (1H, d, J=12 Hz)

Preparation 1-2

The following compound was prepared according to the method of katrisky [J. Org, Chem, 55, 2206 (1990)] in 84.6% yield.

2-(1-benzotriazolyl)-2-benzyloxycarbonylaminoacetic acid $^1$H-NMR (DMSO-$d_6$, δ): 5.01–5.13 (3H, m), 7.20–7.60 (7H, m), 8.00 (1H, d, J=8.0 Hz), 8.08 (1H, d, J=8.8 Hz), 9.39 (1H, d, J=8.8 Hz)

Preparation 1-3

To a suspension of 2-isopropylcarbonyl aniline (15.26 g) and 2-(1-benzotriazolyl)-2-benzyloxycarbonylamino acetic acid (30.70 g) in dry methylene chloride (200 ml) was added dropwise a solution of dicyclohexyl carbodiimide (23.23 g) in dry methylene chloride (160 ml) at 20~25° C. for 1 hour. The mixture was stirred at the same temperature for 1 hour. The resultant mixture was filtered by suction to remove an insoluble material. The filtrate was concentrated in vacuo and the residue was recrystallized from ethyl acetate and isopropyl ether to give 2-isopropylcarbonyl N-{2-(1-benzotriazolyl)-2-benzyloxycarbonylamino}- acetylaniline (40.5 g) as a pale yellow powder.

$^1$H-NMR (DMSO-d$_6$, δ): 1.05 (6H, d, J=8.8 Hz), 3.60–3.70 (1H, m), 5.63 (2H, d, J=12.8 Hz), 5.23 (1H, d, J=12.8 Hz), 7.27–7.66 (9H, m), 7.97–8.11 (3H, m), 8.37 (1H, d, J=8.4 Hz), 9.65 (1H, d, J=8.0 Hz), 12.08 (1H, s)

Preparation 1-4

A suspension of 2-isopropylcarbonyl-N-{2-(1-benzotriazolyl)-2-benzyloxycarbonylamino}acetylaniline (40.5 g) in methanol (150 ml) was treated with a saturated solution of ammonia in methanol (150 ml) at 0~5° C. in an ice bath for 1 hour and then at room temperature for 1 hour. The mixture was concentrated. The residue was treated with a 10% solution of ammonium acetate in acetic acid (300 ml) at room temperature for 2 hours. The resultant mixture was evaporated in vacuo and the residue was partitioned between ethyl acetate (100 ml) and 1N aqueous sodium hydroxide (100 ml). The organic layer was washed with a saturated sodium hydrogen carbonate (100 ml) and a brine (100 ml). Dryness over magnesium sulfate and evaporation afforded a crude product. The crude product was recrystallized from ethyl acetate and isopropyl ether to give (3RS)-3-benzyloxycarbonylamino-2,3-dihydro-5-isopropyl-1H-1,4-benzodiazepin-2-one (26.88 g).

$^1$H-NMR (CDCl$_3$, δ): 0.92 (3H, d, J=6.8 Hz), 1.28 (3H, d, J=6.8 Hz), 3.07–3.17 (1H, m), 5.12 (2H, s), 5.17 (1H, d, J=8.4 Hz), 6.46(1H, d, J=8.4 Hz), 7.11 (1H, d, J=8.4 Hz), 7.22–7.40 (6H, m), 7.46 (1H, t, J=7.2 Hz), 7.59 (1H, d, J=7.6 Hz), 9.13 (1H, s)

Preparation 1-5

To a suspension of sodium hydride (0.123 g of a 65% dispersion in mineral oil) in dry N, N-dimethylformamide (10 ml) was added dropwise a solution of (3RS)-3-benzyloxycarbonylamino-2,3-dihydro-5-isopropyl-1H-1,4-benzodiazepin-2-one (1.00 g) in dry N,N-dimethylformamide (5 ml) under cooling in an ice-bath. The mixture was stirred at the same temperature for 1 hour and then at room temperature for 1 hour. To the mixture was added dropwise a solution of N-bromomethylcarbonyl-3-azabicyclo[3.2.2]nonane (0.77 g) in dry N,N-dimethylformamide (5 ml) and stirred at the same condition for 2 hours. The reaction mixture was concentrated in vacuo and the residue was taken up with ethyl acetate (100 ml) and a saturated aqueous sodium hydrogen carbonate (100 ml). The organic layer was washed with a brine (50 ml) and dried over anhydrous magnesium sulfate. Filtration and evaporation gave (3RS)-1-[(3-azabicyclo[3.2.2]non-3-yl) carbonylmethyl]-3-benzyloxy-carbonylamino-2,3-dihydro-5-isopropyl-1H-1,4-benzodiazepin-2-one.

$^1$H-NMR (CDCl$_3$, δ): 0.98 (3H, d, J=7.2 Hz), 1.00–1.40 (2H, m), 1.31 (3H, d, J=7.2 Hz), 1.60–1.80 (6H, m), 2.04–2.16 (2H, m), 3.10–3.22 (1H, m), 3.44–3.86 (4H, m), 4.34 (1H, d, J=17.2 Hz), 4.94 (1H, d, J=17.2 Hz), 5.04–5.20 (2H, m), 5.10 (1H, d, J=8.0 Hz), 6.60 (1H, d, J=8.0 Hz), 7.20–7.60 (9H, m)

Preparation 1-6

Pd—C (5 wt %, 0.10 g) was added to a suspension of (3RS)-1-[(3-azabicyclo[3.2.2]non-3-yl)carbonylmethyl]-3-benzyloxycarbonylamino-2,3-dihydro-5-isopropyl-1H-1,4-benzodiazepin-2-one (0.718 g) in methanol (20 ml) and then anmonium formate (0.351 g) at room temperature. The mixture was stirred at the same condition for 4 hours and filtered on Celite® to remove the catalyst. The filtrate was concentrated in vacuo and the residue was taken up with ethyl acetate (100 ml) and a saturated aqueous sodium hydrogen carbonate (50 ml). The organic layer was washed with a brine (50 ml) and dried over anhydrous sodium sulfate. Filtration and evaporation gave (3RS)-3-amino-1-[(3-azabicyclo[3.2.2]non-3-yl)carbonylmethyl]-2,3-dihydro-5-isopropyl-1H-1,4-benzodiazepin-2-one (0.39 g) which was used in a following reaction step without further purification.

$^1$H-NMR (CDCl$_3$, δ): 0.97 (3H, d, J=7.2 Hz), 1.30–1.40 (2H, m), 1.31 (3H, d, J=7.2 Hz), 1.60–1.80 (6H, m), 2.00–2.20 (4H, m), 3.07–3.16 (1H, m), 3.47–3.89 (4H, m), 4.24 (1H, d, J=16.4 Hz), 4.42 (1H, s), 5.00 (1H, d, J=16.4 Hz), 7.20–7.53 (4H, m)

Preparation 2-1

To a suspension of Pd—C (5 wt %, 1.60 g) in methanol (60 ml) was added dropwise a solution of (3RS)-3-benzyloxycarbonylamino-2,3-dihydro-5-isopropyl-1H-1,4-benzodiazepin-2-one (8.00 g) in methanol (60 ml) and then ammonium formate (5.56 g) at room temperature. The reaction mixture was stirred at the same temperature for 1 hour. The catalyst was filtered on Celite®. The filtrate was concentrated in vacuo. The residue was taken up with ethyl acetate (100 ml) and saturated aqueous sodium hydrogen carbonate (100 ml). The organic layer was washed with a brine (100 ml). Dryness over sodium sulfate and evaporation gave (3RS)-3-amino-2,3-dihydro-5-isopropyl-1H-1,4-benzodiazepin-2-one (4.21 g). The product was used in a following reaction step without further purification.

$^1$H-NMR (DMSO-d$_6$, δ): 0.79 (3H, d, J=7.2 Hz), 1.20 (3H, d, J=7.2 Hz), 3.16–3.24 (1H, m), 3.20–3.50 (2H, br), 4.02 (1H, s), 7.14 (1H, d, J=8.0 Hz), 7.19 (1H, t, J=7.2 Hz), 7.48 (1H, t, J=7.2 Hz), 7.69 (1H, d, J=7.2 Hz), 10.44 (1H, s)

Preparation 2-2

To a solution of (3RS)-3-amino-2,3-dihydro-5-isopropyl-1H-1,4-benzodiazcpin-2-one (3.98 g) in N,N-dimethylformamidc (100 ml) was added 4-dimethylaminopyridine (0.20 g) and then dropwise a solution of di-tert-butyl dicarbonate (4.09 g) in N,N-dimethylformamide (20 ml) at room temperature. The mixture was stirred at ambient temperature overnight and concentrated in vacuo to dryness. The residue was taken up with ethyl acetate (100 ml) and 1N aqueous hydrochloric acid (100). The aqueous layer was separated, basified with sodium hydrogen carbonate and extracted with ethyl acetate (2×100 ml). The extracts were combined, dried over sodium sulfate and evaporated in vacuo to afford (3RS)-3 -tert-butoxycarbonylamino-2,3-dihydro-5-isopropyl-1H-1,4-benzodiazepin-2-one (4.05 g). The product was used in a following reaction step without further purification.

$^1$H-NMR (CDCl$_3$, δ): 0.93 (3H, d, J=6.8 Hz), 1.30 (3H, d, J=6.8 Hz), 1.45 (9H, s), 3.12–3.19 (1H, m), 5.15 (1H, d, J=8.4 Hz), 6.22 (1H, d, J=8.4 Hz), 7.12 (1H, d, J=8.0 Hz), 7.23 (1H, t, J=8.0 Hz), 7.46 (1H, t, J=8.0 Hz), 7.58 (1H, d, J=8.0 Hz), 8.97 (1H, br)

Preparation 2-3

To a suspension of sodium hydride (0.065 g of a 65% dispersion in mineral oil) in dry N,N-dimethylformamide (5 ml) was added dropwise a solution of (3RS)-3-tert-butoxycarbonylamino-2,3-dihydro-5-isopropyl-1H-1, 4-benzodiazepin-2-one (0.508 g) in dry N,N-dimethylformamide (5 ml) under cooling in an ice-bath. The mixture was stirred under the same condition for 30 minutes and then at ambient temperature for 2 hours. To the mixture was added dropwise a solution of 2-acetyl-3-bromomethylthiophene (0.420 g) in dry N,N-dimethylformamide under cooling in an ice-bath. After completion of the addition, the mixture was stirred under the same condition for 30 minutes and then at ambient temperature overnight. The resultant mixture was concentrated in vacuo. The residue was treated with ethyl acetate (100 ml), washed with water (50 ml) and dried over anhydrous sodium sulfate. Filtration and evaporation gave a crude product. The product was purified by column chromatography on silica gel with an eluent of a mixture of chloroform and ethyl acetate (10: 1) to give (3RS)-1-(2-acetylthiophen-3-yl)methyl-3-tert-butoxycarbonylamino-2,3-dihydro-5-isopropyl-1H-1,4-benzodiazepin-2-one (0.380 g).

$^1$H-NMR (DMSO-d$_6$, δ): 0.86 (3H, d, J=6.0 Hz), 1.28 (3H, d, J=6.0 Hz), 1.46 (9H, s), 3.10–3.20 (1H, m), 5.22 (1H, d, J=9.6 Hz), 5.33 (1H, d, J=17.2 Hz), 5.66 (1H, d, J=17.2 Hz), 6.31 (1H, d, J=8.8 Hz), 6.93 (1H, d, J=4.8 Hz), 7.20–7.30 (3H, m), 7.37–7.43 (2H, m), 7.50 (1H, d, J=8.0 Hz)

Preparation 2-4

A solution of (3RS)-1-(2-acetylthiophen-3-yl)methyl-3-tert-butoxycarbonylamino-2,3-dihydro-5-isopropyl-1H-1,4-benzodiazepin-2-one (0.370 g) in ethyl acetate (50 ml) was treated with gaseous hydrogen chloride at 5~10° C. in an ice-bath for 30 minutes. The resultant mixture was extracted with 3N aqueous hydrochloric acid (2×10 ml). The aqueous layer was basified with sodium hydrogen carbonate and extracted with ethyl acetate (2×50 ml). The extracts were combined, over sodium sulfate, filtered and concentrated in vacuo to afford (3RS)-1-(2-acetylthiophen-3-yl)methyl-3-amino-2,3-dihydro-5-isopropyl-1H-1,4-benzodiazepin-2-one (0.230 g), which was used in a following reaction step without further purification.

$^1$H-NMR (CDCl$_3$, δ): 0.88 (3H, d, J=6.8 Hz), 1.29 (3H, d, J=6.8 Hz), 2.50 (3H, s), 3.08–3.18 (1H, m), 3.25 (1H, br), 4.43 (1H, s), 5.37 (1H, d, J=17.2 Hz), 5.67 (1H, d, J=17.2 Hz), 6.92 (1H, d, J=5.2 Hz), 7.20–7.50 (6H, m)

Preparation 3

To a solution of (3RS)-3-amino-2,3-dihydro-5-isopropyl-1H-1,4-benzodiazcpin-2-one (0.536 g) in methylene chloride (30 ml) was added dropwise a solution of 3-methylphenyl isocyanate (0.361 g) in methylene chloride (5 ml) at room temperature for 10 minutes. The mixture was stirred at the same condition for 2 hours. The resultant precipitate was collected by suction to afford N-[(3RS)-2,3-dihydro-5-isopropyl-2-oxo-1H-1,4-benzodiazcpin-3-yl]-N'-(3-methylphenyl)urea (0.600 g). The filtrate was concentrated in vacuo and the residue was treated with isopropyl ether to give the second crop of the desired compound (0.170 g).

$^1$H-NMR (DMSO-d$_6$, δ): 0.81 (3H, d, J=6.8 Hz), 1.18 (3H, d, J=6.8 Hz), 2.23 (3H, s), 3.20–3.30 (1H, m), 4.49 (1H, d, J=8.0 Hz), 6.72 (1H, d, J=8.0 Hz), 7.06–7.22 (6H, m), 7.55 (1H, t, J=7.2 Hz), 7.77 (1H, d, J=7.2 Hz), 8.88 (1H, s), 10.69 (1H, s)

Preparation 4

To a solution of 3-aminoacetophenone (2.049 g) and pyridine (1.286 g) in tetrahydrofuran (35 ml) was added dropwise a solution of 4-nitrophenylchloroformate (3.288 g) in tetrahydrofuran (10 ml) under cooling in an ice bath. After completion of the addition, the mixture was allowed to stand to ambient temperature and stirred over night. Water was added to the mixture. The resultant precipitate was collected by suction filtration, washed with water and dried in vacuo at 80° C. to afford 4-nitrophenyl N-(3-acetylphenyl) carbamate (3.31 g).

$^1$H-NMR (DMSO-d$_6$, δ): 2.57 (3H, s), 7.50–7.59 (3H, m), 7.71 (1H, d, J=8.0 Hz), 7.76 (1H, d, J=8.0 Hz), 8.13 (1H, s), 8.32 (2H, d, J=9.0 Hz), 10.67 (1H, s)

Preparation 5

The following compound was prepared in a similar manner to that of preparation 4.

4-nitrophenyl N-{3-(tetrazol-5-yl)phenyl}carbamate

Preparation 6-1

The following compound was prepared in a similar manner to that of Preparation 1-1.

2-(2-methyl)propylcarbonylaniline $^1$H-NMR (CDCl$_3$, δ): 0.93 (6H, q, J=8 Hz), 2.04–2.12 (1H, m), 2.93 (2H, d, J=8 Hz), 6.26 (2H, br), 6.60 (2H, d, J=8 Hz), 7.24 (1H, t, J=8 Hz), 7.74 (1H, d, J=8 Hz)

Preparation 6-2

The following compound was prepared in a similar manner to that of Preparation 1-3.

2-(2-methyl)propylcarbonyl-N-{2-(1-benzotriazolyl)-2-benzyloxylcarbonylamino}acetylaniline $^1$H-NMR (CDCl$_3$, δ): 0.83 (6H, q, J=8 Hz), 2.02–2.10 (1H, m), 2.70 (2H, d, J=8 Hz), 5.04–5.14 (3H, m), 6.95 (1H, br), 7.13–7.45 (9H, m), 7.84 (2H, d, J=8 Hz), 8.08 (1H, d, J=8 Hz), 8.62 (1H, d, J=8 Hz), 12.40 (1H, br)

Preparation 6-3

A solution of 2-(2-methyl)propylcarbonyl-N-{2-(1-benzotriazolyl)-2-benzloxycarbonylamino}acetylaniline (31.7 g) in methanol (100 ml) was treated with a saturated solution of ammonia in methanol (200 ml) at 0° C. in a dry ice-acetone bath for 1 hour and then stirred overnight at ambient temperature. The resultant mixture was concentrated and the residue was treated with a 0.5N aqueous sodium hydroxide and chloroform. The organic layer was dried over sodium sulfate, filtered and concentrated in vacuo to give a crude compound. The crude compound was purified by a column chromatography on silica gel with a mixture of chloroform and ethyl acetate to give (3RS)-3-benzyloxycarbonylamino-2,3-dihydro-5-(2-methylpropyl)-1H-1,4-benzodiazepin-2-one as a colorless powder.

$^1$H-NMR (CDCl$_3$, δ): 0.71 (3H, d, J=8 Hz), 0.83 (3H, d, J=8 Hz), 1.21–1.76 (1H, m), 2.45 (1H, dd, J=16 Hz, J=16 Hz), 2.85 (1H, dd, J=8 Hz, J=16 Hz), 5.07–5.21 (3H, m), 6.68 (1H, d, J=8 Hz), 7.14–7.53 (9H, m), 7.87 (1H, d, J=8 Hz)

Preparation 6-4

The following compound was prepared in a similar manner to that of Preparation 2-1.

(3RS)-3-amino-2,3-dihydro-5-(2-methylpropyl)-1H-1,4-benzodiazepin-2-one $^1$H-NMR (CDCl$_3$, δ): 0.76 (3H, d, J=8 Hz), 0.84 (3H, d, J=8 Hz), 1.74–1.83 (1H, m), 2.20 (2H, br), 2.46 (1H, dd, J=16 Hz, J=16 Hz), 2.85 (1H, dd, J=8 Hz, J=16 Hz), 4.32 (1H, s), 7.14 (1H, d, J=8 Hz), 7.24 (1H, t, J=8 Hz), 7.46 (1H, d, J=8 Hz), 7.56 (1H, d, J=8 Hz), 9.04 (1H, s)

Preparation 6-5

The following compound was prepared in a similar manner to that of Preparation 3.

N-[(3RS)-2,3-dihydro-5-(2-methylpropyl)-2-oxo-1H-1,4-benzodiazepin-3-yl]-N'-(3-methylphenyl)urea $^1$H-NMR (DMSO-d$_6$, δ): 0.68 (3H, d, J=8 Hz), 0.84 (3H, d, J=8 Hz), 1.66–1.70 (1H, m), 2.23 (3H, s), 2.34 (1H, dd, J=16 Hz, J=16 Hz), 2.94 (1H, dd, J=8 Hz, J=16 Hz), 4.99 (1H, d, J=14 Hz), 6.72 (1H, d, J=8 Hz), 7.07–7.30 (7H, m), 7.55 (1H, t, J=8 Hz), 7.76 (1H, d, J=14 Hz), 8.85 (1H, s)

Preparation 7-1

The following compound was prepared in a similar manner to that of Preparation 2-2.

(3RS)-3-tert-butoxycarbonylamino-2,3-dihydro-5-(2-methylpropyl)-1H-1,4-benzodiazepin-2-one ¹H-NMR (CDCl₃, δ): 0.72 (3H, d, J=8 Hz), 0.86 (3H, d, J=8 Hz), 1.45 (9H, s), 1.78–1.82 (1H, m), 2.64 (1H, d, J=16 Hz), 2.88 (1H, d, J=8 Hz, 16 Hz), 5.14 (1H, d, J=8 Hz), 6.35 (1H, d, J=8 Hz), 7.21–7.57 (4H, m), 9.71 (1H, s)

Preparation 7-2

The following compound was prepared in a similar manner to that of Preparation 2-3.

(3RS)-1-[(3-azabicyclo[3.2.2]non-3-yl)carbonylmethyl]-3-tert-butoxycarbonylamino-2,3-dihydro-5-(2-methylpropyl)-1H-1,4-benzodiazepin-2-one ¹H-NMR (CDCl₃, δ): 0.76 (3H, d, J=8 Hz), 0.88 (3H, d, J=8 Hz), 1.42 (9H, s), 1.61–1.88 (9H, m), 2.10 (2H, br), 2.48 (1H, dd, J=16 Hz, J=16 Hz), 2.89 (1H, dd, J=8Hz, J=16 Hz), 3.44–3.96 (4H, m). 4.14 (1H, d, J=18 Hz), 5.02 (1H, d, J=18 Hz), 5.25 (1H, d, J=8 Hz), 6.43 (1H, d, J=8 Hz), 7.24–7.54 (4H, m)

Preparation 7-3

The following compound was prepared in a similar manner to that of Preparation 2-4.

(3RS)-3-amino-1-[(3-azabicyclo[3.2.2]non-3-yl)carbonylmethyl]-2,3-dihydro-5-(2-methylpropyl)-1H-1,4-benzodiazepin-2-one ¹H-NMR (CDCl₃, δ): 0.77 (3H, d, J=8 Hz), 0.88 (3H, d, J=8 Hz), 1.70–2.11 (13H, m), 2.50 (1H, dd, J=16 Hz, J=16 Hz), 2.88 (1H, dd, J=8 Hz, J=16 Hz), 3.46–3.92 (4H, m). 4.10 (1H, d, J=18 Hz), 4.43 (1H, s), 5.06 (1H, d, J=18 Hz), 7.21–7.51 (4H, m)

Preparation 8-1

The following compound was prepared in a similar manner to that of Preparation 1-3.

2-methylcarbonyl-N-{2-(1-benzotriazolyl)-2-benzyloxycarbonylamino}acetylaniline

¹H-NMR (CDCl₃, δ): 2.53 (3H, s), 5.04–5.26 (3H, m), 7.07–7.52 (10H, m), 7.78–7.87 (2H, m), 8.05 (1H, d, J=8 Hz), 8.62 (1H, d, J=8 Hz), 12.36 (1H, s)

Preparation 8-2

The following compound was prepared in a similar manner to that of Preparation 6-3.

(3RS)-3-benzyloxycarbonylamino-2,3-dihydro-5-methyl-1H-1,4-benzodiazepin-2-one

¹H-NMR (CDCl₃, δ): 2.42 (3H, s), 5.05–5.15 (3H, m), 6.82 (1H, d, J=8 Hz), 7.08 (1H, d, J=8 Hz), 7.08–7.34 (7H, m), 7.52 (1H, d, J=8 Hz), 10.13 (1H, s)

Preparation 8-3

The following compound was prepared in a similar manner to that of Preparation 2-1.

(3RS)-3-amino-2,3-dihydro-5-methyl-1H-1,4-benzodiazepin-2-one

¹H-NMR (CDCl₃, δ): 2.35–2.64 (2H, br), 2.45 (3H, s), 4.32 (1H, s), 7.18 (1H, d, J=8 Hz), 7.21 (1H, t, J=8 Hz), 7.45 (1H, t, J=8 Hz), 7.58 (1H, d, J=8 Hz), 9.60 (1H, br)

Preparation 8-4

The following compound was prepared in a similar manner to that of Preparation 3.

N-[(3RS)-2,3-dihydro-5-methyl-2-oxo-1H-1,4-benzodiazepin-3-yl]-N'-(3-methylphenyl)urea ¹H-NMR (DMSO-d₆, δ): 2.23 (3H, s), 2.40 (3H, s), 4.95 (1H, d, J=8 Hz), 6.72 (1H, d, J=8 Hz), 7.08–7.31 (6H, m), 7.56 (1H, t, J=8 Hz), 7.78 (1H, d, J=8 Hz), 8.88 (1H, s), 10.77 (1H, s)

Preparation 9-1

The following compound was prepared in a similar manner to that of Preparation 1-1.

2-(3-methyl)butylcarbonylaniline

¹H-NMR (CDCl₃, δ): 0.94 (6H, q, J=8 Hz), 1.62 (2H, q, J=8 Hz), 2.06–2.10 (1H, m), 2.93 (2H, t, J=8 Hz), 6.26 (2H, br), 6.63 (2H, d, J=8 Hz), 7.24 (1H, t, J=8 Hz), 7.74 (1H, d, J=8 Hz)

Preparation 9-2

The following compound was prepared in a similar manner to that of Preparation 1-3.

2-(3-methyl)butylcarbonyl-N-[2-(1-benzotriazolyl)-2-benzyloxylcarbonylamino]acetylaniline ¹H-NMR (CDCl₃, δ): 0.88 (6H, q, J=8 Hz), 1.44 (2H, q, J=8 Hz), 1.80–1.84 (1H, m), 2.40 (2H, t, J=8 Hz), 5.05–5.28 (3H, m), 6.97 (1H, br), 7.26–7.57 (9H, m), 7.85 (2H, d, J=8 Hz), 8.08 (1H, d, J=8 Hz), 8.63 (1H, d, J=8 Hz), 12.40 (1H, br)

Preparation 9-3

The following compound was prepared in a similar manner to that of Preparation 6-3.

(3RS)-3-benzyloxycarbonylamino-2,3-dihydro-5-(3-methylbutyl)-1H-1,4-benzodiazepin-2-one ¹H-NMR (CDCl₃, δ): 0.83–0.86 (6H, m), 1.29–1.53 (3H, m), 2.74–2.79 (2H, m), 4.69 (1H, s), 5.08–5.17 (3H, m), 6.52 (1H, d, J=8 Hz), 7.09 (1H, d, J=8 Hz), 7.23–7.36 (5H, m), 7.44 (1H, t, J=8 Hz), 7.57 (1H, d, J=8 Hz), 9.26 (1H, s)

Preparation 9-4

The following compound was prepared in a similar manner to that of Preparation 2-1.

(3RS)-3-amino-2,3-dihydro-5-(3-methylbutyl)-1H-1,4-benzodiazepin-2-one

¹H-NMR (CDCl₃, δ): 0.83 (3H, dd, J=3.5 Hz, J=4.9 Hz), 0.88 (3H, dd, J=1.4 Hz, J=2.8 Hz), 1.30–1.42 (1H, m), 1.45–1.60 (2H, m), 2.72–2.76 (2H, m), 3.40–3.78 (2H, br), 4.23 (1H, s), 7.02–7.75 (4H, m), 9.70 (1H, br)

Preparation 9-5

The following compound was prepared in a similar manner to that of Preparation 3.

N-[(3RS)-2,3-dihydro-5-(3-methylbutyl)-2-oxo-1H-1,4-benzodiazepin-3-yl]-N'-(3-methylphenyl)urea ¹H-NMR (CDCl₃, δ): 0.73 (6H, t, J=8 Hz), 1.15–1.40 (3H, m), 2.25 (3H, s), 2.6–2.72 (2H, m), 5.35 (1H, d, J=16 Hz), 6.78 (1H, d, J=8 Hz), 7.07–7.32 (7H, m), 7.50 (1H, d, J=8 Hz), 7.78 (1H, d, J=14 Hz), 8.80 (1H, br)

Preparation 10-1

The following compound was prepared in a similar manner to that of Preparation 1-1.

2-ethylcarbonylaniline

¹H-NMR (CDCl₃, δ): 1.20 (3H, t, J=7.0 Hz), 2.97 (2H, q, J=7.0 Hz), 6.27 (2H, br), 6.62–6.66 (2H, m), 7.22–7.27 (1H, m), 7.75 (1H, d J=8 Hz)

Preparation 10-2

The following compound was prepared in a similar manner to that of Preparation 1-3.

2-ethylcarbonyl-N-{2-(1-benzotriazolyl)-2-benzyloxycarbonylamino}acetylaniline

¹H-NMR (CDCl₃, δ): 1.06 (3H, t, J=7.0 Hz), 2.94 (2H, q, J=7.0 Hz), 5.06–5.25 (3H, m), 6.96 (1H, br), 7.14–7.42 (7H, m), 7.52–7.56 (2H, m), 7.86–7.88 (2H, m), 8.93 (1H, d, J=8.0 Hz), 8.63 (1H, d, J=8.0 Hz), 12.45 (1H, s)

Preparation 10-3

The following compound was prepared in a similar manner to that of Preparation 6-3.

(3RS)-3-benzyloxycarbonylamino-2,3-dihydro-5-ethyl-1H-1,4-benzodiazepin-2-one

¹H-NMR (CDCl₃, δ): 1.08 (3H, t, J=7.0 Hz), 2.74–2.86 (2H, m), 5.08–5.16 (2H, m), 5.18 (1H, d, J=8.0 Hz), 6.52 (1H, d, J=8.0 Hz), 7.12 (1H, d, J=8.0 Hz), 7.23–7.38 (6H, m), 7.47 (1H, t, J=8.0 Hz), 7.58 (1H, d, J=8.0 Hz), 9.27 (1H, s)

Preparation 10-4

The following compound was prepared in a similar manner to that of Preparation 2-1.

(3RS)-3-amino-2,3-dihydro-5-ethyl-1H-1,4-benzodiazepin-2-one

¹H-NMR (CDCl₃, δ): 1.10 (3H, t, J=7.0 Hz), 2.00 (2H, br), 2.73–2.83 (2H, m), 4.33 (1H, s), 7.10 (1H, d, J=8.0 Hz), 7.23 (1H, t, J=8.0 Hz), 7.46 (1H, t, J=8.0 Hz), 7.57 (1H, d, J=8.0 Hz), 8.74 (1H, s)

Preparation 10-5

The following compound was prepared in a similar manner to that of Preparation 3.

N-[(3RS)-2,3-dihydro-5-ethyl-2-oxo-1H-1,4-benzodiazepin-3-yl]-N'-(3-methylphenyl)urea ¹H-NMR (DMSO-d₆, δ): 0.99 (3H, t, J=7.0 Hz), 2.23 (3H, s), 2.66–2.72 (1H, m), 2.84–2.88 (1H, m), 5.00 (1H, d, J=8.0 Hz), 6.72 (1H, d, J=7.0 Hz), 7.07–7.30 (6H, m), 7.55 (1H, d, J=7.0 Hz), 7.78 (1H, d, J=8.0 Hz), 8.88 (1H, s), 10.73 (1H, s)

Preparation 11-1

The following compound was prepared in a similar manner to that of Preparation 1-1.

2-(3-butenyl)carbonylaniline

¹H-NMR (CDCl₃, δ): 2.46–2.50 (2H, m), 3.03 (2H, t, J=7 Hz), 5.01 (1H, d, J=13.0 Hz), 5.09 (1H, d, J=18.8 Hz), 5.86–5.98 (1H, m), 6.26 (2H, br), 6.62–6.66 (2H, m), 7.25 (1H, t, J=8.4 Hz), 7.75 (1H, d, J=8.0 Hz)

Preparation 11-2

The following compound was prepared in a similar manner to that of Preparation 1-4 and Preparation 1-5.

(3RS)-3-benzyloxycarbonylamino-5-(3-butenyl)-2,3-dihydro-1H-1,4-benzodiazepin-2-one ¹H-NMR (CDCl₃, δ): 2.24–2.36 (2H, m), 2.88 (2H, t, J=7.6 Hz), 4.90–5.19 (5H, m), 5.71–5.80 (1H, m), 6.65 (1H, d, J=8.0 Hz), 7.12 (1H, d, J=7.6 Hz), 7.25–7.36 (6H, m), 7.49 (1H, t, J=7.6 Hz), 7.59 (1H, d, J=7.6 Hz), 9.17 (1H, br)

Preparation 11-3

The following compound was prepared in a similar manner to that of Preparation 1-6.

(3RS)-3-amino-5-butyl-2,3-dihydro-1H-1,4-benzodiazepin-2-one

¹H-NMR (DMSO-d₆, δ): 0.82 (3H, t, J=7.2 Hz), 1.16–1.20 (2H, m), 1.26–1.40 (2H, m), 2.40 (2H, br), 2.60–2.68 (1H, m), 2.76–2.81 (1H, m), 3.27 (1H, s), 7.14 (1H, d, J=8.0 Hz), 7.19 (1H, t, J=8.0 Hz), 7.48 (1H, t, J=8.0 Hz), 7.67 (1H, d, J=8.0 Hz), 10.47 (1H, br)

Preparation 11-4

The following compound was prepared in a similar manner to that of Preparation 2-2.

(3RS)-3-tert-butoxycarbonylamino-5-butyl-2,3-dihydro-1H 1,4-benzodiazepin-2-one

¹H-NMR (CDCl₃, δ): 0.84 (3H, t, J=7.6 Hz), 1.24–1.29 (2H, m), 1.40–1.47 (2H, m), 1.44 (9H, s), 2.73–2.90 (2H, m), 5.14 (1H, d, J=8.0 Hz), 6.28 (1H, d, J=8.0 Hz), 7.11 (1H, d, J=8.0 Hz), 7.24 (1H, t, J=8.0 Hz), 7.47 (1H, t, J=8.0 Hz), 7.57 (1H, d, J=8.0 Hz), 8.97 (1H, br)

Preparation 11-5

The following compound was prepared in a similar manner to that of Preparation 2-3.

(3RS)-1-[(3-azabicyclo[3.2.2]non-3-yl)carbonylmethyl]-3-tert-butoxycarbonylamino-5-butyl-2,3-dihydro-1H-1,4-benzodiazepin-2-one ¹H-NMR (CDCl₃, δ): 0.86 (3H, t, J=7.6 Hz), 1.24–1.31 (2H, m), 1.42 (9H, s), 1.42–1.52 (2H, m), 1.60–1.80 (8H, m), 2.05–2.15 (2H, m), 2.70–2.90 (2H, m), 3.45–3.90 (4H, m), 4.27 (1H, d, J=16.0 Hz), 4.94 (1H, d, J=16.0 Hz), 5.24 (1H, d, J=8.0 Hz), 6.41 (1H, d, J=8.0 Hz), 7.23–7.54 (4H, m)

Preparation 11-6

The following compound was prepared in a similar manner to that of Preparation 2-4.

(3RS)-3-amino-1-[(3-azabicyclo[3.2.2]non-3-yl)carbonylmethyl]-5-butyl-2,3-dihydro-1H-1,4-benzodiazepin-2-one ¹H-NMR (CDCl₃, δ): 0.86 (3H, t, J=7.6 Hz), 1.24–1.31 (2H, m), 1.44–1.80 (12H, m), 2.00–2.15 (2H, m), 2.70–2.90 (2H, m), 3.40–3.90 (4H, m), 4.26 (1H, d, J=16.0 Hz), 4.40 (1H, s), 4.94 (1H, d, J=16.0 Hz), 7.20–7.60 (4H, m)

Preparation 12-1

The following compound was prepared in a similar manner to that of Preparation 1-1.

2-cyclohexylmethylcarbonylaniline

¹H-NMR (CDCl₃, δ): 0.80–1.40 (6H, m), 1.60–1.80 (4H, m), 1.85–2.00 (1H, m), 2.77 (2H, d, J=6.8 Hz), 6.28 (1H, br), 6.62–6.67 (2H, m), 7.23–7.27 (1H, m), 7.73 (1H, d, J=8.4 Hz)

Preparation 12-2

The following compound was prepared in a similar manner to that of Preparation 1-2.

2-cyclohexylmethylcarbonyl-N-{2-(1-benzotriazolyl)-2-benzyloxycarbonylamino}acetylaniline ¹H-NMR (CDCl₃, δ): 0.80–1.80 (11H, m), 2.69 (2H, d, J=6.8 Hz), 5.00–5.30 (3H, m), 6.91 (1H, br), 7.10–7.50 (7H, m), 7.54 (2H, m), 7.83 (2H, d, J=8.0 Hz), 8.09 (1H, d, J=8.0 Hz), 8.61 (1H, d, J=8.0 Hz), 12.40 (1H, br)

Preparation 12-3

The following compound was prepared in a similar manner to that of Preparation 6-3.

(3RS)-3-benzyloxycarbonylamino-5-cyclohexylmethyl-2,3-dihydro-1H-1,4-benzodiazepin-2-one ¹H-NMR (CDCl₃, δ): 0.80–1.80 (11H, m), 2.49–2.55 (1H, m), 2.82–2.88 (1H, m), 5.10–5.20 (3H, m), 6.49 (1H, d, J=8.0 Hz), 7.08 (1H, d, J=8.0 Hz), 7.30–7.50 (6H, m), 7.46–7.50 (1H, m), 7.58 (1H, d, J=8.0 Hz), 8.33 (1H, s)

Preparation 12-4

The following compound was prepared in a similar manner to that of Preparation 1-5.

(3RS)-1-[(3-azabicyclo[3.2.2]non-3-yl)carbonylmethyl]-3-benzyloxycarbonylamino-5-cyclohexylmethyl-2,3-dihydro-1H-1,4-benzodiazepin-2-one ¹H-NMR (CDCl₃, δ): 0.80–1.80 (19H, m), 2.10 (2H, br), 2.51–2.57 (1H, m), 2.82–2.88 (1H, m), 3.43–3.48 (1H, m), 3.56–3.60 (1H, m), 3.67–3.72 (1H, m), 3.85–3.89 (1H, m), 4.18 (1H, d, J=16 Hz), 4.97 (1H, d, J=16 Hz), 5.04–5.16 (2H, m), 6.65 (1H, d, J=8.0 Hz), 7.2–7.6 (9H, m)

Preparation 12-5

To a solution of (3RS)-1-[(3-azabicyclo[3.2.2]non-3-yl)carbonylmethyl]-3-benzyloxycarbonylamino-5-cyclohexylmethyl-2,3-dihydro-1H-1,4-benzodiazepin-2-one (0.396 g) in methanol (15 ml) was added Pearlman's catalyst (0.111 g). The mixture was stirred under H₂ atmosphere over night. The catalyst was filtered off by suction filtration on Celite®. The filtrate was concentrated in vacuo to give (3RS)-3-amino-1-[(3-azalicyclo[3.2.2]non-3-yl)carbonylmethyl]-5-cyclohexylmethyl-2,3-dihydro-1H-1,4-benzodiazepin-2-one (0.298 g), which was used in a following reaction step without further purification.

¹H-NMR (CDCl₃, δ): 0.80–1.20 (4H, m), 1.4–1.9 (15H, m), 2.00–2.20 (4H, br), 2.57–2.63 (1H, m), 2.78–2.83 (1H, m), 3.50–3.90 (4H, m), 4.13 (1H, d, J=16H), 4.42 (1H, s), 5.05 (1H, d, J=16 Hz), 7.22–7.30 (2H, m), 7.43–7.51 (2H, m)

Preparation 13-1

2-(2-Fluorobenzoyl)-6-methylaniline was prepared in a similar manner to that of Preparation 50-1.

mp: 65.5–67.5° C.

IR (Nujol, cm⁻¹): 3470, 3350, 1610, 1580, 1551, 1375, 1320, 1280, 1218, 1088, 1002, 956, 830, 752

¹H-NMR (CDCl₃, δ): 2.20 (3H, s), 6.38 (2H, br), 6.52 (1H, t, J=7.6 Hz), 7.08–7.46 (6H, m)
APCI-MS (m/z): 230 (M⁺+1)

Preparation 13-2

(3RS)-3- Benzyloxycarbonylamino-5-(2-fluorophenyl)-9-methyl-2,3-dihydro-1H-1,4-benzodiazepin-2-one was prepared in a similar manner to that of Preparation 45-2.
mp: 222.5–225° C.
IR (Nujol, cm⁻¹): 3200, 1715, 1690, 1608, 1530, 1374, 1051, 860, 750
¹H-NMR (DMSO-d₆, δ): 2.40 (3H, s), 5.05 (1H, d, J=8.9 Hz), 5.08 (2H, s), 7.0–7.62 (12H, m), 8.43 (1H, d, J=8.9 Hz), 10.28 (1H, s)
APCI-MS (m/z): 418 (M⁺+1)

Preparation 13-3

(3RS)-3-Benzyloxycarbonylamino-2,3-dihydro-5-(2-fluorophenyl)-1-(2-methoxylphenacyl)-9-methyl-1H-1,4-benzodiazepin-2-one was prepared in a similar manner to that of Preparation 59-3.
IR (Nujol, cm⁻¹): 1710, 1660
¹H-NMR (DMSO-d₆, δ): 2.46 (3H, s), 3.94 (3H, s), 4.60 (1H, d, 18.1 Hz), 5.06 (2H, br, s), 5.24 (1H, d, J=8.6 Hz), 5.44 (1H, d, J=18.1Hz), 6.9–7.8 (15H, m), 8.4–8.6 (1H, m)
Mass (APCI): 566 (M⁺+1)

Preparation 13-4

(3RS)-3-Amino-2,3-dihydro-5-(2-fluorophenyl)-9-methyl-1-(2-methoxyphenacyl)-1H-1,4-benzodiazepin-2-one was prepared in a similar manner to that of Preparation 59-6.
IR (Nujol, cm⁻¹): 1675
¹H-NMR(CDCl₆, δ): 2.45 (3H, s), 3.93 (3H, s), 4.59 (7H, d, J=18.0 Hz), 4.65 (1H, d, J=7.6 Hz), 5.52 (1H, d, J=18.0 Hz), 6.9–7.5 (9H, m), 7.7–8.0 (2H, m)
Mass (APCI): 432 (M⁺+1)

Preparation 14

To a solution of (3RS)-1-[(3-azabicyclo[3.2.2]non-3-yl)carbonylmethyl]-3-benzyloxycarbonylamino-5-acetoxymethyl-9-methyl-2,3-dihydro-1H-1,4-benzodiazepin-2-one (1.9 g) in ethanol (40 ml) was added 1N-sodium hydroxide solution (7 ml) under stirring at ambient temperature. The mixture was stirred for 20 minutes under the same conditions. After removal of the solvent water was added into the mixture, which was adjusted to pH 4 with a diluted hydrochloric acid and extracted with ethyl acetate twice. The combined extract was washed with water and dried over magnesium sulfate. Removal of the solvent gave (3RS)-1-[(3-azabicyclo[3.2.2]non-3-yl)carbonylmethyl]-3 -benzyloxycarbonylamino-5-hydroxymethyl-9-methyl-2,3-dihydro-1H-1,4-benzodiazepin-2-one as an amorphous mass (1.68 g, 95.3%).
¹H-NMR (CDCl₃, δ): 1.4–1.75 (8H, m), 1.9–2.1 (2H, m), 2.36 (3H, s), 3.19–3.34 (2H, m), 3.55–3.89 (2H, m), 4.51 (2H, dd, J=15.8 Hz, 298.4 Hz), 4.75 (2H, dd, J=14.7 Hz, J=27.6 Hz), 5.10 (2H, s), 5.41 (1H, d, J=8.8 Hz), 6.54 (1H, d, J=8.8 Hz), 7.25–7.47 (8H, m)
APCI-MS (m/z): 519 (M⁺+1)

Preparation 15-1

(3RS)-3-Benzyloxycarbonylamino-2,3-dihydro-5-(2-fluorophenyl)-9-methyl-1-(2-nitrophenacyl)-1H-1,4-benzodiazepin-2-one was prepared in a similar manner to that of Preparation 59-3.
IR (Nujol, cm⁻¹): 1710, 1675
¹H-NMR (DMSO-d₆, δ): 2.43 (3H, s), 4.66 (1H, d, J=18.1 Hz), 5.06 (2H, m), 5.26 (1H, d, J=9.1 Hz), 5.45 (1H, d, J=18.0 Hz), 7.07 (1H, d, J=7.7 Hz), 7.2–8.0 (14H, m), 8.0–8.2 (1H, m), 8.4–8.6 (1H, m)
Mass (APCI): 581 (M⁺+1)

Preparation 15-2

(3RS)-3-Amino-1-(2-aminophenacyl)-2,3-dihydro-5-(2-fluorophenyl)-9-methyl-1H-1,4-benzodiazepin-2-one was prepared in a similar manner to that of Preparation 59-6.
mp: 139.7–147.0° C.
IR (Nujol, cm⁻¹): 1680, 1660
¹H-NMR (DMSO-d₆, δ): 2.46 (3H, s), 4.10 (1H, s), 4.49 (1H, d, J=16.8 Hz), 5.74 (1H, d, J=16.8 Hz), 6.0 (2H, m), 6.5–6.7 (2H, m), 7.0–7.3 (7H, m), 7.3–7.6 (2H, m), 7.6–7.7 (1H, m), 7.7–7.9 (1H, m)
Mass (APCI): 417 (M⁺+1)

Preparation 16-1

2-Amino-3-methyl-2'-fluorobenzophenone was prepared in a similar manner to that of Preparation 50-1.
mp: 52.2–55.2° C.
IR (Nujol, cm⁻¹): 3470, 3330. 1620
¹H-NMR (CDCl₃, δ): 2.21 (3H, s), 6.6–6.8 (3H, m), 7.0–7.7 (5H,m)
Mass (APCI): 230 (M⁺+1)

Preparation 16-2

2-Bromoacetylamino-3-methyl-2'-fluorobenzophenone was prepared in a similar manner to that of Preparation 29-2.
mp: 100.1–103.2° C.
IR (Nujol, cm⁻¹): 1660
¹H-NMR (DMSO-d₆, δ): 2.26 (3H, s), 3.70 (2H, s), 7.2–7.4 (4H, m), 7.4–7.8 (3H, m), 9.96 (1H, br, s)
Mass (APCI): 352 (M⁺+1), 350 (M⁺−1)

Preparation 16-3

5-(2-Fluorophenyl)-9-methyl-2,3-dihydro-1H-1,4-benzodiazepin-2-one-4-oxide was prepared in a similar manner to that of Preparation 19-3.
mp: 204.4–205.1° C.
IR (Nujol, cm⁻¹): 1690
¹H-NMR (CDCl₃, δ): 2.48 (3H, s), 4.70 (2H, s), 6.9–7.0 (1H, m), 7.0–7.6 (6H, m), 9.31 (1H, br, s)
Mass (APCI m/z): 285 (M⁺+1)

Preparation 16-4

3-Acetoxy-5-(2-fluorophenyl)-9-methyl-2,3-dihydro-1H-1,4-benzodiazepin-2-one was prepared in a similar manner to that of Preparation 19-4.
IR (Nujol, cm⁻¹): 1745
¹H-NMR (CDCl₃, δ): 2.32 (3H, s), 2.44 (3 H, s), 5.97 (1H, s), 7.0–7.2 (3H, m), 7.2–7.3 (1H, m), 7.3–7.5 (2H, m), 7.6–7.8 (1H, m), 8.62 (1H, br, s)
Mass (APCI): 327 (M⁺+1)

Preparation 16-5

(3RS)-3-Phthalimido-5-(2-fluorophenyl)-9-methyl-2,3-dihydro-1H-1,4-benzodiazepin-2-one was prepared in a similar manner to that of Preparation 20-5.
mp: >250° C.
NMR (CDCl₃, δ): 2.44 (3H, s), 5.93 (1H, s), 6.9–8.0 (11H, m)
Mass (APCI): 414 (M⁺+1)

Preparation 16-6

(3RS)-3-Amino-5-(2-fluorophenyl)-9-methyl-2,3-dihydro-1H-1,4-benzodiazepin-2-one was prepared in a similar manner to that of Preparation 19-6.
mp: 102.2–112.2° C.
IR (Nujol, cm⁻¹): 1685
¹H-NMR (CDCl₃, δ): 2.42 (3H, s), 4.49 (1H, s), 7.0–7.8 (7H, m), 8.64 (1H, m)
Mass (APCI): 284 (M⁺+1)

Preparation 16-7

(3RS)-3-tert-butoxycarbonylamino-5-(2-fluorophenyl)-9-methyl-2,3-dihydro-1H-1,4-benzodiazepin-2-one was prepared in a similar manner to that of Preparation 20-7.
mp: 183.2–186.6° C.

¹H-NMR (CDCl₃, δ): 1.48 (9H, s), 2.41 (3H, s), 5.31 (1H, d, J=8.7 Hz), 6.39 (1H, d, J=8.7 Hz), 7.0–7.2 (3H, m), 7.2–7.3 (1H, m), 7.3–7.6 (2H, m), 7.6–7.8 (1H, m), 8.26 (1H, br, s)

Mass (APCI): 384 (M⁺+1)

Preparation 16-8

(3RS)-1-Ethoxycarbonylmethyl-3-tert-butoxycarbonylamino-5-(2-fluorophenyl)-9-methyl-2,3-dihydro-1H-1,4-benzodiazepin-2-one was prepared in a similar manner to that of Preparation 59-3.

¹H-NMR (CDCl₃, δ): 1.46 (9H, s), 2.40 (3H, s), 3.91(1H, d, J=16.8 Hz), 3.8–4.2 (2H, m), 4.83 (1H, d, J=16.8 Hz), 5.40 (1H, d, J=8.9 Hz), 6.41 (1H, d, J=8.8 Hz), 7.0–7.4 (4H, m), 7.3–7.6 (2H, m), 7.7–7.9 (1H, m)

Mass (APCI): 470 (M⁺+1)

Preparation 16-9

(3RS)-1-Carboxymethyl-3-tert-butoxycarbonylamino-5-(2-fluorophenyl)-2,3-dihydro-9-methyl-1H-1,4-benzodiazepin-2-one was prepared in a similar manner to that of Example 48-2.

mp: 132.1–149.3° C.

IR (Nujol, cm⁻¹): 1700

¹H-NMR (CDCl₃, δ): 1.45 (9H, s), 2.36 (3H, s), 3.89 (1H, d, J=17.2 Hz), 4.82 (1H, d, J=17.2 Hz), 5.38 (1H, d, J=8.9 Hz), 6.40 (1H, d, J=8.9 Hz), 6.9–7.8 (7H, m)

Mass (APCI): 442 (M⁺+1)

Preparation 16-10

(3RS)-1-[(3-Azabicyclo[3.2.2]non-3-yl)carbonylmethyl]-3-tert-butoxycarbonylamino-5-(2-fluorophenyl)-9-methyl-2,3-dihydro-1H-1,4-benzodiazepin-2-one was prepared in a similar manner to that of Preparation 59-5.

mp: 108.1–113.9° C.

¹H-NMR (CDCl₃, δ): 1.45 (9H, s), 1.3–2.2 (10H, m), 2.45(3H, s), 3.2–3.9 (4H, m), 4.04 (1H, d, J=15.5 Hz), 5.05 (1H, d, J=15.5 Hz), 5.42 (1H, d, J=8.9 Hz), 6.40 (1H, d, J=10 Hz), 6.9–7.3 (4H, m), 7.3–7.5 (2H, m), 7.7–7.9 (1H, m)

Mass (APCI): 549 (M⁺+1)

Preparation 16-11

(3RS)-3-Amino-1-[(3-azabicyclo[3.2.2]non-3-yl)carbonylmethyl[-5-(2-fluorophenyl)-9-methyl-2,3-dihydro-1H-1,4-benzodiazepin-2-one was prepared in a similar manner to that of Preparation 30-2.

mp: 102.3–113.4° C.

¹H-NMR (DMSO-d₆, δ): 1.3–2.2 (10H, m), 2.41 (3H, s), 3.0–3.4 (2H, m), 3.6–3.9 (2H, m), 4.06 (1H, d, J=16.2 Hz), 4.36 (1H, s), 5.06 (1H, d, J=16.2 Hz), 6.9–7.0 (1H, m), 7.1–7.4 (3H, m), 7.4–7.6 (2H, m), 7.6–7.8 (1H, m)

Mass (APCI): 449 (M⁺+1)

Preparation 17-1

To a solution of o-toluidine (27.98 g) and cyclohexanecarbonitrile (14.25 g) in toluene (200 ml) was added dropwise 1N-borontrichloride toluene solution (131 ml) under stirring and cooling in an ice-bath below 5° C. After the addition was completed, the mixture was stirred at ambient temperature for 0.5 hour. The mixture was cooled again and aluminum chloride (17.40 g) was added portionwise. The mixture was gradually warmed to ambient temperature and then refluxed under stirring for 7.5 hours. The reaction mixture was cooled in an ice-bath and 2N-hydrochloric acid (180 ml) was added dropwise under stirring. The resultant mixture was refluxed again for 2.5 hours. The reaction mixture was cooled under stirring and the resultant precipitate was filtered off. The filtrate and washings with ethyl acetate were combined and extracted with ethyl acetate. The organic extract was washed with 1N-hydrochloric acid twice and brine successively and dried over magnesium sulfate. Removal of the solvent in vacuo gave an oil, which was subjected to column chromatography on silica gel eluting with a mixture of n-hexane and methylene chloride (2:1). The fractions containing the desired product were combined and evaporated in vacuo to give 2-cyclohexylcarbonyl-6-methylaniline (27.9 g, 98.4% yield) as a light yellow oil.

IR (Film, cm⁻¹): 3470, 3320, 1638, 1608, 1580, 1550, 1424, 1380, 1310, 1240, 1218, 1150, 1004, 980, 891, 740

¹H-NMR (CDCl₃, δ): 1.2–1.95 (8H, m), 2.16 (3H, s), 3.23–3.36 (1H, m), 6.4 (1H, br), 6.60 (1H, t, J=7.3 Hz), 7.18 (1H, d, J=7.3 Hz), 7.68 (1H, d, J=7.3 Hz)

APCI-MS (m/z): 218 (M⁺+1)

Preparation 17-2

To a solution of N-benzyloxycarbonyl-2-(benzotriazol-1-yl)glycine (3.59 g) in dry tetrahydrofuran (THF, 30 ml) was added oxalyl chloride (1.05 ml) at 0–5° C. under stirring and nitrogen stream. After one drop of dimethylformamide was added, the mixture was stirred for 2 hours under the same conditions. To the reaction mixture was added dropwise a mixture of 2-cyclohexylcarbonyl-6-methylaniline (2.17 g) and N-methylmorpholine (2.23 g) in dry THF for 20 minutes under the same conditions. The mixture was allowed to warm to ambient temperature and stirred for 1 hour. THF was removed in vacuo to afford a residue, which was dissolved in ethyl acetate and washed with diluted aqueous sodium bicarbonate, water and brine successively. After drying over magnesium sulfate, the solvent was removed in vacuo to give an amorphous mass (5.77 g), which was dissolved in methanol (4 ml). To the solution was added 9M methanolic ammonia (22 ml) and the mixture was stirred at ambient temperature overnight. The mixture was evaporated in vacuo to give a residue, which was dissolved in ethyl acetate and washed with 1N-sodium hydroxide aqueous solution and water. The organic layer was dried over magnesium sulfate and evaporated in vacuo to give a residue, which was dissolved in acetic acid (60 ml). Ammonium acetate (4.0 g) was added to the solution and the mixture was stirred for 1.5 hour at ambient temperature. Acetic acid was removed in vacuo to give a residue, which was dissolved in ethyl acetate and washed with diluted sodium hydroxide aqueous solution and water successively. After drying over magnesium sulfate, the solvent was removed in vacuo to give a crystalline mass, which was pulverized in a mixture of diisopropyl ether and n-hexane and collected by filtration to give (3RS)-3-benzyloxycarbonylamino-5-cyclohexyl-9-methyl-2,3-dihydro-1H-1,4-benzodiazepin-2-one (2.36 g, 58.3% yield) as a crystalline powder.

mp: 171–173° C.

IR (Nujol, cm⁻¹): 3490 (sh), 3300, 3200, 1710, 1685, 1620, 1520, 1370, 1056, 987, 793, 749, 696

¹H-NMR (DMSO-d₆, δ): 0.8–2.0 (8H, m), 2.33 (3H, s), 2.91 (1H, br, t), 4.86 (1H, d, J=8.7 Hz), 5.03 (2H, s), 7.16–7.60 (8H, m), 8.11 (1H, d, J=8.7 Hz), 9.96 (1H, s)

APCI-MS (m/z): 406 (M⁺+1)

Preparation 17-3

(3RS)-3-Benzyloxycarbonylamino-5-cyclohexyl-2,3-dihydro-1,9-dimethyl-1H-1,4-benzodiazepin-2-one was prepared in a similar manner to that of Preparation 59-3.

¹H-NMR(CDCl₃, δ): 1.0–2.0 (8H, m), 2.34 (3H, s), 2.75–2.80 (1H, m), 3.16 (3H, s), 5.01–5.15 (2H, m), 5.18 (1H, d, J=8.5 Hz), 6.54 (1H, d, J=8.4 Hz), 7.2–7.4 (8H, m)

Mass (APCI): 420 (M⁺+1)

Preparation 17-4

(3RS)-3-Amino-5-cyclohexyl-2,3-dihydro-1,9-dimethyl-1H-1,4-benzodiazepin-2-one was prepared in a similar manner to that of Preparation 59-6.

¹H-NMR (CDCl₃, δ): 0.8–2.0 (10H, m), 2.34 (3H, s), 2.7–2.9 (1H, m), 3.16 (3H, s), 4.34 (1H, br, s), 7.1–7.5 (3H, m)

Mass (APCI): 286 (M⁺+1)

Preparation 18-1

(3RS)-1-(2-methylphenacyl)-3-tert-butoxycarbonylamino-5-(2-fluorophenyl)-9-methyl-2,3-dihydro-1H-1,4-benzodiazepin-2-one was prepared in a similar manner to that of Preparation 59-3.

$^1$H-NMR (CDCl$_3$, δ): 1.47 (9H, s), 2.35 (3H, s), 2.44 (3H, s), 4.36 (1H, d, J=17.2 Hz), 5.49 (1H, d, J=17.2 Hz), 5.51 (1H, d, J=7.3 Hz), 6.42 (1H, d, J=8.9 Hz), 7.0–7.5 (9H, m), 7.5–7.7 (1H, m), 7.8–8.0 (1H, m)

Mass (APCI): 516 (M⁺+1)

Preparation 18-2

(3RS)-3-Amino-1-(2-methylphenacyl)-5-(2-fluorophenyl)-9-methyl-2,3-dihydro-1H-1,4-benzodiazepin-2-one was prepared in a similar manner to that of Preparation 30-2.

mp: 198.1–202.6° C.

IR (Nujol, cm$^{-1}$): 1695, 1665

$^1$H-NMR (DMSO-d$_6$, δ): 2.26 (3H, s), 2.44 (3H, s), 4.44 (1H, s), 4.60 (1H, d, J=17.4 Hz), 5.40 (1H, d, J=17.4 Hz), 7.0 (1H, m), 7.2–8.0 (11H, m)

Mass (APCI): 416 (M⁺+1)

Preparation 19-1

2-Amino-3-ethyl-2'-fluorobenzophenone was prepared in a similar manner to that of Preparation 50-1.

IR (Neat, cm$^{-1}$): 1620

$^1$H-NMR (CDCl$_3$, δ): 1.30 (3H, t, J=7.5 Hz), 2.55 (2H, q, J=7.5 Hz), 6.5–6.7 (3H, m), 7.0–7.7 (5H, m)

Mass (APCI): 244 (M⁺+1)

Preparation 19-2

2-Bromoacetylamino-3-ethyl-2'-fluorobenzophenone was prepared in a similar manner to that of Preparation 29-2.

mp: 90.2–91.6° C.

$^1$H-NMR (CDCl$_3$, δ): 1.26 (3H, t, J=7.5 Hz), 2.69 (2H, q, J=7.5 Hz), 3.87 (2H, s), 7.0–7.4 (4H, m), 7.4–7.7 (3H, m), 9.02 (1H, br, s)

Mass (APCI): 366 (M⁺+2), 364 (M⁺)

Preparation 19-3

A mixture of 2-bromoacetylamino-3-ethyl-2'-fluorobenzophenone (12.0 g), hydroxylamine hydrochloride (17.65 g), sodium hydroxide (8.58 g) in ethanol was stirred at 30–40° C. for 4.5 hours. Concentrated aqueous hydrochloric acid (14.8 ml) was added to the reaction mixture, which was stirred at room temperature overnight. The mixture was evaporated in vacuo to afford precipitates. Water was added to the resultant mixture. The precipitate was collected by filtration and washed with water to afford 5-(2-fluorophenyl)-9-ethyl-2,3-dihydro-1H-1,4-benzodiazepin-2-one-4-oxide (9.25 g, 94.2%).

mp: 170.9–176.2° C.

$^1$H-NMR (CDCl$_3$, δ): 1.30 (3H, t, J=7.4 Hz), 2.82 (2H, q, J=7.4 Hz), 4.69 (2H, s), 6.8–7.0 (1H, m), 7.0–7.6 (6H, m), 9.05 (1H, br, s)

Mass (APCI): 299 (M⁺+1)

Preparation 19-4

A mixture of 9-ethyl-5-(2-fluorophenyl)-2,3-dihydro-1H-1,4-benzodiazepin-2-one-4-oxide (9.0 g) and acetic anhydride (32 ml) in chloroform (32 ml) was stirred at room temperature overnight. The reaction mixture was evaporated to remove chloroform. Diisopropyl ether was added to the residue to afford powder, which was collected by filtration and washed with diisopropyl ether to give (3RS)-3-acetoxy-5-(2-fluorophenyl)-9-ethyl-2,3-dihydro-1H-1,4-benzodiazepin-2-one (6.30 g, 61.3%).

mp: 225.8–228.1° C.

IR (Nujol, cm$^{-1}$): 1730, 1680

$^1$H-NMR (DMSO-d$_6$, δ): 1.18 (3H, t, J=7.4 Hz), 2.20 (3H, s), 2.6–2.8 (1H, m), 2.8–3.1 (1H, m), 5.67 (1H, s), 7.0–7.8 (7H, m)

Mass (APCI): 341 (M⁺+1)

Preparation 19-5

(3RS)-9-Ethyl-3-phthalimido-5-(2-fluorophenyl)-2,3-dihydro-1H-1,4-benzodiazepin-2-one was prepared in a similar manner to that of Preparation 20-5.

IR (Nujol, cm$^{-1}$): 1710, 1670

$^1$H-NMR (DMSO-d$_6$, δ): 1.0–1.3 (3H, m), 2.6–2.9 (1H, m), 2.9–3.2 (1H, m), 5.67 (1H, s), 7.0–7.1 (1H, m), 7.1–7.5 (3H, m), 7.5–7.8 (3H, m), 7.8–8.1 (4H, m)

Mass (APCI): 428 (M⁺+1)

Preparation 19-6

A mixture of (3RS)-3-phthalimido-9-ethyl-5-(2-fluorophenyl)-2,3-dihydro-1H-1,4-benzodiazepin-2-one (6.0 g) and hydrazine hydrate (1.05 g) in a mixture of methanol and tetrahydrofuran (1:1, 60 ml) was refluxed with stirring for 3 hours. The reaction mixture was allowed to cool to room temperature, and the resultant precipitates were filtered off. The filtrate and the washings were combined and evaporated in vacuo to give a residue, which was dissolved in ethyl acetate and washed with a saturated aqueous solution of sodium bicarbonate, water and brine successively. The solvent was dried over sodium sulfate and evaporated in vacuo to afford a pale yellow powder, which was washed with diisopropyl ether and collected by filtration to give (3RS)-3-amino-9-ethyl-5-(2-fluorophenyl)-2,3-dihydro-1H-1,4-benzodiazepin-2-one (3.37 g, 81.0%).

mp: 178.2–180.6° C.

IR (Nujol, cm$^{-1}$): 1620

$^1$H-NMR (DMSO-d$_6$, δ): 1.18 (3H, t, J=7.5 Hz), 2.6–3.1 (2H, m), 4.22 (1H, s), 7.0–7.7 (7H, m)

Mass (APCI): 298 (M⁺+1)

Preparation 19-7

(3RS)-3-Tert-butoxycarbonylamino-5-(2-fluorophenyl)-9-ethyl-2,3-dihydro-1H-1,4-benzodiazepin-2-one was prepared in a similar manner to that of Preparation 20-7.

mp: 88.1–92.1° C.

IR (Nujol, cm$^{-1}$): 1670, 1720

$^1$H-NMR(CDCl$_3$, δ): 1.2–1.4 (3H, m), 1.48 (9H, s), 2.6–2.9 (2H, m), 5.31 (1H, d, J=8.6 Hz), 6.40 (1H, d, J=8.6 Hz), 7.0–7.4 (4H, m), 7.4–7.6 (2H, m), 7.6–7.8 (1H, m), 8.16 (1H, br, s)

Mass (APCI): 398 (M⁺+1)

Preparation 19-8

(3RS)-1-Ethoxycarbonylmethyl-3-tert-butoxycarbonylamino-5-(2-fluorophenyl)-9-ethyl-2,3-dihydro-1H-1,4-benzodiazepin-2-one was prepared in a similar manner to that of Preparation 59-3.

IR (Nujol, cm$^{-1}$): 1750, 1680

$^1$H-NMR (CDCl$_3$, δ): 1.33 (3H, t, J=6.0 Hz), 0.99 (3H, t, J=7.1 Hz), 1.46 (3H, s), 2.6–2.8 (2H, m), 3.7–4.1 (3H, m), 4.88 (1H, d, J=16.6 Hz), 5.39 (1H, d, J=8.8 Hz), 6.42 (1H, d, J=8.8 Hz), 7.0–7.2 (2H, m), 7.2–7.4 (2H, m), 7.4–7.6 (2H, m), 7.7–7.9 (1H, m)

Mass (APCI): 484 (M⁺+1)

Preparation 19-9

(3RS)-1-Carboxymethyl-3-tert-butoxycarbonylamino-5-(2-fluorophenyl)-9-ethyl-2,3-dihydro-1H-1,4-benzodiazepin-2-one was prepared in a similar manner to that of Example 48-2.

IR (Nujol, cm$^{-1}$):1720, 1680

$^1$H-NMR (CDCl$_3$, δ): 1.25 (3H, t, J=7.1 Hz), 1.45 (9H, s), 2.6–2.8 (2H, m), 3.85 (1H, d, J=17.2 Hz), 4.87 (1H, d, J=17.2 Hz), 5.37 (1H, d, J=8.8 Hz), 6.40 (1H, d, J=8.8 Hz), 7.0–7.9 (7H, m)

Mass (APCI): 456 (M⁺+1)

Preparation 19-10

(3RS)-1-[(3-Azabicyclo[3.2.2]non-3-yl)carbonylmethyl]-3-tert-butoxycarbonylamino-5-(2-fluorophenyl)-9-ethyl-2, 3-dihydro-1H-1,4-benzodiazepin-2-one was prepared in a similar manner to that of Preparation 59-5.

IR (Nujol, cm$^{-1}$): 1720, 1650

$^1$H-NMR(CDCl$_3$, δ): 1.34 (3H, t, J=7.5 Hz), 1.45 (9H, s), 1.4–2.2 (10H, m), 2.7–2.9 (2H, m), 3.2–3.8 (4H, m), 3.96 (1H, d, J=15.5 Hz), 5.01 (1H, d, J=15.5 Hz), 5.41 (1H, br, s), 7.0–7.1 (2H, m), 7.1–7.3 (2H, m), 7.3–7.5 (2H, m), 7.7–7.9 (1H, m)

Mass (APCI): 563 (M$^+$+1)

Preparation 19-11

(3RS)-3-Amino-1-[(3-azabicyclo[3.2.2]non-3-yl)carbonylmethyl]-5-(2-fluorophenyl)-9-ethyl-2,3-dihydro-1H-1,4-benzodiazepin-2-one was prepared in a similar manner to that of Preparation 30-2.

mp: 160.4–164.8° C.

$^1$H-NMR (DMSO-d$_6$, δ): 1.26 (3H, t, J=7.4 Hz), 1.3–2.2 (10H, m), 2.75 (2H, q, J=7.4 Hz), 3.0–3.4 (2H, m), 3.4–3.9 (2H, m), 3.97 (1H, d, J=16.1 Hz), 4.36 (1H, br, s), 5.13 (1H, d, J=16.1 Hz), 6.8–7.0 (1H, m), 7.2–7.4 (3H, m), 7.4–7.6 (2H, m), 7.6–7.8 (1H, m)

Mass (APCI): 160.4–164.8° C.

Preparation 20-1

2-Amino-3-isopropyl-2'-fluorobenzophenone was prepared in a similar manner to that of Preparation 50-1.

IR (Neat, cm$^{-1}$): 1620

$^1$H-NMR (CDCl$_3$, δ): 1.26 (3H, d, J=6.8 Hz), 1.30 (3H, d, J=6.8 Hz), 2.7–3.1 (1H, m), 3.64 (1H, br), 6.5–7.6 (7H, m)

Mass (APCI): 258 (M$^+$+1)

Preparation 20-2

2-Bromoacetylamino-3-isopropyl-2-fluorobenzophenone was prepared in a similar manner to that of Preparation 29-2.

mp: 125.8–126.3° C.

IR (Nujol, cm$^{-1}$): 1660

$^1$H-NMR (CDCl$_3$, δ): 1.27 (6H, d, J=6.8 Hz), 3.0–3.3 (1H, m), 3.86 (2H, s), 7.0–7.4 (4H, m), 7.4–7.8 (3H, m), 8.86 (1H, s)

Mass (APCI): 380 (M$^+$+2), 378 (M$^+$)

Preparation 20-3

5-(2-Fluorophenyl)-9-isopropyl-2,3-dihydro-1H-1,4-benzodiazepin-2-one-4-oxide was prepared in a similar manner to that of Preparation 19-3.

mp: 205.5–207.7° C.

$^1$H-NMR (CDCl$_3$, δ): 1.32 (6H, d, J=6.71 Hz), 3.2–3.4 (1H, m), 4.70 (2H, s), 6.8–7.0 (1H, m), 7.0–7.3 (3H, m), 7.3–7.5 (3H, m), 8.91 (1H, br, s)

Mass (APCI): 313 (M$^+$+1)

Preparation 20-4

(3RS)-3-acetoxy-5-(2-fluoropheyl)-9-isopropyl-2,3-dihydro-1H-1,4-benzodiazepin-2-one was prepared in a similar manner to that of Preparation 19-4.

mp: 243.2–247.1° C.

$^1$H-NMR (DMSO-d$_6$, δ): 1.12 (3H, d, J=6.7 Hz), 1.31 (1H, d, J=8.0 Hz), 2.20 (3H, s), 3.3–3.6 (1H, m), 5.65 (1H, s), 7.0–7.1 (1H, m), 7.1–7.5 (3H, m), 7.5–7.7 (3H, m), 10.40 (1H, br, s)

Mass (APCI): 355 (M$^+$+1)

Preparation 20-5

A mixture of (3RS)-3-acetoxy-5-(2-fluorophenyl)-9-isopropyl-2,3-dihydro-1H-1,4-benzodiazepin-2-one (2.73 g), sodium iodide (11.5 g) and phthalimide potassium salt (2.14 g) in N,N-dimethylformamide (18 ml) was stirred at 90° C. for 1.3 hours. The hot reaction mixture was poured into an ice with stirring to afford precipitates, which were collected by filtration, washed with water and air dried at room temperature to afford (3RS)-3-phthalimido-5-(2-fluorophenyl)-9-isopropyl-2,3-dihydro-1H-1,4-benzodiazepin-2-one (3.08 g, 90.6%) as a crystalline powder.

mp: 247.6–252.2° C.

IR (Nujol, cm$^{-1}$): 1680

$^1$H-NMR (DMSO-d$_6$, δ): 1.12 (3H, d, J=6.7 Hz), 1.33 (3H, d, J=6.6Hz), 3.3–3.7 (1H, m), 5.65 (1H, s), 7.0–7.2 (1H, m), 7.2–7.5 (3m), 7.5–7.8 (3H, m), 7.8–8.1 (4H, m)

Mass (APCI): 442 (M$^+$+1)

Preparation 20-6

(3RS)-3-Amino-5-(2-fluorophenyl)-9-isopropyl-2,3-dihydro-1H-1,4-benzodiazepin-2-one was prepared in a similar manner to that of Preparation 19-6.

mp: 192.3–198.6° C.

IR (Nujol, cm$^{-1}$): 1690

$^1$H-NMR (DMSO-d$_6$, δ): 1.11 (3H, d, J=6.7 Hz), 1.29 (1H, d, J=6.7 Hz), 3.3–3.6 (1H, m), 4.20 (1H, s), 6.9–7.7 (7H, m)

Mass (APCI): 312 (M$^+$+1)

Preparation 20-7

A mixture of (3RS)-3-amino-5-(2-fluorophenyl)-9-isopropyl-2,3-dihydro-1H-1,4-benzodiazepin-2-one (1.5 g), a catalytic amount of hydroxylamine hydrochloride, triethylamine (731 mg) and di-tert-butyl dicarbonate (1.57 g) in methylene chloride (30 ml) was stirred at room temperature for 1.5 hours. Chloroform and water were added to the reaction mixture. The separated organic layer was washed with water twice and dried over magnesium sulfate. The solvent was evaporated in vacuo to afford a crude paste, which was dissolved in diisopropyl ether, and allowed to stand at room temperature to afford a pale yellow powder. The powder was collected by filtration and washed with diisopropyl ether to afford (3RS)-3-tert-butoxycarbonylamino-5-(2-fluorophenyl)-9-isopropyl-2,3-dihydro-1H-1,4-benzodiazepin-2-one (1.55 g, 78.1%).

mp: 196.0–199.2° C.

IR (Nujol, cm$^{-1}$): 1715, 1665

$^1$H-NMR (CDCl$_3$, δ): 1.32 (3H, t, J=6.6 Hz), 1.48 (9H, s), 3.1–3.3 (1H, m), 5.32 (1H, d, J=8.6 Hz), 6.41 (1H, d, J=8.6 Hz), 7.0–7.4 (4H, m), 7.4–7.6 (2H, m), 7.6–7.8 (1H, m), 8.15 (1H, br, s)

Mass (APCI): 412 (M$^+$+1)

Preparation 20-8

(3RS)-1-Ethoxycarbonylmethyl-3-tert-butoxycarbonylamino-5-(2-fluorophenyl)-9-isopropyl-2,3-dihydro-1H-1,4-benzodiazepin-2-one was prepared in a similar manner to that of Preparation 59-3.

IR (Nujol, cm$^{-1}$): 1750, 1720, 1670

$^1$H-NMR (CDCl$_3$, δ): 0.99 (1H, t, J=7.1 Hz), 1.20 (3H, d, J=6.7 Hz), 1.4–1.6 (3H, m), 1.46 (9H, s), 3.7–4.2 (3H, m), 3.0–3.2 (1H, m), 4.94 (1H, d, J=16.5 Hz), 5.39 (1H, d, J=8.7 Hz), 6.41 (1H, d, J=8.7 Hz), 7.0–7.2 (2H, m), 7.2–7.4 (2H, m), 7.4–7.6 (2H, m), 7.7–7.9 (1H, m)

Mass (APCI): 498 (M$^+$+1)

Preparation 20-9

(3RS)-1-Carboxymethyl-3-tert-hutoxycarbonylamino-5-(2-fluorophenyl)-9-isopropyl-2,3-dihydro-1H-1,4-benzodiazepin-2-one was prepared in a similar manner to that of Example 48-2.

IR (Nujol, cm$^{-1}$): 1720, 1690

$^1$H-NMR (CDCl$_3$, δ): 1.14 (3H, d, J=7.6 Hz), 1.39 (3H, d, J=6.8 Hz), 1.45 (9H, s), 2.9–3.1 (1H, m), 3.81 (1H, d, J=17.1 Hz), 4.95 (1H, d, J=17.1 Hz), 5.37 (1H, d, J=8.8 Hz), 6.39 (1H, d, J=8.8 Hz), 7.0–7.6 (6H, m), 7.6–7.8 (1H, m)

Mass (APCI): 470 (M$^+$+1)

Preparation 20-10

(3RS)-1-[(3-Azabicyclo[3.2.2]non-3-yl)carbonylmethyl]-3-tert-butoxycarbonylamino-5-(2-fluorophenyl)-9-isopropyl-2,3-dihydro-1H-1,4-benzodiazepin-2-one was prepared in a similar manner to that of Preparation 59-5.

IR (Nujol, cm$^{-1}$): 1720, 1650

$^1$H-NMR (CDCl$_3$, δ): 1.21 (3H, d, J=6.6 Hz), 1.41 (3H, d, J=6.6 Hz), 1.45 (9H, s), 1.4–2.2 (10H, m), 3.1–3.42 (2H, m), 3.42–3.6 (1H, m), 3.7–3.9 (1H, m), 3.92 (1H, d, J=15.4 Hz), 5.16 (1H, d, J=15.4 Hz), 5.41 (1H, d, J=8.9 Hz), 6.39 (1H, d, J=8.9 Hz), 7.0–7.2 (2H, m), 7.2–7.35 (2H, m), 7.35–7.6 (2H, m), 7.7–7.9 (1H, m)

Mass (APCI): 577 (M$^+$+1)

Preparation 20-11

(3RS)-3-Amino-1-[(3-azabicyclo[3.2.2]non-3-yl)carbonylmethyl]-2,3-dihydro-5-(2-fluorophenyl)-9-isopropyl-1H-1,4-benzodiazepin-2-one was prepared in a similar manner to that of Preparation 30-2.

mp: 211.6–214.2° C.

IR (Nujol, cm$^{-1}$): 1080, 1640

$^1$H-NMR (DMSO-d$_6$, δ): 1.10 (3H, d, J=6.6 Hz), 1.38 (1H, d, J=6.6 Hz), 1.4–2.2 (10H, m), 3.0–3.4 (2H, m), 3.6–3.8 (2H, m), 3.84 (1H, d, J=16.3 Hz), 4.36 (1H, br, s), 5.22 (1H, d, J=16.3 Hz), 6.8–7.0 (1H, m), 7.2–7.4 (3H, m), 7.4–7.8 (3H, m)

Mass (APCI): 477 (M$^+$+1)

Preparation 21-1

(3RS)-1-(2-Acetoxyethyl)-3-benzyloxycarbonylamino-5-cyclohexyl-2,3-dihydro-9-methyl-1H-1,4-benzodiazepin-2-one was prepared in a similar manner to that of Preparation 59-3.

IR (Nujol, cm$^{-1}$): 1720, 1675, 1610

$^1$H-NMR(CDCl$_3$, δ): 1.2–2.2 (10H, m), 2.32 (3H, s), 2.84 (1H, m), 3.39 (1H, d, t, J=6.0 Hz and J=14.2 Hz), 3.9–4.0 (2H, m), 4.60 (1H, d, t, J=5.4 Hz and J=14.2 Hz), 5.0–5.2 (3H, m), 6.53 (1H, d, J=8.5 Hz), 7.2–7.5 (8H, m)

Mass (APCI): 492 (M$^+$+1)

Preparation 21-2

(3RS)-3-Amino-1-(2-acetoxyethyl)-5-cyclohexyl-2,3-dihydro-9-methyl-1H-1,4-henzodiazepin-2-one was prepared in a similar manner to that of Preparation 59-6.

$^1$H-NMR (CDCl$_3$, δ): 1.2–2.2 (10H, m), 2.33 (3H, s), 2.7–2.9 (1H, m), 3.3–3.5 (1H, m), 3.8–4.1 (2H, m), 4.29 (1H, br, s), 4.61 (1H, dt, J=5.3 Hz and J=14.1 Hz), 7.2–7.5 (3H, m)

Mass (APCI): 358 (M$^+$+1)

Preparation 22

A mixture of (3RS)-3-amino-1-[(3-azabicyclo[3.2.2]non-3-yl)carbonylmethyl]-2,3-dihydro-9-methyl-5-(2-fluorophenyl)-1H-1,4-benzodiazepin-2-one (1.0 g) and 1,1'-carbonyldiimidazole (723 mg) in tetrahydrofuran (20 ml) was stirred at room temperature overnight. Ethyl acetate and water were added to the reaction mixture. The separated organic layer was washed with water twice, brine and dried over magnesium sulfate. The solvent was evaporated in vacuo to afford (3RS)-1-[(3-azabicyclo[3.2.2]non-3-yl)carbonylmethyl]-2,3-dihydro-5-(2-fluorophenyl)-9-methyl-3-(imidazol-1-yl)carbonylamino-1H-1,4-benzodiazepin-2-one (1.27 g) as a crystalline powder.

mp: 107.3–118.2° C.

IR (Nujol, cm$^{-1}$): 1680, 1645

$^1$H-NMR (DMSO-d$_6$, δ): 1.3–2.2 (10H, m), 2.45 (3H, s), 2.9–3.4 (2H, m), 3.7–4.0 (2H, m), 4.12 (1H, d, J=16.0 Hz), 5.18 (1H, d, J=16.0 Hz), 5.48 (1H, d, J=7.4 Hz), 6.9–7.1 (2H, br, m), 7.2–7.4 (2H, m), 7.5–7.7 (2H, m), 7.7–7.8 (1H, m), 7.91 (1H, br, s), 8.43 (1H, br, s), 9.84 (1H, d, J=7.4 Hz)

Mass (APCI): 475 (M$^+$+1)

Preparation 23-1

(3RS)-3-Benzyloxycarbonylamino-5-cyclohexyl-1-ethoxycarbonyl-methyl-9-methyl-2,3-dihydro-1H-1,4-benzodiazepin-2-one was prepared in a similar manner to that of Preparation 59-3.

IR (Nujol, cm$^{-1}$):1750, 1720, 1670

$^1$H-NMR (CDCl$_3$, δ): 1.1–2.2 (10H, m), 1.21 (3H, t, J=7.1 Hz), 2.33 (3H, s), 2.7–2.9 (1H, m), 3.82 (1H, d, J=16.7 Hz), 4.12 (2H, q, J=7.1 Hz), 4.68 (1H, d, J=16.7 Hz), 5.0–5.2 (2H, br, m), 5.22 (1H, d, J=8.6 Hz), 6.47 (1H, d, J=8.6 Hz), 7.1–7.5 (8H, m)

Mass (APCI): 492 (M$^+$+1)

Preparation 23-2

(3RS)-3-Benzyloxycarbonylamino-5-cyclohexyl-2,3-dihydro-1-carboxymethyl-9-methyl-1H-1,4-benzodiazepin-2-one was prepared in a similar manner to that of Example 48-2.

IR (Nujol, cm$^{-1}$): 1720, 1680

$^1$H-NMR (CDCl$_3$, δ): 1.1–2.2 (10H, m), 2.33 (3H, s), 2.81 (1H, m), 3.84 (1H, d, J=17.1 Hz), 4.72 (1H, d, J=17.1 Hz), 4.9–5.2 (2H, br, m), 5.21 (1H, d, J=8.6 Hz), 6.52 (1H, d, J=8.7 Hz), 7.2–7.5 (8H, m)

Mass (APCI): 464 (M$^+$+1)

Preparation 23-3

(3RS)-1-[(3-Azabicyclo[3.2.2]non-3-yl)carbonylmethyl]-3-benzyloxycarbonylamino-5-cyclohexyl-2,3-dihydro-9-methyl-1H-1,4 -benzodiazepin-2-one was prepared in a similar manner to that of Preparation 59-5.

IR (Nujol, cm$^{-1}$): 1720, 1660

$^1$H-NMR (CDCl$_3$, δ): 1.1–2.2 (20H, m), 2.35 (3H, s), 2.7–3.0 (1H, m), 3.3–3.9 (4H, m), 3.88 (1H, d, J=15.5 Hz), 4.96 (1H, d, J=15.5 Hz), 4.9–5.2 '(2H, m), 5.23 (1H, d, J=8.6 Hz), 6.50 (1H, d, J=8.7 Hz), 7.2–7.6 (8H, m)

Mass (APCI): 571 (M$^+$+1)

Preparation 23-4

(3RS)-3-Amino-1-[(3-azabicyclo[3.2.2]non-3-yl)carbonylmethyl]-5-cyclohexyl-9-methyl-2,3-dihydro-1H-1,4-benzodiazepin-2-one was prepared in a similar manner to that of Preparation 49-2.

IR (Nujol, cm$^{-1}$): 1660

$^1$H-NMR (CDCl$_3$, δ): 1.1–2.2 (10H, m), 2.41 (3H, s), 2.7–3.0 (1H, br, s), 3.3–3.8 (4H, m), 3.91 (1H, d, J=15.8 Hz), 5.09 (1H, d, J=5.2 Hz), 5.14 (1H, d, J=15.8 Hz), 7.2–7.5 (3H, m)

Mass (APCI): 437 (M$^+$+1)

Preparation 24-1

(3RS)-3-Benzyloxycarbonylamino-5-cyclohexyl-9-methyl-1-(2-methylphenacyl)-2,3-dihydro-1H-1,4-benzodiazepin-2-one was prepared in a similar manner to that of Preparation 59-3.

IR (Nujol, cm$^{-1}$): 1720, 1660

$^1$H-NMR(CDCl$_3$, δ): 1.1–2.2 (10H, m), 2.35 (3H, s), 2.38 (3H, s), 2.8–3.0 (1H, m), 4.22 (1H, d, J=17.0 Hz), 5.0–5.2 (2H, br, m), 5.28 (1H, d, J=8.7 Hz), 5.40 (1H, d, J=17.0 Hz), 6.51 (1H, d, J=8.6 Hz), 7.2–7.6 (11H, m), 7.6–7.7 (1H, m)

Mass (APCI): 538 (M$^+$+1)

Preparation 24-2

(3RS)-3-Amino-5-cyclohexyl-2,3-dihydro-9-methyl-1-(2-methylphenacyl)-1H-1,4-benzodiazepin-2-one was prepared in a similar manner to that of Preparation 49-2.

IR (Nujol, cm$^{-1}$): 1680

$^1$H-NMR (CDCl$_3$, δ): 1.2–2.3 (10H, m), 2.38 (3H, s), 2.39 (3H, s), 2.85 (1H, m), 4.22 (1H, d, J=17.1 Hz), 4.66 (1H, br, s), 5.45 (1H, d, J=17.1 Hz), 7.2–7.5 (6H, m), 7.5–7.7 (1H, m)

Mass (APCI): 404 (M$^+$+1)

Preparation 25-1

To a solution of 2-chloroacetyl-6-methylaniline (1.84 g) in methanol (50ml) was added a 15% aqueous solution of sodium methanthiolate (14.01 g, 3 eq. mol) under stirring and cooling in an ice-bath. The mixture was stirred at ambient temperature for 2.5 hours. From the reaction mixture methanol was removed in vacuo and dissolved in ethyl acetate. The solution was washed with water and brine successively and dried over magnesium sulfate. Removal of the solvent in vacuo gave an oil (2.26 g), which was subjected to column chromatography on silica gel eluting with a mixture of n-hexane and chloroform (10:1). The fractions containing the desired product were combined and evaporated to give 2-methylthioacetyl-6-methylaniline (1.75 g, 89.7%) as an oil.

IR (Film, cm$^{-1}$): 3470, 3340, 1635, 1610, 1583, 1555, 1459, 1430, 1380, 1310, 1281, 1250, 1218, 1127, 1030, 980, 740

$^1$H-NMR (CDCl$_3$, δ): 2.18 (6H, s), 3.80 (2H, s), 6.35 (1H, br), 6.59 (1H, t, J=7.2 Hz), 7.21 (1H, d, J=7.2 Hz), 7.62 (1H, d, J=7.2 Hz)

APCI-MS (m/z): 196 (M$^+$+1)

Preparation 25-2

(3RS)-3-Benzyloxycarbonylamino-5-methylthiomethyl-9-methyl-2,3-dihydro-1H-1,4-benzodiazepin-2-one was prepared in a similar manner to that of Preparation 45-2.

mp: 152.6–153.8° C.

IR (Nujol, cm$^{-1}$): 3250 (sh), 3200, 1720, 1695, 1680 (sh), 1460, 1375, 1059, 762, 700

$^1$H-NMR (CDCl$_3$, δ): 2.01 (3H, s), 2.37 (3H, s), 3.72 (2H, dd, J=13.7 Hz, J=44.6 Hz), 5.11 (2H, dd, J=12.3 Hz, J=14.3 Hz), 5.20 (1H, d, J=8.2 Hz), 6.54 (1H, d, J=8.2 Hz), 7.16–7.59 (8H, m), 7.98 (1H, s)

APCI-MS (m/z): 384 (M$^+$+1)

Preparation 25-3

(3RS)-3-Benzyloxycarbonylamino-2,3-dihydro 1-ethoxycarbonyl-methyl-9-methyl-5-methylthiomethyl-1H-1,4-benzodiazepin-2-one was prepared in a similar manner to that of Preparation 59-3.

$^1$H-NMR(CDCl$_3$, δ): 1.1–1.3 (3H, m), 2.18 (3H, s), 2.35 (3H, s), 3.6–4.0 (2H, m), 4.08 (2H, q, J=7.1 Hz), 4.71 (1H, d, J=16.9 Hz), 5.0–5.2 (2H, br, m), 5.30 (1H, d, J=8.6 Hz), 6.55 (1H, d, J=8.5 Hz), 7.2–7.5 (7H, m), 7.74 (1H, d, J=7.5 Hz)

Mass (APCI): 470 (M$^+$+1)

Preparation 25-4

(3RS)-3-Benzyloxycarbonylamino-2,3-dihydro-1-carboxymethyl-9-methyl-5-methylthiomethyl-1H-1,4-benzodiazepin-2-one was prepared in a similar manner to that of Preparation 59-4.

$^1$H-NMR (CDCl$_3$, δ): 2.0–2.2 (3H, m), 2.2–2.4 (3H, m), 3.6–4.0 (2H, m), 4.6–5.0 (1H, br), 5.6–5.2 (3H, m), 5.28 (1H, d, J=8.4 Hz), 7.2–7.6 (7H, m), 7.75 (1H, d, J=6.7 Hz)

Mass (APCI): 442 (M$^+$+1)

Preparation 25-5

(3RS)-1-[(3-Azabicyclo[3.2.2]non-3-yl)carbonylmethyl]-3-benzyloxycarbonylamino-2,3-dihydro-9-methyl-5-methylthiomethyl-1H-1,4-benzodiazepin-2-one was prepared in a similar manner to that of Preparation 59-5.

IR (Nujol, cm$^{-1}$): 1725, 1675, 1640

$^1$H-NMR (CDCl$_3$, δ): 1.5–1.9 (8H, br), 1.9–2.1 (2H, br), 2.30 (3H, s), 2.36 (3H, s), 3.2–3.4 (2H, m), 3.5–3.7 (1H, m), 3.7–3.9 (4H, m), 5.02 (1H, d, J=14.7 Hz), 5.09 (2H, m), 5.32 (1H, d, J=8.5 Hz), 6.54 (1H, d, J=8.5 Hz), 7.2–7.5 (7H, m), 7.76 (1H, d, J=6.5 Hz)

Mass (APCI): 549 (M$^+$+1)

Preparation 26-1

(3RS)-1-[(3-Azabicyclo[3.2.2]non-3-yl)carbonylmethyl]-3 (-[[(S)-N-(tert-butoxycarbonyl)phenylalanyl] amino]-5-(2-fluolophenyl)-9-methyl-2,3-dihydro-1H-1,4-benzodiazepin-2-one was prepared in a similar manner to that of Preparation 59-5.

$^1$H-NMR (CDCl$_3$, δ): 1.38 (18H, s), 1.4–2.2 (20H, m), 2.44 (6H, s), 3.1–3.6 (8H, m), 3.6–4.1 (4H, m), 4.56 (2H, m), 4.9–5.2 (4H, m), 5.62 (1H, d, J=8.2 Hz), 5.64 (1H, d, J=8.1 Hz), 7.0–7.5 (16H, m), 7.5–7.9 (4H, m)

Mass(FAB): 696(M$^+$+1)

Preparation 26-2

A mixture of (3RS)-1-[(3-azabicyclo[3.2.2]non-3-yl) -carbonylmethyl]-3-[[(S)-N-(tert-butoxycarbonyl)phenylalanyl]amino]-5-(2-fluolophenyl)-9-methyl-2,3-dihydro-1H-1,4-benzodiazepin-2-one (900 mg) and 4N-hydrochloric acid in ethyl acetate (6 ml) was stirred at ambient temperature for 1.5 hours. Ethyl acetate and saturated aqueous sodium bicarbonate were added to the reaction mixture at 0° C. The separated organic layer was washed with brine and dried over sodium sulfate. The solvent was evaporated in vacuo to afford a crude white amorphous powder (672 mg) composing two diastereoisomers, which were separated by high-pressure liquid chromatography.

Each fraction containing the respective diastereoisomers was evaporated in vacuo and dissolved in ethyl acetate. Each solution was washed with aqueous sodium hydrogen carbonate respectively. The respective separated organic layer was dried over sodium sulfate and evaporated in vacuo to afford each diastereoisomer of (3R)-and (3S)-1-[(3-azabicyclo[3.2.2]non-3-yl)carbonylmethyl]-3-[(S)-phenylalanylamino]-5-(2-fluorophenyl)-9-methyl-2,3-dihydro-1H-1,4-benzodiazepin-2-one respectively. (S)-isomer: 257 mg, 33.4% yield and (R)-isomer: 251 mg, 32.7% yield.

(S)-isomer

Mass (APCI): 596 (M$^+$+1)

$^1$H-NMR (CDCl$_3$, δ): 1.3–2.2 (10H, m), 2.45 (3H, s), 2.78 (1H, dd, J=9.1 Hz and 13.7 Hz), 3.2–3.6 (4H, m), 3.6–3.9 (2H, m), 4.01 (1H, d, J=15.5 Hz), 5.10 (1H, d, J=15.5 Hz), 5.68 (1H, d, J=8.6 Hz), 7.0–7.6 (1H, m), 7.7-7.9 (1H, m), 8.92 (1H, d, J=8.6 Hz)

(R)-isomer $^1$H-NMR (CDCl$_3$, δ): 1.4–2.2 (10H, m), 2.46 (3H, s), 2.66 (1H, dd, J=10.4 Hz and 13.7 Hz), 3.3–3.6 (4H, m), 3.6–3.9 (2H, m), 4.03 (1H, d, J=15.5 Hz), 5.11 (1H, d, J=15.5 Hz), 5.67 (1H, d, J=8.5 Hz), 7.0–7.6 (11H, m), 7.7–7.9 (1H, m), 8.91 (1H, d, J=8.4 Hz)

Mass (APCI): 596 (M$^+$+1)

Preparation 26-3

A mixture of (3S)-1-[(3-azabicyclo[3.2.2]non-3 -yl)carbonylmethyl]-3-[(S)-phenylalanylamino]-5-5-(2-fluolophenyl)-9-methyl-2,3-dihydro-1H-1,4-benzodiazepin-2-one (235 mg) and triethylamine (42 mg) in tetrahydrofuran (2.0 ml) was stirred at room temperature. Phenylisothioisocyanate (109 mg) was added dropwise to the reaction mixture, stirred for 30 minutes. The mixture was evaporated in vacuo to dryness. A mixture of the residue and trifluoroacetic acid (1.0 ml) was stirred at 50° C. for 45 minutes. The mixture was evaporated in vacuo to afford an oily residue. The oily residue was separated by column chromatography on silica gel to afford either of (3R) or (3S)-3-amino-1-[(3-azabicyclo[3.2.2]non-3-yl)carbonylmethyl]-5-(2-fluorophenyl)-9-methyl-2,3-dihydro-1H-1,4-benzodiazepin-2-one trifluoroacetate (165 mg, 74.4% yield).

$^1$H-NMR (DMSO-d$_6$, δ): 1.3–2.2 (10H, m), 2.44 (3H, s), 2.9–3.1 (1H, m), 3.1–3.4 (1H, m), 3.6–4.0 (2H, m), 4.18 (2H, d, J=16.2 Hz), 5.17 (1H, d, J=16.2 Hz), 5.21 (1H, br, s), 7.0–7.1 (1H, m), 7.2–7.5 (3H, m), 7.5–7.8 (3H, m), 8.98 (2H, m)

Mass (APCI): 449 (M$^+$+1)

Preparation 27

(3R)-3-amino-1-[(3-azabicyclo[3.2.2]non-3-yl)carbonylmethyl]-5-(2-fluorophenyl)-9-methyl-2,3-dihydro- 1H-1,4-benzodiazepin-2-one trifluoroacetate was prepared in a similar manner to that of Preparation 26-3.

$^1$H-NMR (DMSO-d$_6$, δ): 1.3–2.2 (10H, m), 2.44 (3H, s), 2.9–3.1 (1H, m), 3.1–3.4 (1H, m), 3.6–4.0 (4H, m), 4.18 (1H, d, J=16.3 Hz), 5.17 (1H, d, J=16.3 Hz), 5.21 (1H, br, s), 7.0–7.1 (1H, m), 7.2–7.5 (3H, m), 7.5–7.8 (3H, m), 8.98 (2H, m)

Mass (APCI): 449 (M$^+$+1)

Preparation 28-1

(3RS)-2,3-Dihydro-3-tert-butoxycarbonylamino-5-(2-fluorophenyl)-9-methyl-1-(pyridin-2-yl)methyl-1H-1,4-benzodiazepin-2-one was prepared in a similar manner to that of Preparation 59-3.

IR (Nujol, cm$^{-1}$): 1720, 1680

$^1$H-NMR (CDCl$_3$, δ): 1.47 (9H, s), 2.52 (3H, s), 4.53 (1H, d, J=15.1 Hz), 5.37 (1H, d, J=8.7 Hz), 5.71 (1H, d, J=15.1 Hz), 6.45 (1H, d, J=8.6 Hz), 6.9–7.5 (9H, m), 7.5–7.7 (1H, m), 8.2–8.3 (1H, m)

Mass (APCI): 475 (M$^+$+1)

Preparation 28-2

(3RS)-3-Amino-2,3-dihydro-5-(2-fluorophenyl)-9-methyl-1-(pyridin-2-yl)methyl-1H-1,4-benzodiazepin-2-one was prepared in a similar manner to that of Preparation 30-2.

IR (Nujol, cm$^{-1}$): 1670

$^1$H-NMR (CDCl$_3$, δ): 2.52 (3H, s), 4.50 (1H, d, J=15.0 Hz), 4.60 (1H, s), 5.73 (1H, d, J=15.0 Hz), 7.0–7.7 (10H, m), 8.2–8.4 (1H, m)

Mass (APCI): 375 (M$^+$+1)

Preparation 29-1

2-Chloro-6-(2-fluorobenzoyl)aniline was prepared in a similar manner to that of Preparation 50-1.

mp 86–87.5° C.

IR (Nujol, cm$^{-1}$): 3400, 3290, 1620, 1600

$^1$H-NMR (CDCl$_3$, δ): 6.54 (1H, t, J=7.8 Hz), 6.8–7.0 (2H, br), 7.0–7.4 (3H, br. m), 7.4–7.6 (3H, br, m)

Mass (APCI): 250 (M$^+$+1)

Preparation 29-2

To a solution of 2-amino-3-chloro-2'-fluorobenzophenone (4.80 g) and pyridine (3.04 g) in methylene chloride (100 ml) was added dropwise bromoacetyl bromide (3.42 ml) under stirring and cooling in an ice-bath. After the addition was completed, the mixture was stirred at ambient temperature for 0.5 hour and refluxed for 0.5 hour. The mixture was allowed to stand to cool to ambient temperature and evaporated in vacuo to give a residue, which was dissolved in ethyl acetate and washed with water three times and brine successively. After drying over magnesium sulfate and treating with active carbon, the solvent was removed in vacuo to give a crystalline mass. Pulverization in diisopropyl ether and collection by filtration afforded 2-(bromoacetylamino)-3-chloro-2'-fluorobenzophenone (5.86 g, 82.4% yield) as a white crystalline powder.

IR (Nujol, cm$^{-1}$): 3270, 1679 (sh), 1670, 1608, 1594, 1512, 1375, 1304, 1138, 1100, 975, 945, 826, 775, 752, 694

$^1$H-NMR (CDCl$_3$, δ): 3.83 (2H, s), 7.08–7.81 (7H, m), 8.84 (1H, s)

APCI-MS (m/z): 371 (M$^+$+1)

Preparation 29-3

Sodium hydroxide (pellet, 2.82 g) was dissolved in a mixture of methanol (15 ml) and water (25 ml) under stirring. To the mixture was added hydroxylamine hydrochloride (5.50 g). To the clear solution prepared above was portionwise added a suspension of 2-bromoacetylamino-3-chloro-2'-fluorobenzophenone (5.80 g) in methanol (30 ml) under stirring at 30–35° C. After the addition was completed, the mixture was refluxed under stirring for 3 hours. Methanol was removed in vacuo and the residual mixture was extracted with ethyl acetate. The extract was washed with water three times and dried over magnesium sulfate. The solvent was removed in vacuo to afford an oil (5.0 g), which was pulverized in a mixture of diisopropyl ether and ethyl acetate. The resultant crystalline mass was collected by filtration and dried to give 9-chloro-5-(2-fluorophenyl)-2,3-dihydro-2-oxo-1H-1,4-benzodiazepin-4-oxide (1.74 g, 36.5% yield) as a white crystalline powder.

IR (Nujol, cm$^{-1}$): 3350, 1700, 1610, 1490 (sh), 1478, 1350, 1298, 1265, 1230, 1200, 1154, 1100, 992, 860, 819, 792, 750, 730

$^1$H-NMR (DMSO-d$_6$, δ): 4.66 (2H, br, s), 6.9–7.7 (7H, m), 10.73 (1H, s)

APCI-MS (m/z):305 (M$^+$+1), 307 (M$^+$+3)

Preparation 29-4

A suspension of 9-chloro-5-(2-fluorophenyl)-2,3-dihydro-2-oxo-1H-1,4-benzodiazepin-4-oxide (1.475 g) in acetic anhydride (12 ml) was refluxed for 0.5 hour. The resultant clear solution was cooled in an ice-bath to afford precipitate. To the cooled suspension was added diisopropyl ether (20 ml) and the mixture was cooled further. The resultant precipitate was collected by filtration and washed with diisopropyl ether to give (3RS)-3-acetoxy-5-(2-fluorophenyl)-9-chloro-2,3-dihydro-1H-1,4-benzodiazepin-2-one (0.84 g, 50.0% yield) as a colorless crystalline powder.

IR (Nujol, cm$^{-1}$): 3200, 3125, 1736, 1688, 1610, 1593, 1484, 1371, 1322, 1212, 1091, 1060, 926, 794, 770, 748, 705

$^1$H-NMR (DMSO-d$_6$, δ): 2.21 (3H, s), 5.79 (1H, s), 7.18–7.83 (7H, m), 10.72 (1H, s)

APCI-MS (m/z): 347 (M$^+$+1), 349 (M$^+$+3)

Preparation 29-5

A mixture of (3RS)-3-acetoxy-5-(2-fluorophenyl)-9-chloro-2,3-dihydro-1H-1,4-benzodiazepin-2-one (3.60 g), sodium iodide (15.59 g) and potassium phthalimide (2.89 g) in dimethylformamide (25 ml) was stirred at 100° C. for 1 hour. The reaction mixture was poured into ice-water and the resultant precipitate was collected by filtration. After washing with water several times and dried over phosphorus pentoxide under reduced pressure, the crude powder was subjected to column chromatography on silica gel eluting with a mixture of chloroform and methanol (100:1). The fractions containing the desired product were combined and evaporated in vacuo to give (3RS)-3-phthalimido-5-(2-fluorophenyl)-9-chloro-2,3-dihydro-1H-1,4-benzodiazepin-2-one (0.82 g, 18.9% yield) as a crystalline powder.

IR (Nujol, cm$^{-1}$): 3350, 1780, 1720, 1710, 1380, 1125, 886, 746, 712

$^1$H-NMR (DMSO-d$_6$, δ): 5.77 (1H, s), 7.20–8.02 (11H, m), 100.70 (1H, s)

APCI-MS (m/z): 434 (M$^+$+1), 436 (M$^+$+3)

Preparation 29-6

To a suspension of (3RS)-3-phthalimido-5-(2-fluorophenyl)-9-chloro-2,3-dihydro-1H-1,4-benzodiazepin-2-one (0.8 g) in a mixed solvent of tetrahydrofuran and methanol (1:1, 8 ml) was added hydrazine hydrate (0.11 ml) under stirring at ambient temperature. The mixture was stirred at ambient temperature for 0.5 hour and refluxed for 0.5 hours. After allowing to cool to ambient temperature, the resultant precipitate was filtered off and washed with cold methanol. The filtrate and the washings were combined and evaporated in vacuo to afford a residue, which was subjected to column chromatography on silica gel eluting with a mixture of chloroform and methanol (50:1). The fractions containing the desired product were combined and evaporated in vacuo to give a crystalline mass, which was pulverized in diisopropyl ether and collected by filtration to give (3RS)-3-amino-5-(2-fluorophenyl)-9-chloro-2,3-dihydro-1H-1,4-benzodiazepin-2-one (0.54 g, 96.6% yield).

IR (Nujol, cm$^{-1}$): 3350, 3300, 1686, 1608, 1484, 1374, 1320, 1215, 1130, 1018, 968, 830, 746, 715

$^1$H-NMR (CDCl$_3$, δ): 2.27 (2H, br, s), 4.50(1H, s), 7.03–7.68 (7H, m), 8.04 (1H, br, s)

APCI-MS (m/z): 304 (M$^+$+1), 306 (M$^+$+3)

Preparation 29-7

To a suspension of (3RS)-3-amino-5-(2-fluorophenyl)-9-chloro-2,3-dihydro-1H-1,4-benzodiazepin-2-one (538.8 mg), triethylamine (269.2 mg) and a catalytic amount of hydroxylamine hydrochloride in methylene chloride was added dropwise a solution of di-t-butyl dicarbonate (580.5 g) in methylene chloride (1 ml) at ambient temperature under stirring. After the mixture was stirred for 3.5 hours under the same conditions, triethylamine (89.7 mg) and di-t-butyl dicarbonate (193.0 mg) was added. The mixture was stirred overnight at ambient temperature. Methylene chloride was removed in vacuo to afford a residue, which was dissolved in ethyl acetate and washed with water twice. After drying over magnesium sulfate, the solvent was removed in vacuo to give an oil (1.10 g), which was subjected to column chromatography on silica gel eluting with chloroform. Fractions containing the desired product were combined and evaporated in vacuo to give (3RS)-9-chloro-5-(2-fluorophenyl)-3-t-butoxycarbonylamino-2,3-dihydro-1H-1,4-benzodiazepin-2-one (566.1 mg, 79.2% yield) as a white crystalline powder.

mp: 187.1–188.6° C.

IR (Nujol, cm$^{-1}$): 3210, 3150 (sh), 1700 (sh), 1689, 1604, 532, 1365, 1327, 1270, 1254, 1170, 1059, 1020, 957, 945, 880, 834, 763, 746, 680

$^1$H-NMR (DMSO-d$_6$, δ): 1.32 (2H, br, s), 1.41(9H, s), 5.03(1H, d, J=8.6 Hz), 7.17–7.82 (7H, m), 7.91 (1H, d, J=8.6 Hz), 10.56 (1H, s)

APCI-MS (m/z): 404 (M$^+$+1), 406 (M$^+$+3)

Preparation 29-8

(3RS)-9-Chloro-2,3-dihydro-3-tert-butoxycarbonylamino-1-ethoxycarbonylmethyl-5-(2-fluorophenyl)-1H-1,4-benzodiazepin-2-one was prepared in a similar manner to that of Preparation 59-3.

IR (Nujol, cm$^{-1}$): 1680

$^1$H-NMR (CDCl$_3$, δ): 1.00 (3H, t, J=7.1 Hz), 1.46 (9H, s), 3.8–4.2 (2H, m), 4.25 (1H, d, J=17.2 Hz), 4.95 (1H, d, J=17.2 Hz), 5.39 (1H, d, J=8.8 Hz), 6.42 (1H, d, J=8.7 Hz), 7.0–7.2 (1H, br, s), 7.2–7.4 (3H, m), 7.4–7.6 (1H, br, s), 7.6–7.7 (1H, m), 7.7–7.9 (1H, m)

Mass (APCI): 490 (M$^+$+1)

Preparation 29-9

(3RS)-9-Chloro-2,3-dihydro-3-tert-butoxycarbonylamino-5 -(2-fluorophenyl)-1-carboxymethyl]-1H-1,4-benzodiazepin-2-one was prepared in a similar manner to that of Example 48-2.

IR (Nujol, cm$^{-1}$): 1745, 1675

$^1$H-NMR (CDCl$_3$, δ): 1.48 (9H, s), 4.31 (1H, d, J=17.5 Hz), 5.01 (1H, d, J=17.5 Hz), 5.39 (1H, d, J=8.8 Hz), 6.41 (1H, d, J=8.9 Hz), 6.9–7.9 (7H, m)

Mass (APCI): 462 (M$^+$+1)

Preparation 29-10

(3RS)-1-[(3-Azabicyclo[3.2.2]non-3-yl)carbonylmethyl]-9-chloro-2,3-dihydro-5-(2-fluorophenyl)-3-tert-butoxycarbonylamino-1H-1,4-benzodiazepin-2-one was prepared in a similar manner to that of Preparation 59-5.

IR (Nujol, cm$^{-1}$): 1660

$^1$H-NMR(CDCl$_3$, δ): 1.46 (9H, s), 1.4–2.2 (10H, br), 3.2–3.5(2H, m), 3.5–4.0 (2H, m), 4.36 (1H, d, J=16.1 Hz), 5.24 (1H, d, J=16.1 Hz), 5.42 (1H, d, J=9.0 Hz), 6.39 (1H, d, J=8.9 Hz), 7.0–7.3 (3H, m), 7.3–7.5 (1H, m), 7.5–7.7 (1H, m), 7.7–7.9 (1H, m), 8.01 (1H, br, s)

Mass (APCI): 596 (M$^+$+1)

Preparation 29-11

A mixture of (3RS)-1-[(3-azabicyclo[3.2.2]non-3-yl)carbonylmethyl]-9-chloro-2,3-dihydro-5-(2-fluorophenyl)-3-tert-butoxycarbonylamino-1H-1,4-benzodiazepin-2-one (660 mg) and 4N aqueous hydrochloric acid in ethyl acetate (3 ml) was stirred at 0° C. for 5.5 hours. A saturated aqueous solution of sodium bicarbonate and ethyl acetate were added to the reaction mixture. The separated organic layer was washed with water and brine, and then dried over sodium sulfate. The solvent was evaporated in vacuo to afford (3RS)-3-amino-1-[(3-azabicyclo[3.2.2]non-3-yl)carbonylmethyl]-9-chloro-2,3-dihydro-5-(2-fluorophenyl)-1H-1,4-benzodiazepin-2-one (549.0 mg) as a crystalline powder.

IR (Nujol, cm$^{-1}$): 1680, 1650

$^1$H-NMR (CDCl$_3$, δ): 1.4–2.2 (10H, m), 3.2–3.5 (2H, m), 3.5–4.0 (2H, m), 4.36 (1H, d, J=16.1 Hz), 4.61 (1H, br, s), 5.29 (1H, d, J=16.1 Hz), 7.0–7.4 (4H, m), 7.4–7.5 (1H, m), 7.5–7.7 (1H, m), 7.7–7.9 (1H, m)

Mass (APCI): 469 (M$^+$+1)

Preparation 30-1

(3RS)-2,3-Dihydro-1-tert-butylcarbonylmethyl-3-tert-butoxy-carbonylamino-5-(2-fluorophenyl)-9-methyl-1H-1,4-benzodiazepin-2-one was prepared in a similar manner to that of Preparation 59-3.

IR (Nujol, cm$^{-1}$): 1720, 1700, 1635

$^1$H-NMR (CDCl$_3$, δ): 1.13 (9H, s), 1.45 (9H, s), 2.39 (3H, s), 4.03 (1H, d, J=17.1 Hz), 5.09 (1H, d, J=17.1 Hz), 5.40 (1H, d, J=9.0 Hz), 6.36 (1H, d, J=9.0 Hz), 7.0–7.6 (6H, m), 7.7–7.9 (1H, m)

Mass (APCI): 482 (M$^+$+1)

Preparation 30-2

A mixture of (3RS)-2,3-dihydro-5-(2-fluorophenyl)-1-tert-butylcarbonylmethyl-3-tert-butoxycarbonylamino-9-methyl-1H-1,4-benzodiazepin-2-one (130 mg) and 4N HCl in ethyl acetate (1 ml) was stirred at 0° C. for 5 hours. Ethyl acetate and a saturated aqueous solution of sodium bicarbonate were added to the reaction mixture. The separated organic layer was washed with water and brine, and then dried over sodium sulfate. The solvent was evaporated in vacuo to afford (3RS)-3-amino-2,3-dihydro-5-(2-fluorophenyl)-1-tert-butylcarbonylmethyl-9-methyl-1H-1,4-benzodiazepin-2-one (100 mg, 97.1%) as a crystalline powder.

IR (Nujol, cm$^{-1}$): 1720, 1670

$^1$H-NMR (CDCl$_3$, δ): 1.14 (9H, s), 2.39 (3H, s), 3.99 (1H, d, J=17.1 Hz), 4.65 (1H, br, s), 5.16 (1H, d, J=17.1 Hz), 7.0–7.6 (6H, m), 7.7–7.9 (1H, m)

Mass (APCI): 382 (M$^+$+1)

Preparation 31-1

(3RS)-3-Benzyloxycarbonylamino-2,3-dihydro-1-ethoxycarbonylmethyl-5,9-dimethyl-1H-1,4-benzodiazepin-2-one was prepared in a similar manner to that of Preparation 59-3.

$^1$H-NMR (CDCl$_3$, δ): 1.19 (3H, t, J=7.1 Hz), 2.33 (3H, s), 2.56 (3H, s), 3.78 (1H, d, J=16.9 Hz), 4.08 (2H, q, J=7.1 Hz), 4.92 (1H, d, J=16.9 Hz), 5.0–5.2 (2H, m), 5.2–5.3 (1H, m), 6.50 (1H, d, J=8.6 Hz), 7.2–7.5 (8H, m)

Mass (APCI): 424 (M$^+$+1)

Preparation 31-2

(3RS)-3-Benzyloxycarbonylamino-2,3-dihydro-1-carboxymethyl-5,9-dimethyl-1H-1,4-benzodiazepin-2-one was prepared in a similar manner to that of Preparation 59-4.

IR (Nujol, cm$^{-1}$): 1720, 1690, 1618

$^1$H-NMR (CDCl$_3$, δ): 2.29 (3H, s), 2.46 (3H, s), 3.72 (1H, d, J=17.1 Hz), 4.91 (1H, d, J=17.1 Hz), 5.0–5.1 (2H, m), 5.25 (1H, d, J=7.6 Hz), 6.73 (1H, d, J=8.7 Hz), 7.2–7.5 (8H, m), 7.90 (1H, m)

Mass (APCI): 396 (M$^+$+1)

Preparation 31-3

(3RS)-3-Benzyloxycarbonylamino-1-[(3-azabicyclo[3.2.2]non-3-yl)carbonylmethyl]-2,3-dihydro-5,9-dimethyl-1H-1,4-benzodiazepin-2-one was prepared in a similar manner to that of Preparation 59-5.

IR (Nujol, cm$^{-1}$): 1720, 1675, 1650

$^1$H-NMR (CDCl$_3$, δ): 1.5–1.9 (8H, m), 1.9–2.1 (2H, m), 2.35 (3H, s), 2.60 (3H, s), 3.2–3.4 (2H, m), 3.60 (1H, dd, J=4.7 Hz and J=13.7 Hz), 3.77 (1H, d, J=15.8 Hz), 3.87 (1H, d, J=5.0 Hz and J=13.7 Hz), 5.0–5.1 (2H, m), 5.19 (1H, d, J=15.8 Hz), 5.2–5.4 (1H, m), 6.52 (1H, d, J=8.7 Hz), 7.2–7.5 (8H, m)

Mass (APCI): 503 (M$^+$+1)

Preparation 31-4

(3RS)-3-Amino-1-[(3-azabicyclo[3.2.2]non-3-yl)carbonylmethyl]-2,3-dihydro-5,9-dimethyl-1H-1,4-benzodiazepin-2-one was prepared in a similar manner to that of Preparation 59-6.

IR (Nujol, cm$^{-1}$): 3350, 3270, 1665, 1620

$^1$H-NMR (CDCl$_3$, δ): 1.4–1.9 (8H, m), 1.9–2.1 (2H, m), 2.35 (3H, s), 2.58 (3H, s), 3.2–3.5 (2H, m), 3.5–3.9 (2H, br, m), 4.42 (1H, s), 5.23 (1H, d, J=15.6 Hz), 7.2–7.5 (3H, m)

Mass (APCI): 369 (M$^+$+1)

Preparation 31-5

(3RS)-1-[(3-Azabicyclo[3.2.2]non-3-yl)carbonylmethyl]-5,9-dimethyl-2,3-dihydro-3-(imidazol-1-yl)carbonylamino-1H-1,4-benzodiazepin-2-one was prepared in a similar manner to that of Preparation 22.

IR (Nujol, cm$^{-1}$): 1720, 1685, 1650

Mass (APCI): 427 (M$^+$+1)

$^1$H-NMR (DMSO-d$_6$, δ): 1.3–2.2 (10H, m), 2.39 (3H, s), 2.49 (3H, s), 2.9–3.4 (2H, m), 3.6–3.9 (2H, m), 3.95 (1H, d, J=16.2 Hz), 5.13 (1H, d, J=16.2 Hz), 5.2–5.3 (1H, m), 7.0–7.1 (1H, m), 7.2–7.7 (3H, m), 7.86 (1H, br, s), 8.40 (1H, br, s), 9.71 (1H, d, J=7.2 Hz)

Preparation 32

To a suspension of N-{(3RS)-1-[(3-azabicyclo[3.2.2]non-3-yl)-carbonylmethyl]-2,3-dihydro-5,9-dimethyl-2-oxo-1H-1,4-benzodiazepin-3-yl}-N'-(3-methylphenyl)urea (140.5 mg) in methylene chloride (5 ml) was added m-chloroperbenzoic acid (m-CPBA, 72.5 mg, 1.5 eq. mol portionwise under stirring at ambient temperature. After stirring for 5.5 hours, an additional m-CPBA (48 mg) was added and the stirring was continued for 3.5 hours further. From the clear reaction mixture, methylene chloride was removed in vacuo and the residue was dissolved in ethyl acetate. The solution was washed with an aqueous solution of sodium bicarbonate, water and brine. The organic layer was dried over magnesium sulfate and evaporated to afford a reddish oil, which was subjected to preparative thin layer chromatography on silica gel (60F254, 0.5 mm, 20×20 cm; Merek) developed with a mixture of chloroform and methanol (10:1) to give N-[(3RS)-1-(3-azabicyclo[3.2.2]non-3-yl)carbonylmethyl-2,3-dihydro-5,9-dimethyl-2-oxo-1H-1,4-benzodiazepin-4-oxido-3-yl]-N'-(3-methylphenyl)urea as a white crystalline powder (69.5 mg, 48.0%).

mp: 244.1–245.6° C. (dec.)

$^1$H-NMR (CDCl$_3$+CD$_3$OD, δ): 1.53–1.73 (8H, m), 1.94 (1H, br, s), 2.05 (1H, br, s), 2.25 (3H, s), 2.41 (3H, s), 2.56 (3H, s), 3.20–3.36 (2H, m), 3.54–3.81 (2H, m), 4.56 (2H, dd, J=15.8 Hz, J=255.0 Hz), 5.97 (1H, s), 6.76–7.45 (9H, m)

APCI-MS (m/z): 518 (M$^+$+1)

Preparation 33-1

2'-Amino-3'-(N,N-dimethylamino)acetophenone was prepared in a similar manner to that of Preparation 50-1.

IR (Nujol, cm$^{-1}$): 3450, 3320, 1640

$^1$H-NMR (CDCl$_3$, δ): 2.60 (3H, s), 2.64 (3H, s), 6.59 (1H, dd, J=7.7 Hz and J=8.1 Hz), 7.13 (1H, dd, J=1.3 Hz and J=7.5 Hz), 7.48 (1H, dd, J=1.3 Hz and J=8.2 Hz), 6.6–7.0 (2H, m)

Mass (APCI): 179 (M$^+$+1)

Preparation 33-2

(3RS)-3-Benzyloxycarbonylamino-5-methyl-9-(N,N-dimethylamino)-2,3-dihydro-1H-1,4-benzodiazepin-2-one was prepared in a similar manner to that of Preparation 45-2.

IR (Nujol, cm$^{-1}$): 1710, 1680

$^1$H-NMR(CDCl$_3$, δ): 2.46 (3H, s), 2.67 (6H, s), 5.0–5.2 (2H, m), 6.56 (1H, d, J=8.1 Hz), 7.1–7.4 (8H, m), 8.26 (1H, br, s)

Mass (APCI): 367 (M$^+$+1)

Preparation 33-3

To a solution of (3RS)-3-benzyloxycarbonylamino-5-methyl-9-(N,N-dimethylamino)-2,3-dihydro-1H-1,4-benzodiazepin-2-one (820 mg,) in N,N-dimethylformamide (5 ml) was added portionwise 60% sodium hydride suspended in oil (94 mg) under nitrogen stream and cooling in an ice-bath. The mixture was stirred under the same conditions for 3 hours. N-Bromoacetyl-3-azabicyclo[3.2.2]nonane (578 g) was added to the reaction mixture at 0° C. The resultant mixture was stirred at room temperature overnight. Ethyl acetate and water were added to the mixture. The separated organic layer was washed with water twice and brine, and then dried over sodium sulfate. The solvent was evaporated in vacuo to afford a pale yellow residue, which was subjected to column chromatography on silica gel eluting with a mixture of toluene and ethyl acetate (2:1). The fractions containing the desired product were combined and evaporated in vacuo to give (3RS)-1-[(3-azabicyclo[3.2.2]non-3-yl)carbonylmethyl]-3-benzyloxycarbonylamino-5-methyl-9-(N,N-dimethylamino)-2,3-dihydro-1H-1,4-benzodiazepin-2-one (510 mg, 42.8% yield) as a crystalline powder.

IR (Nujol, cm$^{-1}$): 1715, 1680, 1650

$^1$H-NMR (CDCl$_3$, δ): 1.3–2.2 (10H, m), 2.58 (3H, s), 2.74 (6H, s), 3.2–3.4 (2H, m), 3.4–3.8 (2H, m), 4.70 (1H, d, J=16.1 Hz), 5.09 (1H, d, J=16.1 Hz), 5.0–5.2 (2H, m), 5.2–5.4 (1H, m), 6.48 (1H, d, J=8.5 Hz), 7.0–7.4 (8H, m)

Mass (APCI): 532 (M$^+$+1)

Preparation 33-4

(3RS)-3-Amino-1-[(3-azabicyclo[3.2.2]non-3-yl)carbonylmethyl]-5-methyl-9-(N,N-dimethylamino)-2,3-dihydro-1 H-1,4-benzodiazepin-2-one was prepared in a similar manner to that of Preparation 59-6.

IR (Nujol, cm$^{-1}$): 1680, 1640

$^1$H-NMR (CDCl$_3$, δ): 1.3–2.2 (10H, m), 2.35 (2H, m), 2.57 (3H, s), 2.74 (6H, s), 3.2–3.8 (4H, m), 4.46 (1H, br, s), 4.69 (1H, d, J=16.1 Hz), 5.13 (1H, d, J=16.1 Hz), 7.0–7.4 (3H, m)

Mass (APCI): 398 (M$^+$+1)

Preparation 34-1

(3RS)-3-Benzyloxycarbonylamino-2,3-dihydro-5-(2-fluorophenyl)-9-methyl-1-tert-butoxycarbonylmethyl-1H-1,4-benzodiazepin-2-one was prepared in a similar manner to that of Preparation 59-3.

IR (Nujol, cm⁻¹): 1720, 1680
¹H-NMR(CDCl₃, δ): 1.28 (9H, s), 2.36 (3H, s), 3.81 (1H, d, J=16.6 Hz), 4.70 (1H, d, J=16.6 Hz), 5.0–5.3 (2H, m), 5.42 (1H, d, J=8.6 Hz), 6.67 (1H, d, J=8.6 Hz), 7.0–7.6 (11H, m), 7.7–7.9 (1H, m)
Mass (APCI): 532 (M⁺+1)

Preparation 34-2

(3RS)-3-Amino-2,3-dihydro-5-(2-fluorophenyl)-9-methyl-1-tert-butoxycarbonylmethyl-1H-1,4-benzodiazepin-2-one was prepared in a similar manner to that of Preparation 59-6.
¹H-NMR(CDCl₃, δ): 1.29 (9H, s), 2.38 (3H, s), 3.79 (1H, d, J=16.6 Hz), 4.58 (1H, s), 4.73 (1H, d, J=16.6 Hz), 7.0–7.6 (6H, m), 7.7–7.9 (1H, m)
Mass (APCI): 398 (M⁺+1)

Preparation 35-1

(3RS)-1-(Adamantan-1-yl)carbonylmethyl-3-benzyloxycarbonyl-amino-2,3-dihydro-5-(2-fluorophenyl)-9-methyl-1H-1,4-benzodiazepin-2-one was prepared in a similar manner to that of Preparation 59-3.
IR (Nujol, cm⁻¹): 1710, 1670
¹H-NMR (DMSO-d₆, δ): 1.5–2.0 (15H, m), 2.40 (3H, s), 4.06 (1H, d, J=17.4 Hz), 5.04 (2H, br, s), 5.16 (1H, d, J=8.5 Hz), 5.21 (1H, d, J=17.5 Hz), 7.03 (1H, d, J=8.7 Hz), 7.0–7.8 (12H, m)
Mass (APCI): 594 (M⁺+1)

Preparation 35-2

(3RS)-1-(Adamantan-1-yl)carbonylmethyl-3-amino-5-(2-fluorophenyl)-2,3-dihydro-9-methyl-1H-1,4-benzodiazepin-2-one was prepared in a similar manner to that of Preparation 59-6.
IR (Nujol, cm⁻¹): 1710, 1670
¹H-NMR(CDCl₃, δ): 1.5–2.3 (15H, m), 2.38 (3H, s), 3.95 (1H, d, J=17.1 Hz), 4.59 (1H, s), 5.14 (1H, d, J=17.1 Hz), 7.0–7.5 (6H, m), 7.7–7.9 (1H, m)
Mass (APCI): 460 (M⁺+1)

Preparation 36-1

(3RS)-3-Benzyloxycarbonylamino-2,3-dihydro-1,5,9-trimethyl-1H-1,4-benzodiazepin-2-one was prepared in a similar manner to that of Preparation 59-3.
IR (Nujol, cm⁻¹): 1710, 1665, 1620
¹H-NMR (CDCl₃, δ): 2.35 (3H, s), 2.43 (3H, s), 3.19 (3H, s), 5.06 (1H, d, J=12.3 Hz), 5.13 (1H, d, J=12.3 Hz), 5.1–5.2 (1H, m), 6.60 (1H, d, J=8.3 Hz), 7.1–7.5 (8H, m)
Mass (APCI): 352 (M⁺+1)

Preparation 36-2

(3RS)-3-Amino-2,3-dihydro-1,5,9-trimethyl-1H-1,4-benzodiazepin-2-one was prepared in a similar manner to that of Preparation 59-6.
IR (Neat, cm⁻¹): 3350, 1685, 1615
¹H-NMR(CDCl₃, δ): 2.36 (3H, s), 2.47 (3H, s), 3.18 (3H, s), 4.31 (1H, d, J=1.3 Hz), 7.1–7.4 (3H, m)
Mass (APCI): 218 (M⁺+1)

Preparation 37-1

(3RS)-3-Benzyloxycarbonylamino-2,3-dihydro-5,9-dimethyl-1-(2-methylphenacyl)-1H-1,4-benzodiazepin-2-one was prepared in a similar manner to that of Preparation 59-3.
IR (Nujol, cm⁻¹): 1715, 1670
¹H-NMR (CDCl₃, δ): 2.29 (3H, s), 2.39 (3H, s), 2.51 (3H, s), 4.20 (1H, d, J=17.0 Hz), 5.0–5.2 (2H, m), 5.28 (1H, dd, J=1.5 Hz and 8.7 Hz), 5.61 (1H, d, J=17.0 Hz), 6.52 (1H, d, J=8.7 Hz), 7.2–7.5 (11H, m), 7.5–7.6 (1H, m)
Mass (APCI): 470 (M⁺+1)

Preparation 37-2

(3RS)-3-Amino-1-(2-methylphenacyl)-2,3-dihydro-5,9-dimethyl-1H-1,4-benzodiazepin-2-one was prepared in a similar manner to that of Preparation 59-6.
IR (Nujol, cm⁻¹): 1670, 1615
¹H-NMR(CDCl₃, δ): 2.28 (3H, s), 2.41 (3H, s), 2.47 (3H, s), 4.18 (1H, d, J=16.9 Hz), 4.4 (1H, m), 5.64 (1H, d, J=16.9 Hz), 7.1–7.6 (7H, m)
Mass (APCI): 336 (M⁺+1)

Preparation 38

(3RS)-1-(Adamantan-1-yl)carbonylmethyl-3-amino-2,3-dihydro-5,9-dimethyl-1H-1,4-benzodiazepin-2-one was prepared in a similar manner to that of Preparation 59-6.
IR (Nujol, cm⁻¹): 1700, 1670
¹H-NMR(CDCl₃, δ): 1.6–2.3 (15H, br), 2.32 (3H, s), 2.61 (3H, s), 3.74 (1H, d, J=17.2 Hz), 4.4 (1H, m), 5.28 (1H, d, J=17.2 Hz), 7.1–7.5 (3H, m)
Mass (APCI): 380 (M⁺+1)

Preparation 39-1

(3RS)-3-Benzyloxycarbonylamino-1-cyclohexylcarbonylmethyl-2,3-dihydro-5,9-dimethyl-1H-1,4-benzodiazepin-2-one was prepared in a similar manner to that of Preparation 59-3.
IR (Neat, cm⁻¹): 1720, 1670
¹H-NMR (CDCl₃, δ): 1.1–2.0 (10H, m), 2.2–2.4 (1H, m), 2.32 (3H, s), 2.61 (3H, s), 3.74 (1H, d, J=17.2 Hz), 5.0–5.2 (3H, m), 5.24 (1H, d, J=7.3 Hz), 6.46 (1H, d, J=8.8 Hz), 7.1–7.5 (8H, m)
Mass (APCI): 462 (M⁺+1)

Preparation 39-2

(3RS)-3-Amino-1-cyclohexylcarbonylmethyl-2,3-dihydro-5,9-dimethyl-1H-1,4-benzodiazepin-2-one was prepared in a similar manner to that of Preparation 59-6.
IR (Neat, cm⁻¹): 1715, 1670
¹H-NMR (CDCl₃, δ): 1.1–2.0 (10H, m), 2.0–2.4 (1H, m), 2.32 (3H, s), 2.60 (3H, s), 3.72 (1H, d, J=17.2 Hz), 4.4 (1H, m), 5.13 (1H, d, J=17.2 Hz), 7.1–7.5 (3H, m)
Mass (APCI): 328 (M⁺+1)

Preparation 40-1

(3RS)-3-Benzyloxycarbonylamino-2,3-dihydro-5-(2-fluorophenyl)-9-methyl-1-methylcarbonylmethyl-1H-1,4-benzodiazepin-2-one was prepared in a similar manner to that of Preparation 59-3.
IR (Nujol, cm⁻¹): 1705, 1660
¹H-NMR (DMSO-d₆, δ): 2.00 (3H, s), 2.38 (3H, s), 4.23 (1H, d, J=17.6 Hz), 4.91 (1H, d, J=17.6 Hz), 5.05 (2H, br, s), 5.18 (1H, d, J=8.5 Hz), 7.04 (1H, d, J=7.6 Hz), 7.1–7.7 (11H, m), 8.42 (1H, d, J=8.5 Hz)
Mass (APCI): 474 (M⁺+1)

Preparation 40-2

(3RS)-3-Amino-5-(2-fluorophenyl)-2,3-dihydro-9-methyl-1-methylcarbonylmethyl-1H-1,4-benzodiazepin-2-one was prepared in a similar manner to that of Preparation 59-6.
IR (Nujol, cm⁻¹): 1720, 1670
¹H-NMR(CDCl₃, δ): 2.07 (3H, s), 2.39 (3H, s), 3.87 (1H, d, J=17.0 Hz), 4.60 (1H, s), 4.96 (1H, d, J=17.0 Hz), 7.0–7.6 (6H, m), 7.7–7.9 (1H, m)
Mass (APCI): 340 (M⁺+1)

Preparation 41

(3RS)-3-Amino-2,3-dihydro-1-tert-butylcarbonylmethyl-5,9-dimethyl-1H-1,4-benzodiazepin-2-one was prepared in a similar manner to that of Preparation 59-6.
IR (Nujol, cm⁻¹): 1710, 1670, 1615
¹H-NMR(CDCl₃, δ): 1.13 (9H, s), 2.32 (3H, s), 2.61 (3H, s), 3.79 (1H, d, J=17.2 Hz), 4.4 (1H, m), 5.29 (1H, d, J=17.2 Hz), 7.1–7.5 (3H, m)
Mass (APCI): 302 (M⁺+1)

Preparation 42-1

(3RS)-3-Benzyloxycarbonylamino-2,3-dihydro-5-(2-fluorophenyl)-9-methyl-1-(3-nitrophenacyl)-1H-1,4- benzodiazepin-2-one was prepared in a similar manner to that of Preparation 59-3.

mp: 86.1–89.0° C.

IR (Nujol, cm$^{-1}$): 1700, 1670

$^1$H-NMR (DMSO-d$_6$, δ): 4.51 (1H, d, J=17.0 Hz), 5.52 (1H, d, J=8.6 Hz), 5.72 (1H, d, J=17.0 Hz), 6.61 (1H, d, J=8.7 Hz), 7.0–7.8 (12H, m), 7.8–8.0 (1H, m), 8.1–8.3 (1H, m), 8.3–8.5 (1H, m), 8.68 (1H, m)

Mass (APCI): 581 (M$^+$+1)

Preparation 42-2

(3RS)-3-Amino-2,3-dihydro-5-(2-fluorophenyl)-9-methyl-1-(3-nitrophenacyl)-1H-1,4-benzodiazepin-2-one hydrobromide was prepared in a similar procedure to that of Preparation 43.

IR (Nujol, cm$^{-1}$): 1678

$^1$H-NMR (DMSO-d$_6$, δ): 2.50 (3H, s), 5.04 (1H, d, J=17.9 Hz), 5.30 (1H, s ), 5.91 (1H, d, J=17.9 Hz), 7.12 (1H, d, J=7.6 Hz), 7.3–7.5 (3H, m), 7.5–8.0 (4H, m), 8.3–8.5 (2H, m), 8.65 (1H, m), 9.05 (2H, m)

Mass (APCI): 447 (free, M$^+$+1)

Preparation 43

A mixture of (3RS)-3-benzyloxycarbonylamino-2,3-dihydro-5-(2-fluorophenyl)-9-methyl-1-(2-nitrophenacyl)-1H-1,4-benzodiazepin-2-one (300 mg)and 30% hydrobromic acid in acetic acid (3 ml) was stirred at room temperature for 4.5 hours. Water and ice were added to the reaction mixture to afford powder, which was collected by filtration, and washed with water to give (3RS)-3-amino-2,3-dihydro-5-(2-fluorophenyl)-9-methyl-1-(2-nitrophenacyl)-1H-1,4-benzodiazepin-2-one hydrobromide (227 mg, 81.8%).

IR (Nujol, cm$^{-1}$): 1670

$^1$H-NMR (DMSO-d$_6$, δ): 2.43 (3H, s), 4.79 (1H, d, J=18.3 Hz), 5.32 (1H, s), 5.56 (1H, d, J=18.3 Hz), 7.12 (1H, d, J=7.6 Hz), 7.2–7.4 (3H, m), 7.5–7.7 (3H, br), 7.7–8.0 (3H, m), 8.12 (1H, d, J=7.8 Hz), 9.04 (2H, m)

Mass (APCI): 447 (free, M$^+$+1)

Preparation 44-1

(3RS)-3-Benzyloxycarbonylamino-2,3-dithydro-1-ethylcarbonylmethyl-5,9-dimethyl-1H-1,4-benzodiazepin-2-one was prepared in a similar manner to that of Preparation 59-3.

IR (Nujol, cm$^{-1}$): 1715, 1670, 1620

$^1$H-NMR (CDCl$_3$, δ): 1.00 (3H, t, J=7.3 Hz), 2.32 (3H, s), 2.3–2.5 (2H, m), 2.60 (3H, s), 3.72 (1H, d, J=17.2 Hz), 5.0–5.2 (3H, m), 5.25 (1H, dd, J=1.4 Hz and J=8.7 Hz), 6.46 (1H, d, J=8.6 Hz), 7.2–7.5 (8H, m)

Mass (APCI): 408 (M$^+$+1)

Preparation 44-2

(3RS)-3-Amino-2,3-dihydro-1-ethylcarbonylmethyl-5,9-dimethyl-1H-1,4-benzodiazepin-2-one was prepared in a similar manner to that of Preparation 59-6.

IR (Neat, cm$^{-1}$): 1720

$^1$H-NMR (CDCl$_3$, δ): 1.00 (3H, t, J=7.3 Hz), 2.32 (3H, s), 2.3–2.6 (2H, br, m), 2.60 (3H, s), 3.70 (1H, d, J=17.1 Hz), 4.40 (1H, m), 5.06 (1H, d, J=17.1 Hz), 7.1–7.5 (3H, m)

Mass (APCI): 274 (M$^+$+1)

Preparation 45-1

2-Isobutyryl-6-methylaniline was prepared in a similar manner to that of Preparation 50-1.

mp: 47–49° C.

IR (Nujol, cm$^{-1}$): 3470, 3320, 1638, 1607, 1580, 1550, 1422, 1380, 1230, 1094, 1011, 984, 745

$^1$H-NMR (CDCl$_3$, δ): 1.21 (6H, d, J=6.8 Hz), 2.16 (3H, s), 3.62 (1H, hept, J=6.8 Hz), 6.4 (1H, br), 6.60 (1H, t, J=7.3 Hz), 7.19 (1H, d, J=7.3 Hz), 7.69 (1H, d, J=7.3 Hz)

APCI-MS (m/z): 178 (M$^+$+1)

Preparation 45-2

To a solution of N-benzyloxycarbonyl-2-(benzotriazol-1-yl)glycine (10.77 g) in dry tetrahydrofuran (80 ml) were added oxalyl chloride (2.88 ml)and one drop of dimethylformamide at 0° C. under stirring and nitrogen stream. The mixture was stirred for 2 hours under the same conditions. To the reaction mixture was added dropwise a mixture of 2-isobutyryl-6-methylaniline (5.32 g) and N-methylmorpholine (6.68 g) in dry tetrahydrofuran (30 ml) for 20 minutes under the same conditions. After the addition was completed, the mixture was stirred at ambient temperature for 0.5 hour. The resultant precipitate was filtered off and the filtrate and washings were combined and evaporated in vacuo. The residue was dissolved in 20% methanolic ammonia (80 ml) and stirred at ambient temperature overnight. The resultant precipitate was collected by filtration and washed with cold methanol to give the first crop of the desired product (3.25 g, 29.6%). The filtrate and the washings were combined and evaporated in vacuo to afford a residue, which was dissolved in ethyl acetate and washed with 1N-NaOH aqueous solution and water. The organic layer was dried over magnesium sulfate and evaporated to give a residual oil, which was dissolved in acetic acid (70 ml) and treated with ammonium acetate (7.0 g) for 4 hours at ambient temperature. After removal of acetic acid in vacuo, the residue was dissolved in ethyl acetate and washed with diluted hydroxide aqueous solution and water successively. The organic layer was dried over magnesium sulfate and evaporated in vacuo to give an orange oil, which was triturated in methanol overnight to afford the second crop of the desired product (1.01 g, 9.2%), (3RS)-3-benzyloxycarbonylamino-5-isopropyl-9-methyl-2,3-dihydro-1H-1,4-benzodiazepin-2-one.

mp: 169.1–172.8° C.

IR (Nujol, cm$^{-1}$): 3300 (sh), 3200, 1710, 1690, 1614, 1514, 1398, 1367, 1055, 990, 798, 750, 687

$^1$H-NMR (CDCl$_3$, δ): 0.91 (3H, d, J=7.0 Hz), 1.27 (3H, d, J=7 Hz), 2.36 (3H, s), 3.13 (1H, hept, J=7.0 Hz), 5.11 (2H, s), 5.15 (1H, d, J=8.4 Hz), 6.46 (1H, d, J=8.4 Hz), 7.1–7.45 (8H, m), 8.59 (1H, s)

APCI-MS (m/z): 366 (M$^+$+1)

Preparation 45-3

(3RS)-3-Benzyloxycarbonylamino-2,3-dihydro-1-ethoxycarbonyl-methyl-5-isopropyl-9-methyl-1H-1,4-benzodiazepin-2-one was prepared in a similar manner to that of Preparation 59-3.

$^1$H-NMR (CDCl$_3$, δ): 1.1–1.4 (3H, m), 2.34 (3H, s), 3.1–3.4 (1H, m), 3.82 (1H, d, J=16.7 Hz), 4.12 (2H, q, J=7.1 Hz), 4.72 (1H, d, J=16.7 Hz), 5.0–5.2 (2H, m), 5.2–5.3 (1H, m), 6.49 (1H, d, J=8.6 Hz), 7.2–7.5 (8H, m)

Mass (APCI): 452 (M$^+$+1)

Preparation 45-4

(3RS)-3-Benzyloxycarbonylamino-2,3-dihydro-1-carboxymethyl-5-isopropyl-9-methyl-1H-1,4-benzodiazepin-2-one was prepared in a similar manner to that of Preparation 59-4.

$^1$H-NMR (CDCl$_3$, δ): 1.0–1.4 (6H, m), 2.32 (3H, br, s), 3.1–3.3 (1H, m), 3.84 (1H, d, J=17.0 Hz), 4.76 (1H, d, J=17.0 Hz), 5.0–5.2 (2H, m), 5.22 (1H, d, J=8.1 Hz), 6.54 (1H, d, J=8.7 Hz), 7.2–7.5 (8H, m)

Mass (APCI): 424 (M$^+$+1)

Preparation 45-5

(3RS)-1-[(3-Azabicyclo[3.2.2]non-3-yl)carbonylmethyl]-3-benzyloxycarbonylamino-2,3-dihydro-5-isopropyl-9-methyl-1H-1,4-benzodiazepin-2-one was prepared in a similar manner to that of Preparation 59-5.

IR (Nujol, cm$^{-1}$): 1720, 1650

¹H-NMR (CDCl₃, δ): 1.22 (3H, d, J=7.1 Hz), 1.33 (3H, d, J=6.6 Hz), 1.4–1.9 (8H, m), 1.9–2.1 (2H, m), 2.36 (3H, br, s), 3.1–3.9 (5H, m), 3.86 (1H, d, J=15.5 Hz), 5.0–5.2 (2H, m), 5.24 (1H, d, J=8.2 Hz), 6.50 (1H, d, J=8.7 Hz), 7.2–7.5 (8H, m)

Mass (APCI): 531 (M⁺+1)

Preparation 45-6

(3RS)-3-Amino-1-[(3-azabicyclo[3.2.2]non-3-yl)carbonylmethyl]-2,3-dihydro-5-isopropyl-9-methyl-1H-1,4-benzodiazepin-2-one was prepared in a similar manner to that of Preparation 59-6.

IR (Nujol, cm⁻¹): 3330, 3250, 1660, 1630

¹H-NMR (CDCl₃, δ): 1.2–1.3 (3H, m), 1.34 (3H, d, J=6.6 Hz), 1.5–2.3 (10H, m), 2.36 (3H, s), 3.21 (1H, m), 3.4–3.9 (4H, m), 3.87 (1H, d, J=15.5 Hz), 4.38 (1H, s), 5.02 (1H, d, J=15.5 Hz), 7.1–7.5 (3H, m)

Mass (APCI): 397 (M⁺+1)

Preparation 46-1

(3RS)-3-Benzyloxycarbonylamino-2,3-dihydro-5,9-dimethyl-1-methylcarbonylmethyl-1H-1,4-benzodiazepin-2-one was prepared in a similar manner to that of Preparation 59-3.

IR (Neat, cm⁻¹): 1720, 1670

¹H-NMR (CDCl₃, δ): 2.06 (3H, s), 2.32 (3H, s), 2.60 (3H, s), 3.75 (1H, d, J=17.4 Hz), 5.0–5.2 (3H, m), 5.25 (1H, dd, J=1.4 Hz and 8.7 Hz), 6.47 (1H, d, J=8.6 Hz), 7.2–7.5 (8H, m)

Mass (APCI): 394 (M⁺+1)

Preparation 46-2

(3RS)-3-Amino-2,3-dihydro-5,9-dimethyl-1-methylcarbonylmethyl-1H-1,4-benzodiazepin-2-one was prepared in a similar manner to that of Preparation 59-6.

IR (Neat, cm⁻¹): 1720, 1650

¹H-NMR (CDCl₃, δ): 2.07 (3H, s), 2.32 (3H, s), 2.59 (3H, s), 3.72 (1H, d, J=17.4 Hz), 5.4 (1H, m), 5.08 (1H, d, J=17.3 Hz), 7.1–7.5 (3H, m)

Mass (APCI): 260 (M⁺+1)

Preparation 47-1

(3RS)-3-Benzyloxycarbonylamino-5-cyclohexyl-1-cyclopropyl-carbonylmethyl-2,3-dihydro-9-methyl-1H-1,4-benzodiazepin-2-one was prepared in a similar manner to that of Preparation 59-3.

¹H-NMR(CDCl₃, δ): 0.8–1.2 (4H, m), 1.2–2.0 (10H, m), 2.0–2.2 (1H, m), 2.34 (3H, br, s), 2.84 (1H, m), 4.01 (1H, d, J=17.1 Hz), 4.96 (1H, d, J=17.1 Hz), 5.0–5.2 (2H, m), 5.21 (1H, d, J=8.2 Hz), 6.49 (1H, d, J=8.7 Hz), 7.2–7.5 (8H, m)

Mass (APCI): 488 (M⁺+1)

Preparation 47-2

(3RS)-3-Amino-5-cyclohexyl-1-cyclopropylcarbonylmethyl-2,3-dihydro-9-methyl-1H-1,4-benzodiazepin-2-one was prepared in a similar manner to that of Preparation 59-6.

IR (Nujol, cm⁻¹): 1675

¹H-NMR (CDCl₃, δ): 0.8–2.0 (14H, m), 2.0–2.2 (1H, m), 2.34 (3H, s), 2.7–2.9 (1H, m), 4.01 (1H, d, J=17.1 Hz), 4.39 (1H, br, s), 4.95 (1H, d, J=17.1 Hz), 7.1–7.5 (3H, m)

Mass (APCI): 354 (M⁺+1)

Preparation 48

(3RS)-3-Amino-2,3-dihydro-1-ethoxycarbonylmethyl-5,9-dimethyl-1H-1,4-benzodiazepin-2-one was prepared in a similar manner to that of Preparation 59-6.

IR (Neat, cm⁻¹): 3380, 3300, 1738, 1680, 1620

¹H-NMR(CDCl₃, δ): 1.19 (3H, t, J=7.1 Hz), 2.24 (2H, m), 2.33 (3H, s), 2.55 (3H, s), 3.75 (1H, d, J=16.9 Hz), 4.09 (2H, q, J=7.1 Hz), 4.40 (1H, br, s), 4.94 (1H, d, J=16.9 Hz), 7.1–7.7 (3H, m)

Mass (APCI): 290 (M⁺+1)

Preparation 49-1

(3RS)-3-Benzyloxycarbonylamino-5-cyclohexyl-2,3-dihydro-9-methyl-1-(1-triphenylmethylimidazol-4-yl)methyl-1H-1,4-benzodiazepin-2-one was prepared in a similar manner to that of Preparation 59-3.

IR (Nujol, cm⁻¹): 720, 1675

¹H-NMR(CDCl₃, δ): 1.0–2.2 (10H, m), 2.35 (3H, br, s), 2.67 (1H, m), 4.23 (1H, d, J=14.5 Hz), 5.0–5.2 (3H, br), 5.32 (1H, d, J=14.4 Hz), 6.51 (1H, d, J=8.3 Hz), 6.77 (1H, br, s), 6.9–7.5 (24H, m)

Mass (FAB): 728 (M⁺+1)

Preparation 49-2

A mixture of (3RS)-3-benzyloxycarbonylamino-5-cyclohexyl-2,3-dihydro-9-methyl-1-(1-triphenylmethylimidazol-4-yl)methyl-1H-1,4-benzodiazepin-2-one (0.5 g) and 30% hydrobromic acid in acetic acid (2.0 ml) was stirred at room temperature overnight. The reaction mixture was poured into a mixture of an ice and ethyl acetate under stirring. The separated water layer was washed with ethyl acetate once, and neutralized with a saturated aqueous solution of sodium bicarbonate. The resultant aqueous mixture was extracted with ethyl acetate and the extract was dried over sodium sulfate. Removal of the solvent in vacuo afforded (3RS)-3-amino-5-cyclohexyl-2,3-dihydro-1-(imidazol-4-yl)methyl-9-methyl-1H-1,4-benzodiazepin-2-one (174 mg, 72.1%) as a crystalline powder.

IR (Nujol, cm⁻¹): 1670, 1610

¹H-NMR (CDCl₃, δ): 0.9–2.0 (10H, m), 2.42 (3H, s), 2.5–2.7 (1H, m), 4.19 (1H, d, J=14.7Hz), 4.29 (1H, br, s), 5.31 (1H, d, J=14.7 Hz), 6.73 (1H, br, s), 7.1–7.5 (6H, m)

Mass (APCI): 352 (M⁺+1)

Preparation 50-1

To a mixture of 2-toluidine (32.8 g, 0.30 ml) and acetonitrile (6.22 g, 0.15 mol) in dry toluene (200 ml) was added 1N-solution of boron trichloride in toluene (150 ml) dropwise under stirring and cooling in an ice-bath for 2 hours. After the addition was completed, the mixture was stirred for 1 hour at ambient temperature and cooled again. To the cooled mixture was added aluminum chloride (20.0 g, 0.15 mol) portionwise. The resultant mixture was stirred at ambient temperature for 1 hour and refluxed for 5 hours. After cooling the reaction mixture in an ice-bath, 2N-HCl (200 ml) was added. The mixture was then refluxed for 2.5 hours. After cooling the mixture, ethyl acetate was added. The separated organic layer was washed with water twice and dried over magnesium sulfate. Removal of the solvent in vacuo Save crystals, which was washed with n-hexane with stirring and collected by filtration to give 2-acetyl-6-methylaniline as a yellow crystal (8.91 g, 39.8%).

mp 51.1–52.9° C.

IR (Nujol, cm⁻¹): 3410, 3300, 1630 (sh), 1610, 960, 740

¹H-NMR (CDCl₃, δ): 2.16 (3H, s), 2.59 (3H), 6.4 (1H, br), 6.59 (1H, t, J=7.9 Hz), 7.19 (1H, d, J=7.9 Hz), 7.63 (1H, d, J=7.9 Hz)

APCI-MS (m/z): 150 (M⁺+1)

Preparation 50-2

To a solution of N-benzyloxycarbonyl-2-(benzotriazol-1-yl)glycine (14.11 g) in dry tetrahydrofuran (100 ml) were added oxalyl chloride (3.77 ml) and dimethylformamide (3 drops) under stirring at 0° C. in an ice-salt bath under nitrogen stream. After the mixture was stirred under the same conditions for 2 hours, a mixture of 2-acetyl-6-methylaniline (4.30 g) and N-methylmorpholine (8.74 g) in tetrahydrofuran (20 ml) was added dropwise for 20 minutes. After the addition was completed, the mixture was allowed to warm to ambient temperature with stirring. Tetrahydrofuran was removed in vacuo and the residue was dissolved in ethyl acetate. The mixture was washed with water twice and dried over magnesium sulfate. Removal of the solvent gave an intermediate product as an oil, to which was added 20% methanolic ammonia (75 ml) and stirred at ambient temperature overnight. The resultant precipitate was collected by filtration and washed with cold methanol and diisopropyl ether successively, and dried to give (3RS)-3-benzyloxycarbonylamino-5,9-dimethyl-2,3-dihydro-1H-1,4-benzodiazepin-2-one as a white crystalline powder (6.17 g, 63.5%).

mp 238–239.5° C.

IR (Nujol, cm$^{-1}$): 3210, 1718, 1690, 1678, 1628, 1059, 742, 699

$^1$H-NMR (CDCl$_3$, δ): 2.36 (3H, s), 2.46 (3H, s), 5.11 (2H, s), 5.14 (1H, d, J=8.3 Hz), 6.50 (1H, d, J=8.3 Hz), 7.13–7.47 (8H, m), 8.48 (1H, s)

APCI-MS (m/z): 338 (M$^+$+1)

Preparation 50-3

To a suspension of (3RS)-3-benzyloxycarbonylamino-5,9-dimethyl-2,3-dihydro-1H-1,4-benzodiazepin-2-one (3.22 g) in methylene chloride (50 ml) was added m-chloroperbenzoic acid (2.50 g, 1.5 eq. mol) portionwise under stirring at ice-bath cooling. The mixture was stirred for 3 days at ambient temperatures. From the reaction mixture methylene chloride was removed in vacuo and to the residue was added an aqueous solution of sodium bicarbonate and stirred for several minutes. The mixture was extracted with ethyl acetate twice and the combined extract was washed with aqueous sodium bicarbonate, water twice and brine. The organic layer was dried over magnesium sulfate and evaporated in vacuo to afford an amorphous mass, which was triturated in methanol and collected by filtration to give (3RS)-3-benzyloxycarbonylamino-5,9-dimethyl-2,3-dihydro-1H-1,4-benzodiazepin-2-one-4-oxide (2.59 g) as a crystalline powder. From the mother liquid, the second crop (0.25 g) of the desired powder was prepared by crystallization in a mixture of methanol and diisopropyl ether (3:1).

$^1$H-NMR (DMSO-d$_6$, δ): 2.38 (6H, s), 5.08 (2H, dd, J=12.9 Hz, 14.8 Hz), 5.45 (1H, d, J=9.3 Hz), 7.15–7.52 (8H, m), 7.89 (1H, d, J=9.3 Hz), 10.49 (1H, s)

APCI-MS (m/z): 354 (M$^+$+1)

Preparation 50-4

A mixture of (3RS)-3-benzyloxycarbonylamino-5,9-dimethyl-2,3-dihydro-1H-1,4-benzodiazepin-2-one-4-oxide (2.83 g,) and acetic anhydride (7.6 ml, 10 eq.mol) in methylene chloride (60 ml) was stirred for 4 days. From the reaction mixture methylene chloride was removed in vacuo. To the residue was added a mixture (60 ml) of diisopropyl ether and n-hexane (1:1). The resultant crystalline powder was collected by filtration and washed with diisopropyl ether to give (3RS)-3-benzyloxycarbonylamino-5-acetoxymethyl-9-methyl-2,3-dihydro-1H-1,4-benzodiazepine-2-one (2.26 g, 71.1%) as a crystalline powder.

$^1$H-NMR (CDCl$_3$, δ): 2.01 (3H, s), 2.36 (3H, s), 4.95–5.29 (5H, m), 6.48 (1H, d, J=8.3 Hz), 7.12–7.47 (8H, m), 7.94 (1H, s)

APCI-MS (m/z): 396 (M$^+$+1)

IR (Nujol, cm$^{-1}$): 3200, 1740, 1686

Preparation 50-5

To a solution of (3RS)-3-benzyloxycarbonylamino-5-acetoxymethyl-9-methyl-2,3-dihydro-1H-1,4-benzodiazepin-2-one (2.24 g) in dimethylformamide (40 ml) was added portionwise sodium hydride (60% suspension in mineral oil, 0.227 g) under stirring and ice-bath cooling. After the addition was completed, the suspension was stirred for 1 hour at ambient temperature. Then to the mixture after ice-bath cooling again was added dropwise a solution of t-butyl bromoacetate (1.11 g) in dimethylformamide (5 ml). The mixture was stirred for 10 minutes under cooling and for 3.5 hours at ambient temperature.

The reaction mixture was poured into ice-water and extracted with ethyl acetate. The extract was washed with water three times and dried over magnesium sulfate. Removal of the solvent afforded (3RS)-3-benzyloxycarbonylamino-1-t-butoxycarbonylmethyl-5-acetoxymethyl-9-methyl-2,3-dihydro-1H-1,4-benzodiazepin-2-one (2.75 g, 95.2%) as an amorphous mass which was used in a following reaction without further purification.

$^1$H-NMR (CDCl$_3$, δ): 1.37 (9H, s), 2.09 (3H, s), 2.34 (3H, s), 4.22 (2H, dd, J=16.8 Hz, 210.1 Hz), 5.09 (2H, s), 5.20 (2H, s), 5.29 (1H, d, J=8.6 Hz), 6.52 (1H, d, J=8.6 Hz), 7.25–7.52 (8H, m)

APCI-MS (m/z): 510 (M$^+$+1)

Preparation 50-6

To a solution of (3RS)-3-benzyloxycarbonylamino-1-t-butoxycarbonylmethyl-5-acetoxymethyl-9-methyl-2,3-dihydro-1H-1,4-benzodiazepin-2-one (3.02 g) in methylene chloride (45 ml) was added trifluoroacetic acid (4.6 ml) under stirring at ambient temperature. The mixture was stirred for 20 hours under the same conditions. Methylene chloride was removed in vacuo and the residue was dissolved in ethyl acetate. The solution was washed with water four times and dried over magnesium sulfate. Removal of the solvent afforded an amorphous mass (2.82 g), which was subjected to column chromatography on silica gel eluting with a mixture of chloroform and methanol (30:1). The fractions containing the desired product were combined and evaporated to give (3RS)-3-benzyloxycarbonylamino-1-carboxymethyl-5-acetoxymethyl-9-methyl-2,3-dihydro-1H-1,4-benzodiazepin-2-one (1.89 g, 70.3%) as a crystalline powder.

IR (Nujol, cm$^{-1}$): 3300, 2800–2200 (br), 1740 (sh), 1720, 1690, 1375, 1230, 1060, 750

$^1$H-NMR (DMSO-d$_6$, δ): 2.04 (3H, s), 2.33 (3H, s), 4.25 (2H, dd, J=17.0 Hz, 139.4 Hz), 4.96 (1H, d, J=8.32 Hz), 5.02 (2H, s), 5.17 (2H, dd, J=14.4 Hz, 57.4 Hz), 7.3–7.65 (8H, m), 8.31 (1H, d, J=8.32 Hz)

APCI-MS (m/z): 454 (M$^+$+1)

Preparation 50-7

A mixture of (3RS)-3-benzyloxycarbonylamino-1-carboxymethyl-5-acetoxymethyl-9-methyl-2,3-dihydro-1H-1,4-benzodiazepin-2-one (343.0 mg), 3-azabicyclo[3.2.2]nonane (106.3 mg), 1-hydroxybenzotriazole (HOBT, 112.4 mg), 1-(3-dimethylaminopropyl)-3-ethylcarbodiimide hydrochloride (WSCD, 160.3 mg) and triethylamine (84.1 mg) in dimethylformamide (7 ml) was stirred for 12 hours at ambient temperature. The reaction mixture was poured into water and the mixture was extracted with ethyl acetate twice. The organic extract was washed with water three times and dried over magnesium sulfate. Removal of the solvent afforded an oil (0.45 g), which was pulverized in diisopropyl ether and collected by filtration to give (3RS)-3-benzyloxycarbonylamino-1-(3-azabicyclo[3.2.2]non-3-yl)carbonylmethyl-5-acetoxymethyl-9-methyl-2,3-dihydro-1H-1,4-benzodiazepin-2-one (339.0 mg, 80.0%) as a light yellow crystalline powder.

IR (Nujol, cm$^{-1}$): 3370, 1751, 1729, 1677, 1642, 1508, 1230, 1056, 760

¹H-NMR (DMSO-d₆, δ): 1.4–1.8 (8H, m), 1.85–2.15 (2H, m), 2.07 (3H, s), 2.37 (3H, s), 3.04–3.31 (2H, m), 3.60–3.82 (2H, m), 4.68 (2H, dd, J=14.7 Hz, 288.3 Hz), 4.90–5.14 (5H, m), 7.34–7.62 (8H, m), 8.26 (1H, d, J=8.6 Hz)

APCI-MS (m/z): 561 (M⁺+1)

Preparation 50-8

A mixture of (3RS)-1-[(3-azabicyclo[3.2.2]non-3-yl)carbonylmethyl]-3-benzyloxycarbonylamino-5-acetoxymethyl-9-methyl-2,3-dihydro-1H-1,4-benzodiazepin-2-one (320 mg), ammonium formate (144 mg) and 10% Pd—C(wet) (80 mg) in 99% ethanol (5 ml) was stirred for 4 hours. The catalyst was removed by filtration through Celite® and the filtrate and the washings were combined and evaporated in vacuo to afford a residue, which was subjected to column chromatography on silica gel eluting with a mixture of chloroform and methanol (20:1). The fractions containing the desired product were combined and evaporated to give (3RS)-3-amino-1-[(3-azabicyclo[3.2.2]non-3-yl)carbonylmethyl]-5,9-dimethyl-2,3-dihydro-1H-1,4-benzodiazepin-2-one as an amorphous mass (178.8 mg, 85.1%).

¹H-NMR (CDCl₃, δ): 1.55–1.77 (8H, m), 1.95–2.17 (2H, m), 2.35 (3H, s), 2.57 (3H, m), 3.29(2H, br, s), 3.36 (2H, m), 3.56–3.86 (2H, m), 4.44 (1H, s), 4.50 (2H, dd, J=15.7 Hz, 295.5 Hz), 7.18–7.40 (3H, m)

APCI-MS (m/z): 369 (M⁺+1)

Preparation 51-1

(3RS)-1-(2-Acetylbenzyl)-3-benzyloxycarbonylamino-5-cyclohexyl-2,3-dihydro-9-methyl-1H-1,4-benzodiazepin-2-one was prepared in a similar manner to that of Preparation 59-3.

IR (Nujol, cm⁻¹): 1660

¹H-NMR (CDCl₃, δ): 1.2–2.2 (10H, m), 2.38 (3H, s), 2.41 (3H, s), 2.8–3.0 (1H, m), 4.21 (1H, d, J=17.1 Hz), 5.0–5.2 (2H, m), 5.28 (1H, d, J=8.2 Hz), 5.40 (1H, d, J=17.1 Hz), 6.51 (1H, d, J=8.6 Hz), 7.2–7.5 (11H, m), 7.60 (1H, d, J=77 Hz)

Mass (APCI): 538 (M⁺+1)

Preparation 51-2

(3RS)-1-(2-Acetylbenzyl)-3-amino-5-cyclohexyl-2,3-dihydro-9-methyl-1H-1,4-benzodiazepin-2-one was prepared in a similar manner to that of Preparation 59-6.

¹H-NMR (CDCl₃, δ): 1.2–2.3 (10 H, m), 2.37 (3H, s), 2.38 (3H, s), 2.8–3.0 (1H, m), 4.21 (1H, d, J=17.0 Hz), 4.43 (1H, br, s), 5.39 (1H, d, J=17.0 Hz), 5.2–5.6 (6H, m), 7.6–7.7 (1H, m)

Mass (APCI): 404 (M⁺+1)

Preparation 52-1

To a solution of 3-azabicyclo[3.2.2]nonane (1.1 g) and triethylamine (0.88 g) in methylene chloride (25 ml) was added portionwise 2-chloroacetyl-6-methylaniline (1.47 g) under stirring and cooling in an ice-bath. After the addition was completed, the mixture was stirred at ambient temperature overnight. Removal of the solvent afforded a residue, which was dissolved in ethyl acetate and washed with water and brine. The organic layer was dried over magnesium sulfate and evaporated in vacuo to give a crystalline mass, which was pulverized in a mixture of n-hexane and diisopropyl ether. A dark yellow crystal was collected by filtration to give 2-[(3-azabicyclo[3.2.2]non-3-yl)acetyl]-6-methylaniline (1.92 g, 88.2%).

IR (Nujol, cm⁻¹): 3440, 3325, 1630, 1608, 1580, 1552, 1374, 1312, 1136, 1000, 944, 868, 857, 749

¹H-NMR (CDCl₃, δ): 1.48–1.9 (10H, m), 2.16 (3H, s), 2.68 (4H, d, J=4.2 Hz), 3.68 (2H, s), 6.38 (1H, br), 6.58 (1H, t, J=7.3 Hz), 7.19 (1H, d, J=7.3 Hz), 8.10 (1H, d, J=7.3 Hz)

APCI-MS (m/z): 273 (M⁺+1)

Preparation 52-2

(3RS)-3-Benzyloxycarbonylamino-5-(3-azabicyclo[3.2.2]non-3-yl)methyl-9-methyl-2,3-dihydro-1H-1,4-benzodiazepin-2-one was prepared in a similar manner to that of Preparation 45-2.

mp: 149.2–151.4° C.

IR (Nujol, cm⁻¹): 3400 (sh), 3220, 1718, 1700, 1681, 1532, 1374, 1058, 980, 778, 749, 691

¹H-NMR (CDCl₃, δ): 1.2–1.8 (10H, m), 2.36 (3H, s), 2.35–2.7 (4H, m), 3.45 (1H, br, d, J=14.3 Hz), 3.90 (1H, d, J=14.3 Hz), 5.11 (2H, s), 5.19 (1H, d, J=8.2 Hz), 6.54 (1H, d, J=8.2Hz), 7.1–7.8 (8H, m), 8.02 (1H, s)

APCI-MS (m/z): 461 (M⁺+1)

Preparation 52-3

(3RS)-5-[(3-Azabicyclo[3.2.2]non-3-yl)methyl]-3-benzyloxy-carbonylamino-2,3-dihydro-1,9-dimethyl-1H-1,4-benzodiazepin-2-one was prepared in a similar manner to that of Preparation 59-3.

IR (Nujol, cm⁻¹): 1720, 1670, 1620

¹H-NMR (CDCl₃, δ): 1.2–1.8 (10H, m), 2.35 (3H, s), 2.4–2.7 (4H, m), 3.15 (3H, s), 3.3–3.5 (1H, br, s), 3.9–4.1 (1H, br, s), 5.0–5.2 (2H, m), 5.23 (1H, d, J=8.4 Hz), 6.64 (1H, d, J=8.5 Hz), 7.2–7.6 (8H, m)

Mass (APCI): 475 (M⁺+1)

Preparation 52-4

(3RS)-3-Amino-5-[(3-azabicyclo[3.2.2]non-3-yl)methyl]-2,3-dihydro-1,9-dimethyl-1H-1,4-benzodiazepin-2-one was prepared in a similar manner to that of Preparation 59-6.

¹H-NMR (CDCl₃, δ): 1.2–1.8 (10H, m), 2.35 (3H, s), 2.3–2.6 (4H, m), 3.15 (3H, s), 3.2–3.4 (1H, m), 3.9–4.1 (1H, br, s), 4.40 (1H, m), 3.2–3.6 (3H, m)

Mass (APCI): 341 (M⁺+1)

Preparation 53-1

To a solution of 2-chloroacetyl-6-methylaniline (1.84 g) in methanol (50 ml) was added 28% methanolic sodium methoxide (5.79 g, 3 eq.mol.) under stirring and cooling in an ice-bath. The mixture was stirred for 0.5 hour under cooling and at ambient temperature overnight. Methanol was removed in vacuo to afford a residue, which was dissolved in ethyl acetate and washed with water and brine successively. The organic layer was dried over magnesium sulfate and evaporated in vacuo to give an oil which was subjected to column chromatography on silica gel eluting with chloroform. The fractions containing the desired product were combined and evaporated to give 2-methoxyacetyl-6-methylaniline (1.07 g, 59.7%, yield) as an oil.

IR (Film, cm⁻¹): 3410, 3340, 1655, 1620 (sh), 1610, 1585, 1560, 1460, 1429, 1380, 1235, 1200, 1120, 1025, 982, 963, 930, 770 (sh), 744

¹H-NMR (CDCl₃, δ): 2.17 (3H, s), 3.51 (3 H, s), 4.70 (2H, s), 6.41 (1H, br), 6.58 (1H, t, J=7.3 Hz), 7.19 (1H, d, J=7.3 Hz), 7.49 (1H, d, J=7.3 Hz)

APCI-MS (m/z): 180 (M⁺+1)

Preparation 53-2

(3RS)-3-Benzyloxycarbonylamino-5-methoxymethyl-9-methyl-2,3-dihydro-1H-1,4-benzodiazepin-2-one was prepared in a similar manner to that of Preparation 45-2.

IR (Nujol, cm⁻¹): 3250 (sh), 3210, 1719, 1696, 1685 (sh), 1530, 1394, 1374, 1085, 1060, 985, 970, 780, 750

¹H-NMR (CDCl₃, δ): 2.37 (3H, s), 3.31 (3H, s), 4.50 (2H, dd, J=13.5 Hz, J=49.8 Hz), 5.11 (2H, s), 5.18 (1H, br, d), 6.58 (1H, br, d), 7.15–7.6 (8H, m), 8.30 (1H, s)

APCI-MS (m/z): 368 (M⁺+1)

Preparation 53-3

(3RS)-3-Benzyloxycarbonylamino-2,3-dihydro-1-ethoxycarbonyl-methyl-5-methoxymethyl-9-methyl-1H-1, 4-benzodiazepin-2-one was prepared in a similar manner to that of Preparation 59-3.

¹H-NMR(CDCl₃, δ): 1.22 (3H, t, J=7.1 Hz), 2.34 (3H, br, s), 3.46–3.48 (3H, m), 3.6–4.0 (2H, m), 4.12 (2H, q, J=7.1 Hz), 4.0–4.3 (1H, br), 4.8–5.1 (1H, br, s), 5.1–5.3 (2H, m), 5.3–5.7 (1H, m), 6.5–6.8 (1H, m), 7.2–7.6 (8H, m)

Mass (APCI): 454 (M⁺+1)

Preparation 53-4

(3RS)-3-Benzyloxycarbonylamino-2,3-dihydro-1-carboxymethyl-9-methyl-5-methoxymethyl-1H-1,4-benzodiazepin-2-one was prepared in a similar manner to that of Preparation 59-4.

IR (Neat, cm⁻¹): 1720, 1680

¹H-NMR (CDCl₃, δ): 2.34 (3H, s), 3.4–3.9 (6H, m), 5.0–5.3 (2H, m), 5.4–5.7 (1H, m), 6.6–6.8 (1H, m), 7.2–7.6 (8H, m)

Mass (APCI): 426 (M⁺+1)

Preparation 53-5

(3RS)-1-[(3-Azabicyclo[3.2.2]non-3-yl)carbonylmethyl]-3-benzyloxycarbonylamino-2,3-dihydro-5-methoxymethyl]-9-methyl-1H-1,4-benzodiazepin-2-one was prepared in a similar manner to that of Preparation 59-5.

¹H-NMR (CDCl₃, δ): 1.4–1.9 (8H, m), 1.9–2.2 (2H, m), 2.36 (3H, s), 3.2–3.4 (2H, m), 3.49 (3H, s), 3.5–3.7 (2H, br), 3.7–3.9 (2H, m), 4.6–4.8 (1H, m), 5.1–5.3 (3H, m), 5.3–5.4 (1H, m), 6.5–6.6 (1H, br), 7.2–7.6 (8H, m)

Mass (APCI): 533 (M⁺+1)

Preparation 53-6

(3RS)-3-Amino-1-[(3-azabicyclo[3.2.2]non-3-yl)carbonylmethyl]-2,3-dihydro-5-methoxymethyl-9-methyl-1H-1,4-benzodiazepin-2-one was prepared in a similar manner to that of Preparation 59-6.

¹H-NMR (CDCl₃, δ): 1.4–2.1 (10H, m), 2.35 (3H, s), 3.2–3.5 (2H, m), 3.61 (3H, s), 3.6–3.9 (4H, m), 4.5–4.8 (2H, m), 5.21 (1H, d, J=15.6 Hz), 7.1–7.6 (3H, m)

Mass (APCI): 399 (M⁺+1)

Preparation 54-1

To a solution of (3RS)-3-benzyloxycarbonylamino-5-cyclohexyl-2,3-dihydro-9-methyl-1-[N-methyl-N-(2-pyridyl)amino]carbonylmethyl-1H-1,4-benzodiazepin-2-one (400 mg) in tetrahydrofuran (4 ml) was added cyclohexyl magnesium chloride (1.08 ml) under stirring, at 0° C. The mixture was stirred for twenty minutes under the same conditions and at room temperature overnight. Ethyl acetate and a saturated aqueous solution of ammonium chloride were added to the reaction mixture. The separated organic layer was washed with 0.1N aqueous hydrochloric acid, water, a saturated aqueous sodium bicarbonate solution and brine successively and dried under magnesium sulfate. The solvent was removed in vacuo to afford a residue, which was subjected to column chromatography on silica gel eluting with a mixture of toluene and ethyl acetate (20:1) to give (3RS)-3-benzyloxycarbonylamino-5-cyclohexyl-1-cyclohexylcarbonylmethyl-2,3-dihydro-9-methyl-1H-1,4-benzodiazepin-2-one.

¹H-NMR (CDCl₃, δ): 1.1–2.0 (20H, m), 2.0–2.2 (1H, m), 2.31 (3H, s), 2.85 (1H, br, s), 3.81 (1H, d, J=17.0 Hz), 4.88 (1H, d, J=17.0 Hz), 5.07–5.08 (2H, m), 5.19 (1H, d, J=9 Hz), 6.42 (1H, d, J=9 Hz), 7.1–7.5 (8H, br, m)

Mass (APCI): 530 (M⁺+1)

Preparation 54-2

(3RS)-3-Amino-5-cyclohexyl-1-cyclohexylcarbonylmethyl-2,3-dihydro-9-methyl-1H-1,4-benzodiazepin-2-one was prepared in a similar manner to that of Preparation 59-6.

¹H-NMR(CDCl₃, δ): 1.1–2.2 (10H, m), 2.31 (3H, s), 2.3–2.5 (1H, br, s), 3.82 (1H, d, J=16.9 Hz), 4.35 (1H, s), 4.86 (1H, d, J=16.9 Hz), 7.2–7.5 (3H, m)

Mass (APCI): 396 (M⁺+1)

Preparation 55-1

2-Chloroacetyl-6-methylaniline was prepared in a similar manner to that of Preparation 50-1.

IR (Nujol, cm⁻¹): 3400, 3340, 1655, 1610, 1587, 1560, 1380, 788, 738, 700

¹H-NMR (CDCl₃, δ): 2.17 (3H, s), 4.70 (2H, s), 6.2 (1H, br), 6.60 (1H, t, J=7.2 Hz), 7.22 (1H, d, J=7.2 Hz), 7.53 (1H, d, J=7.2 Hz)

APCI-MS (m/z): 184 (M⁺+1), 186 (M⁺+3)

Preparation 55-2

To a solution of 2-chloroacetyl-6-methylaniline (2.0 g) in methylene chloride (20 ml) was added 1-methylpiperazine (2.29 g) under stirring and cooling in an ice-bath. The mixture was stirred overnight at ambient temperature. Methylene chloride was removed in vacuo and to the residue were added ethyl acetate and diluted aqueous solution of sodium bicarbonate. From the aqueous layer the desired product was extracted with ethyl acetate five times and combined organic extract was washed with brine. After drying over magnesium sulfate, the solvent was removed in vacuo to give 2-[(4-methylpiperazin-1-yl)acetyl]-6-methylaniline (2.07 g, 76.9% yield) as a crystalline mass.

IR (Nujol, cm⁻¹): 3380, 3280, 1654, 1610, 1588, 1562, 1375, 1280, 1141, 1005, 974, 780, 740

¹H-NMR (CDCl₃, δ): 2.16 (3H, s), 2.31 (3H, s), 2.55 (4H, br, m), 2.65 (4H, br, m), 3.79 (2H, s), 6.41 (1H, br, s), 6.57 (1H, t, J=7.3 Hz), 7.20 (1H, d, J=7.3 Hz), 7.72 (1H, d, J=7.3 Hz)

APCI-MS (m/z): 248 (M⁺+1)

Preparation 55-3

(3RS)-3-Benzyloxycarbonylamino-5-(4-methylpiperazin-1-yl)methyl-9-methyl-2,3-dihydro-1H-1,4-benzodiazepin-2-one was prepared in a similar manner to that of Preparation 45-2.

¹H-NMR (CDCl₃, δ): 2.25 (3H, s), 2.35 (3H, s), 2.2–2.5 (8H, m), 3.58 (2H, dd, J=13.7 Hz, 45.9 Hz), 5.10 (2H, s), 5.16 (1H, d, J=8.2 Hz), 6.56 (1H, d, J=8.2 Hz), 7.1–7.73 (8H, m), 8.05 (1H, s)

APCI-MS (m/z): 436 (M⁺+1)

Preparation 55-4

(3RS)-3-Benzyloxycarbonylamino-2,3-dihydro-1,9-dimethyl-5-(4-methylpiperazin-1-yl)methyl-1H-1,4-benzodiazepin-2-one was prepared in a similar manner to that of Preparation 59-3.

IR (Nujol, cm⁻¹): 1710, 1680

¹H-NMR(CDCl₃, δ): 2.27 (3H, s), 2.35 (3 H, s), 3.17 (31H, s), 2.4–2.6 (8H, m), 3.40 (1H, d, J=13.5 Hz), 3.81 (1H, d, J=13.5 Hz), 5.0–5.3 (3H, br, m), 6.63 (1H, d, J=8.2 Hz), 7.2–7.6 (8H, m)

Mass (APCI): 450 (M⁺+1)

Preparation 56-1

Dimethylamine aqueous solution (50%, 5.41 g) was added to a solution of 2-chloroacetyl-6-methylaniline (3.67 g) in methanol (50 ml) under stirring and cooling in an ice-bath. The mixture was stirred for 3 hours at ambient temperature. Methanol was removed in vacuo to give a residue, which was dissolved in ethyl acetate and washed with water. From the organic layer a basic substance was extracted with 1N-hydrochloric acid twice. The aqueous extract was washed with ethyl acetate and basidified with 1N-sodium hydroxide aqueous solution. The mixture was extracted with ethyl acetate twice and washed with water and brine. The organic extract was dried over magnesium sulfate and evaporated in vacuo to afford an oil (2.58 g), which was pulverized in a mixture of n-hexane and diisopropyl ether (1:1) and collected by filtration to give 2

- N,N-dimethylamino)acetyl-6-methylaniline (2.03 g, 52% yield) as a yellow crystalline powder.

IR (Nujol, cm$^{-1}$): 3410, 3300, 1640, 1612, 1585, 1552, 1378, $^1$H-NMR (CDCl$_3$, δ): 2.16 (3H, s), 2.37 (6H, s), 3.71 (2H, s), 6.41 (1H, br), 6.58 (1H, dd, J=7.2 Hz, 8.1 Hz): 7.18 (1H, d, J=7.2 Hz ), 7.71 (1H, d, J=7.2 Hz)

APCI-MS (m/z): 193 (M$^+$+1)

Preparation 56-2

(3RS)-3-Benzyloxycarbonylamino-5-(N,N-dimethylamino)methyl-9-methyl-2,3-dihydro-1H-1,4-benzodiazepin-2-one was prepared in a similar manner to that of Preparation 45-2.

mp: 204.1–205.2° C.

IR (Nujol, cm$^{-1}$): 3250 (sh), 3200, 1718, 1695, 1685, 1615, 1530, 1391, 1370, 1058, 855, 785, 752, 690

$^1$H-NMR (CDCl$_3$, δ): 2.18 (6H, s), 2.34 (3H, s), 3.52 (2H, dd, J=13.7 Hz, 101.6 Hz), 5.11 (2H, s), 5.19 (1H, d, J=8.4 Hz), 6.53 (2H, d, J=8.4 Hz), 7.18–7.4 (7H, m), 7.58 (1H, d, J=7.8Hz), 8.07 (1H, s)

APCI-MS (m/z): 381 (M$^+$+1)

Preparation 56-3

(3RS)-3-Benzyloxycarbonylamino-2,3-dihydro-1-ethoxycarbonyl-methyl-5-(N,N-dimethylamino)methyl-9-methyl-1H-1,4-benzodiazepin-2-one was prepared in a similar manner to that of Preparation 59-3.

IR (Neat, cm$^{-1}$): 1750, 1720, 1675, 1620

$^1$H-NMR(CDCl$_3$, δ): 1.20 (3H, t, J=7.1 Hz), 2.34 (3H, s), 2.35 (6H, s), 3.59 (2H, s), 3.82 (1H, d, J=16.9 Hz), 4.09 (2H, q, J=7.1 Hz), 4.76 (1H, d, J=16.9 Hz), 5.29 (1H, d, J=8.7 Hz), 6.54 (1H, d, J=8.6 Hz), 7.2–7.5 (8H, m)

Mass (APCI): 467 (M$^+$+1)

Preparation 56-4

(3RS)-3-Benzyloxycarbonylamino-2,3-dihydro-1-carboxymethyl-9-methyl-5-(N,N-dimethylamino)methyl-1H-1,4-benzodiazepin-2-one was prepared in a similar manner to that of Preparation 59-4.

IR (Nujol, cm$^{-1}$): 1715, 1685, 1600

$^1$H-NMR (DMSO-d$_6$, δ): 2.27 (3H, s), 2.31 (3H, s), 2.46 (3H, s), 3.5–3.8 (3H m), 3.42 (1H, d, J=16.5 Hz), 4.98 (1H, d, J=9.6 Hz), 5.01 (2H, s), 7.1–7.4 (5H, m), 7.45 (1H, d, J=7.1 Hz), 7.76 (1H, d, J=7.3 Hz), 8.07 (1H, d, J=8.6 Hz), 8.31 (1H, s)

Mass (APCI): 439 (M$^+$+1)

Preparation 56-5

(3RS)-1-[(3-Azabicyclo[3.2.2]non-3-yl)carbonylmethy]-3-benzyloxycarbonylamino-2,3-dihydro-9-methyl-5-(N,N-dimethylamino)-methyl-1H-1,4-benzodiazepin-2-one was prepared in a similar manner to that of Preparation 59-5.

IR (Neat, cm$^{-1}$): 735, 1655, 1625

$^1$H-NMR(CDCl$_3$, δ): 1.5–1.9 (8H, m), 1.9–2.2 (2H, m), 2.22 (3H, s), 2.34 (6H, s), 3.1–3.5 (4H, m), 3.6–3.8 (2H, m), 3.82 (1H, d, J=15.5 Hz), 4.97–5.31 (4H, m), 7.1–7.5 (7H, m), 7.7–7.9 (1H, m)

Mass (APCI): 546 (M$^+$+1)

Preparation 56-6

(3RS)-3-Amino-1-[(3- azabicyclo[3.2.2non-3-yl)carbonylmethyl]-2,3-dihydro-9-(N,N-dimethylamino)methyl-9-methyl-1H-1,4-benzodiazepin-2-one was prepared in a similar manner to that of Preparation 59-6.

IR (Neat, cm$^{-1}$): 3320, 1645

$^1$H-NMR(CDCl$_3$, δ): 1.2–2.6 (19H, m), 3.2–4.0 (6H, m), 4.13 (1H, m), 4.47 (1H, m), 5.10 (1H, m), 7.25 (2H, m), 7.70 (1H, m)

Mass (APCI): 412 (M$^+$+1)

Preparation 57-1

2-(4-chlorobutanoyl)-6-methylaniline was prepared in a similar manner to that of Preparation 50-1.

$^1$H-NMR (CDCl$_3$, δ): 2.16 (3H, s), 2.20 (2H, m), 3.15 (2H, t, J=7.0 Hz), 3.66 (2H, t J=6.3 Hz), 6.38 (1H, br, s), 6.5–6.7 (1H, m), 7.1–7.3 (1H, m), 7.6–7.8 (11H, m)

Mass (APCI): 212 (M$^+$+1)

Preparation 57-2

A mixture of 2-(4-chlorobutanoyl)-6-methylaniline (538 mg) and potassium t-butoxide (285 mg) in tetrahydrofuran (8 ml) was stirred at room temperature for 1.5 hour. Ethyl acetate and 0.1 N aqueous hydrochloric acid were added to the reaction mixture. The separated organic layer was washed with water, saturated aqueous sodium bicarbonate and brine successively and dried over magnesium sulfate. Removal of the solvent in vacuo gave 2-cyclopropylcarbonyl-6-methylaniline (445 mg, 100.0%) as a crystalline powder.

IR (Nujol, cm$^{-1}$): 3450, 3300, 1610

$^1$H-NMR (CDCl$_3$, δ): 0.90–1.00 (2H, m), 1.14–1.21 (3H, m), 2.17 (3H, s), 2.5–2.8 (1H, m), 6.25 (2H, m), 6.64 (1H, t, J=7.2 Hz), 7.22 (1H, J=7.2 Hz), 7.88(1H, d, J=8.2 Hz)

Mass (APCI): 176 (M$^+$+1)

Preparation 57-3

(3RS)-3-Benzyloxycarbonylamino-5-cyclopropyl-2,3-dihydro-9-methyl-1H-1,4-benzodiazepin-2-one was prepared in a similar manner to that of Preparation 45-2.

IR (Nujol, cm$^{-1}$): 1715, 1675, 1620

$^1$H-NMR (DMSO-d$_6$, δ): 0.7–1.2 (4H, m), 2.03 (1H, m), 2.34 (3H, s), 4.79 (1H, d, J=8.6 Hz), 5.02 (2H, br, s), 7.1–7.5 (6H, m), 7.6–7.8 (1H, m), 7.9–8.2 (1H, m), 9.96 (2H, br, s)

Mass (APCI): 364 (M$^+$+1)

Preparation 57-4

(3RS)-3-Benzyloxycarbonylamino-5-cyclopropyl-2,3-dihydro-1-ethoxycarbonylmethyl-9-methyl-1H-1,4-benzodiazepin-2-one was prepared in a similar manner to that of Preparation 59-3.

IR (Neat, cm$^{-1}$): 750, 1700, 1630

$^1$H-NMR (CDCl$_3$, δ): 0.83–0.94 (2H1, m), 0.98–1.10 (2H, m), 1.19 (3H, t, J=7.1 Hz), 1.9–2.4 (1H, m), 2.33 (3H, s), 3.80 (1H, d, J=16.8 Hz), 4.10 (2H, q, J=7.1 Hz), 4.85 (1H, d, J=16.8 Hz), 5.01–5.14 (2H, m), 5.18 (1H, d, J=8.7 Hz), 6.36 (1H, d, J=8.6 Hz), 7.2–7.4 (7H, m), 7.63–7.68 (1H, m)

Mass (APCI): 450 (M$^+$+1)

Preparation 57-5

(3RS)-3-Benzyloxycarbonylamino-5-cyclopropyl-2,3-dihydro-1-carboxymethyl-9-methyl-1H-1,4-benzodiazepin-2-one was prepared in a similar manner to that of Preparation 59-4.

IR (Nujol, cm$^{-1}$): 1730, 1680, 1610

$^1$H-NMR (CDCl$_3$, δ): 0.82–0.90 (2H, m), 0.96–1.07 (2H, m), 1.26 (3H, t, J=7.1 Hz), 1.90–2.04 (1H, m), 2.31 (3H, s), 3.80 (1H, d, J=17.3 Hz), 4.89 (1H, d, J=17.3 Hz), 4.93–5.12 (2H, m), 5.18 (1H, d, J=8.7 Hz), 6.40 (1H, d, J=8.7 Hz), 7.2–7.4 (7H, m), 7.5–7.6 (1H, m)

Mass (APCI): 422 (M$^+$+1)

Preparation 57-6

(3RS)-1-[(3-Azabicyclo[3.2.2]non-3-yl)carbonylmethyl]-3-benzyloxycarbonylamino-5-cyclopropyl-2,3-dihydro-9-methyl-1H-1,4-benzodiazepin-2-one was prepared in a similar manner to that of Preparation 59-5.

IR (Nujol, cm$^{-1}$): 1725, 1675, 1650, 1615

$^1$H-NMR (CDCl$_3$, δ): 0.87–1.09 (4H, m), 1.25–1.73 (8H, m), 2.03–2.15 (3H, m), 2.36 (3H, s), 3.31–3.80 (4H, m), 3.84 (1H, d, J=15.5 Hz), 5.10 (2H, m), 5.14 (1H, d, J=15.5 Hz), 5.19 (1H, d, J=8.7 Hz), 6.38 (1H, d, J=8.6 Hz), 7.2–7.5 (7H, m), 7.6–7.7 (1H, m)

Mass (APCI): 529 (M$^+$+1)

Preparation 57-7

(3RS)-3-Amino-1-[(3-azabicyclo[3.2.2]non-3-yl)carbonylmethyl]-5-cyclopropyl-2,3-dihydro-9-methyl-1H-

1,4-benzodiazepin-2-one was prepared in a similar manner to that of Preparation 59-6.

IR (Nujol, cm$^{-1}$): 1675, 1645, 1600

$^1$H-NMR (CDCl$_3$, δ): 0.85–1.06 (4H, m), 1.4–1.8 (8H, m), 1.9–2.2 (2H, m), 2.23 (1H, br, s), 2.37 (3H, s), 3.35–3.67 (4H, m), 3.86 (1H, d, J=15.5 Hz), 4.34 (1H, s), 5.17 (1H, d, J=15.5 Hz), 7.1–7.4 (2H, m), 7.6–7.7 (1H, m)

Mass (APCI): 395 (M$^+$+1)

Preparation 58-1

2-methyl-6-isovalerylaniline was prepared in a similar manner to that of Preparation 50-1.

IR (Nujol, cm$^{-1}$): 3475, 3330, 1638, 1610, 1580, 1555, 1025, 951, 742

$^1$H-NMR (CDCl$_3$, δ): 0.99 (6H, d, J=6.6 Hz), 2.17 (3H, s), 2.27 (1H, m), 2.81 (2H, d, J=6.9 Hz), 6.4 (1H, br), 6.59 (1H, dd, J=7.3 Hz, J=8.0 Hz), 7.16–7.3 (2H, m), 7.66 (1H, d, J=8.0 Hz)

APCI-MS (m/z): 192 (M$^+$+1)

Preparation 58-2

(3RS)-3-Benzyloxycarbonylamino-5-isobutyl-9-methyl-2,3-dihydro-1H-1,4-benzodiazepin-2-one was prepared in a similar manner to that of Preparation 45-2.

mp: 208.4–209.1° C.

IR (Nujol, cm$^{-1}$): 3250 (sh), 3200, 1718, 1690 (sh), 1680, 1526, 1390, 1367, 1057, 983, 761, 698

$^1$H-NMR (CDCl$_3$, δ): 0.75 (3H, d, J=6.6 Hz), 0.86 (3H, d, J=6.6 Hz), 1.79 (1H, m), 2.36 (3H, s), 2.46 (1H, dd, J=9.4 Hz, J=13.9 Hz), 2.87 (1H, dd, J=3.9 Hz, J=13.9 Hz), 5.10 (2H, s), 5.15 (1H, d, J=8.4 Hz), 6.48 (1H, d, J=8.4 Hz), 7.12–7.45 (8H, m), 8.24 (1H, br, s)

APCI-MS (m/z): 380 (M$^+$+1)

Preparation 58-3

(3RS)-3-Benzyloxycarbonylamino-2,3-dihydro-1-ethoxycarbonylmethyl-5-isobutyl-9-methyl-1H-1,4-benzodiazepin-2-one was prepared in a similar manner to that of Preparation of 59-3.

IR (Neat, cm$^{-1}$): 1750, 1720, 1620

$^1$H-NMR (CDCl$_3$, δ): 0.96 (6H, d, J=6.6 Hz), 1.21 (3H, t, J=7.1 Hz), 2.13–2.28 (1H, m), 2.35 (3H, s), 2.57–2.88 (2H, m), 3.89 (1H, d, J=16.9 Hz), 4.12 (2H, q, J=7.1 Hz), 4.64 (1H, d, J=16.9 Hz), 5.06 (1H, d, J=12.4 Hz), 5.13 (1H, d, J=12.4 Hz), 5.25 (1H, d, J=8.6 Hz), 6.50 (1H, d, J=8.6 Hz), 7.2–7.4 (8H, m)

Mass (APCI): 466 (M$^+$+1)

Preparation 58-4

(3RS)-3-Benzyloxycarbonylamino-2,3-dihydro-1-carboxymethyl-5-isobutyl-9-methyl-1H-1,4-benzodiazepin-2-one was prepared in a similar manner to that of Preparation 59-4.

IR (Nujol, cm$^{-1}$): 1715, 1680, 1610

$^1$H-NMR (CDCl$_3$, δ): 0.91 (3H, d, J=6.6 Hz), 0.93 (3H, d, J=6.6 Hz), 2.1–2.2 (1H, m), 2.34 (3H, s), 2.55–2.73 (2H, m), 3.91 (1d, J=17.2 Hz), 4.68 (1H, d, J=17.2 Hz), 5.04 (1H, d, J=12.4 Hz), 5.12 (1H, d, J=12.4 Hz), 6.56 (1H, d, J=8.6 Hz), 5.24 (1H, d, J=8.6 Hz), 7.2–7.4 (8H, m)

Mass (APCI): 438 (M$^+$+1)

Preparation 58-5

(3RS)-1-[(3-Azabicyclo[3.2.2]non-3-yl)carbonylmethyl]-3-benzyloxycarbonylamino-2,3-dihydro-9-methyl-5-isobutyl-1H-1,4-benzodiazepin-2-one was prepared in a similar manner to that of Preparation 59-5.

IR (Nujol, cm$^{-1}$): 1710, 1675, 1650

$^1$H-NMR(CDCl$_3$, δ): 0.15 (6H, d, J=6.6 Hz), 1.5–1.8 (8H, br), 1.9–2.2 (2H, m), 2.2–2.3 (1H, m), 2.36 (3H, s), 2.58–2.95 (2H, m), 3.31–3.40 (2H, m), 3.53–3.82 (2H, m), 3.91 (1H, d, J=15.7 Hz), 4.95 (1H, d, J=15.7 Hz), 5.05 (1H, d, J=12.4 Hz), 5.12 (1H, d, J=12.4 Hz), 5.27 (1H, d, J=8.6 Hz), 6.51 (1H, d, J=8.6 Hz), 7.1–7.5 (8H, m)

Mass (APCI): 545 (M$^+$+1)

Preparation 58-6

(3RS)-3-Amino-1-[(3-Azabicyclo[3.2.2]non-3-yl)carbonylmethyl]-5-isobutyl-2,3-dihydro-9-methyl-1H-1,4-benzodiazepin-2-one was prepared in a similar manner to that of Preparation 59-6.

IR (Nujol, cm$^{-1}$): 3380, 1680, 1650

$^1$H-NMR(CDCl$_3$, δ): 0.98 (3H, d, J=6.5 Hz), 0.99 (3H, d, J=6.5 Hz), 1.5–1.8 (8H, m), 1.9–2.1 (2H, m), 2.2–2.3 (1H, m), 2.36 (3H, s), 2.56–2.68 (1H, m), 2.77–2.88 (1H, m), 3.35–3.44 (2H, m), 3.53–3.63 (1H, m), 3.77–3.85 (1H, m), 3.82 (1H, d, J=15.7 Hz), 4.41(1H, s), 4.97 (1H, d, J=15.7 Hz), 7.1–7.4 (3H, m)

Mass (APCI): 411 (M$^+$+1)

Preparation 59-1

2-Propanoyl-6-methylaniline was prepared in a similar manner to that of Preparation 50-1.

$^1$H-NMR (CDCl$_3$, δ): 1.21 (3H, t, J=7.3 Hz), 2.16 (3H, s), 2.98 (2H, q, J=7.3 Hz), 6.40 (2H, m), 6.5–6.6 (1H, m), 7.18 (1H, d, J=7.1 Hz), 7.66 (1H. d, J=8.1 Hz)

Mass (APCI): 164 (M$^+$+1)

Preparation 59-2

(3RS)-3-Benzyloxycarbonylamino-2,3-dihydro-5-ethyl-9-methyl-1H-1,4-benzodiazepin-2-one was prepared in a similar manner to that of Preparation 50-2.

IR (Nujol, cm$^{-1}$): 1705, 1675, 1610

$^1$H-NMR (DMSO-d$_6$, δ): 0.99 (3H, t, J=7.4 Hz), 2.34 (3H, s), 2.65–2.90 (2H, m), 4.86 (1H, d, J=8.6 Hz), 5.03 (2H, s), 7.1–7.5 (7H, m), 7.58 (1H, d, J=7.9 Hz), 8.09 (1H, d, J=8.6 Hz), 9.95 (1H, s)

Mass (APCI): 352 (M$^+$+1)

Preparation 59-3

A mixture of (3RS)-3-benzyloxycarbonylamino-5-ethyl-2,3-dihydro-9-methyl-1H-1,4-benzodiazepin-2-one (1.0 g) and 60% sodium hydride (120 mg) in N,N-dimethylformamide was stirred at 0° C. for 1 hour and at room temperature for 3 hours. To the resultant mixture was added dropwise ethyl bromoacetate (476 mg) under cooling at 0–5° C. in an ice-bath. The mixture was stirred for 5.5 hours under the same conditions. The reaction mixture was poured into 0.1N aqueous hydrochloric acid and extracted with ethyl acetate. The extract was washed with water twice, saturated aqueous sodium bicarbonate and brine successively and dried over magnesium sulfate. The solvent was evaporated in vacuo to afford (3RS)-3-benzyloxycarbonylamino-5-ethyl-2,3-dihydro-1-ethoxycarbonylmethyl-9-methyl-1H-1,4-benzodiazepin-2-one (1.55 g) as an oil.

IR (Neat, cm$^{-1}$): 1750, 1720, 1622

$^1$H-NMR (CDCl$_3$, δ): 1.0–1.35 (61H, m), 2.33 (3H, s), 3.78 (1H, d, J=16.8 Hz), 2.75–2.98 (2H, m), 4.85 (1H, d, J=16.8 Hz), 4.10 (2H, q, J=7.1 Hz), 5.06 (1H, d, J=12.3 Hz), 5.13 (1H, d, J=12.3 Hz), 5.27 (1H, d, J=8.7 Hz), 6.49 (1H, d, J=8.6 Hz), 7.2–7.4 (8H, m)

Mass (APCI): 438 (M$^+$+1)

Preparation 59-4

A mixture of (3RS)-3-benzyloxycarbonylamino-2,3-dihydro-5-ethyl-1-ethoxycarbonylmethyl-9-methyl-1H-1,4-benzodiazepin-2-one (1.55 g) and 1N sodium hydroxide (7.0 ml) in 1,2-dimethoxyethane (10 ml) was stirred at room temperature overnight. The reaction mixture was evaporated in vacuo to afford a residue, which was dissolved in a mixture of ethyl acetate and 1N aqueous hydrochloric acid. The separated organic layer was washed with water and brine, and then dried over magnesium sulfate. The solvent was evaporated in vacuo to afford a residue, which was triturated in diisopropyl ether and collected by filtration to give (3RS)-3-benzyloxycarbonylamino-5-ethyl-1-carboxymethyl-2,3-dihydro-9-methyl-1H-1,4-benzodiazepin-2-one (1.22 g, 84.2% yield) as a white crystalline powder.

IR (Nujol, cm$^{-1}$): 1720, 1670, 1615
$^1$H-NMR (CDCl$_3$, δ): 1.14 (3H, t, J=7.4 Hz), 2.31 (3H, s), 2.74–2.95 (2H, m), 3.79 (1H, d, J=17.1 Hz), 4.86 (1H, d, J=17.1 Hz), 5.03 (1H, d, J=12.4 Hz), 5.01 (1H, d, J=12.4 Hz), 5.26 (1H, d, J=8.7 Hz), 6.62 (1H, d, J=8.7 Hz), 7.2–7.4 (8H, m). 7.87 (1H, br)
Mass (APCI): 410 (M$^+$+1)

Preparation 59-5

A mixture of (3RS)-3-benzyloxycarbonylamino-5-ethyl-2,3-dihydro-1-carboxymethyl-9-methyl-1H-1,4-benzodiazepin-2-one (1.22 g), N-ethyl-N'-(3-dimethylaminopropyl)carbodiimide hydrochloride (642 mg), 1-hydroxybenzotriazole (453 mg), 3-azabicyclo[3.2.2]nonane (419 mg) and triethylamine (1.55 ml) in N,N-dimethylformamide (30 ml) was stirred at room temperature overnight. Ethyl acetate and 0.1N aqueous hydrochloric acid were added to the reaction mixture, which was stirred for several minutes. The separated organic layer was washed with 1N aqueous hydrochloric acid, water twice, a saturated aqueous solution of sodium bicarbonate and brine, successively, and then dried over magnesium sulfate. The solvent was evaporated in vacuo, and the residue was triturated in diisopropyl ether and collected by filtration to afford (3RS)-1-[(3-azabicyclo[3.2.2]non-3-yl)carbonylmethyl]-3-benzyloxycarbonylamino-2,3-dihydro-5-ethyl-9-methyl-1H-1,4-benzodiazepin-2-one (1.23 g, 79.9%) as a crystalline powder.

IR (Nujol, cm$^{-1}$): 1718, 1675, 1650
$^1$H-NMR (CDCl$_3$, δ): 1.26 (3H, t, J=7.4 Hz), 1.5–1.8 (10H, m), 2.34 (3H, s), 2.90 (2H, q, J=7.4 Hz), 3.29–3.36 (2H, m), 3.55–3.64 (1H, m), 3.79 (1H, d, J=15.6 Hz), 3.7–3.86 (1H, m), 5.05 (1H, d, J=12.4 Hz), 5.12 (1H, d, J=12.4 Hz), 5.14 (1H, d, J=15.6 Hz), 5.28 (1H, d, J=8.7 Hz), 6.50 (1H, d, J=8.7 Hz), 7.2–7.4 (8H, m)
Mass (APCI): 517 (M$^+$+1)

Preparation 59-6

A mixture of (3RS)-3-benzyloxycarbonylamino-1-[(3-azabicyclo[3.2.2]non-3-yl)-carbonylmethyl]-5-ethyl-2,3-dihydro-9-methyl-1H-1,4-benzodiazepin-2-one (1.23 g), 10% palladium on carbon (50% wet, 250 mg) and ammonium formate (600 mg) in ethanol (15 ml) was stirred at room temperature for 1 hour. The catalyst was filtered off and the filtrate was evaporated in vacuo to afford a residue, which was dissolved in ethyl acetate and washed with saturated aqueous sodium bicarbonate, water and brine successively. After drying over sodium sulfate, the solvent was evaporated in vacuo to afford a residue, which was triturated in diisopropyl ether and collected by filtration to give (3RS)-3-amino-1-[(3-azabicyclo[3.2.2]non-3-yl)carbonylmethyl]-5-ethyl-2,3-dihydro-9-methyl-1H-1,4-benzodiazepin-2-one (792 mg, 87.0% yield) as a crystalline powder.

IR (Nujol, cm$^{-1}$): 3360, 3370, 1680, 1655
$^1$H-NMR (CDCl$_3$, δ): 1.27 (3H, t, J=7.3 Hz), 1.5–1.8 (8H, m), 1.8–2.1 (2H, m), 2.35 (3H, s), 2.89 (2H, q, J=7.3 Hz), 3.3–3.42 (2H, m), 3.5–3.6 (2H, m), 3.79 (1H, d, J=15.5 Hz), 4.41 (1H, s), 5.17 (1H, d, J=15.5 Hz), 7.1–7.4 (3H, m)
Mass (APCI): 383 (M$^+$+1)

Preparation 60-1

(3RS)-3-Benzyloxycarbonylamino-2,3-dihydro-1-ethoxycarbonyl-methyl-5-(2-fluorophenyl)-9-methyl-1H-1,4-benzodiazepin-2-one was prepared in a similar manner to that of Preparation 59-3.

IR (Nujol, cm$^{-1}$): 1720, 1675
$^1$H-NMR (DMSO-d$_6$, δ): 0.97 (3H, t, J=7.1 Hz), 2.39 (3H, s), 3.89 (2H, q, J=7.1 Hz), 4.21 (1H, d, J=16.7 Hz), 4.68 (1H, d, J=16.7 Hz), 5.05 (1H, br, s), 5.20 (H, d, J=8.6 Hz), 7.06 (1H, d, J=7.6 Hz), 7.2–7.8 (11H, m), 8.4–8.6 (1H, m)
Mass (APCI): 504 (M$^+$+1)

Preparation 60-2

(3RS)-3-Benzyloxycarbonylamino-2,3-dihydro-5-(2-fluorophenyl)-1-carboxymethyl-9-methyl-1H-1,4-benzodiazepin-2-one was prepared in a similar manner to that of Example 48-2.

IR (Nujol, cm$^{-1}$): 1720, 1680
$^1$H-NMR(CDC$_3$, δ): 2.35 (3H, s), 3.88 (1H, d, J=17.2 Hz), 4.84 (1H, d, J=17.2 Hz), 5.0–5.3 (2H, m), 5.42 (1H, d, J=8.7 Hz), 6.67 (1H, d, J=8.7 Hz), 6.9–7.5 (1H, m), 7.6–7.8 (1H, m)
Mass (FAB): 476 (M$^+$+1)

Preparation 61-1

(3RS)-3-Benzyloxycarbonylamino-1-cyclohexylcarbonylmethyl-2,3-dihydro-5-ethyl-9-methyl-1H-1,4-benzodiazepin-2-one was obtained in a similar manner to that of Preparation 59-3.

IR (Nujol, cm$^{-1}$): 3350, 1710, 1670, 1620
$^1$H-NMR (CDCl$_3$, δ): 1.27 (3H, t, J=7.4 Hz), 1.1–2.0 (10H, m), 2.2–2.4 (1H, m), 2.32 (3H, s), 2.92 (2H, q, J=7.4 Hz), 3.75 (1H, d, J=17 Hz), 5.05 (1H, d, J=17 Hz), 5.0–5.2 (2H, m), 5.25 (1H, d, J=8.7 Hz), 6.45 ((1H, d, J=8.6 Hz), 7.1–7.5 (8H, m)
Mass (APCI)(e/z): 476 (M$^+$+1)

Preparation 61-2

(3RS)-3-Amino-1-cyclohexylcarbonylmethyl-2,3-dihydro-5-ethyl-9-methyl-1H-1,4-benzodiazepin-2-one was obtained in a similar manner to that of Preparation 59-6.

IR (Neat, cm$^{-1}$): 3380, 3320, 1720, 1680
$^1$H-NMR (CDCl$_3$, δ): 1.29 (3H, t, J=7.1 Hz), 1.1–1.4 (5H, m), 1.5–2.0 (5H, m), 2.0–2.2 (2H, m), 2.2–2.4 (1H, m), 2.32 (3H, s), 2.8–3.0 (2H, m), 3.74(1H, d, J=17.0 Hz), 4.39 (1H, t, J=1.5 Hz), 5.06 (1H, d, J=17.0 Hz), 7.1–7.4 (3H, m)
Mass (APCI)(e/z): 342 (M$^+$+1)

Preparation 62-1

(3RS)-3-Benzyloxycarbonylamino-1-cyclohexylcarbonylmethyl-2,3-dihydro-5-isopropyl-9-methyl-1H-1,4-benzodiazepin-2-one was obtained in a similar manner to that of Preparation 59-3.

IR (Nujol, cm$^{-1}$): 3350, 1720, 1670, 1610
$^1$H-NMR(CDCl$_3$, δ): 1.19 (3H, d, J=7.1 Hz), 1.33 (3H, d, J=6.6 Hz), 1.1–2.0 (10H, m), 2.32 (3H, s), 2.2–2.4 (1H, m), 3.1–3.3 (1H,m), 3.79 (1H, d, J=17.0 Hz), 4.93 (1H, d, J=17.0 Hz), 5.05 (1H, d, J=12.6 Hz)(5.12, d, J=12.6 Hz), 5.20 (1H, d, J=8.7 Hz), 6.42 (1H, d, J=8.6 Hz), 7.1–7.5 (8H, m)
Mass (APCI)(e/z): 490 (M$^+$+1)

Preparation 62-2

(3RS)-3-Amino-1-cyclohexylcarbonylmethyl-2,3-dihydro-5-isopropyl-9-methyl-1H-1,4-benzodiazepin-2-one was obtained in a similar manner to that of Preparation 59-6.

IR (Neat, cm$^{-1}$): 3380, 3320, 1725, 1680, 1620
$^1$H-NMR (CDCl$_3$, δ): 1.21 (3H, d, J=7.0 Hz), 1.35 (3H, d, J=6.6 Hz), 1.1–1.5 (5H, m), 1.5–2.2 (5H, m), 2.2–2.4 (1H, m), 2.35 (3H, s), 3.1–3.3 (1H, m), 3.80(1H, d, J=17.0 Hz), 4.34 (1H, s), 4.92 (1H, d J=17,0Hz), 7.1–7.4 (3H, m)
Mass (APCI)(e/z): 356 (M$^+$+1)

Preparation 63-1

(3RS)-3-Benzyloxycarbonylamino-1-cycloheptylcarbonylmethyl-2,3-dihydro-5,9-dimethyl-1H-1,4-benzodiazepin-2-one was obtained in a similar manner to that of Preparation 54-1.

IR (Nujol, cm$^{-1}$): 3400, 1720, 1670, 1620

Mass (APCI)(e/z): 476 (M$^+$+1)

$^1$H-NMR(CDCl$_3$, δ): 1.3–2.0 (12H, m), 2.32 (3H, s), 2.4–2.6 (1H, m), 2.61 (3H,s), 3.75 (1H, d, J=17 Hz), 5.10 (1H, d, J=17 Hz), 5.0–5.2 (2H, m), 5.24 (1H, d, J=8.7 Hz), 6.48 (1H, d, J=8.7 Hz), 7.1–7.5 (8H, m)

Preparation 63-2

(3RS)-3-Amino-1-cycloheptylcarbonylmethyl-2,3-dihydro-5,9-dimethyl-1H-1,4-benzodiazepin-2-one was obtained in a similar manner to that of Preparation 59-6.

IR (Nujol, cm$^{-1}$): 3360, 3320, 1720, 1670, 1620

$^1$H-NMR (CDCl$_3$, δ): 1.3–2.3 (12H, br), 2.32 (3H, s), 2.4–2.6 (1H, m), 2.60 (3H, s), 3.74 (1H, d, J=17 Hz), 4.39 (1H, s), 5.12 (1H, d, J=17 Hz), 7.1–7.5 (3H, m)

Mass (APCI)(e/z): 342 (M$^+$+1)

Preparation 64-1

(3RS)-3-Benzyloxycarbonylamino-1-cyclohexylcarbonylmethyl-5-cyclopropyl-2,3-dihydro-9-methyl-1H-1,4-benzodiazepin-2-one was obtained in a similar manner to that of Preparation 59-3.

IR (Nujol, cm$^{-1}$): 3300, 1715, 1665, 1605

$^1$H-NMR (CDCl$_3$, δ): 0.8–1.5 (10H, m), 1.5–1.9 (4H, m), 2.0–2.2 (1H, m), 2.2–2.4 (1H, m), 2.32 (3H, s), 3.78 (1H, d, J=17.0 Hz), 5.01 (1H, d, J=17.0 Hz), 5.0–5.2 (2H, m), 5.17 (1H, d, J=9 Hz), 6.33 (1H, d, J=9 Hz), 7.1–7.4 (7H, m), 7.6–7.7 (1H, m)

Mass (APCI)(e/z): 488 (M$^+$+1)

Preparation 64-2

(3RS)-3-Amino-1-cyclohexylcarbonylmethyl-5-cyclopropyl-2,3-dihydro-9-methyl-1H-1,4-benzodiazepin-2-one was obtained in a similar manner to that of Preparation 59-6.

IR (Nujol, cm$^{-1}$): 3400, 3310, 1720, 1680, 1610

$^1$H-NMR (CDCl$_3$, δ): 0.8–2.4 (16H, m), 2.32 (3H, s), 2.2–2.4 (1H, br), 2.7–2.9 (1H, m), 3.88 (1H, d, J=17 Hz), 4.32 (1H, s), 5.01 (1H, d, J=17 Hz), 7.1–7.4 (3H, m)

Mass (APCI)(e/z): 356 (M$^+$+1)

Preparation 65-1

(3RS)-3-Benzyloxycarbonylamino-1-cyclopentylcarbonylmethyl-2,3-dihydro-5,9-dimethyl-1H-1,4-benzodiazepin-2-one was obtained in a similar manner to that of Preparation 54-1.

Mass (APCI)(e/z): 448 (M$^+$+1)

Preparation 65-2

(3RS)-3-Amino-1-cyclopentylcarbonylmethyl-2,3-dihydro-5,9-dimethyl-1H-1,4-benzodiazepin-2-one was obtained in a similar manner to that of Preparation 59-6.

Preparation 66-1

(3RS)-1-(Azacyclooctan-1-yl)carbonylmethyl-3-benzyloxycarbonylmethyl-2,3-dihydro-5-ethyl-9-methyl-1H-1,4-benzodiazepin-2-one was obtained in a similar manner to that of Preparation 59-5.

IR (Nujol, cm$^{-1}$): 3380, 1700, 1670, 1640

$^1$H-NMR (CDCl$_3$, δ): 1.25 (3H, t, J=7.3 Hz), 1.3–1.9 (10H, m), 2.34 (3H, s), 2.8–3.0 (2H, m), 3.2–3.5 (4H, m), 3.71(1H, d, J=15.4 Hz), 5.0–5.2 (3H, m), 5.27 (1H, d, J=8.7 Hz), 6.50 (1H, d, J=8.7 Hz), 7.1–7.4 (8H, m)

Mass (APCI)(e/z): 505 (M$^+$+1)

Preparation 66-2

(3RS)-3-Amino-1-(azacyclooctan-1-yl)carbonylmethy-2,3-dihydro-5-ethyl-9-methyl-1H-1,4-benzodiazepin-2-one was obtained in a similar manner to that of Preparation 59-6.

IR (Nujol, cm$^{-1}$): 3380, 3270, 1670, 1640

$^1$H-NMR (CDCl$_3$, δ): 1.27 (3H, t, J=7.3 Hz), 1.3–2.0 (10H, br), 2.26 (2H, br), 2.34 (3H,s), 2.8–3.0 (2H, m), 3.2–3.6 (4H, m), 3.70 (1H, d, J=15.3 Hz), 4.41 (1H, s), 5.07 (1H, d, J=15.3 Hz), 7.1–7.4 (3H, m)

Mass (APCI)(e/z): 371 (M$^+$+1)

Preparation 67-1

(3RS)-1-(Azacyclooctan-1-yl)carbonylmethyl-3-benzyloxycarbonylamino-2,3-dihydro-5-isopropyl-9-methyl-1H-1,4-benzodiazepin-2-one was obtained in a similar manner to that of Preparation 59-5.

IR (Nujol, cm$^{-1}$): 3370, 1710, 1670, 1645

$^1$H-NMR (CDCl$_3$, δ): 1.22 (3H, d, J=7.0 Hz), 1.33 (3H, d, J=6.6 Hz), 1.3–1.9 (10H, m), 2.35 (3H, s), 3.1–3.6 (5H, m), 3.76 (1H, d, J=15.3 Hz), 4.96 (1H, d, J=15.3 Hz), 5.0–5.2 (2H, m), 5.22 (1H, d J=9 Hz), 6.48 (1H, d, J=9 Hz), 7.1–7.5 (8H, m)

Mass (APCI)(e/z): 519 (M$^+$+1)

Preparation 67-2

(3RS)-3-Amino-1-(azacyclooctan-1-yl)carbonylmethyl-2,3-dihydro-5-isopropyl-9-methyl-1H-1,4-benzodiazepin-2-one was obtained in a similar manner to that of Preparation 59-6.

IR (Nujol, cm$^{-1}$): 3350, 3280, 1675, 1640

$^1$H-NMR (CDCl$_3$, δ): 1.22 (3H, d, J=7.0 Hz), 1.34 (3H, d, J=6.6 Hz), 1.3–1.9 (10H, m), 2.23 (2H, br, s), 2.35 (3H, s), 3.1–3.6 (5H, m), 3.77 (1H, d, J=15.2 Hz), 4.36 (1H, s), 4.96 (1H, d, J=15.2 Hz), 7.1–7.4 (3H, m)

Mass (APCI)(e/z): 385 (M$^+$+1)

Preparation 68-1

(3RS)-1-(Azacyclooctan-1-yl)carbonylmethyl-3-benzyloxycarbonylamino-5-cyclopropyl-2,3-dihydro-9-methyl-1H-1,4-benzodiazepin-2-one was obtained in a similar manner to that of Preparation 59-5.

IR (Nujol, cm$^{-1}$): 3370, 1705, 1660, 1640

$^1$H-NMR (CDCl$_3$, δ): 0.8–1.1 (4H,m), 1.2–1.9 (10H, m), 2.0–2.2 (1H, m), 2.35 (3H, s), 3.3–3.5 (4H, m), 3.74 (1H, d, J=15.3 Hz), 5.02 (1H,d, J=15.3 Hz), 5.0–5.2 (2H, m), 5.19 (1H, d, J=9 Hz), 6.37 (1H, d, J=9 Hz), 7.2–7.4 (7H, m), 7.6–7.7 (1H, m)

Mass (APCI)(e/z): 517 (M$^+$+1)

Preparation 68-2

(3RS)-3-Amino-1-(azacyclooctan-1-yl)carbonylmethyl-5-cyclopropyl-2,3-dihydro-9-methyl-1 H-1,4-benzodiazepin-2-one was obtained in a similar manner to that of Preparation 59-6.

IR (Nujol, cm$^{-1}$): 3780, 3280, 1675, 1650

$^1$H-NMR (CDCl$_3$, δ): 0.8–1.1 (4H, m), 1.2–1.9 (10H, m), 1.9–2.2 (3H, m), 2.35 (3H, s), 3.2–3.6 (4H, m), 3.74 (1H, d, J=15.2 Hz), 3.97 (1H, s), 5.04 (1H, d, J=15.2 Hz), 7.1–7.4 (2H, m), 7.4–7.5 (1H, m)

Mass (APCI)(e/z): 383 (M$^+$+1)

Preparation 69-1

(3RS)-1-(Azacyclooctan-1-yl)carbonylmethyl-3-benzyloxycarbonylamino-2,3-dihydro-5-isobutyl-9-methyl-1H-1,4-benzodiazepin-2-one was obtained in a similar manner to that of Preparation 59-5.

IR (Nujol, cm$^{-1}$): 3400, 1710, 1670, 1640

$^1$H-NMR (CDCl$_3$, δ): 0.98 (6H, d, J=6.6 Hz), 1.4–1.9 (10H, m), 2.2–2.4 (1H, m), 2.36 (3H, s), 2.5–3.0 (2H, m), 3.3–3.5 (4H, m), 3.81(1H, d, J=5.5 Hz), 4.89 (1H, d, J=15.5 Hz), 5.0–5.2 (2H, m), 5.25 (1H, d, 9 Hz), 6.50 (1H, d, J=9 Hz), 7.1–7.5 (8H, m)

Mass (APCI)(e/z): 533 (M$^+$+1)

Preparation 69-2

(3RS)-3-Amino-1-(azacyclooctan-1-yl)carbonylmethyl-2,3-dihydro-5-isobutyl-9-methyl-1H-1,4-henzodiazepin-2-one was obtained in a similar manner to that of Preparation 59-6.

mp. 138.1–140.2° C.

IR (Nujol, cm$^{-1}$): 3370, 3300, 1675, 1635

$^1$H-NMR (CDCl$_3$, δ): 0.98 (6H, d, J=6.6 Hz), 1.4–1.9 (10H, m), 2.1–2.3 (3H, m), 2.36 (3H, s), 2.5–2.9 (2H, m), 3.3–3.5 (4H, m), 3.81 (1H, d, J=15.4 Hz), 4.40 (1H, s), 4.89 (1H, d, J=15.4 Hz), 7.1–7.4 (3 H, m)

Mass (APCI)(e/z): 399 (M$^+$+1)

Preparation 70-1

(3RS)-1-(Azacyclooctan-1-yl)carbonylmethyl-3-benzyloxycarbonylamino-5-cyclohexyl-2,3-dihydro-9-methyl-1H-1,4-benzodiazepin-2-one was obtained in a similar manner to that of Preparation 59-5.

IR (Nujol, cm$^{-1}$): 3380, 1710, 1670, 1645

$^1$H-NMR (CDCl$_3$, δ): 1.1–2.2 (20H, m), 2.35 (3H, s), 2.7–3.0 (1H, m), 3.2–3.6 (4H, m), 3.78 (1H, d, J=15.3 Hz), 4.91 (1H, d J=15.3 Hz), 5.0–5.2 (2H, m), 5.21 (1H, d, J=8.6 Hz), 6.49 (1H, d, J=8.6 Hz), 7.1–7.5 (8H, m)

Mass (APCI)(e/z): 559 (M$^+$+1)

Preparation 70-2

(3RS)-3-Amino-1-(azacyclooctan-1-yl)carbonylmethyl-5-cyclohexyl-2,3-dihydro-9-methyl-1H-1,4-benzodiazepin-2-one was obtained in a similar manner to that of Preparation 59-6.

mp. 174.1–175.6° C.

IR (Nujol, cm$^{-1}$): 3350, 3280, 1670, 1635

$^1$H-NMR (CDCl$_3$, δ): 1.2–2.1 (20H, m), 2.35 (3H, s), 2.7–2.9 (1H, m), 3.2–3.6 (4H, m), 3.79 (1H, d, J=15.2 Hz), 4.69 (1H, s), 4.92 (1H, d, J=15.2 Hz), 7.1–7.4 (3H, m)

Mass (APCI)(e/z): 425 (M$^+$+1)

Preparation 71

N-[(3RS)-1-(Azacyclooctan-1-yl)carbonylmethyl-2,3-dihydro-5,9-dimethyl-2-oxo-4-oxide-1H-1,4-benzodiazepin-3-yl]-N'-(3-methylphenyl)urea was obtained in a similar manner to that of Preparation 32.

mp. 253.6–255.4° C.

IR (Nujol, cm$^{-1}$): 3340, 1692, 1640

$^1$H-NMR (DMSO-d$_6$, δ): 1.2–1.9 (10H, m), 2.23 (3H, s), 2.38 (3H, s), 2.41 (3H, s), 2.9–3.6 (4H, m), 4.07 (1H, d, J=16 Hz), 4.99 (1H, d, J=16 Hz), 5.70 (1H, d, J=9.5Hz), 6.7–6.8 (1H, m), 7.0–7.6 (7H, m), 9.26 (1H, s)

Mass (APCI)(e/z): 506 (M$^+$+1)

Preparation 72-1

(3RS)-3-Benzyloxycarbonylamino-1-cyclooctylcarbonylmethyl-2,3-dihydro-5,9-dimethyl-1H-1,4-benzodiazepin-2-one was obtained in a similar manner to that of Preparation 54-1.

IR (Neat, cm$^{-1}$): 3400, 1730, 1690, 1670

$^1$H-NMR (CDCl$_3$, δ): 1.3–2.0 (14H, m), 2.33 (3H1, s), 2.61 (3H, s), 2.4–2.6 (1H, m), 3.75 (1H, d, J=17 Hz), 5.10 (1H, d, J=17 Hz), 5.0–5.2 (2H, m), 5.24 (1H, m), 6.48 (1H, d, J=8.7 Hz), 7.1–7.5 (8H, m)

Mass (APCI)(e/z): 490 (M$^+$+1)

Preparation 72-2

(3RS)-3-Amino-1-cyclooctylcarbonylmethyl-2,3-dihydro-5,9-dimethyl-1H-1,4-benzodiazepin-2-one was obtained in a similar manner to that of Preparation 59-6.

IR (Neat, cm$^{-1}$): 3400, 3300, 1725, 1690, 1660

$^1$H-NMR (CDCl$_3$, δ): 1.3–2.0 (14H, m), 2.16 (2H, s), 2.33 (3H, s), 2.4–2.6 (1H, m), 2.60 (3H, s), 3.74 (1H, d, J=17 Hz), 4.39 (1H, m), 5.12 (1H, d, J=17 Hz), 7.1–7.5 (3H, m)

Mass (APCI)(e/z): 356 (M$^+$+1)

Preparation 73-1

(3RS)-3-Benzyloxycarbonylamino-1-clohexylcarbonylmethyl-2,3-dihydro-5-isobutyl-9-methyl-1H-1,4-benzodiazepin-2-one was obtained in a similar manner to that of Preparation 59-3.

IR (Nujol, cm$^{-1}$): 3300, 1710, 1665

$^1$H-NMR (CDCl$_3$, δ): 0.97 (6H, d, J=6.6 Hz), 1.1–2.0 (10H, m), 2.1–2.3 (2H, m), 2.31 (3H, s), 2.5–3.0 (2H, m), 3.90 (1H, d, J=17.3 Hz), 4.83 (1H, d, J=17.3 Hz), 5.0–5.2 (2H, m), 5.23 (1H, d, J=8.7 Hz), 6.46 (1H, d, J=8.5 Hz), 7.1–7.5 (8H, m)

Mass (APCI)(e/z): 504 (M$^+$+1)

Preparation 73-2

(3RS)-3-Amino-1-cyclohexylcarbonylmethyl-2,3-dihydro-5-isobutyl-9-methyl-1H-1,4-benzodiazepin-2-one was obtained in a similar manner to that of Preparation 59-6.

IR (Neat, cm$^{-1}$): 3380, 3320, 1720, 1680, 1620

$^1$H-NMR (CDCl$_3$, δ): 0.98 (6H, d, J=6.6 Hz), 1.1–2.0 (10H, m), 2.0–2.4 (4H, m), 2.31 (3H, s), 2.5–2.9 (2H, m), 3.90 (1H, d, J=17 Hz), 3.38 (1H, m), 4.83 (1H, d, J=17 Hz), 7.1–7.4 (3H, m)

Mass (APCI)(e/z): 370 (M$^+$+1)

Preparation 74-1

(3RS)-1-Cyclohexylcarbonylmethyl-3-[N-t-butoxycarbonyl-(S)-phenylalanyl]amino-5-ethyl-9-methyl-2,3-dihydro-1H-1,4-benzodiazepin-2-one was obtained by reacting (3RS)-1-cyclohexylcarbonylmethyl-3-amino-5-ethyl-9-methyl-2,3-dihydro-1H-1,4-benzodiazepin-2-one with N-t-butoxycarbonyl-(S)-phenylalanine in a similar manner to that of Preparation 59-5.

$^1$H-NMR (CDCl$_3$, δ): 1.15–1.35 (9H, m), 1,37 (9H, s), 1.6–1.85 (4 H, m), 1.85–2.0 (1H, m), 2.2–2.4 (1H, m), 2.34 (3H, s), 2.85–3.1 (2H, m), 3.14–3.29 (1H, m), 3.75 (1H, d, J=17.2 Hz), 4.50 (1H, br, s), 4.94 (1H, hr, d), 5.06 (1H, d, J=17.2 Hz), 5.39–5.46 (1H, m), 7.19–7.5 (8H m), 7.61 (1H, br, d)

APCI-MS (m/z): =589 (M$^+$+1)

Preparation 74-2

A mixture of (3RS)-1-cyclohexylcarbonylmethyl-3-[N-t-butoxy-carbonyl-(S)-phenylalanyl]amino-5-ethyl-9-methyl-2,3-dihydro-1H-1,4-benzodiazepin-2-one (47.70 g, 81.02mmol) and 4N-solution of hydrogen chloride in ethyl acetate (800 ml) was stirred for 0.5 hour under cooling in an ice-bath and stirred for 3 hours at ambient temperature. After removal of hydrogen chloride as completely as possible by babbling of nitrogen gas, the solution was washed with a dilute aqueous solution of sodium bicarbonate twice and with water. After drying over magnesium sulfate, the solvent was evaporated in vacuo to give an oily mixture of diastereoisomers (35.51 g), which was separated by medium pressure liquid chromatography on silica gel eluting with a mixture of chloroform and methanol (20:1). The fractions containing the following A-isomer and B-isomer were collected and evaporated in vacuo to afford amorphous masses of pure A-isomer (11.81 g) and B-isomer (14.30 g) respectively.

A-isomer: (3R)-1-cyclohexylcarbonylmethyl-3-[(S)-phenylalanyl]amino-5-ethyl-9-methyl-2,3-dihydro-1H-1,4-benzodiazepin-2-one $^1$H-NMR (CDCl$_3$, δ): 1.05–1.45 (5H, m), 1,28 (31H, t, J=7.41 Hz), 1.60 (2H, s), 1.6–2.0 (51H, m), 2.25–2.43 (1H, m), 2.35 (3H, s), 2.60 (1H, dd, J=10.5 Hz, J=13.7 Hz), 2.93 (2H, q, J=7.4 Hz), 3.34 (1H, dd, J=3.5 Hz, J=13.7 Hz), 3.66 (1H, dd, J=3.5 Hz, J=10.5 Hz), 3.75 (1H, d, J=17.1 Hz), 5.08 (1H, d, J=17.1 Hz), 5.48 (1H, d, J=8.5 Hz), 7.15–7.45 (8H, m), 8.77 (1H, d, J=8.5 Hz)

APCI-MS (m/z): =489 (M$^+$+1)

B-isomer: (3S)-1-cyclohexylcarbonylmethyl-3-[(S)-phenylalanyl]amino-5-ethyl-9-methyl-2,3-dihydro-1H-1,4-benzodiazepin-2-one $^1$H-NMR (CDCl$_3$, δ): 1.05–1.45 (5H, m), 1,28 (3H, 1, J=7.4 Hz), 1.63 (2H, s), 1.6–2.0 (5H, m), 2.25–2.43 (1H, m), 2.34 (3H, s), 2.70 (1H, dd, J=10.5 Hz, J=13.7 Hz), 2.94 (2H, q, J=7.4 Hz), 3.31 (1H, dd, J=3.8 Hz, J=10.1 Hz), 3.64 (1H, dd, J=3.8 Hz, J=10.1 Hz), 3.74 (1H, d, J=17.1 Hz), 5.06 (1H, d, J=17.1 Hz), 5.46 (1H, d, J=8.5 Hz), 7.15–7.45 (8H, m), 8.73 (1H, d, J=8.5 Hz)

APCI-MS (m/z): 489 (M$^+$+1)

Preparation 74-3(1)

A mixture of (3S)-1-cyclohexylcarbonylmethyl-3-[(S)-phenylalanyl]-amino-5-ethyl-9-methyl-2,3-dihydro-1H-1,4-benzediazepin-2-one (14.30 g) and phenyl isothiocyanate (4.35 g) in methylene chloride (250 ml) was heated under stirring with vaporizing spontaneously. This vaporizing procedure was repeated three times. The resultant reaction mixture was evaporated in vacuo to remove methylene chloride completely. To the oil obtained above was added trifluoroacetic acid (200 ml) and the mixture was heated under stirring at 50° C. for 20 minutes. The mixture was evaporated in vacuo. The resultant residue was subjected to column chromatography on silica gel eluting with a mixture of chloroform and methanol (20:1). The fractions containing the desired product were combined and evaporated in vacuo to give an oily product, which was dissolved in ethyl acetate and washed with a diluted aqueous sodium bicarbonate. After drying over magnesium sulfate, the organic extract was concentrated in vacuo to afford (3S)-3-amino-1-cyclohexylcarbonylmethyl-5-ethyl-9-methyl-2,3-dihydro-1H-1,4-benzodiazepin-2-one (6.30 g, 63.1%) as an amorphous mass.

$^1$H-NMR (CDCl$_3$, δ): 1.05–1.4 (5H, m), 1.26 (3H, t, J=7.1 Hz), 1.55–1.95 (5H, m), 2.25–2.45 (1H, m), 2.32 (3H, s), 2.90 (2H, q, J=7.1 Hz), 2.96 (2H, br, s), 3.75 (1H, d, J=17.1 Hz), 4.46 (1H, s), 5.07 (1H, d, J=17.1 Hz), 7.15–7.4 (3H, m)

APCI-MS (m/z): 342 (M$^+$+1)

$[α]_D^{29.2}$=−6.59° (C=1.41, CHCl$_3$)

Preparation 74-3(2)

(3R)-3-Amino-1-cyclohexylcarbonylmethyl-5-ethyl-9-methyl-2,3-dihydro-1H-1,4-benzodiazepin-2-one was obtained in a similar manner to that of Preparation 74-3(1).

$^1$H-NMR (CDCl$_3$, δ): 1.05–1.4 (5H, m), 1.26 (3H, t, J=7.1 Hz), 1.55–1.95 (5H, m), 2.25–2.45 (1H, m), 2.32 (3H, s), 2.90 (2!H, q, J=7.1 Hz), 3.47 (2H, br, s), 3.75 (1H, d, J=17.1 Hz), 4.48 (1H, s), 5.07 (1H, d, J=17.1 Hz), 7.15–7.4 (3H, m)

APCI-MS (m/z): 342 (M$^+$+1)

$[α]_D^{30.4}$=5.78° (C=1.21, CHCl$_3$)

EXAMPLE 1(1)

To a solution of (3RS)-3-amino-1-[3-azabicyclo[3.2.2]non-3-yl)carbonylmethyl]-2,3-dihydro-5-isopropyl-1H-1,4-benzodiazepin-2-one (0.200 g) in dry methylene chloride (10 ml) was added dropwise a solution of 3-methoxyphenyl isocyanate (0.086 g) in dry methylene chloride (5 ml) at 5–10° C. in an ice-bath. The mixture was allowed to warm to room temperature and stirred overnight.

The reaction mixture was washed with a saturated aqueous sodium hydrogen carbonate (10 ml) and a brine (10 ml). The organic layer was dried over anhydrous magnesium sulfate and evaporated in vacuo. The residue was subjected by column chromatography on silica gel with a mixture of chloroform and methanol (10:1) as an eluent to afford N-[(3RS)-1-(3-azabicyclo[3.2.2]non-3-yl)carbonylmethyl-2,3-dihydro-5-isopropyl-2-oxo-1H-1,4-benzodiazepin-3-yl]-N'-(3-methoxyphenyl)urea (0.270 g).

mp: 139–142° C.

IR(KBr): 3350, 2933, 2864, 1659, 1601, 1548, 1492, 1428, 1201, 762cm$^{-1}$ $^1$H-NMR (CDCl$_3$, δ): 1.02 (3H, d, J=7.2 Hz), 1.29 (3H, d, J=7.2 Hz), 1.55–1.80 (8H, m), 2.02–2.10 (2H, m), 3.15–3.24 (1H, m), 3.44–3.80 (4H, m), 4.42 (1H, d, J=17.2 Hz), 4.89 (1H, d, J=17.2 Hz), 5.50 (1H, d, J=8.0 Hz), 6.55 (1H, d, J=8.4 Hz), 6.81 (1H, d, J=8.4 Hz), 6.90 (1H, d, J=8.4 Hz), 7.07–7.32 (8H, m), 7.47 (1H, 1, J=7.2 Hz), 7.57 (1H, d, J=7.2 Hz)

Mass: m/e=532 (M$^+$+1)

EXAMPLE 1(2)

The following compound was prepared in a similar manner to that of Example 1(1).

N-[(3RS)-1-(3-azabicyclo[3.2.2]non-3-yl)carbonylmethyl-2,3-dihydro-5-isopropyl-2-oxo-1H-1,4-benzodiazepin-3-yl]-N'-(3-methylthiophenyl)urea mp: 134–135° C.

IR(KBr): 3350, 2931, 1659, 1541, 1451, 1201, 766cm$^{-1}$ $^1$H-NMR (CDCl$_3$, δ): 0.99 (3H, d, J=6.8 Hz), 1.29 (3H, d, J=6.8 Hz), 1.50–1.90 (8H, m), 2.00–2.10 (2H, m), 2.41 (3H, s), 3.10–3.22 (1H, m), 3.40–3.84 (4H, m), 4.41 (1H, d, J=16.0 Hz), 4.91 (1H, d, J=16.0 Hz), 5.48 (1H, d, J=7.6 Hz), 6.85–7.31 (7H, m), 7.37 (1H, s), 7.46 (1H, t, J=7.2 Hz), 7.55 (1H, t, J=7.2 Hz)

Mass: m/e=548 (M$^+$+1)

EXAMPLE 1(3)

The following compound was prepared in a similar manner to at of Example 1(1).

N-[(3RS)-1-(3-azabicyclo[3.2.2]non-3-yl)carbonylmethyl-2,3-dihydro-5-isopropyl-2-oxo-1H-1,4-benzodiazepin-3-yl]-N'-phenylurea mp: 132–135° C.

IR(KBr): 3362, 2932, 1657, 1598, 1546, 1496, 1449, 1201, 756cm$^{-1}$ $^1$H-NMR (CDCl$_3$, δ): 0.99 (3H, d, J=6.8 Hz), 1.28 (3H, d, J=6.8 Hz), 1.50–1.90 (8H, m), 1.90–2.10 (2H, m), 3.10–3.20 (1H, m), 3.13–3.75 (4H, m), 4.43 (1H, d, J=16.0 Hz), 4.76 (1H, d, J=16.0 Hz), 5.48 (1H, d, J=8.0 Hz), 6.90–7.53 (11H, m)

Mass: m/e=502 (M$^+$+1)

EXAMPLE 1(4)

The following compound was prepared in a similar manner to that of Example 1(1).

N-[(3RS)-1-(3-azabicyclo[3.2.2]non-3-yl)carbonylmethyl-2,3-dihydro-5-isopropyl-2-oxo-1H-1,4-benzodiazepin-3-yl]-N'-cyclohexylurea mp: 138–140° C.

IR(KBr): 3373, 2930, 2861, 1658, 1546, 1451, 1201, 762 cm$^{-1}$ $^1$H-NMR (CDCl$_3$, δ): 0.98 (3H, d, J=6.8 Hz), 1.00–1.20 (6H, m), 1.28 (3H, d, J=6.8 Hz), 1.40–2.10 (14H, m), 3.10–3.20 (1H, m), 3.40–3.84 (2H, m), 4.37 (1H, d, J=16.4 Hz), 4.54 (1H, d, J=7.2 Hz), 4.86 (1H, d, J=16.4 Hz), 5.40 (1H, d, J=7.6 Hz), 6.17 (1H,d, J=7.6 Hz), 7.20–7.60 (4H, m)

Mass: m/e=508 (M$^+$+1)

EXAMPLE 2

To a solution of (3RS)-1-(2-acetylthiophen-3-yl)methyl-3-amino-2,3-dihyro-5-isporopyl-1H-1,4-benzodiazepin-2-one (0.230 g) in dry tetrahydrofuran (20 ml) was added dropwise a solution of 3-methylphenyl isocyanate (0.095 g) in dry tetrahydrofuran (5 ml) at 5~10° C. in an ice-bath for 10 minutes. The mixture was allowed to warm to room temperature and stirred at ambient temperature for 3 hours. The resultant mixture was concentrated in vacuo and the residue was subjected by column chromatography on silica gel with a mixture of chloroform and ethyl acetate (10:1). The fractions containing the desired compound were combined and evaporated in vacuo to afford N-[(3RS)-1-(2-acetylthiophen-3-yl)methyl-2,3-dihydro-5-isopropyl-2-oxo-1H-1,4-benzodiazepin-3-yl]-N'-(3 -methylphenyl)urea (0.210 g).

mp: 219–221° C. (dec.)

IR(KBr): 3324, 2968, 2926, 1661, 1649, 1559, 1491, 1415, 1381, 1247, 1165, 774, 692cm$^{-1}$ $^1$H-NMR (CDCl$_3$, δ): 0.89 (3H, d, J=6.8 Hz), 1.29 (3H, d, J=6.8 Hz), 2.26(3H, s), 2.49(3H, s), 3.10–3.20 (1H, m), 5.32(1H, d, J=17.2 Hz), 5.50 (1H, d, J=8.0 Hz), 5.68 (1H, d, J=17.2 Hz), 6.80–7.55 (12H, m)

Mass: m/e=489 (M$^+$+1)

EXAMPLE 3

To a suspension of sodium hydride (0.030 g of a 65% dispersion in mineral oil) in dry N,N-dimethylformamide (5 ml) was added gradually N-[(3RS)-2,3-dihydro-5-isopropyl-2-oxo-1H-1,4-benzodiazepin-3-yl]-N'-(3-methylphenyl) urea (0.250 g) at 5~10° C. in an ice-bath for 30 minutes. The mixture was stirred at the same temperature for 1 hour and then at room temperature for 2 hours. To the above mixture was added dropwise a solution of N-bromomethylcarbonyl-3-azabicyclo[3.2.2]nonane (0.200 g) in dry N,N-dimethylformamide (5 ml) for 10 minutes and stirred at ambient temperature overnight. The reaction mixture was concentrated in vacuo and the residue was taken up with ethyl acetate (100 ml) and a saturated aqueous sodium hydrogen carbonate (50 ml). The organic layer was separated, washed with a brine (50 ml), dried over anhydrous magnesium sulfate and evaporated in vacuo to give a crude product. The product was purified by column chromatography on silica gel with a mixture of chloroform and ethyl acetate (10:1) as an eluent. The fractions containing the desired compound were combined and evaporated in vacuo to afford N-[(3RS)-1-(3-azabicyclo[3.2.2]non-3-yl) carbonylmethyl-2,3-dihydro-5-isopropyl-2-oxo-1H-1,4-benzodiazepin-3-yl]-N'-(3-methylphenyl)urea (0.160 g).

mp: 123–126° C.

IR(KBr): 3364, 2929, 2862, 1660, 1616, 1554, 1451, 1201cm$^{-1}$ $^1$H-NMR (CDCl$_3$, δ): 0.99 (3H, d, J=7.2 Hz), 1.29 (3H, d, J=7.2 Hz), 1.50–1.80 (8H, m), 2.00–2.10 (2H, m), 2.28 (3H, s), 3.10–3.22 (1H, m), 3.42–3.82 (4H, m), 4.42 (1H, d, J=17.2 Hz), 4.87 (1H, d, J=17.2 Hz), 5.47 (1H, d, J=8.0 Hz), 6.72 (1H, d, J=8.4 Hz), 6.81 (1H, d, J=7.4 Hz), 7.07–7.56 (8H, m)

Mass: m/e=516 (M$^+$+1)

EXAMPLE 4

To a solution of (3RS)-3-amino-1-(3-azabicyclo[3.2.2] non-3-yl)carbonylmethyl-2,3-dihydro-5-isopropyl-1H-1,4-benzodiazepin-2-one (0.165 g) in N,N-dimethylformamide (5 ml) was added gradually 4-nitrophenyl N-(3-acetylphenyl)carbonate (0.155 g) and then dropwise triethylamime (0.087 g) at 5~10° C. in an ice-bath and the mixture was stirred at ambient temperature overnight. The resultant mixture was concentrated in vacuo. The residue was taken up with ethyl acetate (100 ml) and a saturated aqueous sodium hydrogen carbonate (50 ml) and washed with a brine (50 ml). Dryness over anhydrous magnesium sulfate and evaporation gave a crude product. The crude product was purified by column chromatography on silica gel with a mixture of chloroform and methanol (50:1) as an eluent to afford N-[(3RS)-1-(3-azabicyclo[3.2.2]non-3-yl) carbonylmethyl-2,3-dihydro-5-isopropyl-2-oxo-1H-1,4-benzodiazepin-3-yl]-N'-(3-acetylphenyl)urea (0.190 g).

mp: 138–140° C.

IR(KBr): 3363, 2933, 2865, 1682, 1661, 1550, 1488, 1217, 1202cm$^{-1}$ $^1$H-NMR (CDCl$_3$, δ): 0.99 (3H, d, J=7.2 Hz), 1.29 (3H, d, J=7.2 Hz), 1.56–1.80 (8H, m), 2.00–2.16 (2H, m), 2.49 (3H, s), 3.14–3.22 (1H, m), 3.44–3.84 (4H, m), 4.49 (1H, d, J=16.0 Hz), 4.98 (1H, d, J=16.0 Hz), 5.51 (1H, d, J=7.6 Hz), 7.10–7.64 (9H, m), 7.93 (1H, s)

Mass: m/e=534 (M$^+$+1)

EXAMPLE 5

To a solution of (3RS)-3-amino-1-(3-azabicyclo[3.2.2] non-3-yl)carbonylmethyl-2,3-dihydro-5-isopropyl-1H-1,4-benzodiazepin-2-one (0.170 g) in dry tetrahydrofuran was added gradually 4-nitrophenyl N-[3-(tetrazol-5-yl)phenyl] carbamate (0.152 g) and then dropwise a solution of triethylamime (0.090 g) in tetrahydrofuran (5 ml) at room temperature. The mixture was stirred at ambient temperature overnight. The mixture was concentrated in vacuo and the residue was subjected by column chromatography on silica gel with a mixture of chloroform and methanol (100:1) as an eluent to afford N-[(3RS)-1-(3-azabicyclo[3.2.2]non-3-yl) carbonylmethyl-2,3-dihydro-5-isopropyl-2-oxo-1H-1,4-benzodiazepin-3-yl]-N'-[3-(tetrazo]-5-yl)phenyl]urea (0.150 g).

mp: 220° C. (dec.)

IR(KBr): 3347, 2933, 2866, 1655, 1584, 1452, 1273, 1204, 758cm$^{-1}$ $^1$H-NMR (DMSO-d$_6$, δ): 0.91 (3H, d, J=7.2 Hz), 1.29 (3H, d, J=7.2 Hz), 1.40–1.80 (8H, m), 1.90–2.10 (2H, m), 3.20–3.30 (1H, m), 3.30–3.80 (4H, m ), 4.64 (1H, d, J=16.8 Hz ), 4.93 (1H, d, J=16.8 Hz), 5.17 (1H, d, J=8.4 Hz), 7.28–7.60 (9H, m), 7.99 (1H, s) 9.14 (1H, s)

Mass: m/e=558 (M$^+$+1)

EXAMPLE 6(1)

To a suspension of sodium hydride (0.027 g of a 64% dispersion in mineral oil) in N,N-dimethylformamide (3 ml) was added gradually N-[(3RS)-2,3-dihydro-5-(2-methylpropyl)-2-oxo-1H-1,4-benzodiazepin-3-yl]-N'-(3-methylphenyl)urea (0.200 g) at ambient temperature and the mixture was stirred for 1 hour under the same conditions. To the mixture was added sodium iodide (0.107 g) and followed dropwise a solution of 2-chloromethyl-3-methylpridine (0.093 g,) in N,N-dimethylformamide (2 ml) at the same temperature. The resultant mixture was concentrated in vacuo and the residue was taken up with ethyl acetate and water. The aqueous layer was extracted with another ethyl acetate. The combined organic layer was dried over sodium sulfate, filtered and concentrated in vacuo to give a crude compound. The crude compound was recrystallized with isopropyl ether and chloroform to give N-[(3RS)-2,3-dihydro-5-(2-methylpropyl)-1-(3-methylpyridin-2-yl) methyl-2-oxo-1H-1,4-benzodiazepin-3-yl]-N'-(3-methylphenyl)urea (0.23 g) as a colorless powder.

mp: 185–187° C.

IR(KBr): 2956, 1695, 1649, 1614, 1564, 1492, 1447, 1384, 1214, 778cm$^{-1}$ $^1$H-NMR (DMSO-d$_6$, δ): 0.79 (3H, d, J=8 Hz), 0.87 (3H, d, J=8 Hz), 1.82–1.88 (1H, m), 2.24 (3H, s), 2.35 (3H, s), 2.46 (1H, dd, J=16 Hz, J=16 Hz), 2.86 (1H, dd, J=8 Hz, J=16 Hz), 5.15 (2H, q, J=18 Hz), 5.20 (1H, s), 6.73 (1H, d, J=8 Hz), 7.10–7.57 (9H, m), 7.74 (1H, d, J=8 Hz), 8.23 (1H, d, J=8 Hz), 8.87 (1H, s)

Mass: m/e=469 (M$^+$+1)

EXAMPLE 6(2)

The following compound was prepared in a similar manner to that of Example 3.

N-[(3RS)-2,3-dihydro-5-(2-methylpropyl)-1-(3-azabicyclo[3.2.2]non-3-yl)methyl-2-oxo-1H-1,4-benzodiazepin-3-yl]-N'-(3-methylphenyl)urea mp: 95–100° C.

IR(KBr): 2932, 1653, 1558, 1456, 1204, 774cm$^{-1}$ $^1$H-NMR (CDCl$_3$, δ): 0.78 (3H, d, J=8 Hz), 0.88 (3H, d, J=8 Hz), 1.57–1.88 (8H, m), 2.08 (3H, br), 2.78 (3H, s), 2.50 (1H, dd, J=16 Hz, J=16 Hz), 2.88 (1H, dd, J=8 Hz, J=16 Hz), 3.48–3.85 (4H, m), 4.20 (1H, d, J=18 Hz), 5.00 (1H, d, J=18 Hz), 5.48 (1H, d, J=8 Hz), 6.69–7.55 (10H, m)

Mass: m/e=530 (M$^+$+1)

EXAMPLE 6(3)

The following compound was prepared in a similar manner to that of Example 3.

N-[(3RS)-2,3-dihydro-5-(2-methylpropyl)-1-(2-methylcarbonylthiophen-3-yl)methyl-2-oxo-1,4-benzodiazepin-3-yl]-N'-(3-methylphenyl)urea mp: 215–218° C.

IR(KBr): 3347, 2954, 1664, 1646, 1561, 1490, 1448, 1415, 1384, 1310, 1216, 1165, 772cm$^{-1}$ $^1$H-NMR (DMSO-d$_6$, δ): 0.70 (3H, d, J=8 Hz), 0.80 (3H, d, J=8 Hz), 1.70–1.80 (1H, m), 2.18 (3H, s), 2.40 (3H, s), 2.50 (1H, dd, J=16 Hz, J=16 Hz), 2.78 (1H, dd, J=8 Hz, J=16 Hz), 5.10 (1H, d, J=18 Hz), 5.16 (1H, d, J=8 Hz), 5.40 (1H, d, J=16 Hz), 6.68 (1H, d, J=8 Hz), 6.85 (1H, d, J=8 Hz), 7.03–7.13 (3H, m), 7.23–7.33 (3H, m), 7.49 (1H, t, J=8 Hz), 7.71 (1H, d, J=10 Hz), 7.78 (1H, d, J=6 Hz), 8.81 (1H, s)

Mass: m/e=502 (M$^+$+1)

EXAMPLE 7

The following compound was prepared in a similar manner to that of Example 4.

N-[(3RS)-1-(3-azabicyclo[3.2.2]non-3-yl)carbonylmethyl-2,3-dihydro-5-(2-methylpropyl)-2-oxo-1H-1,4-benzodiazepin-3-yl]-N'-(3-tetrazolyphenyl)urea mp: 212–215° C.

IR(KBr): 3364, 2935, 1659, 1569, 1452, 1385, 1215, 1016, 761cm$^{-1}$ $^1$H-NMR (DMSO-d$_6$, δ): 0.74 (3H, d, J=8 Hz), 0.85 (3H, d, J=8 Hz), 1.03 (2H, d, J=6 Hz), 1.20–1.82 (8H, m), 2.02 (2H, br), 2.43 (1H, dd, J=16 Hz, J=16 Hz), 2.95 (1H, dd, J=8 Hz, J=16 Hz), 3.47 (2H, d, J=18 Hz), 3.66 (1H, dd, J=8HZ, J=16 Hz), 3.83 (1H, dd, J=8 Hz, J=16 Hz), 4.52 (1H, d, J=18 Hz), 4.95 (1H, d, J=18 Hz), 5.18 (1H, d, J=8 Hz), 7.27–7.79 (8H, m), 8.05 (1H, s), 9.22 (1H, s)

Mass: m/e=584 (M$^+$+1)

EXAMPLE 8(1)

The following compound was prepared in a similar manner to that of Example 6(1).

N-[(3RS)-2,3-dihydro-5-methyl-1-(3-methylpyridin-2-yl)methyl-2-oxo-1H-1,4-benzodiazepin-3-yl]-N'-(3-methylphenyl)urea mp: 225–229° C.

IR(KBr): 3323, 1677, 1644, 1611, 1562, 1492, 1449, 1387, 1312, 1217, 1165, 776cm$^{-1}$ $^1$H-NMR (DMSO-d$_6$, δ): 1.58 (3H, d, J=8 Hz), 2.26 (3H, s), 4.27 (1H, d, J=16 Hz), 4.60 (1H, d, J=16 Hz), 5.33 (1H, q, J=8 Hz), 6.76 (1H, s ), 6.78 (1H, d, J=8 Hz ), 6.99–7.26 (13H, m ), 9.01 (1H, s)

Mass m/e=427 (M$^+$)

EXAMPLE 8(2)

The following compound was prepared in a similar manner to that of Example 3.

N-[(3RS)-1-(3-azabicyclo[3.2.2]non-3-yl)carbonylmethyl-2,3-dihydro-5-methyl-2-oxo-1H-1,4-benzodiazepin-3-yl]-N'-(3-methylphenyl)urea mp: 150–153° C.

IR(KBr): 3343, 2931, 1959, 1675, 1554, 1206, 1167cm$^{-1}$ $^1$H-NMR (DMSO-d$_6$, δ): 1.03 (2H, d, J=6 Hz), 1.50–1.70 (8H,m), 1.98 (1H, br), 2.04 (1H, br), 2.23 (3H, s), 2.40 (3H, s), 3.48 (1H, br), 3.58–3.69 (21, m), 4.65 (1H, d, J=16 Hz), 4.90 (1H, d, J=16 Hz), 5.10 (1H, d, J=8 Hz), 6.72 (1H, J=8 Hz), 7.07–7.18 (3H, m), 7.31–7.38 (2H, m), 7.60 (1H, t, J=8 Hz), 7.78 (1H, d, J=8 Hz), 8.90 (1H, s)

Mass: m/e=487 (M$^+$+1)

EXAMPLE 8(3)

The following compound was prepared in a similar manner to that of Example 3.

N-[(3RS)-1-(2-acetylthiophen-3-yl)methyl-2,3-dihydro-5-methyl-2-oxo-1H-1,4-benzodiazepin-3-yl]-N'-(3-methylphenyl)urea mp: 215–219° C.

IR(KBr): 3307, 1676, 1554, 1491, 1449, 1415, 1382, 1311, 1217, 1165, 770cm$^{-1}$ $^1$H-NMR (DMSO-d$_6$, δ): 2.23 (3H, s), 2.44 (3H, s), 5.18 (1H, d, J=8 Hz), 5.30 (1H, d, J=16 Hz), 5.41 (1H, d, J=16 Hz), 6.72–6.76 (2H, m), 7.08–7.37 (9H, m), 7.56 (1H, t, J=8 Hz), 7.79 (1H, d, J=8 Hz), 7.83 (1H, d, J=6 Hz), 8.91 (1H, s)

Mass: m/e=461 (M$^+$+1)

EXAMPLE 9(1)

The following compound was prepared in a similar manner to that of Example 6(1).

N-[(3RS)-2,3-dihydro-5-(3-methylbutyl)-1-(3-methylpyridin-2-yl)methyl-2-oxo-1H-1,4-benzodiazepin-3-yl]-N'-(3-methylphenyl)urea mp: 151–154° C.

IR(KBr): 2955, 1644, 1612, 1555, 1492, 1384, 1308, 1206, 1165, 778, 692cm$^{-1}$ $^1$H-NMR (DMSO-d$_6$, δ): 0.74 (3H, q, J=8 Hz), 0.81 (3H, d, J=8 Hz), 1.17–1.50 (3H, m), 2.17 (3H, s), 2.45–2.76 (2H, m), 3.33 (3H, s), 4.92 (1H, d, J=16 Hz), 5.05 (1H, d, J=18 Hz), 5.12 (1H, d, J=16 Hz), 5.20 (1H, d, J=18 Hz), 6.67 (1H, d, J=8 Hz), 7.02–7.27 (5H, m), 7.46–7.51 (2H, m), 7.66 (1H, d, J=8 Hz), 7.71 (1H, d, J=8 Hz), 8.11 (1H, d, J=6 Hz), 8.83 (1H, d, J=16 Hz)

Mass: m/e=484 (M$^+$+1)

EXAMPLE 9(2)

The following compound was prepared in a similar manner to that of Example 6(3).

N-[(3RS)-1-(2-acetylthiophen-3-yl)methyl-2,3-dihydro-5-(3-methylbutyl)-2-oxo-1H-1,4-benzodiazepin-3-yl]-N'-(3-methylphenyl)urea mp: 190–195° C.

IR(KBr): 3329, 2955, 1645, 1551, 1492, 1413, 1383, 1215, 1165, 774cm$^{-1}$ $^1$H-NMR (CDCl$_3$, δ): 0.80 (3H, t, J=8 Hz), 0.85 (3H, d, J=8 Hz), 1.20–1.54 (3H, m), 1.68 (2H, s), 2.27 (3H, s), 2.49 (3H, s), 2.75 (2H, d, J=10 Hz), 5.34 (1H, d, J=18 Hz), 5.52 (1H, d, J=8 Hz), 5.65 (1H, d, J=18 Hz), 6.80–7.56 (10, m)

Mass: m/e=517 (M$^+$+1)

EXAMPLE 10

The following compound was prepared in a similar manner to that of Example 3.

N-[(3RS)-1-(3-azabicyclo[3.2.2]non-3-yl)carbonylmethyl-2,3-dihydro-5-ethyl-2-oxo-1H-1,4-benzodiazepin-3-yl]-N'-(3-methylphenyl)urea mp: 115–120° C.

IR(KBr): 3358, 2963, 2932, 2866, 1659, 1630, 1569, 1489, 1451, 1265, 1214, 1204, 1016cm$^{-1}$ $^1$H-NMR (CDCl$_3$, δ): 1.14 (3H, t, J=7.2 Hz), 1.50–1.80 (8H, m), 2.00–2.10 (2H, m), 2.27 (3H, s), 2.73–2.95 (2H1, m), 3.40–3.80 (4H, m), 4.50 (1H, d, J=16.0 Hz), 4.87 (1H, d, J=16.0 Hz), 5.51 (1H, d, J=7.2 Hz), 6.66 (1H, s), 6.80–7.60 (9H, m)

EXAMPLE 11

The following compound was prepared in a similar manner to that of Example 2.

N-[(3RS)-1-(3-azabicyclo[3.2.2]non-3-yl)carbonylmethyl-5-butyl-2,3-dihydro-2-oxo-1H-1,4-benzodiazepin-3-yl]-N'-(3-methylphenyl)urea mp: 121–123° C.

IR(KBr): 3348, 2931, 2864, 1659, 1599, 1555, 1490, 1451, 202, 774cm$^{-1}$ $^1$H-NMR (CDCl$_3$, δ): 0.85 (3H, t, J=7.6 Hz), 1.29 (2H, q, J=7.2 Hz), 1.40–1.80 (10H, m), 2.00–2.10 (2H, m), 2.27 (3H, s), 2.72–2.88 (2H, m), 3.44–3.80 (4H, m), 4.39 (1H, d, J=16.4 Hz), 4.91 (1H, d, J=16.4 Hz), 5.49 (1H, d, J=7.2 Hz), 6.80–7.57 (10H, m)

Mass: m/e=530 (M$^+$+1)

EXAMPLE 12(1)

The following compound was prepared in a similar manner to that of Example 1(1).

N-[(3RS)-1-(3-azabicyclo[3.2.2]non-3-yl)carbonylmethyl-5-cyclohexylmethyl-2,3-dihydro-2-oxo-1H-1,4-benzodiazepin-3-yl]-N'-(3-methylphenyl)urea mp: 164–166° C.

IR(KBr): 2916, 2846, 2400, 1678, 1657, 1592, 1556, 1476, 1444, 1194cm$^{-1}$ $^1$H-NMR (DMSO-d$_6$, δ): 0.80–1.20 (4H, m), 1.50–1.80 (15H, m), 1.99–2.05 (2H, m), 2.23 (3H, s), 2.50–2.55 (1H, m), 2.95–2.98 (1H, m), 3.43–3.79 (4H, m), 4.64 (1H, d, J=17 Hz), 4.93 (1H, d, J=17 Hz), 5.20 (1H, d, J=4.0 Hz), 6.73 (1H, d, J=7.0 Hz), 7.07–7.24 (3H, m), 7.35–7.42 (3H, m), 7.65 (1H, t, J=8 Hz), 7.82 (1H, d, J=7.0 Hz), 9.04 (1H, s)

Mass: m/e=571 (M$^+$+1)

EXAMPLE 12(2)

The following compound was prepared in a similar manner to that of Example 4.

N-[(3RS)-1-(3-azabicyclo[3.2.2]non-3-yl)carbonylmethyl-5-cyclohexylmethyl-2,3-dihydro-2-oxo-1H-1,4-benzodiazepin-3-yl]-N'-[3-(tetrazol-5-yl)phenyl]urea mp: 218–222° C. (dec.)

IR(KBr): 3370, 3354, 2925, 2862, 1689, 1740, 1630, 1489, 1450, 1214, 1204cm$^{-1}$ $^1$H-NMR (DMSO-d$_6$, δ): 0.80–1.2 (4H, m), 1.50–1.80 (15H, m), 1.90–2.40 (2H, m), 2.40–2.50 (1H, m), 2.80–2.90 (1H, m), 3.50–3.80 (4H, m), 4.56 (1H, d, J=17 Hz), 4.95 (1H, d, J=17 Hz), 5.14 (1H, d, J=8.0 Hz), 7.29 (1H, d, J=8.0 Hz), 7.36–7.48 (4H, m), 7.56–7.63 (2H, m), 7.76 (1H, d, J=8.0 Hz), 8.07 (1H, s), 9.20 (1H, s)

Mass: m/e=623 (M$^+$)

EXAMPLE 13-1

N-[(3RS)-2,3-dihydro-5-(2-fluorophenyl)-1-(2-methoxyphenacyl)-9-methyl-2-oxo-1H-1,4-benzodiazepin-3-yl]-N'-[3-(tetrazol-5-yl)phenyl]urea was prepared in a similar manner to that of Example 51.

mp: 193.9–195.2° C.

IR (Nujol, cm$^{-1}$): 1650

$^1$H-NMR (DMSO-d$_6$, δ): 2.5 (3H, br, s), 3.95 (3H, s), 4.66 (1 H, d, J=18.0 Hz), 5.40 (1H, d, J=0.3 Hz), 5.46 (1H, d, J=18.0 Hz), 6.9–7.8 (15H, m ), 7.95 (1H, br, s ), 8.21 (1H, br, s ), 9.35 (1H, br, s)

Mass (APCI): 619 (M$^+$+1)

EXAMPLE 13-2

A mixture of N-[(3RS)-2,3-dihydro-5-(2-fluorophenyl)-1-(2-methoxyphenacyl)-9-methyl-2-oxo-1H-1,4-benzodiazepin-3-yl]-N'-[3-(tetrazol-5-yl)phenyl]urea (200 mg) and 1N boron tribromide in methylene chloride (3.87 ml) was stirred at 0° C. under nitrogen stream for 4 hours and allowed to stand in a refrigerator overnight. Ethyl acetate and water were added to the reaction mixture. The separated organic layer was washed with water and brine, and then dried over magnesium sulfate. The solvent was evaporated in vacuo to afford a pale brown powder, which was washed with diisopropyl ether and collected by filtration to give N-[(3RS)-2,3-dihydro-5-(2-fluorophenyl)-1-(2-hydroxyphenacyl)-9-methyl-2-oxo-1H-1,4-benzodiazepin-3-yl]-N'-[3-(tetrazol-5-yl)phenyl]urea (202.0 mg) as a crystalline powder.

mp: 220.8–225.0° C.

IR (Nujol, cm$^{-1}$): 1640

$^1$H-NMR (DMSO-d$_6$, δ): 4.67 (1H, d, J=18.1 Hz), 5.56 (1H, d, J=18.1 Hz), 6.7–7.9 (15H, m), 8.22 (1H, br, s), 9.37 (1H, br, s)

Mass (FAB): 605 (M$^+$+1)

EXAMPLE 13-3

A mixture of N-[(3RS)-2,3-dihydro-5-(2-fluorophenyl)-1-(2-hydroxyphenacyl)-9-methyl-2-oxo-1H-1,4-benzodiazepin-3-yl]-N'-[3-(tetrazol-5-yl)phenyl]urea (150 mg), triethylamine (75 mg) and chlorotriphenylmethane (69 mg) in a mixture of N,N-dimethylformamide and tetrahydrofuran (1:3, 4 ml) was stirred overnight. Ethyl acetate and a saturated aqueous solution of sodium bicarbonate were added to the reaction mixture. The separated organic layer was washed with water and brine, and then dried over sodium sulfate. The solvent was evaporated in vacuo to afford an amorphous mass, which was triturated in diisopropyl ether and collected by filtration to afford N-[(3RS)-

2,3-dihydro-5-(2-fluorophenyl)-1-(2-hydroxyphenacyl)-9-methyl-2-oxo-1H-1,4-benzodiazepin-3-yl]-N'-{3-[1-(triphenylmethyl)tetrazol-5-yl]phenyl}urea (186.0 mg, 88.6% yield) as a crystalline powder.

mp: 132.1–146.0° C.

IR (Nujol, cm$^{-1}$): 1640

$^1$H-NMR (DMSO-d$_6$, δ): 2.5 (3H, br, s), 4.81 (1H, d, J=18.4 Hz), 5.39 (1H, d, J=8.4 Hz), 5.68 (1H, d, J=18.0 Hz), 6.8–7.8 (30H, m), 8.08 (1H, br, s)

Mass (FAB): 847 (M$^+$+1)

EXAMPLE 13-4

N-[(3RS)-1-(2-Ethoxycarbonylmethoxyphenyl)carbonylmethyl-2,3-dihydro-5-(2-fluorophenyl)-9-methyl-2-oxo-1H-1,4-benzodiazepin-3-yl]-N'-{3-[1-(triphenylmethyl)tetrazol-5-yl]phenyl}urea was prepared in a similar manner to that of Preparation 59-3.

IR (Neat, cm$^{-1}$): 1700

$^1$H-NMR (DMSO-d$_6$, δ): 0.97 (3H, t, J=7.1 Hz), 2.30 (3H, s), 3.89 (2H, q, J=7.1 Hz), 4.21 (1H, d, J=16.8 Hz), 4.68 (1H, d, J=16.8 Hz), 5.05 (2H, s), 5.20 (1H, d, J=8.6 Hz), 7.0–7.8 (30H, m), 8.50 (1H, d, J=8.5 Hz)

EXAMPLE 13-5

A mixture of N-[(3RS)-1-(2-ethoxycabonylmethoxyphenyl)-carbonylmethyl-2,3-dihydro-5-(2-fluorophenyl)-9-methyl-2-oxo-1H-1,4-benzodiazepin-3-yl]-N'-{3-[1-(triphenylmethyl)tetrazol-5-yl]phenyl}urea (196 mg) and 1N NaOH in 1,2-dimethoxyethane (2 ml) was stirred at room temperature overnight. 4N-HCl in ethyl acetate (2 ml) was added to the reaction mixture and stirred at room temperature for three days. Ethyl acetate and water were added to the reaction mixture. The separated organic layer was washed with water and brine successively, and dried over magnesium sulfate. Removal of the solvent in vacuo afforded N-[(3RS)-2,3-dihydro-5-(2-fluorophenyl)-1-(2-carboxymethoxyphenyl)-carbonylmethyl-9-methyl-2-oxo-1H-1,4-benzodiazepin-3-yl]-N'-[3-(tetrazol-5-yl)phenyl]urea (66.0 mg, 47.4%).

mp: 109.6–113.0° C.

$^1$H-NMR (DMSO-d$_6$, δ): 4.04 (1H, d, J=17.0 Hz), 4.64 (1H, d, J=17.0 Hz), 5.05 (2H, s), 5.18 (1H, d, J=8.6 Hz), 7.03 (1H, d, J=7.6 Hz), 7.2–7.7 (13H, m), 8.46 (1H, d, J=8.6 Hz)

Mass (FAB): 662 (M$^+$)

EXAMPLE 14-1

A mixture of N-[(3RS)-1-(3-azabicyclo[3.2.2]non-3-yl)carbonylmethyl-2,3-dihydro-5-(2-fluorophenyl)-9-methyl-2-oxo-1H-1,4-benzodiazepin-3-yl]-N'-(3-hydroxymethylphenyl)urea (190 mg) and activated manganese dioxide (1.5 g) in acetone (10 ml) was stirred at room temperature for 4 hours.

The reaction mixture was filtered. The filtrate and the washings were combined and evaporated in vacuo to afford a colorless oil, which was triturated in diisopropyl ether and collected by filtration to afford N-[(3RS)-1-(3-azabicyclo[3.2.2]non-3-yl)carbonylmethyl-2,3-dihydro-5-(2-fluorophenyl)-9-methyl-2-oxo-1H-1,4-benzodiazepin-3-yl]-N'-(3-formylphenyl)urea (146 mg, 77.1%) as a crystalline powder.

mp: 236.8–242.1° C.

IR (Nujol, cm$^{-1}$): 1700, 1680, 1635

$^1$H-NMR (DMSO-d$_6$, δ): 1.4–2.2 (10H, m), 2.44 (3H, s), 2.9–3.4 (2H, m), 3.7–4.0 (2H, m), 4.13 (1H, d, J=16.1 Hz), 5.13 (1H, d, J=16.1 Hz), 5.32 (1H, d, J=8.3 Hz), 7.03 (1H, d, J=7.6 Hz), 7.1–7.4 (3H, m), 7.4–7.8 (6H, m), 8.0 (1H, br, s), 9.32 (1H, br, s), 9.94 (1H, br, s)

Mass (APCI):596 (M$^+$+1)

EXAMPLE 14-2

N-[(3RS)-1-(3-azabicyclo[3.2.2]non-3-yl)carbonylmethyl-2,3-dihydro-5-(2-fluorophenyl)-9-methyl-2-oxo-1H-1,4-benzodiazepin-3-yl]-N'-(3-hydroxyiminomethylphenyl)urea was prepared in a similar manner to that of Example 16(7)-2.

mp: 196.0–199.0° C.

IR (Nujol, cm$^{-1}$): 3300, 1680, 1640

$^1$H-NMR (DMSO-d$_6$, δ): 1.3–2.2 (10H, m), 2.44 (3H, s), 2.9–3.4 (2H, m), 3.6–4.0 (2H, m), 4.12 (1H, d, J=16.2 Hz), 5.13 (1H, d, J=16.2 Hz), 5.31 (1H, d, J=8.4 Hz), 7.0–7.8 (12H, m), 8.05 (1H, s), 11.18 (1H, s)

Mass (APCI): 611 (M$^+$+1)

EXAMPLE 15-1

N-[(3RS)-1-(2-aminophenacyl)-2,3-dihydro-5-(2-fluorophenyl)-9-methyl-2-oxo-1H-1,4-benzodiazepin-3-yl]-N'-[3-(tetrazol-5-yl)phenyl]urea was prepared in a similar manner to that of Example 51.

mp: 164.1–186.2° C.(dec.)

IR (Nujol, cm$^{-1}$): 1650

$^1$H-NMR (DMSO-d$_6$, δ): 2.5 (3H, br, s), 4.69 (1H, d, J=17.4 Hz), 5.41 (1H, d, J=8.3 Hz), 5.69 (1H, d, J=17.4 Hz), 6.5–8.2 (16H, m), 9.37 (1H, br, s)

Mass (APCI): 604 (M$^+$+1)

EXAMPLE 15-2

A mixture of N-[(3RS)-1-(2-aminophenacyl)-2,3-dihydro-5-(2-fluorophenyl)-9-methyl-2-oxo-1H-1,4-benzodiazepin-3-yl]-N'-[3-(tetrazol-5-yl)phenyl]urea (180 mg) and acetic anhydride (2 ml) in methylene chloride (2 ml) was stirred at room temperature for 6 hours. The reaction mixture was evaporated in vacuo to afford a residue, which was triturated in diisopropyl ether and collected by filtration to give N-[(3RS)-1-(2-(N,N-diacetylamino)phenacyl)-2,3-dihydro-5-(2-fluorophenyl)-9-methyl-2-oxo-1H-1,4-benzodiazpin-3-yl]-N'-[3-(tetrazol-5-yl)phenyl]urea (125.0 mg, 61.0% yield) as a crystalline powder.

mp: 192.0–216.6° C. (dec.)

IR (Nujol, cm$^{-1}$): 1670, 1645

$^1$H-NMR (DMSO-d$_6$, δ): 1.91 (6H, s), 2.49 (3H, s), 4.75 (1H, d, J=17.8 Hz), 5.44 (1H, d, J=8.3 Hz), 5.85 (1H, d, J=17.8 Hz), 7.0–7.8 (13H, m), 8.0–8.4 (3H, m), 9.37(1H, br, s)

Mass (FAB): 688 (M$^+$+1)

EXAMPLE 1 6(1)

N-[(3RS)-1-(3-Azabicyclo[3.2.2]non-3-yl)carbonylmethyl-2,3-dihydro-5-(2-fluorophenyl)-9-methyl-1H-1,4-benzodiazepin-3-yl]-N'-(3-bromophenyl)urea was prepared in a similar manner to that of Example 59.

mp: >250° C.

IR (Nujol, cm$^{-1}$): 1690, 1630

$^1$H-NMR (DMSO-d$_6$, δ): 1.3–2.2 (10H, m), 2.44 (3H, s), 2.8–3.4 (2H, m), 3.4–4.0 (2H, m), 4.13 (1H, d, J=16.2 Hz), 5.13 (1H, d, J=16.2 Hz), 5.30 (1H, d, J=8.4 Hz), 7.0–7.9 (11H, m), 9.22 (1H, br, s)

Mass (APCI):648, 646

EXAMPLE 16(2)

N-[(3RS)-1-(3-Azabicyclo[3.2.2]non-3-yl)carbonylmethyl-2,3-dihydro-5-(2-fluorophenyl)-9-methyl-2-oxo-1H-1,4-benzodiazepin-3-yl]-N'-(3-chlorophenyl)urea was prepared in a similar manner to that of Example 59.

mp: >250° C.

IR (Nujol, cm$^{-1}$): 1680, 1630

$^1$H-NMR (DMSO-d$_6$, δ): 1.3–2.2 (10H, m), 2.44 (3H, s), 2.9–3.4 (2H, m), 3.5–4.0 (2H, m), 4.13 (1H, d, J=16.2 Hz), 5.13 (1H, d, J=16.2 Hz ), 5.31 (1H, d, J=8.3 Hz ), 6.9–7.8 (11H, m ), 9.24 (1H, s)

Mass (APCI): 602 (M$^+$+1)

EXAMPLE 16(3)

N-[(3RS)-1-(3-Azabicyclo[3.2.2]non-3-yl)carbonylmethyl-5-(2-fluorophenyl)-2,3-dihydro-9-methyl-2-oxo-1H-1,4-benzodiazepin-yl]-N'-(3-methoxyphenyl)urea was prepared in a similar manner to at of Example 59.

mp: 240.9–243.1° C.

IR (Nujol, cm$^{-1}$): 1680, 1640

$^1$H-NMR (DMSO-d$_6$, δ): 1.3–2.2 (1OH, m), 2.44 (3H, s), 2.8–3.1 (1H, m), 3.1–3.3 (1H, m), 3.5–4.0 (2H, m), 3.69 (3H, s), 4.12 (1H, d, J=16.2 Hz), 5.13 (1H, d, J=16.1 Hz), 5.32 (1H, d, J=8.5 Hz), 6.50 (1H, d, J=7.8 Hz ), 6.7–7.0 (1H, m), 7.0–7.8 (10H, m), 9.04 (1H, br, s)

Mass (APCI): 598 (M$^+$+1)

EXAMPLE 16(4)

N-[(3RS)-(3-Azabicyclo[3.2.2]non-3-yl)carbonylmethyl-2,3-dihydro-5-(2-fluorophenyl)-9-methyl-2-oxo-1H-1,4-benzodiazepin-3-yl]-N'-[3-(tetrazol-5-yl)methylphenyl]urea was prepared in a similar manner to that of Example 51.

mp: 153.8–167.7° C.

IR (Nujol, cm$^{-1}$): 1650

$^1$H-NMR (DMSO-d$_6$, δ): 1.4–2.1 (10H, m), 2.44 (3H, s), 2.9–4.0 (4H, m), 4.12 (1H, d, J=16.2 Hz), 4.22 (2H, br, s), 2.12 (1H, d, J=16.2 Hz), 5.30 (1H, d, J=8.4 Hz), 6.8–7.8 (12H, m), 8.0–8.2 (1H, m), 9.05 (1H, br, s)

Mass (APCI): 650 (M$^+$+1)

EXAMPLE 16(5)

N-[(3RS)-1-(3-Azabicyclo[3.2.2]non-3-yl)carbonylmethyl-2,3-dihydro-5-(2-fluorophenyl)-9-methyl-2-oxo-1H-1,4-benzodiazepin-3-yl]-N'-(3-methylthiophenyl)urea was prepared in a similar manner to that of Example 59.

mp: 234.2–236.6° C.

IR (Nujol, cm$^{-1}$): 1700, 1675, 1630

$^1$H-NMR (DMSO-d$_6$, δ): 1.3–2.2 (10H, m), 2.42 (3H, s), 2.44 (3H, s), 2.9–3.4 (2H, m), 3.7–4.0 (2H, m), 4.12 (1H, d, J=16.2 Hz), 5.13 (1H, d, J=16.2 Hz), 5.32 (1H, d, J=8.4 Hz), 6.7–6.9 (1H, m), 6.9–7.1 (2H, m ), 7.1–7.4 (4H, m ), 7.4–7.8 (4H, m ), 9.08 (1H, br, s)

Mass (APCI): 614 (M$^+$+1)

EXAMPLE 16(6)

N-[(3RS)-1-(3-Azabicyclo[3.2.2]non-3-yl)carbonylmethyl-2,3-dihydro-5-(2-fluorophenyl)-9-methyl-1H-1,4-benzodiazepin-3-yl]-N'-(3-methylphenyl)urea was prepared in a similar manner to that of Example 59.

mp: 246.2–247.2° C.

IR (Nujol, cm$^{-1}$): 1700, 1680, 1635

$^1$H-NMR (DMSO-d$_6$, δ): 1.3–2.2 (10H, m), 2.23 (3H, s), 2.44 (3H, s), 2.9–3.4 (2H, m), 3.6–4.0 (2H, m), 4.12 (1H, d, J=16.2 Hz), 5.12 (1H, d, J=16.2 Hz), 5.32 (1H, d, J=8.5 Hz), 6.73(1H, d, J=6.6 Hz), 7.0–7.8 (11H, m), 8.94 (1H, br, s)

Mass (APCI): 582 (M$^+$+1)

EXAMPLE 16(7)-1

N-[(3RS)-1-(3-Azabicyclo[3.2.2]non-3-yl)carbonylmethyl-2,3-dihydro-9-methyl-5-(2-fluorophenyl)-2-oxo-1H-1,4-benzodiazepin-3-yl]-N'-(3-acetylphenyl)urea was prepared in a similar manner to that of Example 59.

mp: >250° C.

IR (Nujol, cm$^{-1}$): 1700, 1680, 1640

$^1$H-NMR (DMSO-d$_6$, δ): 1.4–2.2 (10H, m), 2.44 (3H, s), 2.53 (3H, s), 2.9–3.3 (2H, m), 3.7–4.1 (2H, m), 4.13 (1H, d, J=16.2 Hz), 5.13 (1H, d, J=16.2 Hz), 5.33 (1H, d, J=8.4 Hz), 7.03 (1H, d, J=7.6 Hz) 7.2–7.9 (10H, m), 8.01 (1H, br, s), 9.26 (1H, br, s)

Mass (APCI): 610 (M$^+$+1)

EXAMPLE 16(7)-2

A mixture of N-[(3RS)-1-(3-azabicyclo[3.2.2]non-3-yl)carbonylmethyl-2,3-dihydro-9-methyl-5-(2-fluorophenyl)-2-oxo-1H-1,4-benzodiazepin-3-yl]-N'-(3-acetylphenyl)urea (217 mg) and hydroxylamine-hydrochloride (124 mg), triethylamine (180 mg) in tetrahydrofuran (4 ml) was stirred at room temperature overnight. Ethyl acetate and 1N aqueous hydrochloric acid solution were added the reaction mixture. The separated organic layer was washed with 1N aqueous hydrochloric acid twice, saturated aqueous sodium bicarbonate and brine successively and then dried over magnesium sulfate. The solvent was evaporated in vacuo to afford N-[(3RS)-1-(3-azabicyclo[3.2.2]non-3-yl)carbonylmethyl-2,3-dihydro-9-methyl-5-(2-fluorophenyl)-2-oxo-1H-1,4-benzodiazepin-3-yl]-N'-[3-(1-hydroxyiminoethyl)phenyl]urea (235.0 mg) as a crystalline powder.

mp: 199.1–207.8° C.

IR (Nujol, cm$^{-1}$): 1650

$^1$H-NMR (DMSO-d$_6$, δ): 1.3–2.2 (10H, m), 2.11 (3H, s), 2.44 (3H, s), 2.8–3.4 (2H, m), 3.6–4.0 (2H, m), 4.13 (1H, d, J=16.3 Hz), 5.13 (1H, d, J=16.3 Hz), 5.33 (1H, d, J=8.4 Hz), 7.02 (1H, d, J=7.6 Hz), 7.2–7.8 (11H, m), 9.10 (1H, br, s), 11.14 (1H, br, s)

Mass (APCI): 625 (M$^+$+1)

EXAMPLE 16(8)

N-[(3RS)-1-(3-Azabicyclo[3.2.2]non-3-yl)carbonylmethyl-5-(2-fluorophenyl)-9-methyl-2,3-dihydro-2-oxo-1H-1,4-benzodiazepin-3-yl]-N'-[3-(tetrazol-5-yl)phenyl]urea was prepared in a similar manner to that of Example 51.

mp: 182.2–190.9° C.

$^1$H-NMR (DMSO-d$_6$, δ) 1.3–2.2 (10H, m), 2.45 (3H, s), 2.9–3.4 (2H, m), 3.6–4.0 (2H, m), 4.13 (1H, d, J=16.3 Hz), 5.14 (1H, d, J=16.3 Hz), 5.35 (1H, d, J=8.3 Hz), 6.9–7.1 (2H, m), 7.2–7.4 (3H, m), 7.4–7.8 (5H, m ), 8.0–8.2 (1H, m ), 8.20 (1H, br, s ), 9.30 (1H, br, s)

Mass (APCI): 636 (M$^+$+1)

EXAMPLE 16(9)-1

N-[(3RS)-1-(3-Azabicyclo[3.2.2]non-3-yl)carbonylmethyl-5-(2-fluorophenyl)-9-methyl-2,3-dihydro- 2-oxo-1H-1,4-benzodiazepin-3-yl]-N'-(3-tert-butoxycarbonylphenyl)urea was prepared in a similar manner to that of Example 51.

mp: 230.4–232.2° C.

IR (Nujol, cm$^{-1}$): 1720, 1680

$^1$H-NMR (DMSO-d$_6$, δ): 1.3–2.2 (10H, m), 2.44 (3H, s), 1.52 (9H, s), 2.9–3.4 (2H, m), 3.6–4.0 (2H, m), 4.13 (1H, d, J=16.2 Hz), 5.13 (1H, d, J=16.2 Hz), 5.32 (1H, d, J=8.4 Hz), 7.03 (1H, d, J=7.5 Hz), 7.2–7.8 (11H, m), 7.95 (1H, br, s), 9.52 (1H, br, s)

Mass (APCI): 668 (M$^+$+1)

EXAMPLE 16(9)-2

N-[(3RS)-1-(3-Azabicyclo[3.2.2]non-3-yl)carbonylmethyl-5-(2-fluorophenyl)-9-methyl-2,3-dihydro-2-oxo-1H-1,4-benzodiazepin-3-yl]-N'-(3-carboxyphenyl)urea was prepared in a similar manner to that of Example 18(3)-2.

mp: 197.1–204.2° C.

$^1$H-NMR (DMSO-d$_6$, δ): 1.3–2.2 (10H, m), 2.45 (3H, s), 2.9–3.4 (2H, m), 3.8–4.0 (2H, m), 4.13 (1H, d, J=16.2 Hz), 5.13 (1H, d, J=16.2 Hz), 5.32 (1H, d, J=8.3 Hz), 7.0–7.1 (1H, m), 7.2–7.8 (10H, m), 8.05 (1H, br, s), 9.24 (1H, br, s)

EXAMPLE 17(1)

N-[(3RS)-5-Cyclohexyl-2,3-dihydro-1,9-dimethyl-2-oxo-1H-1,4-benzodiazepin-3-yl]-N'-[3-(tetrazol-5-yl)phenyl]urea was prepared in a similar manner to that of Example 51.

mp: 198.9–200.7° C.

IR (Nujol, cm$^{-1}$): 1655

$^1$H-NMR (DMSO-d$_6$, δ) 0.8–2.0 (10H, m), 2.3–2.5 (3H, br, s), 2.9–3.1 (1H, m), 3.09 (3H, s), 5.12 (1H, d, J=8.4 Hz), 7.3–7.7 (7H, m), 8.18 (1H, br, s), 9.31(1H, br, s)

Mass (APCI): 473 (M$^+$+1)

EXAMPLE 17(2)

N-[(3RS)-5-Cyclohexyl-2,3-dihydro-1,9-dimethyl-2-oxo-1H-1,4-benzodiazepin-3-yl]-N'-(3-methylphenyl)urea was prepared in a similar manner to that of Example 59.

mp: 196.4–197.5° C.

IR (Nujol, cm$^{-1}$): 1685, 1640, 1610

$^1$H-NMR (DMSO-d$_6$, δ): 0.8–2.0 (10H, m), 2.22 (3H, s), 2.34 (3H, s), 3.04 (1H, m), 3.07 (3H, s), 5.08 (1H, d, J=8.3 Hz), 6.73 (1H, m), 7.0–7.6 (7H, m), 8.91 (1H, br, s)

Mass (APCI): 419 (M$^+$+1)

EXAMPLE 18(1)

N-[(3RS)-1-(2-Methylphenacyl)-9-methyl-5-(2-fluorophenyl)-2,3-dihydro-2-oxo-1H-1,4-benzodiazepin-3-yl]-N'-(3-methylphenyl)urea was prepared in a similar manner to that of Example 59.

mp: 190.2–196.2° C.

IR (Nujol, cm$^{-1}$): 1680, 1635

$^1$H-NMR (DMSO-d$_6$, δ): 2.24 (3H, s), 2.27 (3H, s), 2.46 (3H, s), 4.70 (1H, d, J=17.5 Hz), 5.37 (1H, d, J=8.6 Hz), 5.45 (1H, d, J=17.5 Hz ), 6.73 (1H, d, J=6.6 Hz ), 7.0–8.0 (15H, m), 8.96 (1H, br, s)

Mass (APCI): 549 (M$^+$+1)

EXAMPLE 18(2)

N-[(3RS)-1-(2-Methylphenacyl)-5-(2-fluorophenyl)-9-methyl-2,3-dihydro-2-oxo-1H-1,4-benzodiazepin-3-yl]-N'-[3-(tetrazol-5-yl)phenyl]urea was prepared in a similar manner to that of Example 51.

mp: 215.8–220.3° C.

IR (Nujol, cm$^{-1}$): 1670, 1635

$^1$H-NMR (DMSO-d$_6$, δ): 2.28 (3H, s), 2.49 (3H, s), 4.72 (1H, d, J=17.5 Hz), 5.41 (1H, d, J=8.3 Hz), 5.47 (1H, d, J=17.5 Hz), 7.0–8.0 (15H, m), 8.21 (1H, br, s), 9.33 (1H, br, s)

Mass (APCI): 603 (M$^+$+1)

EXAMPLE 18(3)-1

N-[(3RS)-2,3-dihydro-5-(2-fluorophenyl)-9-methyl-1-(2-ethyl-phenacyl)-2-oxo-1H-1,4-benzodiazepin-3-yl]-N'-13-(tert-butoxycarbonyl)-phenyl]urea was prepared in a similar manner to that Example 51.

IR (Nujol, cm$^{-1}$): 1710, 1660

$^1$H-NMR (CDCl$_3$, δ): 1.56 (9H, s), 2.31 (3H, s), 2.45 (3H, s), 4.38 (1H, d, J=17.2 Hz), 5.58 (1H, d, J=17.2 Hz), 5.73 (1H, d, J=8.3 Hz), 6.8–8.1 (15H, m)

Mass (APCI): 635 (M$^+$+1)

EXAMPLE 18(3)-2

A mixture of N-[(3RS)-2,3-dihydro-5-(2-fluorophenyl)-9-methyl-1-(2-methylphenacyl)-2-oxo-1H-1,4-benzodiazepin-3-yl]- N'-(3-tert-butoxycarbonylphenyl)urea (170 mg) and trifluoroacetic acid (1.0 ml) in methylene chloride (2.0 ml) was stirred at 0° C. for 2 hours. The reaction mixture was evaporated in vacuo to give a residue, which was washed with diisopropyl ether to afford N-[(3RS)-2,3-dihydro-5-(2-fluorophenyl)-9-methyl-1-(2-methylphenacyl)-2-oxo-1H-1,4-benzodiazepin-3-yl]-N'-(3-carboxyphenyl)urea (152.0 mg,98.0%) as a crystalline powder.

mp: 168.1–176.3° C.

IR (Nujol, cm$^{-1}$): 1650

$^1$H-NMR (DMSO-d$_6$, δ): 2.27 (3H, s), 2.48 (3H, s), 4.70 (1H, d, J=17.5 Hz), 5.38 (1H, d, J=8.4 Hz), 5.46 (1H, d, J=17.5 Hz), 7.0–7.8 (14H, m), 7.8–7.9 (1H, m), 8.05 (1H, br, s), 9.24 (1H, br, s)

Mass (FAB): 579 (M$^+$+1)

EXAMPLE 19(1)

N-[(3RS)-1-(3-Azabicyclo[3.2.2]non-3-yl)carbonylmethyl-2,3-dihydro-9-ethyl-5-(2-fluorophenyl)-2-oxo-1H-1,4-benzodiazepin-3-yl]-N'-(3-methylphenyl)urea was prepared in a similar manner to that of Example 59.

mp: 162.8–168.1° C.

IR (Nujol, cm$^{-1}$): 1680, 1640

$^1$H-NMR (DMSO-d$_6$, δ): 1.23 (3H, t, J=7.4 Hz), 1.3–2.2 (10H, br), 2.78 (2H, q, J=7.4 Hz), 2.9–3.5 (2H, m), 3.7–4.0 (2H, m), 4.03 (1H, d, J=16.2 Hz), 5.19 (1H, d, J=16.2 Hz), 5.31 (1H, d, J=8.5 Hz), 6.73(1H, d, J=6.7 Hz), 6.9–7.8 (11H, m), 8.94 (1H, br, s)

Mass (APCI): 596 (M$^+$+1)

EXAMPLE 19(2)

N-[(3RS)-1-(3-Azabicyclo[3.2.2]non-3-yl)carbonylmethyl-2,3-dihydro-9-ethyl-5-(2-fluorophenyl)-2-oxo-1H-1,4-benzodiazepin-3-yl]-N'-[3-(tetrazol-5-yl)phenyl]urea was prepared in a similar manner to that of Example 51.

mp: 226.4–231.6° C.

Mass (APCI): 650 (M$^+$+1)

IR (Nujol, cm$^{-1}$): 1680, 1630

$^1$H-NMR (DMSO-d$_6$, δ): 1.24 (3H, t, J=7.4 Hz), 1.3–2.2 (10H, br), 2.79 (2H, q, J=7.4 Hz), 2.9–3.4 (2H, m), 3.6–4.0 (2H, m), 4.04 (1H, d, J=16.4 Hz), 5.21 (1H, d, J=16.4 Hz), 5.34 (1H, d, J=8.3 Hz), 7.03(1H, d, J=7.6 Hz), 7.2–7.8 (11H, m), 8.20 (1H, br, s), 9.31 (1H, br, s)

EXAMPLE 20(1)

N-[(3RS)-1-(3-azabicyclo[3.2.2]non-3-yl)carbonylmethyl-2,3-dihydro-5-(2-fluorophenyl)-9-isopropyl-2-oxo-1H-1,4-benzodiazepin-3-yl]-N'-[3-(tetrazol-5-yl)phenyl]urea was prepared in a similar manner to that of Example 51.

mp: 212.2–222.1° C.

IR (Nujol, cm$^{-1}$): 1650

$^1$H-NMR (DMSO-d$_6$, δ): 1.12 (3H, d, J=6.5 Hz), 1.41 (3H, d, J=6.6 Hz), 1.3–2.2 (10H, m), 2.9–4.0 (6H, m), 5.32 (1H, d, J=17.9 Hz), 5.34 (1H, d, J=8.2 Hz), 6.9–7.1 (1H, m), 7.1–7.8 (11H, m), 8.19 (1H, br, s), 9.31 (1H, br, s)

Mass (APCI): 664 (M$^+$+1)

EXAMPLE 20(2)

N-[(3RS)-1-(3-Azabicyclo[3.2.2]non-3-yl)carbonylmethyl-2,3-dihydro-5-(2-fluorophenyl)-9-isopropyl-2-oxo-1H-1,4-benzodiazepin-3-yl]-N'-(3-methylphenyl)urea was prepared in a similar manner to that of Example 59.

mp: 183.3–186.8° C.

IR (Nujol, cm$^{-1}$): 1655

$^1$H-NMR (DMSO-d$_6$, δ): 1.11 (3H, d, J=6.5 Hz), 1.40 (3H, d, J=6.7 Hz), 1.4–2.2 (10H, m), 2.8–3.4 (3H, m), 3.6–4.0 (3H, m), 5.30 (1H, d, J=14.9 Hz), 5.31 (1H, d, J=8.6 Hz), 6.74 (1H, d, J=6.5 Hz), 6.9–7.8 (11H, m), 8.92 (1H, br, s)

Mass (APCI): 610 (M$^+$+1)

EXAMPLE 21-1

N-[(3RS)-1-(2-Acetoxyethyl)-5-cyclohexyl-2,3-dihydro-9-methyl-2-oxo-1H-1,4-benzodiazepin-3-yl]-N'-[3-(tetrazol-5 -yl)phenyl]urea was prepared in a similar manner to that of Example 51.

mp: 165.2–168.4° C.

IR (Nujol, cm$^{-1}$): 1745, 1660

$^1$H-NMR (DMSO-d$_6$, δ): 1.0–2.0 (10H, m), 1.79 (3H, s), 2.34 (3H, s), 3.00 (1H, m), 3.3–3.6 (1H, m), 3.7–3.9 (2H, m), 4.4–4.6 (1H, m), 5.06 (1H, d, J=8.3 Hz), 7.3–7.7 (7H, m), 8.16 (1H, br, s), 9.27 (1H, br, s)

Mass (APCI): 545 (M$^+$+1)

EXAMPLE 21-2

N-[(3RS)-5-Cyclohexyl-2,3-dihydro-1-(2-hydroxyethyl)-9-methyl-2-oxo-1H-1,4-benzodiazcpin-3-yl]-N'-[3-(tetrazol-5-yl)phenyl]urea was prepared in a similar manner to that of Preparation 59-–4.

mp: 223.5–224.2° C.

IR (Nujol, cm$^{-1}$): 1640

$^1$H-NMR (DMSO-d$_6$, δ): 0.9–2.0 (10H, m), 2.34 (3H, s), 2.9–3.6 (4H, m), 4.2–4.4 (1H, m), 5.02 (1H, d, J=8.2 Hz), 7.3–7.7 (7H, m), 8.17 (1H, s), 9.29 (1H, br, s)

Mass (APCI): 503 (M$^+$+1)

EXAMPLE 22(1)

Potassium salt of N-[(3RS)-1-(3-azabicyclo[3.2.2]non-3-yl)carbonylmethyl-2,3-dihydro-5-(2-fluorophenyl)-9-methyl-2-oxo-1H-1,4-benzodiazepin-3-yl]-N'-[3-(1-sulfoethyl)phenyl]urea was prepared in a similar manner to that of Example 22(3).

mp: 247.2–255.6° C.

IR (Nujol, cm$^{-1}$): 1650, 1615

$^1$H-NMR (DMSO-d$_6$, δ): 1.2–2.2 (10H, m), 1.43 (3H, d, J=7.1 Hz), 2.44 (3H, s), 2.9–3.4 (2H, m), 3.58 (1H, d, J=6.6 Hz), 3.6–4.0 (2H, br, m), 4.11 (1H, d, J=16.2 Hz), 5.14 (1H, d, J=16.2 Hz), 5.32 (1H, d, J=8.6 Hz), 6.8–7.0 (1H, br), 7.0–7.2 (2H, m), 7.2–7.8 (10H, m), 8.99 (1H, m)

Mass (FAB): 714 (M$^+$+1)

EXAMPLE 22(2)

N-[(3RS)-1-(3-Azabicyclo[3.2.2]non-3-yl)carbonylmethyl-2,3-dihydro-5-(2-fluorophenyl)-9-methyl-2-oxo-1H-1,4-benzodiazepin-3-yl]-N'-(3-hydroxymethylphenyl)urea was prepared in a similar manner to that of Example 22(3).

mp: 188.2–202.2° C.

IR (Nujol, cm$^{-1}$): 3320, 1640

$^1$H-NMR (DMSO-d$_6$, δ): 1.2–2.0 (10H, m), 2.26 (3H, s), 2.7–3.2 (2H, m), 3.7–3.9 (2H, m), 4.04 (1H, d, J=17.8 Hz), 4.25 (1H, d, J=5.7 Hz), 4.8–5.1 (3H, m), 5.14 (1H, d, J=8.5 Hz), 6.6–6.8 (1H, m), 6.8–6.9 (1H, m), 6.9–7.6 (10H, m), 8.82 (1H, br, s)

Mass (APCI): 598 (M$^+$+1)

EXAMPLE 22(3)

A mixture of (3RS)-1-[(3-azabicyclo[3.2.2]non-3-yl)carbonylmethyl]-2,3-dihydro-5-(2-fluorophenyl)-3-(imidazol-1-yl)carbonylamino-9-methyl-1H-1,4-benzodiazepin-2-one (250 mg), 3-aminophenol (55 mg) and triethylamine (93 mg) in N,N-dimethylformamide (1 ml) was stirred at 100° C. for 1 hour. After the reaction mixture was allowed to cool to room temperature, ethyl acetate and 1N aqueous hydrochloric acid were added thereto. The separated organic layer was washed with 1N aqueous hydrochloric acid, water, saturated aqueous sodium bicarbonate and brine successively, and then dried over magnesium sulfate. The solvent was evaporated in vacuo to give a colorless paste, which was washed with diisopropyl ether and collected by filtration to afford N-[(3RS)-1-(3-azabicyclo[3.2.2]non-3-yl)carbonylmethyl-2,3-dihydro-9-methyl-5-(2-fluorophenyl)-2-oxo-1H-1,4-benzodiazepin-3-yl]-N '-(3-hydroxyphenyl)urea (184.0 mg, 68.5% yield) as a crystalline.

mp: 192.8–203.9° C.

IR (Nujol, cm$^{-1}$): 3300, 1650

$^1$H-NMR (DMSO-d$_6$, δ): 1.3–2.2 (10H, m), 2.44 (3H, s), 2.8–3.4 (2H, m), 3.7–4.0 (2H, m), 4.12 (1H, d, 16.2 Hz), 5.13 (1H, d, J=16.2 Hz), 5.30 (1H, d, J=8.5 Hz), 6.2–6.4 (1H, m), 6.7–7.7 (10H, m), 9.24 (1H, m)

Mass (APCI): 584 (M$^+$+1)

EXAMPLE 23(1)

(3RS)-1-[(3-Azabicyclo[3.2.2]non-3-yl)carbonylmethyl]-5-cyclohexyl-2,3-dihydro-3-(indol-2-yl)carbonylamino-9-methyl-1H-1,4-benzodiazepin-2-one was prepared in a similar manner to that of Preparation 59-5.

mp: 206.2–212.2° C.

IR (Nujol, cm$^{-1}$): 1680, 1640

$^1$H-NMR (DMSO-d$_6$, δ): 1.0–2.2 (10H, m), 2.40 (3H, s), 2.8–3.4 (2H, m), 2.5–4.0 (2H, m), 4.02 (1H, d, J=16.0 Hz), 5.02 (1H, d, J=16.1 Hz), 5.46 (1H, d, 8.1 Hz), 7.0–7.8 (8H, m), 9.20 (1H, d, J=8.1 Hz)

Mass (FAB): 580 (M$^+$+1)

EXAMPLE 23(2)

N-[(3RS)-1-(3-Azabicyclo[3.2.2]non-3-yl) carbonylmethyl-5 -cyclohexyl-2,3-dihydro-9-methy]-2-oxo-1H-1,4-benzodiazepin-3-yl]-N'-[3-(tetrazol-5-yl) phenyl]urea was prepared in a similar manner to that of Example 51.

mp: 186.2–197.6° C.

IR (Nujol, cm$^{-1}$): 1650

$^1$H-NMR (DMSO-d$_6$, δ): 0.9–2.2 (20H, m), 2.38 (4H, m), 2.8–4.0 (4H, m), 4.04 (1H, d, J=16.0 Hz), 4.98 (1H, d, J=16.0 Hz), 5.02 (1H, d, J=8.2 Hz), 6.94 (1H, d, J=9.1 Hz), 7.3–7.8 (5H, m), 8.1–8.3 (2H, m), 9.25 (1H, br, s)

Mass (FAB): 624 (M$^+$+1)

EXAMPLE 23(3)

N-[(3RS)-1-(3-azabicyclo[3.2.2]non-3-yl) carbonylmethyl-5-cyclohexyl-9-methy]-2-oxo-2,3-dihydro-1H-1,4-benzodiazepin-3-yl]-N'-(3-methylphenyl)urea was obtained in a similar manner to that of Example 59.

mp: 212–214° C.

IR (Nujol, cm$^{-1}$): 3390, 3275, 1705, 1688, 1634

$^1$H-NMR (DMSO-d$_6$, δ): 1.05–2.1 (20H, m), 2.22 (3H, s), 2.37 (3H, s), 2.90 (1H, m), 3.05–3.35 (2H, m), 3.65–3.87 (2H, m), 4.49 (2H, d, d, J=16.2 Hz, J=187 Hz), 5.08 (1H, d, J=8.4 Hz), 6.69–7.57 (8H, m), 8.85 (1H, s)

APCI-MS(e/z): 570 (M$^+$+1)

EXAMPLE 24(1)

N-[(3RS)-5-Cyclohexyl-9-methyl-2,3-dihydro-1-(2-methylphenacyl)-2-oxo-1H-1,4-benzodiazepin-3-yl]-N'-[3-(tetrazol-yl)phenyl]urea was prepared in a similar manner to that of Example 1.

mp: 165.0–176.6° C.

IR (Nujol, cm$^{-1}$): 1660, 1635

$^1$H-NMR (DMSO-d$_6$, δ): 1.0–2.2 (10H, m), 2.32 (3H, s), 2.41 (3H, s), 2.9–3.2 (1H, m), 4.58 (1H, d, J=17.3 Hz), 5.18 (1H, d, J=8.4 Hz), 5.33 (1H, d, J=17.3 Hz), 6.9–7.0 (1H, m), 7.2–7.7 (9H, m), 7.7–7.9 (1H, m), 8.0–8.2 (2H, m), 9.22 (1H, br, s)

Mass (FAB): 591 (M$^+$+1)

EXAMPLE 24(2)

(3RS)-5-Cyclohexyl-2,3-dihydro-3-(indol-2-yl) carbonylamino-9-methyl-1-(2-methylphenacyl)-1H-1,4-benzodiazepin-2-one was prepared in a similar manner to that of Preparation 59-5.

mp: 126.7–145.2° C.

IR (Nujol, cm$^{-1}$): 1640

$^1$H-NMR (DMSO-d$_6$, δ): 1.0–2.3 (10H, m), 2.32 (3H, s), 2.43 (3H, s), 3.05 (1H, m), 4.58 (1H, d, J=17.4 Hz), 5.37 (1H, d, =17.3 Hz), 5.52 (1H, d, J=8.1 Hz), 7.0–8.1 (12H, m), 9.2–9.3 (1H, m)

Mass (APCI): 547 (M$^+$+1)

EXAMPLE 25-1

A mixture of N-[(3RS)-1-(3-azabicyclo[3.2.2]non-3-yl)-carbonylmethyl-5-acetoxymethyl-9-methyl-2,3-dihydro-2-oxo-1H-1,4-benzodiazepin-3-yl]-N'-(3-methylphenyl)urea (208 mg) and 15% aqueous solution of sodium thiomethoxide in N,N-dimethylformamide was stirred at room temperature for 8 hours. Ethyl acetate and water were added to the reaction mixture. The separated organic layer was washed with water and brine, and then dried over magnesium sulfate. The solvent was evaporated in vacuo to afford a paste (214 mg), which was washed with diisopropyl ether and collected by filtration to give N-[(3RS)-1-(3-azabicyclo [3.2.2]non-3-yl)carbonylmethyl-5-hydroxymethyl-9-methyl-2,3-dihydro-2-oxo-1H-1,4-benzodiazepin-3-yl]-N'-(3-methylphenyl)urea (127 mg, 66.0% yield) as a crystalline powder.

mp: 151.7–153.2° C.

IR (Nujol, cm$^{-1}$): 1640

$^1$H-NMR (DMSO-d$_6$, δ): 1.3–2.2 (10H, m), 2.22 (3H, s), 2.48 (3H, s), 2.9–3.4 (2H, m), 3.6–4.0 (2H, m), 4.01 (1H, d, J=16.3 Hz), 4.5–4.6 (2H, m), 5.11 (1H, d, J=16.3 Hz), 5.23 (1H, d, J=8.5 Hz), 6.72 (1H, d, J=6.5 Hz), 7.0–7.2 (3H, m), 7.2–7.7 (4H, m), 8.90 (1H, br, s)

Mass (APCI): 518 (M$^+$+1)

EXAMPLE 25--2

To a mixture of N-[(3RS)-1-(3-azabicyclo[3.2.2]non-3-yl)carbonylmethyl-5-hydroxymethyl-9-methyl-2-oxo-2,3-dihydro-1H-1,4-benzodiazepin-3-yl]-N'-(3-methylphenyl) urea (147 mg) and diisopropylethylamine (55.1 mg) in methylene chloride (2 ml) was added dropwise a solution of methanesulfonyl chloride (48.7 mg) in methylene chloride (1 ml) under stirring and cooling at 0–5° C. in an ice-bath. The mixture was stirred for 1.5 hours under the same conditions. The reaction mixture was evaporated in vacuo to afford a residue, which was dissolved in tetrahydrofuran (2 ml) and cooled in an ice-bath. To the solution prepared above was added 15% aqueous solution of sodium methylmercaptide (0.5 g). The mixture was stirred under cooling for 0.5 hour and at ambient temperature for 2 hours. The reaction mixture was evaporated in vacuo to afford a residue, which was dissolved in ethyl acetate and washed with water twice. The separated organic layer was dried over magnesium sulfate and evaporated in vacuo to afford an amorphous mass, which was subjected to preparative thin-layer chromatography on silica gel developing with a mixture of chloroform and methanol (10:1) to give N-[(3RS)-1-(3-azabicyclo[3.2.2]non-3-yl)carbonylmethyl-5-methylthiomethyl-9-methyl-2-oxo-2,3-dihydro-1H-1,4-benzodiazepin-3-yl]-N'-(3-methyphenyl)urea as an amorphous mass. This was triturated in diisopropyl ether and collected by filtration to give a crystalline powder (71.9 mg, 41.7% yield).

mp: 172–175.5° C.(dec.)

$^1$H-NMR (CDC$_3$, δ): 1.45–2.1 (10H, m), 2.20 (3H, s), 2.29 (3H, s), 2.38 (3H, s), 3.25–3.55 (4H, m), 3.7–3.95 (3H, m), 5.03 (1H, d, J=15.8 Hz), 5.54 (1H, d, J=8.2 Hz), 6.7–7.8 (9H, m)

APCI-MS(m/z): 548 (M$^+$+1)

EXAMPLE 26

N-[(S)-1-(3-azabicyclo[3.2.2]non-3-yl)carbonylmethyl-2,3-dihydro-5-(2-fluorophenyl)-9-methyl-2-oxo-1H-1,4-benzodiazepin-3-yl]-N'-[3-(tetrazol-5-yl)phenyl]urea was prepared in a similar manner to that of Example 51.

mp: 210.3–213.4° C.

[α]$_D^{30.4}$=+6.6° (C=0.50, EtOH)

IR (Nujol, cm$^{-1}$): 1650

¹H-NMR (DMSO-d₆, δ): 1.4–2.2 (10H, m), 2.45 (3H, s), 2.9–3.4 (2H, m), 3.4–4.0 (2H, m), 4.14 (1H, d, J=16.2 Hz), 5.14 (1H, d, J=10.2 Hz), 5.35 (1H, d, J=8.3 Hz), 6.8–7.8 (12H, m), 8.21 (1H, br, s), 9.31 (1H, br, s)

Mass (APCI): 636 (M⁺+1)

EXAMPLE 27

N-[(R)-1-(3-azabicyclo[3.2.2]non-3-yl)carbonylmethyl-2,3-dihydro-5-(2-fluorophenyl)-9-methyl-2-oxo-1H-1,4-benzodiazepin-3-yl]-N'-[3-(tetrazol-5-yl)phenyl]urea was prepared in a similar manner to that of Example 51.

mp: 209.9–215.2° C.

$[\alpha]_D^{30.4}$=10.96° (C=0.52, EtOH)

IR (Nujol, cm⁻¹): 1650, 1620

¹H-NMR (DMSO-d₆, δ): 1.3–2.2 (10H, m), 2.45 (3H, s), 2.8–4.0 (4H, m), 4.14 (1H, d, 16.3 Hz), 5.14 (1H, d, 16.3 Hz), 5.35 (1H, d, 8.3 Hz), 7.03 (1H, d, 7.5 Hz), 7.2–7.8 (11H, m), 8.21 (1H, br, s), 9.32 (1H, br, s)

Mass (APCI): 636 (M⁺+1)

EXAMPLE 28

N-[(3RS)-2,3-dihydro-5-(2-fluorophenyl)-9-methyl-1-(pyridin-2-yl)methyl-2-oxo-1H-1,4-benzodiazepin-3-yl]-N'-[3-(tetrazol-5-yl)phenyl]urea was prepared in a similar manner to that of Example 51.

mp: 173.9–182.0° C.

IR (Nujol, cm⁻¹): 1640

¹H-NMR (DMSO-d₆, δ): 4.59 (1H, d, J=15.3 Hz), 5.35 (1H, d, J=8.3 Hz), 5.49 (1H, d, J=15.3 Hz), 6.9–7.8 (13H, m), 7.95 (1H, br, s), 8.0–8.3 (2H, m), 9.33 (1H, br, s)

Mass (FAB):562 (M⁺+1)

EXAMPLE 29

N-[(3RS)-1-(3-Azabicyclo[3.2.2]non-3-yl)carbonylmethyl-9-chloro-2,3-dihydro-5-(2-fluorophenyl)-2-oxo-1H-1,4-benzodiazepin-3-yl]-N'-[3-(tetrazol-5-yl)phenyl]urea was prepared in a similar manner to that of Example 51.

mp: 172.0–180.5° C.

IR (Nujol, cm⁻¹): 1650

¹H-NMR (DMSO-d₆, δ): 1.4–2.2 (10H, m), 2.9–3.1 (1H, m), 3.1–3.5 (1H, m), 3.6–4.0 (2H, m), 4.41 (1H, d, J=16.4 Hz), 5.22 (1H, d, J=16.8 Hz), 5.38 (1H, d, J=8.3 Hz), 6.93 (1H, d, J=9.2 Hz), 7.2–8.3 (11H, m), 9.30 (1H, br, s)

Mass (APCI): 657 (M⁺+1)

EXAMPLE 30

N-[(3RS)-2,3-Dihydro-5-(2-fluorophenyl)-9-methyl-1-tert-butylcarbonylmethyl-2-oxo-1H-1,4-benzodiazepin-3-yl]-N'-[3-(tetrazol-5-yl)phenyl]urea was prepared in a similar manner to that of Example 51.

mp: 160.4–180.7° C.(dec.)

IR (Nujol, cm⁻¹): 1720, 1650

¹H-NMR (DMSO-d₆, δ): 1.09 (9H, s), 2.43 (3H, s), 4.19 (1H, d, J=17.3 Hz), 5.24 (1H, d, J=17.4 Hz), 5.32 (1H, d, J=8.4 Hz), 7.07 (1H, d, J=7.2 Hz), 7.2–7.8 (11H, m), 8.19 (1H, br, s), 9.27 (1H, br, s)

Mass (FAB): 569 (M⁺+1)

EXAMPLE 31(1)

Potassium salt of N-[(3RS)-1-(3-azabicyclo[3.2.2]non-3-yl)carbonylmethyl-5,9-dimethyl-2,3-dihydro-2-oxo-1H-1,4-benzodiazepin-3-yl]-N'-[3-(1-sulfoethyl)phenyl]urea was prepared in a similar manner to that of Example 22(3).

mp: 246.9–249.1° C.

IR (Nujol, cm⁻¹): 1670, 1660

¹H-NMR (DMSO-d₆, δ): 1.3–2.2 (10H, m), 1.41 (1H, d, J=7.1 Hz), 2.37 (3H, s), 2.44 (3H, s), 3.0–3.4 (2H, m), 3.5–3.9 (3H, m), 3.96 (1H, d, J=16.5 Hz), 5.12 (1H, d, J=16.5 Hz), 5.0–5.2 (1H, m), 6.8–6.9 (1H, m), 6.9–7.6 (7H. m), 8.9–9.0 (1H, m)

Mass (FAB): 634 (M⁺+1)

EXAMPLE 31(2)

N-[(3RS)-1-(3-Azabicyclo[3.2.2]non-3-yl)carbonylmethyl-5.9-dimethyl-2,3-dihydro-2-oxo-1H-1,4-benzodiazepin-3-yl]-N'-(2-methylpyridin-6-yl)urea was prepared in a similar manner to that of Example 22(3).

mp: 150.8–152.1° C.

IR (Nujol, cm⁻¹): 1670

¹H-NMR (DMSO-d₆, δ): 1.3–2.2 (10H, m), 2.36 (3H, s), 2.44 (3H, s), 2.42 (3H, s), 3.0–3.5 (2H, br), 3.5–3.9 (2H, m), 3.96 (1H, d, J=16.3 Hz), 5.0–5.2 (2H, m), 6.7–7.7 (6H, m), 9.43 (1H, br, s)

Mass (APCI): 503 (M⁺+1)

EXAMPLE 31(3)

N-[(3RS)-1-(3-Azabicyclo[3.2.2]non-3-yl)carbonylmethyl-5,9-dimethyl-2,3-dihydro-2-oxo-1H-1,4-benzodiazcpin-3-yl]-N'-(4-methylpyridin-2-yl)urea was prepared in a similar manner to that of Example 22(3).

mp: 152.0–154.1° C.

IR (Nujol, cm⁻¹): 1680, 1660

¹H-NMR (DMSO-d₆, δ): 1.3–2.2 (10H, m), 2.24 (3H, s), 2.36 (3H, s), 2.44 (3H, s), 2.44 (3H, s), 2.9–3.4 (2H, br), 3.5–3.9 (2H, m), 3.95 (1H, d, J=16.4 Hz), 5.09 (1H, d, J=16.4 Hz), 5.18 (1H, d, J=7.1 Hz), 6.8 (1H, br), 7.0–7.6 (5H, m), 8.0–8.2 (1H, m), 9.39 (1H, br, s)

Mass (APCI): 503 (M⁺+1)

EXAMPLE 31(4)

A mixture of (3RS)-1-(3-azabicyclo[3.2.2]non-3-yl)carbonylmethyl-5,9-dimethyl-3-(imidazol-1-yl)carbonylamino-2,3-dihydro-1H-1,4-benzodiazepin-2-one (300 mg), N,N-dimethyl-1,3-phenylenediamine dihydrochloride (149 mg) and triethylamine (2 ml) in N,N-dimethylformamide (6 ml) was stirred at 100° C. for 2 hours. After allowing to cool to room temperature, ethyl acetate and water were added to the reaction mixture under stirring. The separated organic layer was washed with water and brine, and then dried over sodium sulfate. The solvent was evaporated in vacuo to afford an amorphous powder, which was washed with diisopropyl ether and collected by filtration to give a pale gray powder (320 mg). To the powder dissolved in 1,4-dioxane was added 4N-hydrogen chloride in 1,4-dioxane (0.5 ml) at ambient temperature under stirring. The resultant mixture was evaporated in vacuo to dryness to afford a residue, which was washed with diisopropyl ether and collected by filtration to give N-[(3RS)-1-(3-azabicyclo[3.2.2]non-3-yl)carbonylmethyl-5,9-dimethyl-2,3-dihydro-2-oxo-1H-1,4-benzodiazepin-3-yl]-N'-[3-(N,N-dimethyl amino)phenyl]urea hydrochloride (280 mg, 67.1% yield).

mp: 190.9–193.1° C.

IR (Nujol, cm⁻¹): 1690, 1630

¹H-NMR (DMSO-d₆, δ): 1.3–2.2 (10H, m), 2.43 (3H, s), 2.73 (3H, s), 2.86 (3H, s), 2.7–3.4 (2H, m), 3.6–4.0 (2H, m), 4.06 (1H, d, J=16.4 Hz), 5.23 (1H, d, J=16.4 Hz), 5.61 (1H, d, J=6.2 Hz), 6.7–7.0 (1H, m), 7.2–8.0 (7H, m), 10.04 (1H, br, s)

Mass (APCI): 531(free σ M⁺+1)

EXAMPLE 32

N-[(3RS)-1-(3-azabicyclo[3.2.2]non-3-yl)carbonylmethyl-2,3-dihydro-5,9-dimethyl-1H-1,4-benzodiazepin-2-one-4-oxide-3-yl]-N'-(3-methylephenyl)urea (45.3 mg) was treated with acetic anhydride (1.8 ml) at 50° C. for 5 hours. After the reaction was completed, acetic anhydride was removed under reduced pressure. The residue was subjected to preparative thin layer chromatography on silica gel (60F₂₅₄, 0.5 mm, 20×20 cm; Merck) developed with a mixture of CHCl₃, AcOEt and MeOH (14:1:0.4) to give N-[(3RS)-1-(3-azabicyclo[3.2.2]non-3-yl)-carbonylmethyl-2,3-dihydro-5-acetoxymethyl-9-methyl-2-oxo-1H-1,4-benzodiazepin-3-yl]-N'-(3-methylphenyl)urea as an amorphous mass (59.9 mg), which was powdered by triturated in diisopropyl ether and collected by filtration (26.5 mg; 59.3%).

mp: 133–134.5° C.

¹H-NMR(CDCl₃, δ): 1.50–2.17 (10H, m), 2.10 (3H, s), 2.29 (3H, s), 2.38 (3H, s), 3.28–3.74 (4H, m), 4.62 (2H, d, d, J=15.6 Hz, J=319.0 Hz), 5.17 (2H, d, d, J=9.45 Hz, J=15.7 Hz), 5.59 (1H, d, J=7.82 Hz), 6.76–7.56 (9H, m)

APCI-MS (m/z): 560.3 (M⁺+1)

EXAMPLE 33

To a solution of (3RS)-3-amino-1-[(3-azabicyclo[3.2.2]non-3-yl)-carbonylmethyl]-5-methyl-9-(N,N-dimethylamino)-2,3-dihydro-1H-1,4-benzodiazepin-2-one (285 mg) in tetrahydrofuran (4 ml) was added dropwise 3-tolyl isocyanate (100 mg) under stirring at room temperature. The mixture was stirred at room temperature for 2 hours. Removal of the solvent in vacuo afforded a residue, which was triturated in diisopropyl ether and collected by filtration to give a white powder. To a solution of the powder in ethyl acetate was added 4N-hydrogen chloride in ethyl acetate (0.25 ml) under cooling. The mixture was evaporated in vacuo to dryness. The residue was washed with diisopropyl ether and collected by filtration to afford N-[(3RS)-1-(3-azabicyclo[3.2.2]non-3-yl)carbonylmethyl-5-methyl-9-(N,N-dimethylamino)-2,3-dihydro-2-oxo-1H-1,4-benzodiazepin-3-yl]-N'-(3-methylphenyl)urea hydrochloride (250 mg,61.5%) as a crystalline powder.

mp: 216.5–218.7° C.

IR (Nujol, cm⁻¹): 1680, 1630

¹H-NMR (DMSO-d₆, δ): 1.3–2.2 (10H, m), 2.24 (3H, s), 2.80 (6H, br, s), 3.0–3.2 (1H, m), 3.2–3.4 (1H, m), 3.5–3.9 (2H, br, m), 4.56 (1H, d, J=16.7 Hz), 5.11 (1H, d, J=16.7 Hz), 5.67 (1H, m), 6.7–6.8 (1H, m), 7.0–7.3 (3H, m), 7.4–7.7 (3H, m), 7.72 (1H, m), 9.56 (1H, br, s)

Mass (FAB): 531 (hydrochloride free M⁺+1)

EXAMPLE 34

N-[(3RS)-2,3-Dihydro-5-(2-fluorophenyl)-9-methyl-1-tert-butoxycarbonylmethyl-2-oxo-1H-1,4-benzodiazepin-3-yl]-N'-[3-(tetrazol-5-yl)phenyl]urea was prepared in a similar manner to that of Example 51.

mp: 151.4–174.2° C.(dec.)

IR (Nujol, cm⁻¹): 1745, 1650

¹H-NMR (DMSO-d₆, δ): 1.25 (9H, s), 2.46 (3H, s), 4.11 (1H, d, J=16.8 Hz), 4.60 (1H, d, J=16.7 Hz), 5.34 (1H, d, J=8.4 Hz), 6.9–7.8 (10H, m), 8.1–8.3 (2H, m), 9.32 (1H, br, s)

Mass (APCI): 585 (M⁺+1)

EXAMPLE 35

N-[(3RS)-1-(Adamantan-1-yl)carbonylmethyl-2,3-dihydro-5-2-fluorophenyl)-9-methyl-2-oxo-1H-1,4-benzodiazepin-3-yl]-N'-[3-(tetrazol-5-yl)phenyl]urea was prepared in a similar manner to that Example 51.

mp: 195.0–218.4° C.(dec.)

IR (Nujol, cm⁻¹): 1650

¹H-NMR (DMSO-d₆, δ): 1.5–2.2 (15H, m), 2.42 (3H, br, s), 4.12 (1H, d, J=17.1 Hz), 5.23 (1H, d, J=17.5 Hz), 5.31 (1H, d, J=8.3 Hz), 6.9–7.8 (11H, m), 8.1 (1H, m), 9.28 (1H, br, s)

Mass (FAB): 647 (M⁺+1)

EXAMPLE 36

N-[(3RS)-2,3-Dihydro-1,5–9-trimethyl-2-oxo-1H-1,4-benzodiazepin-3-yl]-N'-(3-methylphenyl)urea was prepared in a similar manner to that of Example 59.

mp: 204.2–206.6° C.

IR (Nujol, cm⁻¹): 1685, 1645, 1610

¹H-NMR (DMSO-d₆, δ): 2.22 (3H, s), 2.35 (3H, s), 2.42 (3H, s), 3.10 (3H, s), 5.03 (1H, dd, J=1.4 Hz, J=8.5 Hz), 6.72 (1H, d, J=6.4 Hz), 7.0–7.7 (7H, m), 8.93 (1H, br, s)

Mass (APCI): 351 (M⁺+1)

EXAMPLE 37

N-[(3RS)-2,3-Dihydro-5,9-dimethyl-1-(2-methylphenacyl)-2-oxo-1H-1,4-benzodiazepin-3-yl]-N'-(3-methylphenyl)urea was prepared in a similar manner to that of Example 59.

mp: 128.4–136.2° C.

IR (Nujol, cm⁻¹): 1650

¹H-NMR (DMSO-d₆, δ): 2.22 (3H, s), 2.27 (3H, s), 2.40 (3H, s), 2.42 (3H, s), 4.55 (1H, d, J=17.1 Hz), 5.12 (1H, d, J=8.5 Hz), 5.37 (1H, d, J=17.2 Hz), 6.7–6.8 (1H, m), 7.0–7.8 (11H, m), 8.86 (1H, br, s)

Mass (APCI): 469 (M⁺+1)

EXAMPLE 38

N-[(3RS)-1-(Adamantan-1-yl)carbonylmethyl-2,3-dihydro-5,9-dimethyl-2-oxo-1H-1,4-benzodiazepin-3-yl]-N'-(3-methylphenyl)urea was prepared in a similar manner to that of Example 59.

mp: 182.2–184.2° C.

IR (Nujol, cm⁻¹): 1700, 1658, 1638

¹H-NMR (DMSO-d₆, δ): 1.6–2.1 (15H, m), 2.22 (3H, s), 2.34 (3H, s), 3.96 (1H, d, J=17.5 Hz), 5.0–5.1 (1H, m), 5.21 (1H, d, J=17.5 Hz), 6.72 (1H, d, J=6.3 Hz), 7.1–7.7 (7H, m), 8.84 (1H, br, s)

Mass (APCI): 513 (M⁺+1)

EXAMPLE 39

N-[(3RS)-1-Cyclohexylcarbonylmethyl-2,3-dihydro-5,9-dimethyl-2-oxo-1H-1,4-benzodiazepin-3-yl]-N'-(3-methylphenyl)urea was prepared in a similar manner to that of Example 59.

mp: 179.2–180.9° C.

IR (Nujol, cm$^{-1}$): 1710, 1655, 1638

$^1$H-NMR (DMSO-d$_6$, δ): 1.0–1.8 (10H, m), 1.8–2.0 (1H, m), 2.22 (3H, s), 2.33 (3H, s), 4.06 (1H, d, J=17.6 Hz), 5.02 (1H, d, J=17.3 Hz), 5.08 (1H, d, J=7.0 Hz), 6.72 (1H, d, J=6.0 Hz), 7.0–7.6 (7H, m), 8.84 (1H, br, s)

Mass (APCI): 461 (M$^+$+1)

EXAMPLE 40

N-[(3RS)-2,3-Dihydro-5-(2-fluorophenyl)-9-methyl-1 -methylcarbonylmethyl-2-oxo-1H-1,4-benzodiazepin-3-yl]-N'-[3-(tetrazol-5-yl)phenyl]urea was prepared in a similar manner to that of Example 51.

mp: 173.5–189.8° C.

IR (Nujol, cm$^{-1}$): 1730, 1680, 1650

$^1$H-NMR (DMSO-d$_6$, δ):2.03 (3H, s), 2.41 (3H, s), 4.29 (1H, d, J=17.7 Hz), 4.96 (1H, d, J=17.6 Hz), 6.9–7.8 (11H, m), 8.20 (1H, m), 9.35 (1H, br, s)

Mass (APCI): 527 (M$^+$+1)

EXAMPLE 41

N-[(3RS)-2,3-Dihydro-5,9-dimethyl-1-tert-butylcarbonylmethyl-2-oxo-1H-1,4-benzodiazepin-3-yl]-N'-(3-methylphenyl)urea was prepared in a similar manner to that of Example 59.

mp: 179.6–181.2° C.

IR (Nujol, cm$^{-1}$): 1720, 1670, 1645

$^1$H-NMR (DMSO-d$_6$, δ): 1.08 (9H, s), 2.22 (3H, s), 2.34 (3H, s), 4.01 (1H, d, J=17.4 Hz), 5.08 (1H, dd, J=1.4 Hz and J=8.5 Hz), 5.22 (1H, d, J=17.4 Hz), 6.72 (1H, d, J=6.5 Hz), 7.0–7.7 (7H, m), 8.84 (1H, br, s)

Mass (APCI): 435 (M$^+$+1)

EXAMPLE 42

N-[(3RS)-2,3-Dihydro-5-(2-fluorophenyl)-9-methyl-1-(3-nitrophenacyl)-2-oxo-1H-1,4-benzodiazepin-3-yl]-N'-[3-(tetrazol-5-yl)phenyl]urea was prepared in a similar manner to that of Example 51.

mp: 194.4–198.1° C.

IR (Nujol, cm$^{-1}$): 1655, 1620

$^1$H-NMR (DMSO-d$_6$, δ): 2.50 (3H, s), 4.96 (1H, d, J=17.7 Hz), 5.43 (1H, d, J=8.3 Hz), 5.84 (1H, d, J=17.8 Hz), 7.0–8.5 (15H, m), 8.65 (1H, m), 9.33 (1H, m)

Mass (APCI): 634 (M$^+$+1)

EXAMPLE 43

N-[(3RS)-2,3-Dihydro-5-(2-fluorophenyl)-9-methyl-1-(2-nitrophenacyl)-2-oxo-1H-1,4-benzodiazepin-3-yl]-N'-[3-(tetrazol-5-yl)phenyl]urea was prepared in a similar manner to that of Example 51.

mp: 192.2–197.1° C.

IR (Nujol, cm$^{-1}$): 1650, 1620

$^1$H-NMR (DMSO-d$_6$, δ): 2.45 (3H, s), 4.73 (1H, d, J=18.1 Hz), 5.3–5.5 (2H, m), 7.0–8.2 (16H, m)

EXAMPLE 44

N-[(3RS)-2,3-Dihydro-1-ethylcarbonylmethyl-5,9-dimethyl-2-oxo-1H-1,4-benzodiazepin-3-yl]-N'-(3-methylphenyl)urea was prepared in a similar manner to that of Example 59.

mp: 125.1–127.5° C.

IR (Nujol, cm$^{-1}$): 1720, 1640

$^1$H-NMR (DMSO-d$_6$, δ): 0.87 (3H, t, J=7.2 Hz), 2.22 (3H, s), 2.33 (3H, s), 2.3–2.5 (2H, m), 4.08 (1H, d, J=17.5 Hz), 4.92 (1H, d, J=17.5 Hz), 5.10 (1H, dd, J=1.4 Hz and 8.5 Hz), 6.7–6.9 (1H, m), 7.0–7.7 (7H, m), 8.90 (1H, br, s)

Mass (APCI): 407 (M$^+$+1)

EXAMPLE 45

N-[(3RS)-1-(3-Azabicyclo[3.2.2]non-3-yl) carbonylmethyl-2,3-dihydro-5-isopropyl-9-methyl-2-oxo-1H-1,4-benzodiazepin-3-yl]-N'-(3-methylphenyl)urea was prepared in a similar manner to that of Example 59.

mp: 189.9–192.8° C.

IR (Nujol, cm$^{-1}$): 1650, 1610, 1700

$^1$H-NMR (DMSO-d$_6$, δ): 1.11 (3H, d, J=7.0 Hz), 1.21 (3H, d, J=6.5 Hz), 1.4–2.1 (10H, m), 2.22 (3H, s), 2.37 (3H, s), 3.0–3.4 (2H, m), 3.6–4.0 (2H, m), 4.04 (1H, d, J=16.1 Hz), 5.00 (1H, d, J=16.2 Hz), 5.09 (1H, d, J=8.4 Hz), 6.72 (1H, d, J=6.2 Hz), 7.0–7.7 (7H, m), 8.85(1H, br, s)

Mass (APCI): 530 (M$^+$+1)

EXAMPLE 46

N-[(3RS)-2,3-Dihydro-5,9-dimethyl-1-methylcarbonylmethyl-2-oxo-1H-1,4-benzodiazcpin-3-yl]-N'-(3-methylphenyl)urea was prepared in a similar manner to that of Example 59.

mp: 126.1–127.7° C.

IR (Nujol, cm$^{-1}$): 1720, 1650

$^1$H-NMR (DMSO-d$_6$, δ): 2.00 (3H, s), 2.22 (3H, s), 2.33 (3H, s), 2.47 (3H, s), 4.11 (1H, d, J=17.8 Hz), 4.93 (1H, d, J=17.6 Hz), 5.0–5.2 (1H, m), 6.7–6.8 (1H, m), 7.0–7.6 (7H, m), 8.90 (1H, br, s)

Mass (APCI): 393 (M$^+$+1)

EXAMPLE 47

N-[(3RS)-5-Cyclohexyl-1-cyclopropylcarbonylmethyl-2,3-dihydro-9-methyl-2-oxo-1H-1,4-benzodiazepin-3-yl]-N'-[3-(tetrazol-5-yl)phenyl]urea was prepared in a similar manner to that of Example 51.

mp: 227.1–233.2° C.

IR (Nujol, cm$^{-1}$): 1715, 1650

$^1$H-NMR (DMSO-d$_6$, δ): 0.7–2.1 (15H, m), 2.36 (3H, s), 2.8–3.0 (1H, m), 4.30 (1H, d, J=17.6 Hz), 4.96 (1H, d, J=17.5 Hz), 5.10 (1H, d, J=8.2 Hz), 7.3–7.7 (7H, m), 8.15 (1H, br), 9.23 (1H, br, s)

Mass (APCI): 541 (M$^+$+1)

EXAMPLE 48-1

N-[(3RS)-2,3-Dihydro-1-ethoxycarbonylmethyl-5,9-dimethyl-2-oxo-1H-1,4-benzodiazepin-3-yl]-N'-(3-methylphenyl)urea was prepared in a similar manner to that of Example 59.

mp: 229.7–231.0° C.

IR (Nujol, cm$^{-1}$): 1755, 1685, 1645, 1615

$^1$H-NMR (DMSO-d$_6$, δ): 1.27 (3H, t, J=7.1 Hz), 2.22 (3H, s), 2.33 (3H, s), 2.45 (3H, s), 4.02 (2H, q, J=7.1 Hz), 4.08 (1H, m), 4.68 (1H, d, J=16.8 Hz), 5.09–5.14 (1H, m), 6.72 (1H, d, J=6.4 Hz), 7.0–7.7 (7H, m), 8.87 (1H, br, s)

Mass (APCI): 423 (M$^+$+1)

EXAMPLE 48-2

A mixture of N-[(3RS)-2,3-dihydro-1-ethoxycarbonymethyl-5,9-dimethyl-2-oxo-1H-1,4- benzodiazepin-3-yl]-N'-(3-methylphenyl)urea (1.3 g) and 1N aqueous sodium hydroxide (15 ml) in 1,2-dimethoxyethane (15 ml) was stirred at room temperature overnight. 1N aqueous hydrochloric acid was added to the reaction mixture. The mixture was evaporated to dryness to afford a residue, which was triturated in water and collected by filtration to give the first crop of the desired product as a white powder (417 mg, 34.3%). To the filtrate were added ethyl acetate and 0.1N aqueous hydrochloric acid. The separated organic layer was washed with water and brine, and then dried over magnesium sulfate. The solvent was evaporated in vacuo to afford the second crop of N-[(3RS)-2,3-dihydro-1-carboxymethyl-5,9-dimethyl-2-oxo-1H-1,4-benzodiazepin-3-yl]-N'-(3-methylphenyl)urea (631 mg, 51.9%) as a white crystalline powder.

IR (Nujol, cm$^{-1}$): 1690, 1658, 1620 Anal: $C_{21}H_{22}N_4O_4 \cdot 0.5H_2O$ calc. C; 62.52; H, 5.75; N, 13.89 found C; 62.86; H, 5.58; N,6745 13.84

$^1$H-NMR (DMSO-$d_6$, δ): 2.22 (3H, s), 2.33 (3H, s), 2.41 (3H, s), 3.94 (1H, d, J=17.0 Hz), 4.65 (1H, d, J=17.0 Hz), 5.10 (1H, d, J=7.2 Hz), 6.72 (1H, d, J=6.4 Hz), 7.0–7.6 (7H, m), 8.91 (1H, s)

Mass (APCI): 395 (M$^+$+1)

EXAMPLE 48-3(1)

N-[(3RS)-1-[4-(Piperidino)piperidin-1-yl] carbonylmethyl-5,9-dimethyl-2,3-dibydro-2-oxo-1H-1,4-benzodiazepin-3-yl]-N'-(3-methylphenyl)urea was prepared in a similar manner to that of Preparation 59-5.

mp: 214.5–217.3° C.

IR (Nujol, cm$^{-1}$): 1660

$^1$H-NMR (DMSO-$d_6$, δ): 1.0–1.9 (10H, m), 2.22 (3H, s), 2.35 (3H, s), 2.43 (3H, s), 2.3–2.6 (6H, m), 2.8–3.1 (1H, m), 3.7–4.0 (2H, m), 4.1–4.3 (1H, m), 4.9–5.2 (2H, m), 6.71 (1H, d, J=6.4 Hz), 7.0–7.7 (7H, m), 8.92 (1H, br, s)

Mass (APCI): 545 (M$^+$+1)

EXAMPLE 48-3(2)

N-[(3RS)-2,3-Dihydro-5,9-dimethyl-1-(4-methylpiperazin-1-yl)carbonylmethyl-2-oxo-1H-1,4-benzodiazepin-3-yl]-N'-(3-methylphenyl)urea was prepared in a similar manner to that of Preparation 59-5.

IR (Nujol, cm$^{-1}$): 1675, 1640, 1610

$^1$H-NMR (DMSO-$d_6$, δ): 2.15 (3H, s), 2.22 (3H, s), 2.35 (3H, s), 2.43 (3H, s), 3.3–3.5 (4H, br), 3.91 (1H, d, J=16.4 Hz), 5.04 (1H, d, J=16.1 Hz), 5.11–5.12 (1H, m), 6.71 (1H, d, J=6.3 Hz), 7.0–7.6 (7H, m), 8.92 (1H, br, s)

Mass (APCI): 477 (M$^+$+1)

EXAMPLE 48-3(3)

N-[(3RS)-5,9-Dimethyl-1-[(pyrrolidin-1-yl) carbonylmethyl]-2-oxo-1H-1,4-benzodiazepin-3-yl]-N'-(3-methylphenyl)urea was prepared in a similar manner to that of Preparation 59-5.

IR (Nujol, cm$^{-1}$): 1650

$^1$H-NMR (DMSO-$d_6$, δ): 1.6–2.0 (2H, m), 2.22 (3H, s), 2.35 (3H, s), 2.43 (3H, s), 3.1–3.3 (2H, m), 3.88 (1H, d, J=16.4 Hz), 4.86 (1H, d, J=16.4 Hz), 5.10 (1H, d, J=7.2 Hz), 6.72 (1H, d, J=6.3 Hz), 7.0–7.6 (7H, m), 8.92 (1H, s)

Mass (APCI): 448 (M$^+$+1)

EXAMPLE 48-3(4)

N-[(3RS)-1-(Azacyclooctan-1-yl)carbonylmethyl-5,9-dimethyl-2,3-dihydro-2-oxo-1H-1,4-benzodiazepin-3-yl]-N'-(3-methylphenyl)urea was prepared in a similar manner to that of Preparation 59-5.

IR (Nujol, cm$^{-1}$): 1650, 1610

$^1$H-NMR (DMSO-$d_6$, δ): 1.2–1.8 (10H, m), 2.22 (3H, s), 2.36 (3H, s), 2.44 (3H, s), 2.9–3.3 (2H, m), 3.3–3.6 (2H, m), 3.93 (1H, d, J=16.1 Hz), 4.95 (1H, d, J=16.1 Hz), 5.09 (1H, d, J=7.1 Hz), 6.71 (1H, d, J=6.5 Hz), 7.0–7.6 (7H, m), 8.86 (1H, br, s)

Mass (APCI): 490 (M$^+$+1)

EXAMPLE 48-3(5)

N-{(3RS)-1-[(3RS)-3-(N,N-Diethylaminocarbonyl) piperidin-1-yl]-carbonylmethyl-5,9-dimethyl-2,3-dihydro-2-oxo-1H-1,4-benzodiazepin-3-yl}-N'-(3-methylphenyl) urea was prepared in a similar manner to that of Preparation 59-5.

mp: 150.8–154.7° C.

IR (Nujol, cm$^{-1}$): 1655, 1610

$^1$H-NMR (DMSO-$d_6$, δ): 0.9–1.3 (8H, m), 1.4–2.0 (2H, m), 2.22 (3H, s), 2.35 (3H, s), 2.43 (3H, s), 2.9–3.5 (7H, m), 3.7–4.3 (3H, m), 5.0–5.2 (2H, m), 6.71 (1H, d, J=6.2 Hz), 7.0–7.8 (7H, m), 8.90 (1H, m)

Mass (APCI): 561 (M$^+$+1)

EXAMPLE 48-3(6)

N-[(3RS)-1-(4-Hydroxy-4-phenylpiperidin-1-yl) carbonylmethyl-5,9-dimethyl-2,3-dihydro-2-oxo-1H-1,4 -benzodiazepin-3-yl]-N'-(3-methylphenyl)urea was prepared in a similar manner to that of Preparation 59-5.

mp: 163.2–164.9° C.

IR (Nujol, cm$^{-1}$): 1665, 1645

$^1$H-NMR (DMSO-$d_6$, δ): 1.4–2.0 (4H, m), 2.22 (3H, s), 2.37 (3H, s), 2.45 (3H, s), 2.8–3.0 (1H, m), 3.2–3.6 (2H, m), 3.6–4.3 (3H, m), 4.9–5.2 (2H, m), 6.71 (1H, d, J=6.5 Hz), 7.0–7.6 (12H, m), 8.94 (1H, m)

Mass (APCI): 554 (M$^+$+1)

EXAMPLE 48-3(7)

N-[(3RS)-2,3-dihydro-5,9-dimethyl-1-(morpholin-1-yl)-carbonylmethyl-2-oxo-1H-1,4-benzodiazepin-3-yl]-N'-(3-methylphenyl)urea was prepared in a similar manner to that of Preparation 59-5.

mp: 219.0–220.1° C.

IR (Nujol, cm$^{-1}$): 1675, 1640

$^1$H-NMR (DMSO-$d_6$, δ) 2.22 (3H, s), 2.36 (3H, s), 2.43 (3H, s), 3.3–3.6 (8H, m), 3.94 (1H, d, J=16 Hz), 5.04 (1H, d, J=16 Hz), 5.10 (1H, d, J=6.9 Hz), 6.72 (1H, d, J=6.3 Hz), 7.0–7.6 (7H, m), 8.92 (1H, s)

Mass (APCI): 464 (M$^+$+1)

EXAMPLE 48-3(8)

N-{(3RS)-2,3-Dihydro-5,9-dimethyl-1-[4-methylpiperazin-1-yl)carbonylmethyl]-2-oxo-1H-1,4-benzodiazepin-3-yl}-N'-(3-methylphenyl)urea was prepared in a similar manner to that of Preparation 59-5.

IR (Nujol, cm$^{-1}$): 1675, 1640, 1610

$^1$H-NMR (DMSO-$d_6$, δ) 2.15 (3H, s), 2.22 (3H, s), 2.35 (3H, s), 2.43 (3H, s), 3.3–3.5 (4H, br), 3.91 (1H, d, J=16.4 Hz), 5.04 (1H, d, J=16.1 Hz), 5.11–5.12 (1H, m), 6.71 (1H, d, J=6.3 Hz), 7.0–7.6 (7H, m), 8.92 (1H, br, s)

Mass (APCI): 477 (M$^+$+1)

EXAMPLE 48-3(9)

N-[(3RS)-1-(N,N-Diethylamino)carbonylmethyl-2,3-dihydro-5,9-dimethyl-2-oxo-1H-1,4-benzodiazepin-3-yl]-

N'-(3-methylphenyl)urea was prepared in a similar manner to that of Preparation 59-5.

IR (Nujol, cm$^{-1}$): 1670, 1625

$^1$H-NMR (DMSO-d$_6$, δ): 0.92 (3H, t, J=7.0 Hz), 1.13 (3H, t, J=7.0 Hz), 2.22 (3H, s), 2.36 (3H, s), 2.43 (3H, s), 3.0–3.5 (4H, m), 3.88 (1H, d, J=16.1 Hz), 4.97 (1H, d, J=16.1 Hz), 5.08 (1H, d, J=7.1 Hz), 6.71 (1H, d, J=6.5 Hz), 7.0, 7.6 (7H, m), 8.89 (1H, br, s)

Mass (APCI): 450 (M$^+$+1)

EXAMPLE 48-3(10)

N-[(3RS)-2,3-Dihydro-1-(N-ethylamino)carbonylmethyl-5,9-dimethyl-2-oxo-1H-1,4-benzodiazepin-3-yl]-N'-(3-methylphenyl)urea was prepared in a similar manner to that of Preparation 59-5.

IR (Nujol, cm$^{-1}$): 1658, 1610

$^1$H-NMR (DMSO-d$_6$, δ): 0.93 (3H, t, J=7.2 Hz), 2.22 (3H, s), 2.32 (3H, s), 2.42 (3H, s), 2.9–3.0 (2H, m), 3.76 (1H, d, J=15.8 Hz), 4.63 (1H, d, J=15.8 Hz), 5.07 (1H, d, J=8.5 Hz), 6.71 (1H, d, J=6.2 Hz), 7.0–7.3 (3H, m), 7.3–7.4 (1H, m), 7.4–7.6 (2H, m), 7.8–8.0 (1H, m), 8.91 (1H, br, s)

Mass (APCI): 422 (M$^+$+1)

EXAMPLE 48-3(11)

N-[(3RS)-2,3-Dihydro-5,9-dimethyl-1-(N-tert-butylamino-carbonylmethyl)-2-oxo-1H-1,4-benzodiazepin-3-yl]-N'-(3-methylphenyl)urea was prepared in a similar manner to that of Preparation 59-5.

mp: 243.4–244.4° C.

IR (Nujol, cm$^{-1}$): 3310, 1645

$^1$H-NMR (DMSO-d$_6$, δ): 1.13 (9H, s), 2.22 (3H, s), 2.32 (3H, s), 2.43 (3H, s), 3.68 (1H, d, J=15.7 Hz), 4.62 (1H, d, J=15.7 Hz), 5.07 (1H, dd, J=1.4 Hz and 8.6 Hz), 6.72 (1H, d, J=6.5 Hz), 7.0–7.6 (7H, m), 8.87 (1H, br, s)

Mass (APCI): 450 (M$^+$+1)

EXAMPLE 48-3(12)

N-[(3RS)-1-(Azacycloheptan-1-yl)carbonylmethyl-2,3-dihydro-5,9-dimethyl-2-oxo-1H-1,4-benzodiazepin-3-yl]-N'-(3-methylphenyl)urea was prepared in a similar manner to that of Preparation 59-5.

mp: 203.6–204.2° C.

IR (Nujol, cm$^{-1}$): 1670, 1630

$^1$H-NMR (DMSO-d$_6$, δ): 1.3–1.9 (8H, m), 2.22 (3H, s), 2.36 (3H, s), 2.44 (3H, s), 3.0–3.2 (1H, m), 3.2–3.4 (1H, m), 3.4–3.7 (2H, m), 3.92 (1H, d, J=16.2 Hz), 4.96 (1H, d, J=16.1 Hz), 5.09 (1H, d, J=7.4 Hz), 6.71 (1H, d, J=6.4 Hz), 7.0–7.6 (7H, m), 8.87 (1H, br, s)

Mass (APCI): 476 (M$^+$+1)

EXAMPLE 48-3(13)

N-[(3RS)-1-(4-Aminocarbonylpiperidin-1-yl)carbonylmethyl-2,3-dihydro-5,9-dimethyl-2-oxo-1H-1,4-benzodiazepin-3-yl]-N'-(3-methylphenyl)urea was prepared in a similar manner to that of Preparation 59-5.

mp: 196.8–198.0° C.

IR (Nujol, cm$^{-1}$): 1650

$^1$H-NMR (DMSO-d$_6$, δ): 1.1–1.8 (4H, m), 2.22 (3H, s), 2.36 (3H, s), 2.43 (3H, s), 2.6–2.8 (1H, m), 2.8–3.2 (2H, m), 3.7–4.2 (3H, m), 4.9–5.2 (2H, m), 6.7–6.9 (1H, br, s), 7.0–7.6 (7H, m), 8.93 (1H, br, s)

Mass (APCI): 505 (M$^+$+1)

EXAMPLE 48-3(14)

N-[(3RS)-2,3-Dihydro-1-[4-(2-hydroxyethyl)piperazin-1-yl]carbonylmethyl-5,9-dimethyl-2-oxo-1H-1,4-benzodiazepin-3-yl]-N'-(3-methylphenyl)urea was prepared in a similar manner to that of Preparation 59-5.

mp: 221.7–224.2° C.

IR (Nujol, cm$^{-1}$): 1660, 1635

$^1$H-NMR (DMSO-d$_6$, δ): 2.22 (3H, s), 2.35 (3H, s), 2.43 (3H, s), 2.2–2.6 (8H, m), 3.3–3.6 (4H, m), 3.91 (1H, d, J=16.4 Hz), 4.3–4.5 (1H, m), 5.0–5.2 (2H, m), 6.73 (1H, m), 7.0–7.6 (7H, m), 8.92 (1H, br, s)

Mass (APCI): 507 (M$^+$+1)

EXAMPLE 48-3(15)

N-[(3RS)-2,3-Dihydro-1-(N,N-diisobutylamino)carbonylmethyl-5,9-dimethyl-2-oxo-1H-1,4-benzodiazepin-3-yl]-N'-(3-methylphenyl)urea was prepared in a similar manner to that of Preparation 59-5.

mp: 226.9–228.1° C.

IR (Nujol, cm$^{-1}$): 1680, 1660

$^1$H-NMR (DMSO-d$_6$, δ): 0.7–0.8 (6H, m), 0.8–1.0 (6H, m), 2.22 (3H, s), 2.36 (3H, s), 2.43 (3H, s), 2.9–3.2 (4H, m), 3.89 (1H, d, J=16.0 Hz), 4.99 (1H, d, J=16.0 Hz), 5.07 (1H, d, J=7.1 Hz), 6.71 (1H, d, J=6.3 Hz), 7.0–7.6 (7H, m), 8.85 (1H, br, s)

Mass (APCI): 506 (M$^+$+1)

EXAMPLE 48-3(16)

N-[(3RS)-2,3-Dihydro-1-(N,N-bis-(2-hydroxyethyl)amino)-carbonylmethyl-5,9-dimethyl-2-oxo-1H-1,4-benzodiazepin-3-yl]-N'-(3-methylphenyl)urea was prepared in a similar manner to that of Preparation 59-5.

mp: 160.5–161.1° C.

IR (Nujol, cm$^{-1}$): 1650, 3300

$^1$H-NMR (DMSO-d$_6$, δ): 2.22 (3H, s), 2.34 (3H, s), 2.43 (3H, s), 2.9–3.8 (6H, m), 4.15 (1H, d, J=16.5 Hz), 4.5–4.7 (1H, m), 4.8–5.0 (1H, br), 5.0–5.2 (2H, br), 6.72 (1H, d, J=6.3 Hz), 7.0–7.6 (7H, m), 8.92 (1H, br, s)

Mass (APCI): 482 (M$^+$+1)

EXAMPLE 49

N-[(3RS)-5-Cyclohexyl-2,3-dihydro-1-(imidazol-4-yl)methyl-9-methyl-2-oxo-1H-1,4-benzodiazepin-3-yl]-N'-[3-(tetrazol-5-yl)phenyl]urea was prepared in a similar manner to that of Example 51.

mp: 168.2–179.2° C.

IR (Nujol, cm$^{-1}$): 1650

$^1$H-NMR (DMSO-d$_6$, δ): 0.9–1.9 (10H, m), 2.45 (3H, s), 2.73 (1H, br, s), 4.23 (1H, d, J=14.7 Hz), 5.03 (1H, d, J=8.3 Hz), 5.36 (1H, d, J=14.7 Hz), 6.8–7.0 (1H, br, s), 7.2–7.6 (8H, m), 8.0–8.2 (2H, m), 9.25 (1H, br, s)

Mass (FAB): 539 (M$^+$+1)

EXAMPLE 50(1)

N-[(3RS)-1-(3-Azabicyclo[3.2.2]non-3-yl)carbonylmethyl-5,9-dimethyl-2,3-dihydro-2-oxo-1H-1,4-benzodiazepin-3-yl]-N'-(3-bromophenyl)urea was prepared in a similar manner to that of Example 59.

mp: 168.1–171.1° C.

IR (Nujol, cm$^{-1}$): 1645

$^1$H-NMR (DMSO-d$_6$, δ): 1.3–2.2 (10H, m), 2.36 (3H, s), 2.45 (3H, s), 2.9–3.4 (2H, m), 3.5–3.9 (2H, m), 3.96 (1H, d,

J=16.5 Hz), 5.11 (1H, d, J=16.5 Hz), 5.09 (1H, d, J=8.6 Hz), 7.0–7.6 (7H, m), 7.75 (1H, br, s), 9.16 (1H, br, s)

Mass (APCI): 568 ($M^++2$), 564 ($M^+$)

EXAMPLE 50(2)

N-[(3RS)-1-(3-Azabicyclo[3.2.2]non-3-yl)carbonylmethyl-5,9-dimethyl-2,3-dihydro-2-oxo-1H-1,4-benzodiazepin-3-yl]-N'-(3-chlorophenyl)urea was prepared in a similar manner to that of Example 59.

mp: 181.2–185.1° C.

IR (Nujol, $cm^{-1}$): 1680, 1640

$^1$H-NMR (DMSO-$d_6$, δ): 1.3–2.2 (10H, m), 2.36 (3H, s), 2.44 (3H, s), 2.9–3.3 (2H, m), 3.5–3.9 (2H, m), 3.96 (1H, d, J=16.4 Hz), 5.11 (1H, d, J=16.4 Hz), 5.0–5.2 (1H, m), 6.94 (1H, d, J=8.5 Hz), 7.0–7.7 (7H, m), 9.17 (1H, br, s)

Mass (APCI): 522 ($M^++1$)

EXAMPLE 50(3)

N-[(3RS)-1-(3-Azabicyclo[3.2.2]non-3-yl)carbonylmethyl-5,9-dimethyl-2,3-dihydro-2-oxo-1H-1,4-benzodiazepin-3-y]-N'-(3-methylthiophenyl)urea was prepared in a similar manner to that of Example 59.

mp: 237.2–238.5° C.

IR (Nujol, $cm^{-1}$): 1680, 1660, 1645

$^1$H-NMR (DMSO-$d_6$, δ): 1.3–2.2 (10H, m), 2.36 (3H, s), 2.40 (3H, s), 2.44 (3H, s), 2.9–3.4 (2H, m), 3.5–3.9 (2H, m), 3.96 (1H, d, J=16.5 Hz), 5.11 (1H, d, J=16.5 Hz), 5.0–5.2 (1H, m)

Mass (APCI): 534 ($M^++1$)

EXAMPLE 50(4)

N-[(3RS)-1-(3-Azabicyclo[3.2.2]non-3-yl)carbonylmethyl-5,9-dimethyl-2,3-dihydro-2-oxo-1H-1,4-benzodiazepin-3-yl]-N'-(3-methoxyphenyl)urea was prepared in a similar manner to that of Example 59.

mp: 169.6–170.7° C.

IR (Nujol, $cm^{-1}$): 1700, 1675, 1640

$^1$H-NMR (DMSO-$d_6$, δ): 1.3–2.2 (10H, m), 2.36 (3H, s), 2.44 (3H, s), 2.9–3.3 (2H, m), 3.5–3.9 (2H, m), 3.67 (3H, s), 3.96 (1H, d, J=16.5 Hz), 5.11 (1H, d, J=16.5 Hz), 5.0–5.2 (1H, m), 6.4–6.6 (1H, m), 6.7–6.9 (1H, m), 7.0–7.6 (6H, m), 8.98 (1H, br, s)

Mass (APCI): 518 ($M^++1$)

EXAMPLE 50(5)

N-[(3RS)-1-(3-Azabicyclo[3.2.2]non-3-yl)carbonylmethyl-2,3-dihydro-5,9-dimethyl-2-oxo-1H-1,4-benzodiazepin-3-yl]-N'-(3-methylphenyl)urea was prepared in a similar manner to that of Example 59.

mp: 176.9–179.1° C.

IR (Nujol, $cm^{-1}$): 1670, 1640

$^1$H-NMR (DMSO-$d_6$, δ): 1.4–1.8 (8H, m), 1.9–2.1 (2H, m), 2.22 (3H, s), 2.36 (3H, s), 2.44 (3H, s), 3.0–3.4 (2H, m), 3.6–4.0 (2H, m), 3.96 (1H, d, J=16 Hz), 5.11 (1H, d, J=16 Hz), 5.0–5.1 (1H, br, m), 6.71 (1H, d, J=6.6 Hz), 7.0–7.6 (7H, m), 8.87 (1H, br, s)

Mass (APCI): 502 ($M^++1$)

EXAMPLE 51

A mixture of 3-amino-1-(2-acetylbenzyl)-5-cyclohexyl-2,3-dihydro-9-methyl-1H-1,4-benzodiazepin-2-one (280 mg), 4-nitrophenyl N-{3-(tetrazol-5-yl)phenyl}carbamate (249 mg) and triethylamine (281 mg) in NN-dimethylformamide was stirred at room temperature for 50 minutes. Ethyl acetate and 0.1N aqueous hydrochloric acid were added to the reaction mixture. The separated organic layer was washed with water and brine, and then dried over magnesium sulfate. The solvent was evaporated in vacuo to afford a residue, which was washed with diisopropyl ether to give N-[(3RS)-1-(2-acetylbenzyl)-5-cyclohexyl-2,3-dihydro-9-methyl-2-oxo-1H-1,4-benzodiazcpin-3-yl]-N'-[3-(tetrazol-5-yl)phenyl]urea (348 mg, 84.9%) as a crystalline powder.

mp: 199.0–208.0C.

IR (Nujol, $cm^{-1}$): 1635

$^1$H-NMR (DMSO-$d_6$, δ): 1.0–2.2 (10H, m), 2.33 (3H, s), 2.41 (3H, s), 3.00 (1H, br, s), 4.57 (1H, d, J=17.4 Hz), 5.19 (1H, d, J=8.1 Hz), 5.33 (1H, d, J=17.4 Hz), 7.0–8.0 (1H, m), 9.22 (1H, br, s)

Mass (APCI): 591 ($M^++1$)

EXAMPLE 52

N-[(3RS)-5-(3-Azabicyclo[3.2.2]non-3-yl)methyl-2,3-dihydro-1,9-dimethyl-2-oxo-1H-1,4-benzodiazepin-3-yl]-N'-(3-methylphenyl)urea was prepared in a similar manner to that of Example 59.

mp: 145.6–149.2° C.

IR (Nujol, $cm^{-1}$): 1670, 1635, 1600

$^1$H-NMR (DMSO-$d_6$, δ): 1.1–1.6 (8H, m), 1.6–1.8 (2H, m), 2.22 (3H, br, s), 2.35 (3H, s), 3.06 (3H, s), 3.06–3.10 (1H, m), 4.23 (1H, d, J=13.8 Hz), 5.12 (1H, d, J=7.9 Hz), 6.72 (1H, d, J=6.3 Hz), 7.0–7.3 (3H, m), 7.3–7.45 (2H, m), 7.45–7.6 (1H, d, J=6.9 Hz), 7.67 (1H, d, J=7.5 Hz), 8.94 (1H.s)

Mass (APCI): 474 ($M^++1$)

EXAMPLE 53

N-[(3RS)-1-(3-Azabicyclo[3.2.2]non-3-yl)carbonylmethyl-2,3-dihydro-5-methoxymethyl-9-methyl-2-oxo-1H-1,4-benzodiazepin-3-yl]-N'-(3-methylphenyl)urea was prepared in a similar manner to that of Example 59.

mp: 178.1–182.1° C.

IR (Nujol, $cm^{-1}$): 1640

$^1$H-NMR (DMSO-$d_6$, δ): 1.4–1.9 (8H, m), 1.9–2.1 (2H, m), 2.22 (3H, s), 2.38 (3H, s), 3.35 (3H, s), 3.3–4.1 (4H, m), 4.00 (1H, d, J=16.9 Hz), 4.52 (2H, m), 5.0–5.3 (2H, m), 6.74 (1H, br, s), 7.0–7.7 (7H, m), 8.88 (1H, br, s)

Mass (APCI): 532 ($M^++1$)

EXAMPLE 54

N-[(3RS)-5-Cyclohexyl-1-cyclohexylcarbonylmethyl-2,3-dihydro-9-methyl-2-oxo-1H-1,4-benzodiazepin-3-yl]-N'-(3-methylphenyl)urea was prepared in a similar manner to that of Example 59.

mp: 159.3–169.6° C.

IR (Nujol, $cm^{-1}$): 1710, 1640, 1600

$^1$H-NMR (DMSO-$d_6$, δ): 1.0–2.1 (20H, m), 2.22 (3H, s), 2.33 (3H, s), 2.3–2.6 (1H, br, s), 2.94 (1H, br, s), 4.10 (1H, d, J=17.4 Hz), 4.89 (1H, d, J=17.4 Hz), 5.06 (1H, d, J=8.4 Hz), 6.71 (1H, d, J=5.5 Hz), 7.0–7.6 (7H, m), 8.81 (1H, br, s)

Mass (APCI): 530 ($M^++1$)

EXAMPLE 55

N-[(3RS)-2,3-Dihydro-1, 9-dimethyl-5-(4-methylpiperazin-1-yl)-methyl-2-oxo-1H-1,4- benzodiazepin-3-yl]-N'-(3-methylphenyl)urea was prepared in a similar manner to that of Example 59.

mp: 136.2–140.1° C.

IR (Nujol, cm$^{-1}$): 1650, 1600

$^1$H-NMR (DMSO-d$_6$, δ): 2.07 (3H, s), 2.21 (3H, s), 2.27 (3H, s), 2.35 (3H, s), 2.0–2.6 (4H, m), 2.9–3.2 (5H, m), 4.11 (1H, d, J=11.6 Hz), 5.07 (1H, d, J=8,1 Hz), 6.7–6.9 (1H, br, s), 7.0–7.8 (7H, m)

Mass (APCI): 449 (M$^+$+1)

EXAMPLE 56

N-[(3RS)-1-(3-azabicyclo[3.2.2]non-3-yl)carbonylmethyl-2,3-dihydro-5-(N,N-dimethyaminomethyl)-9-methyl-2-oxo-1H-1,4-benzodiazepin-3-yl]-N'-(3-methylphenyl)urea was prepared in a similar manner to that of Example 59.

mp: 154.0–156.9° C.

IR (Nujol, cm$^{-1}$): 1650, 1610

$^1$H-NMR (DMSO-d$_6$, δ): 1.4–1.8 (8H, m), 1.9–2.1 (2H, m), 2.22 (3H, br, s), 2.25 (6H, br, s), 2.37 (3H, br, s), 3.0–3.2 (1H, m), 3.4–3.9 (5H, m), 3.9–4.1 (1H, m), 4.9–5.1 (1H, m), 5.13 (1H, d, J=8.0 Hz), 6.73 (1H, m), 7.0–7.2 (2H, m), 7.2–7.4 (2H, m), 7.4–7.5 (1H, m), 7.8–7.9 (1H, m), 8.88 (1H, br, s)

Mass (APCI): 545

EXAMPLE 57

N-[(3RS)-1-(3-azabicyclo[3.2.2]non-3-yl)carbonylmethyl-5 -cyclopropyl-2,3-dihydro-9-methyl-2-oxo-1H-1,4-benzodiazepin-3-yl]-N'-(3-methylphenyl)urea was prepared in a similar manner to that of Example 59.

mp: 172.0–174.4° C.

IR (Nujol, cm$^{-1}$): 1680, 1650, 1610

$^1$H-NMR (DMSO-d$_6$, δ): 0.7–0.9 (2H, m), 0.9–1.3 (2H, m), 1.4–1.9 (8H, m), 1.9–2.2 (3H, m), 2.22 (3H, s), 3.38 (3H, s), 3.1–3.4 (2H, m), 3.6–3.9 (2H, m), 4.00 (1H, d, J=16 Hz), 5.04 (1H, d, J=16 Hz), 5.06 (1H, d, J=8.5 Hz), 6.71 (1H, d, J=5.6 Hz), 7.0–7.3 (4H, m), 7.3–7.45 (1H, m), 7.45–7.6 (1H, m), 7.6–7.8 (1H, m), 8.82 (1H, br, s)

Mass (APCI): 528 (M$^+$+1)

EXAMPLE 58

N-[(3RS)-1-(3-Azabicyclo[3.2.2]non-3-yl)carbonylmethyl-2,3-dihydro-5-isobutyl-9-methyl-2-oxo-1H-1,4-benzodiazepin-3-yl]-N'-(3-methylphenyl)urea was prepared in a similar manner to that of Example 59.

mp: 133.6–135.4° C.

IR (Nujol, c$^{-1}$): 1650, 1610

$^1$H-NMR (DMSO-d$_6$, δ): 0.94 (6H, d, J=6.6 Hz), 1.4–1.9 (8H, m), 1.9–2.1 (2H, m), 2.22 (3H, br, s), 3.37 (3H, br, s), 2.1–2.2 (1H, m), 2.6–2.8 (2H, m), 3.0–3.2 (1H, m), 3.5–4.0 (3H, m), 4.01 (1H, d, J=16 Hz), 5.00 (1H, d, J=16 Hz), 5.11 (1H, d, J=8.6 Hz), 6.73 (1H, m), 7.0–7.6 (7H, m), 8.85 (1H, br, s)

Mass (APCI): 544 (M$^+$+1)

EXAMPLE 59

A mixture of (3RS)-3-amino-1-[(3-azabicyclo[3.2.2]non-3-yl)-carbonylmethyl]-2,3-dihydro-5-ethyl-9-methyl-1H-1,4-benzodiazepin-2-one (310 mg) and 3-methylphenyl isocyanate (113 mg) in tetrahydrofuran (8 ml) was stirred at room temperature for 1 hour. The reaction mixture was evaporated in vacuo to dryness. The residue was triturated in diisopropyl ether and collected by filtration to afford N-[(3RS)-1-(3-azabicyclo[3.2.2]non-3-yl)carbonylmethyl 2,3-dihydro-5-ethyl-9-methyl-2-oxo-1H-1,4-benzodiazepin-3-yl]-N'-(3-methylphenyl)urea (360 mg, 86.2% yield) as a crystalline powder.

mp: 130.1–133.0° C.

IR (Nujol, cm$^{-1}$): 1650, 1610

$^1$H-NMR (DMSO-d$_6$, δ): 1.26 (3H, t, J=7.3 Hz), 1.4–1.9 (8H, m), 1.9–2.1 (2H, m), 2.22 (3H, s), 2.37 (3H, s), 2.7–3.0 (2H, m), 3.0–3.4 (2H, m), 3.7–3.9 (2H, m), 3.98 (1H, d, J=16.2 Hz), 5.08 (1H, d, J=16.0 Hz), 5.14 (1H, d, J=7.7 Hz), 6.71 (1H, d, J=6.5 Hz), 7.0–7.6 (7H, m), 8.86 (1H, br, s)

Mass (APCI): 516 (M$^+$+1)

EXAMPLE 60(1)

N-[(3 RS)-1-(Piperidin-1-yl)carbonylmethyl-5,9-dimethyl-2,3-dihydro-2-oxo-1H-1,4-benzodiazepin-3-yl]-N'-(3-methylphenyl)urea was prepared in a similar manner to that of Preparation 59-5.

EXAMPLE 60(2)

N-[(3RS)-1-(cis-2,6-Dimethylpiperidin-1-yl)carbonylmethyl-5,9-dimethyl-2,3-dihydro-2-oxo-1H-1,4-benzodiazepin-3-yl]-N'-(3-methylphenyl)urea was prepared in a similar manner to that of Preparation 59-5.

EXAMPLE 60(3)

N-[(3RS)-1-((2RS)-2-Hydroxymethylpiperidin-1-yl)carbonylmethyl-5,9-dimethyl-2,3-dihydro-2-oxo-1H-1,4-benzodiazepin-3-yl]-N'-(3-methylphenyl)urea was prepared in a similar manner to that of Preparation 59-5.

EXAMPLE 60(4)

N-[(3RS)-1-((3RS)-3-Carbamoylpiperidin-1-yl)carbonylmethyl-5,9-dimethyl-2,3-dihydro-2-oxo-1H-1,4-benzodiazepin-3-yl]-N'-(3-methylphenyl)urea was prepared in a similar manner to that of Preparation 59-5.

EXAMPLE 60(5)

N-[(3RS)-1-((3RS)-3-Hydroxymethylpiperidin-1-yl)carbonylmethyl-5,9-dimethyl-2,3-dihydro-2-oxo-1H-1,4-benzodiazepin-3-yl]-N'-(3-methylphenyl)urea was prepared in a similar manner to that of Preparation 59-5.

EXAMPLE 60(6)

N-[(3RS)-1-(4-Hydroxypiperidin-1-yl)carbonylmethyl-5,9-dimethyl-2,3-dihydro-2-oxo-1H-1,4-benzodiazepin-3-yl]-N'-(3-methylphenyl)urea was prepared in a similar manner to that of Preparation 59-5.

EXAMPLE 60(7)

N-[(3RS)-1-(4-Oxopiperidin-1-yl)carbonylmethyl-5,9-dimethyl-2,3-dihydro-2-oxo-1H-1,4-benzodiazepin-3-yl]-N'-(3-methylphenyl)urea was prepared in a similar manner to that of Preparation 59-5.

EXAMPLE 60(8)

N-[(3RS)-1-(4-Phenylpiperidin-1-yl)carbonylmethyl-5,9-dimethyl-2,3-dihydro-2-oxo-1H-1 ,4-benzodiazepin-3-yl]-N'-(3-methylphenyl)urea was prepared in a similar manner to that of Preparation 59-5.

EXAMPLE 60(9)

N-[(3RS)-1-(4-Benzylpiperidin-1-yl)carbonylmethyl-5,9-dimethyl-2,3-dihydro-2-oxo-1H-1,4-benzodiazepin-3-yl]-

N'-(3-methylphenyl)urea was prepared in a similar manner to that of Preparation 59-5.

EXAMPLE 60(10)

N-[(3RS)-1-(4-Acetylpiperidin-1-yl)carbonylmethyl-5,9-dimethyl-2,3-dihydro-2-oxo-1H-1,4-benzodiazepin-3-yl]-N'-(3-methylphenyl)urea was prepared in a similar manner to that Preparation 59-5.

EXAMPLE 60(11)

N-[(3RS)-1-(N,N-Diisopropylamino)carbonylmethyl-5,9-dimethyl-2,3-dihydro-2-oxo-1H-1,4-benzodiazepin-3-yl]-N'-(3-methylphenyl)urea was prepared in a similar manner to that of Preparation 59-5.

EXAMPLE 60(12)

N-[(3RS)-1-(2-Hydroxyethylamino)carbonylmethyl-5,9-dimethyl-2,3-dihydro-2-oxo-1H-1,4-benzodiazepin-3-yl]-N'-(3-methylphenyl)urea was prepared in a similar manner to that of Preparation 59-5.

EXAMPLE 60(13)

N-[(3RS)-1-(1-Methyl-1-phenylethylamino)carbonylmethyl-5,9-dimethyl-2,3-dihydro-2-oxo-1H-1,4-benzodiazepin-3-yl]-N'-(3-methylphenyl)urea was prepared in a similar manner to that of Preparation 59-5.

EXAMPLE 60(14)

N-[(3RS)-1-(2-(2-Hydroxyethyl)piperidin-1-yl)carbonylmethyl-5,9-dimethyl-2,3-dihydro-2-oxo-1H-1,4-benzodiazepin-3-yl]-N'-(3-methylphenyl)urea was prepared in a similar manner to that of Preparation 59-5.

EXAMPLE 60(15)

N-[(3RS)-1-(N, N-Diisobutylamino)carbonylmethyl-5,9-dimethyl-2,3-dihydro-2-oxo-1H-1,4-benzodiazepin-3-yl]-N'-(3-methylphenyl)urea was prepared in a similar manner to that of Preparation 59-5.

EXAMPLE 60(16)

N-[(3RS)-1-(4-Phenylpiperazin-1-yl)carbonylmethyl-5,9-dimethyl-2,3-dihydro-2-oxo-1H-1,4-benzodiazepin-3-yl]-N'-(3-methylphenyl)urea was prepared in a similar manner to that of Preparation 59-5.

EXAMPLE 60(17)

N-[{(3RS)-1-[4-[(Pyrrolidin-1-yl)carbonylmethyl]piperazin-1-yl]carbonylmethyl-5,9-dimethyl-2,3-dihydro-2-oxo-1H-1,4-benzodiazepin-3-yl}-N'-(3-methylphenyl)urea was prepared in a similar manner to that of Preparation 59-5.

EXAMPLE 60 (18)

N-{ (3RS)-1-[4-(Pyridin-2-yl)piperazin-1-yl]carbonylmethyl-5,9-dimethyl-2,3-dihydro-2-oxo-1H-1,4-benzodiazepin-3-yl}-N'-(3-methylphenyl)urea was prepared in a similar manner to that of Preparation 59-5.

EXAMPLE 60(19)

N-{(3RS)-1-[4-(Pyrimidin-2-yl)piperazin-1-yl]carbonylmethyl-5,9-dimethyl-2,3-dihydro-2-oxo-1H-1,4-benzodiazepin-3-yl}-N'-(3-methylphenyl)urea was prepared in a similar manner to that of Preparation 59-5.

EXAMPLE 61

N-[(3RS)-1-Cyclohexylcarbonylmethyl-2,3-dihydro-5-ethyl-9-methyl-2-oxo-1H-1,4-benzodiazepin-3-yl]-N'-(3-methylphenyl)urea was obtained in a similar manner to that of Example 59.

mp: 161.2–164.0° C.

IR (Nujol, cm$^{-1}$): 3350, 1730, 1680, 1650

$^1$H-NMR (DMSO-d$_6$, δ): 1.0–1.4 (8H, m), 1.5–2.0 (5H, m), 2.22 (3H, s), 2.35 (3H, s), 2.2–2.5 (1H, m), 2.8–3.1 (2H, m), 4.11 (1H, d, J=17.6 Hz), 5.04 (1H, d, J=17.6 Hz), 5.21 (1H, d, J=7.4 Hz), 6.72 (1H, d, J=6.6 Hz), 7.0–7.7 (7H, m), 8.99 (1H, s)

Mass (APCI)(e/z): 475 (M$^+$+1)

EXAMPLE 62

N-[(3RS)-1-Cyclohexylcarbonylmethyl-2,3-dihydro-5-isopropyl-9-methyl-2-oxo-1H-1,4-benzodiazepin-3-yl]-N'-(3-methylphenyl)urea was obtained in a similar manner to that of Example 59.

mp: 142.4–146.1° C.

IR (Nujol, cm$^{-1}$): 3320, 1730, 1680, 1650

$^1$H-NMR (DMSO-d$_6$, δ): 1.09 (3H, d, J=7.7 Hz), 1.22 (3H, d, J=6.5 Hz), 1.0–1.4 (5H, m), 1.5–1.8 (4H, m), 1.8–2.0 (1H, m), 2.22 (3H, s), 2.34 (3H, s), 2.3–2.5 (1H, m), 3.2–3.5 (1H, m), 4.11 (1H, d, J=17.4 Hz), 4.94 (1H, d, J=17.4 Hz), 5.08 (1H, d, J=7.8 Hz), 6.6–6.8 (1H, m), 7.0–7.6 (7H, m), 8.84 (1H, s)

Mass (APCI)(e/z): 489 (M$^+$+1)

EXAMPLE 63

N-[(3RS)-1-Cycloheptylcarbonylmethyl-2,3-dihydro-5,9-dimethyl-2-oxo-1H-1,4-benzodiazepin-3-yl]-N'-(3-methylphenyl)urea was obtained in a similar manner to that of Example 59.

mp: 171.3–174.6° C.

IR (Nujol, cm$^{-1}$): 3360, 1720, 1660, 1640

$^1$H-NMR (DMSO-d$_6$, δ): 1.2–2.0 (2H, m), 2.22 (3H, s), 2.33 (3H, s), 2.4–2.7 (1H, m), 4.09 (1H, d, J=18 Hz), 5.00 (1H, d, J=18 Hz), 5.06 (1H, d, J=8.3 Hz), 6.7–6.8 (1H, m), 7.0–7.7 (7H, m), 8.86 (1H, s)

Mass (APCI)(e/z): 475 (M$^+$+1)

EXAMPLE 64

N-[(3RS)-1-Cyclohexylcarbonylmethyl-5-cyclopropyl-2,3-dihydro-9-methyl-2-oxo-1H-1,4-benzodiazepin-3-yl]-N'-(3-methylphenyl)urea was obtained in a similar manner to that of Example 59.

mp: 143.6–144.2° C.

IR (Nujol, cm$^{-1}$): 3370, 1720, 1680, 1650

$^1$H-NMR (DMSO-d$_6$, δ): 0.8–1.4 (9H, m), 1.5–2.0 (5H, m), 2.1–2.5 (2H, m), 2.22 (3H, s), 2.34 (3H, s), 2.8–3.0 (1H, m), 4.09 (1H, d, J=17 Hz), 4.94 (1H, d, J=17 Hz), 5.06 (1H, d, J=8.3 Hz), 6.7–6.8 (1H, m), 7.0–7.8 (7H, m), 8.8–9.0 (1H, m)

Mass (APCI)(e/z): 487 (M$^+$+1)

EXAMPLE 65

N-[(3RS)-1-Cyclopentylcarbonylmethyl-2,3-dihydro-5,9-dimethyl-2-oxo-1H-1,4-benzodiazepin-3-yl]-N'-(3-methylphenyl)urea was obtained in a similar manner to that of Example 59.

mp: 150.1–155.5° C.

IR (Nujol, cm$^{-1}$): 3280, 1720, 1670, 1645

$^1$H-NMR (DMSO-d$_6$, δ): 1.4–1.9 (8H, m), 2.22 (3H, s), 2.33 (3H, s), 2.47 (3H, s), 2.8–3.0 (1H, m), 4.10 (1H, d, J=17.5 Hz), 4.97 (1H, d, J=17.5 Hz), 5.08 (1H, m), 6.7–6.8 (1H, m), 7.0–7.7 (7H, m), 8.86 (1H, s)

Mass (APCI)(e/z): 447 (M$^+$+1)

EXAMPLE 66

N-[(3RS)-1-(Azacyclooctan-1-yl)carbonylmethyl-2,3-dihydro-5-ethyl-9-methyl-2-oxo-1H-1,4-benzodiazepin-3-yl]-N'-(3-methylphenyl)urea was obtained in a similar manner to that of Example 59.

mp: 189.0–189.5° C.

IR (Nujol, cm$^{-1}$): 3350, 1690, 1630

$^1$H-NMR (DMSO-d$_6$, δ): 1.23 (3H, t, J=7.3 Hz), 1.3–1.9 (10H, m), 2.22 (3H, s), 2.36 (3H, s), 2.7–2.95 (2H, m), 2.95–3.35 (2H, m), 3.35–3.60 (2H, m),3.15 (1H, d, J=16.0 Hz), 4.94 (1H, d, J=16.0 Hz), 5.13 (1H, d, J=8.5 Hz), 6.71 (1H, d, J=6.4 Hz), 7.0–7.6 (6H, m), 8.83 (1H, s)

Mass (APCI)(e/z): 504 (M$^+$+1)

EXAMPLE 67

N-[(3RS)-1-(Azacyclooctan-1-yl)carbonylmethyl-2,3-dihydro-5-isopropyl-9-methyl-2-oxo-1H-1,4-benzodiazepin-3-yl]-N'-(3-methylphenyl)urea was obtained in a similar manner to that of Example 59.

mp: 131.7–132.8° C.

IR (Nujol, cm$^{-1}$): 3320, 1685, 1645, 1605

$^1$H-NMR (DMSO-d$_6$, δ): 1.12 (3H, d, J=7.0 Hz), 1.21 (3H, d, J=6.5 Hz), 1.3–1.9 (10H, m), 2.22 (3H, s), 2.37 (3H, s), 3.0–3.6 (5H, m), 3.98 (1H, d, J=16.0 Hz), 4.87 (1H, d, J=16.0 Hz), 5.09 (1H, d, J=8.5 Hz), 6.72 (1H, d, J=6.2 Hz), 7.0–7.6 (7H, m), 8.82 (1H, s)

Mass (APCI)(e/z): 518 (M$^+$+1)

EXAMPLE 68

N-[(3RS)-1-(Azacyclooctan-1-yl)carbonylmethyl-5-cyclopropyl-2,3-dihydro-9-methyl-2-oxo-1H-1,4-benzodiazcpin-3-yl]-N'-(3-methylphenyl)urea was obtained in a similar manner to that of Example 59.

mp: 177.7–179.2° C.

IR (Nujol, cm$^{-1}$): 3300, 1660, 1630, 1605

$^1$H-NMR (DMSO-d$_6$, δ): 0.7–1.3 (4H, m), 1.3–1.9 (10H, m), 2.0–2.2 (1H, m), 2.22 (3H, s), 2.37 (3H, s), 3.0–3.6 (4H, m), 3.96 (1H d, J=16.0 Hz), 4.90 (1H, d, J=16.0 Hz), 5.05 (1H, d, J=8.5 Hz), 6.7–6.9 (1H, m), 7.0–7.8 (7H, m), 8.79 (1H, s)

Mass (APCI)(e/z): 516 (M$^+$+1)

EXAMPLE 69

N-[(3RS)-1-(Azacyclooctan-1-yl)carbonylmethyl-2,3-dihydro-5-isobutyl-9-methyl-2-oxo-1H-1,4-benzodiazepin-3-yl]-N'-(3-methylphenyl)urea was obtained in a similar manner to that of Example 59.

mp: 131.6–133.4° C.

IR (Nujol, cm$^{-1}$): 3370, 3320, 1700, 1635, 1605

$^1$H-NMR (DMSO-d$_6$, δ): 0.94 (6H, d, J=6.4 Hz), 1.3–1.9 (10H, m), 2.1–2.3 (1H, m), 2.22 (3H, s), 2.37 (3H, s), 2.68 (2H, d, J=6.7 Hz), 3.0–3.6 (4H, m), 3.97 (1H, d, J=16.1 Hz), 4.88 (1H, d, J=16.1 Hz), 5.12 (1H, d, J=8.5 Hz), 6.72 (1H, d, J=6.3 Hz), 7.0–7.6 (7H, m), 8.84 (1H, s)

Mass (APCI)(e/z): 532 (M$^+$+1)

EXAMPLE 70

N-[(3RS)-1-(Azacyclooctan-1-yl)carbonylmethyl-5-cyclohexyl-2,3-dihydro-9-methyl-2-oxo-1H-1,4-benzodiazcpin-3-yl]-N'-(3-methylphenyl)urea was obtained in a similar manner to that of Example 59.

mp: 153.6–155.3° C.

IR (Nujol, cm$^{-1}$): 3360, 3330, 1695, 1650, 1630

$^1$H-NMR (DMSO-d$_6$, δ): 1.1–2.1 (20H, m), 2.22 (3H, s), 3.37 (3H, s), 2.8–3.0 (1H, m), 3.0–3.6 (4H, m), 3.98 (1H, d, J=16.0 Hz), 4.84 (1H, d, J=16.0 Hz), 5.08 (1H, d, J=8.3 Hz), 6.7–6.8 (1H, m), 7.0–7.6 (7H, m), 8.83 (1H, s)

Mass (APCI)(e/z): 558 (M$^+$+1)

EXAMPLE 71-1

N-[(3RS)-5-Acetoxymethyl-1-(azacyclooctan-1-yl) carbonylmethyl-2,3-dihydro-9-methyl-2-oxo-1H-1,4-benzodiazepin-3-yl]-N'-(3-methylphenyl)urea was obtained in a similar manner to that of Example 32.

mp: 112.2–114.2° C.

IR (Nujol, cm$^{-1}$): 3330, 1735, 1680, 1640

$^1$H-NMR (DMSO-d$_6$, δ): 1.2–1.8 (10H, m), 2.06 (3H, s), 2.22 (3H, s), 2.30 (3H, s), 2.9–3.6 (4H, m), 3.97 (1H, d, J=16 Hz), 4.8–5.0 (2H, m), 5.18 (1H, d, J=8.4 Hz), 5.35 (1H, d, J=16 Hz), 6.7–6.8 (1H, m ), 7.0–7.2 (3H, m ), 7.2–7.4 (2H, m ), 7.4–7.7 (2H, m ), 8.87 (1H, s)

Mass (APCI)(e/z): 506 (M$^+$+1)

EXAMPLE 71-2

N-[(3RS)-1-(Azacyclooctan-1-yl)carbonylmethyl-2,3-dihydro-5-hydroxymethyl-9-methyl-2-oxo-1H-1,4-benzodiazepin-3-yl]-N'-(3-methylphenyl)urea was obtained in a similar manner to that of Preparation 14.

mp: 214.5–216.0° C.

IR (Nujol, cm$^{-1}$): 3380, 3280, 1690, 1615

$^1$H-NMR (DMSO-d$_6$, δ): 1.2–1.9 (10H, m), 2.22 (3H, s), 2.38 (3H, s), 2.9–3.2 (1H, m), 3.2–3.4 (3H, m), 3.99 (1H, d, J=16 Hz), 4.56 (1H, s), 4.57 (2H, s), 4.97 (1H, d, J=16 Hz), 5.22 (1H, d, J=8.5 Hz), 6.72 (1H, d, J=6.6 Hz), 7.0–7.7 (7H, m), 8.89 (1H, s)

Mass (APCI)(e/z): 506 (M$^+$+1)

EXAMPLE 71-3(1)

To a solution of N-[(3RS)-1-(azacyclooctan-1-yl) carbonylmethyl-2,3-dihydro-5-hydroxymethyl-9-methyl-2-oxo-1H-1,4-benzodiazepin-3-yl]-N'-(3-methylphenyl)urea (300 mg) and diisopropylethylamine (115 mg) in methylene chloride (4 ml) was added methanesulfonyl chloride (102 mg) under stirring and cooling in an ice-bath. The mixture was stirred under the same conditions for 4 hours. A mixture of 50% aqueous dimethylamine (2 ml) and tetrahydrofuran (2 ml) was added to the reaction mixture obtained above and the resultant mixture was stirred under cooling in an ice-bath for 3.5 hours. Ethyl acetate and water were added to the reaction mixture. The separated organic layer was washed with water and brine, and dried over sodium sulfate. The solvent was evaporated in vacuo to afford a residue, which was triturated in diisopropyl ether and collected by filtration to give N-[(3RS)-1-(azacyclooctan-1-yl)carbonylmethyl-2, 3-dihydro-5-(N,N-dimethylamino)methyl-9-methyl-2-oxo-1H-1,4-benzodiazepin-3-yl]-N'-(3-methylphenyl)urea as crystalline powder (209 mg, 66.2% yield).

mp: 147.9–149.1° C.

IR (Nujol, cm$^{-1}$): 3450, 1670, 1650, 1610

$^1$H-NMR (DMSO-d$_6$, δ) 1.2–1.9 (10H, m), 2.22 (3H, s), 2.25 (6H, s), 2.37 (3H,s), 3.0–3.6 (4H, m), 3.52 (2H, s), 3.97 (1H, d, J=16 Hz), 4.86 (1H, d, J=16 Hz), 5.13 (1H, d, J=8.4 Hz), 6.7–6.8 (1H, m), 7.0–7.5 (6H, m), 7.7–7.9 (1H, m), 8.87 (1H, s)

Mass (APCI)(e/z): 533 (M$^+$+1)

EXAMPLE 71-3(2)

A mixture of N-[(3RS)-1-(Azacyclooctan-1-yl) carbonylmethyl-2,3-dihydro-5-hydroxymethyl-9-methyl-2-oxo-1H-1,4-benzodiazepin-3-yl]-N'-(3-methylphenyl)urea (1.50 mg) and manganese dioxide (15.0 g) in acetone (40 ml) was stirred at ambient temperature for 5 hours. The undissolved substances were removed by filtration. The filtrate was evaporated in vacuo to afford a residue, which was triturated in diisopropyl ether and collected by filtration to give N-[(3RS)-1-(azacyclooctan-1-yl)carbonylmethyl-2,3-dihydro-5-formyl-9-methyl-2-oxo-1H-1,4-benzodiazepin-3-yl]-N'-(3-methylphenyl)urea as crystalline powder (1.20 g, 80.2% yield).

mp: 137.9–141.0° C.

IR (Nujol, cm$^{-1}$): 3350, 1710, 1680, 1640

$^1$H-NMR (DMSO-d$_6$, δ): 1.2–1.9 (10H, m), 2.23 (3H, s), 2.39 (3H, s), 2.8–3.6 (4H, br), 3.98 (1H, d, J=16 Hz), 4.94 (1H, d, J=16 Hz), 5.47 (1H, d, J=8.3 Hz), 6.7–6.8 (1H, m), 7.0–7.7 (7H, m), 8.97 (1H, s), 9.64 (1H, s)

Mass (APCI)(e/z): 504 (M$^+$+1)

EXAMPLE 72

N-[(3RS)-1-Cyclooctylcarbonylmethyl-2,3-dihydro-5,9-dimethyl-2-oxo-1H-1,4-benzodiazepin-3-yl]-N'-(3-methylphenyl)urea was obtained in a similar manner to that of Example 59.

mp: 162.9–164.4° C.

IR (Nujol, cm$^{-1}$): 3350, 1720, 1680, 1640, 1605

$^1$H-NMR (DMSO-d$_6$, δ) 1.3–2.0 (14H, m), 2.22 (3H, s), 2.33 (3H, s), 2.47 (3H, s), 2.5–2.7 (1H, m), 4.09 (1H, d, J=18 Hz), 5.00 (1H, d, J=18 Hz), 5.07 (1H, d, J=9.4 Hz), 6.7–6.8 (1H, m), 7.0–7.6 (7H, m), 8.85 (1H, s)

Mass (APCI)(e/z): 489 (M$^+$+1)

EXAMPLE 73

N-[(3RS)-1-Cyclohexylcarbonylmethyl-2,3-dihydro-5-isobutyl-9-methyl-2-oxo-1H-1,4-benzodiazepin-3-yl]-N'-(3-methylphenyl)urea was obtained in a similar manner to that of Example 59.

mp: 152.3–154.8° C.

IR (Nujol, cm$^{-1}$): 3410, 3250, 1730, 1680, 1650

$^1$H-NMR (DMSO-d$_6$, δ): 0.94 (6H, d, J=6.6 Hz), 1.1–1.4 (5H, m), 1.5–2.0 (5H, m), 2.0–2.2 (1H, m), 2.22 (3H, s), 2.32 (3H, s), 3.3–3.6 (1H, m), 3.6–3.8 (2H, m), 4.72 (1H, d, J=17.6 Hz), 4.89 (1H, d, J=17.6 Hz), 5.09 (1H, d, J=8.5 Hz), 6.7–6.8 (1H, m), 7.0–7.6 (7H, m), 8.83 (1H, s)

Mass (APCT)(e/z): 503 (M$^+$+1)

EXAMPLE 74

N-{(3RS)-2,3-dihydro-5,9-dimethyl-1-[N-methyl-N-(2-pyridyl)amino]carbonylmethyl-2-oxo-1H-1,4-benzodiazepin-3-yl}-N'-(3-methylphenyl)urea was obtained in a similar manner to that of Example 59.

mp: 222.3–224.2° C.

IR (Nujol, cm$^{-1}$): 3280, 1680, 1670, 1650

$^1$H-NMR (DMSO-d$_6$, δ): 2.21 (3H, s), 2.25 (3H, s), 3.23 (3H, s), 2.47 (3H, s), 4.13 (1H, d, J=17 Hz), 4.91 (1H, d, J=17 Hz), 5.09 (1H, d, J=7.9 Hz), 6.6–6.8 (1H, br), 7.0–7.7 (9H, m), 7.8–8.0 (1H, m), 8.4–8.6 (1H, m), 8.91 (1H, s)

Mass (APCI)(e/z): 485 (M$^+$+1)

EXAMPLE 75(1)-1

To a suspension of sodium hydride (31 mg, 60% in mineral oil) in tetrahydrofuran was added ethyl diethylphosphonoacetate (195 mg) under stirring and cooling in an ice-bath. After stirring for 15 minutes, a solution of N-[(3RS)-1-(azacyclooctan-1-yl)carbonylmethyl-2,3-dihydro-5-formyl-9-methyl-2-oxo-1H-1,4-benzodiazepin-3-yl]-N'-(3-methylphenyl)urea (300 mg) in tetrahydrofuran (5 ml) was added to the reaction mixture under the same conditions. The mixture was stirred at ambient temperature for 4 hours. To a reaction mixture was added 0.1N aqueous hydrochloric acid (20 ml) and the resultant mixture was extracted with ethyl acetate. The separated organic layer was washed with water and brine, and dried over magnesium sulfate. The solvent was evaporated in vacuo to afford a residue, which was subjected to column chromatography on silica gel eluting with a mixture of toluene and ethyl acetate (3:1) to give N-[(3RS)-1-(azacyclooctan-1-yl)carbonylmethyl-2,3-dihydro-5-((EZ)-2-(ethoxycarbonyl) ethenyl)-9-methyl-2-oxo-1H-1,4-benzodiazepin -3-yl]-N'-(3-methylphenyl)urea (266 mg, 77.8% yield) as crystalline powder.

mp: 175.2–177.7° C.

IR (Nujol, cm$^{-1}$): 3260, 1730, 1700, 1665, 1620

$^1$H-NMR (DMSO-d$_6$, δ): 1.21 (3H, t, J=7.1 Hz), 1.2–1.8 (10H, m), 2.27 (3H, s), 2.34 (3H, s), 3.0–3.6 (4H, m), 4.10 (2H, q, J=7.1 Hz), 3.9–4.1 (1H, m), 4.86 (1H, d, J=16 Hz), 5.3–5.5 (1H, m), 6.8–6.9 (1H, m), 7.0–7.4 (9H, m), 9.54 (1H, s), 10.22 (1H, s)

Mass (APCI)(e/z): 574 (M$^+$+1)

EXAMPLE 75(1)-2

A mixture of N-[(3RS)-1-(azacyclooctan-1-yl) carbonylmethyl-5-((EZ)-2-(ethoxycarbonyl)ethenyl)-2,3-dihydro-9-methyl-2-oxo-1H-1,4-benzodiazcpin-3-yl]-N'-(3-methylphenyl)urea (230 mg) and 1N sodium hydroxide (1.6 ml) in, 1,2-dimethoxyethane (6.0 ml) was stirred at ambient temperature overnight. Ethyl acetate and water were added to the reaction mixture. The separated aqueous layer was made acidic with 1N aqueous hydrochloric acid and extracted with ethyl acetate. The extract was dried over magnesium sulfate and evaporated in vacuo to afford a residue, which was triturated in diisopropyl ether and collected by filtration to give N-[(3RS)-1-(azacyclooctan-1-yl) carbonylmethyl-2,3-dihydro-5-((EZ)-2-carboxylethenyl)-9-methyl-2-oxo-1H-1,4-benzodiazepin-3-yl]-N'-(3-methylphenyl)urea (80 mg. 36.6% yield) as crystalline powder.

mp: 129.3–134.1° C.

IR (Nujol, cm$^{-1}$): 3200, 1710, 1660, 1630

$^1$H-NMR (DMSO-d$_6$, δ) 1.2–1.8 (10H, m), 2.34 (3H, s), 2.26 (3H, s), 3.0–3.6 (4H, m), 4.05 (1H, d, J=17 Hz), 4.86 (1H, d, J=17 Hz), 5.4–5.6 (1H, m), 6.8–6.9 (1H, m), 7.0–7.4 (9H, m), 10.26 (1H, s)

Mass (APCI)(e/z): 546 (M$^+$+1)

EXAMPLE 75(2)

A mixture of N-[(3RS)-1-(Azacyclooctan-1-yl) carbonylmethyl-2,3-dihydro-5-formyl-9-methyl-2-oxo-1H-

1,4-benzodiazepin-3-yl]-N'-(3-methylphenyl)urea (300 mg), hydroxylamine hydrochloride (41 mg) and sodium acetate (51 mg) in acetic acid (1.5 ml) was stirred at ambient temperature for 2.5 hours. Acetic anhydride (0.4 ml) was added to the reaction mixture, and the resultant mixture was stirred at 90° C. for 11.5 hours. After the reaction mixture was allowed to cool to ambient temperature, ethyl acetate and aqueous sodium hydrogen carbonate were added into the mixture successively under stirring. The separated organic layer was washed with aqueous sodium hydrogen carbonate and brine, and dried over magnesium sulfate. The solvent was evaporated in vacuo to afford a residue, which was subjected to column chromatography on silica gel eluting with a mixture of toluene and ethyl acetate (4:1) to give N-[(3RS)-1-(azacyclooctan-1-yl)carbonylmethyl-5-cyano-2,3-dihydro-9-methyl-2-oxo-1H-1,4-benzodiazepin-3-yl]-N'-(3-methylphenyl)urea as crystalline powder (80 mg).

mp: 213.4–216.7° C.

IR (Nujol, cm$^{-1}$): 3300, 2210, 1690, 1656

$^1$H-NMR (DMSO-d$_6$, δ): 1.2–1.9 (10H, m), 2.25 (3H, s), 2.38 (3H, s), 2.9–3.8 (4H, m), 4.22 (1H, d, J=16 Hz), 5.06 (1H, d, J=16 Hz), 5.37 (1H, d, J=8.1 Hz), 6.7–6.9 (1H, m), 7.0–7.8 (9H, m), 9.4–9.7 (1H m)

Mass (APCI)(e/z): 501 (M$^+$+1)

EXAMPLE 76(1)

To a solution of (3S)-3-amino-1-cyclohexylcarbonylmethyl-5-ethyl-9-methyl-2,3-dihydro-1H-1,4-benzodiazepin-2-one (6.30 g) in tetrahydrofuran (100 ml) was added m-tolyl isocyanate (2.62 g) under stirring at ambient temperature. The mixture was stirred for 3 hours further under the same conditions. After removal of the solvent in vacuo, the residue was dissolved in ethyl acetate and washed with a diluted hydrochloric acid, a diluted aqueous sodium bicarbonate and water successively. The organic extract was dried over magnesium sulfate and evaporated in vacuo to afford an oil (9.36 g), which was subjected to column chromatography on silica gel eluting with a mixture of methylene chloride and methanol (50:1). The fractions containing the desired product were combined and evaporated in vacuo to give N-[(3S)-1-cyclohexylcarbonylmethyl-5-ethyl-9-methyl-2-oxo-2,3-dihydro-1H-1,4-benzodiazepin-3-yl]-N'-(3-methylphenyl)urea (6.34 g, 72.4%) as an amorphous mass.

$^1$H-NMR (CDCl$_3$, δ): 1.05–1.4 (5H, m), 1.26 (3H, t, J=7.4 Hz), 1.55–1.9 (5H, m), 2.02 (1H, br, s), 2.2–2.35 (1H, m), 2.29 (3H, s), 2.33 (3H, s), 2.92 (2H, q, J=7.4 Hz), 3.77 (1H, d, J=17.2 Hz), 5.06 (1H, d, J=17.2 Hz),5.48(1H, d, J=8.3 Hz), 6.7–7.4 (8H, m)

APCI-MS(m/z): 475 (M$^+$+1)

[α]$_D^{30}$=−53.36° (C=1.16, CHCl$_3$)

EXAMPLE 76(2)

N-[(3R)-1-cyclohexylcarbonylmethyl-5-ethyl-9-methyl-2-oxo-2,3-dihydro-1H-1,4-benzodiazepin-3-yl]-N'-(3-methylphenyl)urea was obtained in a similar manner to that of Example 76(1).

$^1$H-NMR (CDCl$_3$, δ): 1.05–1.4 (5H, m), 1.26 (3H, t, J=7.4 Hz), 1.55–1.9 (5H, m), 1.95–2.35 (2H, m), 2.29 (3H, s), 2.32 (3H, s), 2.92 (2H, q, J=7.4 Hz), 3.77 (1H, d, J=17.2 Hz), 5.06 (1H, d, J=17.2 Hz), 5.48 (1H, d, J=8.3 Hz), 6.7–7.4 (8H, m)

APCI-MS(m/z): 475 (M$^+$+1)

[α]$_D^{30}$=−50.92° (C=1.08, CHCl$_3$)

What is claimed is:

1. A compound represented by the formula:

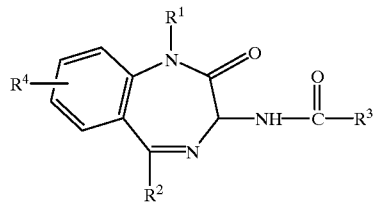

wherein

R$^1$ is
(5) aryl(lower)alkyl which may have one or more suitable substituent(s), or

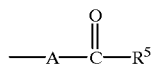

(8)

wherein
A is lower alkylene and
R$^5$ is
(a) lower alkyl,
(b) C$_3$–C$_8$ cycloalkyl,
(c) adamantyl, or
(d) aryl which may have one or more suitable substituent(s), R$^2$ is
(1) lower alkyl,
(3) lower alkoxy(lower)alkyl,
(5) N,N-di(lower)alkylamino(lower)alkyl,
(6) lower alkylpiperazinyl(lower)alkyl,
(7) lower alkylthio(lower)alkyl,
(8) hydroxy(lower)alkyl,
(9) protected hydroxy(lower)alkyl,
(10) azabicyclo[3.2.2]nonyl(lower)alkyl,
(12) cyano,
(13) lower alkanoyl,
(14) carboxy(lower)alkenyl, or
(15) protected carboxy(lower)alkenyl, R$^3$ is indolyl or —NH—R$^6$ wherein R$^6$ is
(1) aryl which may have one or more suitable substituent(s),
(2) pyridyl which may have one or more suitable substituent(s), or
(3) C$_3$–C$_8$ cycloalkyl, and R$^4$ is
(1) hydrogen,
(2) lower alkyl,
(3) halogen, or
(4) di(lower)alkylamino, with proviso that when R$^4$ is hydrogen, then R$^2$ is lower alkyl, or a pharmaceutically acceptable salt thereof.

2. The compound of claim 1, wherein
R$^1$ is
(5) aryl(lower)alkyl which may have one or more acyl(s), or

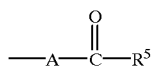
(8)

wherein
    A is lower alkylene and
    $R^5$ is
        (a) lower alkyl,
        (b) $C_3$–$C_8$ cycloalkyl,
        (c) adamantyl, or
        (d) acyl which may have one or more substituent(s), $R^2$ is
    (1) lower alkyl,
    (3) lower alkoxy(lower)alkyl,
    (5) N,N-di(lower)alkylamino(lower)alkyl,
    (6) lower alkylpiperazinyl(lower)alkyl,
    (7) lower alkylthio(lower)alkyl,
    (8) hydroxy(lower)alkyl,
    (9) acyloxy(lower)alkyl,
    (10) azabicyclo[3.2.2]nonyl(lower)alkyl,
    (12) cyano,
    (13) lower alkanoyl,
    (14) carboxy(lower)alkenyl, or
    (15) esterified carboxy(lower)alkenyl, $R^3$ is indolyl or —NH—$R^6$ wherein $R^6$ is
    (1) aryl which may have one or more substituent(s) selected from the group consisting of lower alkyl, hydroxy, lower alkoxy, lower alkylthio, hydroxy(lower)alkyl, acyl, halogen, carboxy, protected carboxy, tetrazolyl, triphenyl(lower)alkyltetrazoyl, hydroxyimino(lower)alkyl, sulfo(lower)alkyl, tetrazolyl(lower)alkyl and di(lower)alkylamino,
    (2) pyridyl which may have one or more lower alkyl(s), or
    (3) $C_3$–$C_8$ cycloalkyl, $R^4$ is
    (1) hydrogen,
    (2) lower alkyl,
    (3) halogen or
    (4) di(lower)alkylamino,
with proviso that when $R^4$ is hydrogen, then $R^2$ is lower alkyl,
or a pharmaceutically acceptable salt thereof.

3. The compound of claim 1, wherein
$R^1$ is
    (5) aryl(lower)alkyl which may have one or more lower alkanoyl(s), or

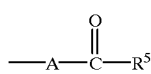
(8)

wherein
    A is lower alkylene and
    $R^5$ is
        (a) lower alkyl,
        (b) $C_3$–$C_8$ cycloalkyl,
        (c) adamantyl, or
        (d) aryl which may have one or more substituent(s) selected from the group consisting of lower alkyl, hydroxy, lower alkoxy, carboxy(lower)alkoxy, lower alkoxycarbonyl(lower)alkoxy, nitro, amino and di(lower alkanoyl)amino, $R^2$ is
    (1) lower alkyl,
    (3) lower alkoxy(lower)alkyl,
    (5) N,N-di(lower)alkylamino(lower)alkyl,
    (6) lower alkylpiperazinyl(lower)alkyl.
    (7) lower alkylthio(lower)alkyl,
    (8) hydroxy(lower)alkyl,
    (9) lower alkanoyloxy(lower)alkyl,
    (10) azabicyclo[3.2.2]nonyl(lower)alkyl,
    (12) cyano,
    (13) lower alkanoyl,
    (14) carboxy(lower)alkenyl, or
    (15) lower alkoxycarbonyl(lower)alkenyl, $R^3$ is indolyl or —NH—$R^6$ wherein $R^6$ is
    (1) aryl which may have one or more substituent(s) selected from the group consisting of lower alkyl, hydroxy, lower alkoxy, lower alkylthio, hydroxy(lower)alkyl, lower alkanoyl, halogen, carboxy, esterified carboxy, tetrazolyl, triphenyl(lower)alkyltetrazolyl, hydroxyimino(lower)alkyl, sulfo(lower)alkyl, tetrazolyl(lower)alkyl, and di(lower)alkylamido,
    (2) pyridyl which may have one or more lower alkyl(s), or
    (3) $C_3$–$C_8$ cycloalkyl, $R^4$ is
    (1) hydrogen,
    (2) lower alkyl,
    (3) halogen or
    (4) di(lower)alkylamino,
with proviso that when $R^4$ is hydrogen, then $R^2$ is lower alkyl,
or a pharmaceutically acceptable salt thereof.

4. A compound of claim 1, wherein
$R^1$ is
    (5) benzyl which may have one or more acetyl substituents, or

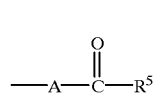
(8)

wherein
    A is methylene, and
    $R^5$ is
        (a) methyl, ethyl or t-butyl,
        (b) cyclopropyl, cyclopentyl, cyclohexyl, cycloheptyl or cyclooctyl,
        (c) adamantyl,
        (d) phenyl which may have one or more substituent(s) selected from the group consisting of methyl, hydroxy, methoxy, carboxymethoxy, ethoxycarbonylmethoxy, nitro, amino and diacetylamino, $R^2$ is
    (1) methyl, ethyl, isopropyl, isobutyl, butyl or isopentyl,
    (3) methoxymethyl,
    (5) N,N-dimethylaminomethyl,
    (6) methylpiperazinylmethyl,
    (7) methylthiomethyl,
    (8) hydroxymethyl,
    (9) acetoxymethyl,
    (10) (3-azabicyclo[3.2.2]non-3-yl)methyl,
    (12) cyano,

(13) formyl,
(14) carboxyvinyl, or
(15) ethoxycarbonylvinyl, $R^3$ is indolyl or —NH—$R^6$ wherein $R^6$ is
  (1) phenyl which may have one or more substituent(s) selected from the group consisting of methyl, hydroxy, methoxy, methylthio, hydroxymethyl, formyl, acetyl, chlorine, bromine, carboxy, t-butoxycarbonyl, tetrazolyl, triphenylmethyltetrazolyl, hydroxyimino methyl, hydroxyimino ethyl, sulfoethyl, tetrazolylmethyl and N,N-dimethylamino,
  (2) pyridyl which may have one or more methyl(s), or
  (3) cyclohexyl, $R^4$ is
  (1) hydrogen,
  (2) methyl, ethyl or isopropyl,
  (3) chlorine, or
  (4) N,N-dimethylamino, with proviso that when $R^4$ is hydrogen, then $R^2$ is isopropyl, isobutyl, methyl, isopentyl, ethyl, butyl or cyclohexylmethyl, or a pharmaceutically acceptable salt thereof.

5. A compound of claim 1, which is represented by the formula:

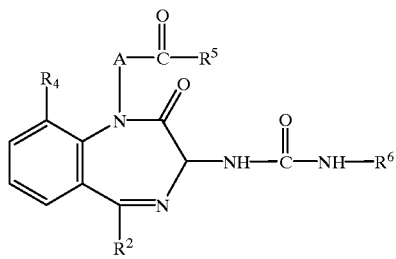

wherein $R^2$ is lower alkyl,
$R^4$ is lower alkyl,
$R^5$ is $C_3$–$C_8$ cycloalkyl,
$R^6$ is lower alkylphenyl and
A is lower alkylene, or a pharmaceutically acceptable salt thereof.

6. The compound of claim 1, which is represented by the formula:

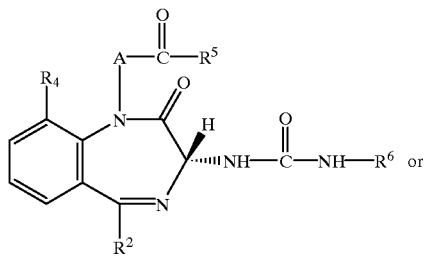

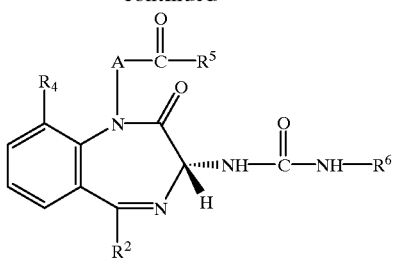

wherein $R^2$ is lower alkyl,
$R^4$ is lower alkyl,
$R^5$ is $C_3$–$C_8$ cycloalkyl,
$R^6$ is lower alkylphenyl and
A is lower alkylene.

or a pharmaceutically acceptable salt thereof.

7. The compound of claim 1, wherein $R^2$ is lower alkyl, or a pharmaceutically acceptable salt thereof.

8. A process for preparing a compound represented by the formula:

(I)

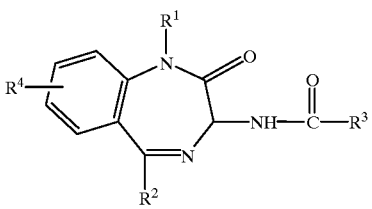

wherein $R^1$ is
  (5) aryl(lower)alkyl which may have one or more suitable substituent(s), or (8)

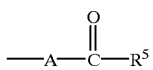

wherein

A is lower alkylene, and
$R^5$ is
  (a) lower alkyl,
  (b) $C_3$–$C_8$ cycloalkyl,
  (c) adamantyl, or
  (d) aryl which may have one or more suitable substituent(s), $R^2$ is
  (1) lower alkyl,
  (3) lower alkoxy(lower)alkyl,
  (5) N,N-di(lower)alkylamino(lower)alkyl,
  (6) lower alkylpiperazinyl(lower)alkyl,
  (7) lower alkylthio(lower)alkyl,
  (8) hydroxy(lower)alkyl,
  (9) protected hydroxy(lower)alkyl,
  (10) azabicyclo[3.2.2]nonyl(lower)alkyl,
  (12) cyano,
  (13) lower alkanoyl,
  (14) carboxy(lower)alkenyl, or
  (15) esterified carboxy(lower)alkenyl, $R^3$ is indolyl or —NH—$R^6$ wherein $R^6$ is
(1) aryl which may have one or more suitable substituent(s),
(2) pyridyl which may have one or more suitable substituent(s), or
(3) $C_3$–$C_8$ cycloalkyl, and $R^4$ is
(1) hydrogen,
(2) lower alkyl,
(3) halogen, or
(4) di(lower)alkylamino, with proviso that when $R^4$ is hydrogen, then $R^2$ is lower alkyl, or a salt thereof,
which comprises:

(1) reacting a compound of the formula (II):

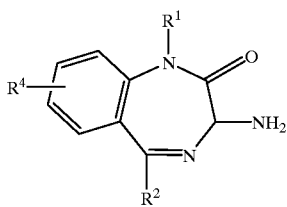

(II)

wherein $R^1$, $R^2$ and $R^4$ are each as defined above, or its reactive derivatives at the amino group or a salt thereof with a compound of the formula (III):

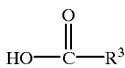

(III)

wherein $R^3$ is each as defined above, or its reactive derivative or a salt thereof to produce a compound of the formula (I):

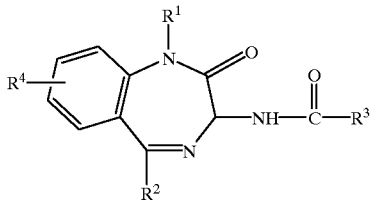

(I)

wherein $R^1$, $R^2$, $R^3$ and $R^4$ are each as defined above, or a salt thereof, or (2) reacting a compound of the formula (IV):

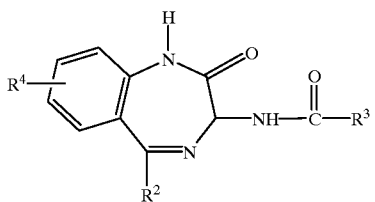

(IV)

wherein $R^2$, $R^3$, and $R^4$ are each as defined above, or a salt thereof with a compound of the formula (V):

X—$R^1$ (V)

wherein $R^1$ is as defined above, X is halogen, or a salt thereof to produce a compound of the formula (I):

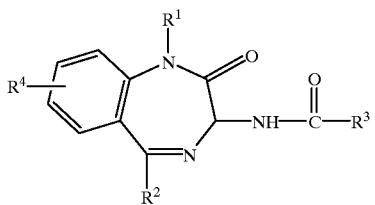

(I)

wherein $R^1$, $R^2$, $R^3$ and $R^4$ are each as defined above, or a salt thereof.

9. A pharmaceutical composition which comprises, as an active ingredient, a compound of claim 1 or a pharmaceutically acceptable salt thereof in admixture with a pharmaceutically acceptable carrier.

10. A process for preparing a pharmaceutical composition which comprises admixing a compound of claim 1 or a pharmaceutically acceptable salt thereof with a pharmaceutically acceptable carrier.

11. A method of treating a disease selected from the group consisting of ulcers, excess gastric secretion, zollinger-Ellison syndrome, non-ulcer dyspepsia, and gastroesophageal reflux disease, comprising administering a compound of claim 1 or a pharmaceutically acceptable salt thereof to an animal.

12. The method of claim 11, wherein the animal is a human.

* * * * *

UNITED STATES PATENT AND TRADEMARK OFFICE
CERTIFICATE OF CORRECTION

PATENT NO.      : 6,291,452 B1
DATED           : September 18, 2001
INVENTOR(S)     : Sato et al.

It is certified that error appears in the above-identified patent and that said Letters Patent is hereby corrected as shown below:

<u>Title page,</u>
Item [73], the Assignee's information should read:
-- [73]   Assignees:   Fujisawa Pharmaceutical Co., Ltd.;
                      Nippon Shokubai Co., Ltd., both of
                      Osaka-shi (JP) --

Signed and Sealed this

Thirty-first Day of December, 2002

JAMES E. ROGAN
*Director of the United States Patent and Trademark Office*